United States Patent
Dyck et al.

(10) Patent No.: US 8,293,729 B2
(45) Date of Patent: Oct. 23, 2012

(54) COMPOUNDS, PHARMACEUTICAL COMPOSITION AND METHODS RELATING THERETO

(75) Inventors: Brian Dyck, San Diego, CA (US); Joe A. Tran, San Marcos, CA (US); Junko Tamiya, Carlsbad, CA (US); Florence Jovic, Los Angeles, CA (US); Troy Vickers, San Diego, CA (US); Chen Chen, San Diego, CA (US); Nicole Harriott, San Diego, CA (US); Timothy Coon, Carlsbad, CA (US); Neil J. Ashweek, Escondido, CA (US)

(73) Assignees: Boehringer Ingelheim International GmbH, Ingelheim am Rhein (DE); Neurocrine Biosciences Inc., San Diego, CA (US)

( * ) Notice: Subject to any disclaimer, the term of this patent is extended or adjusted under 35 U.S.C. 154(b) by 261 days.

(21) Appl. No.: 12/821,231

(22) Filed: Jun. 23, 2010

(65) Prior Publication Data
US 2011/0166116 A1 Jul. 7, 2011

Related U.S. Application Data

(60) Provisional application No. 61/220,133, filed on Jun. 24, 2009.

(51) Int. Cl.
C07D 211/68 (2006.01)
C07D 401/10 (2006.01)
C07D 413/14 (2006.01)
A61K 31/15 (2006.01)

(52) U.S. Cl. .......... 514/218; 514/237.2; 514/253.01; 514/253.13; 514/255.05; 514/260.1; 514/264.11; 514/269; 514/273; 514/275; 514/303; 514/316; 540/575; 544/128; 544/278; 544/279; 544/298; 544/320; 544/323; 544/364; 544/409; 546/118; 546/187; 546/188

(58) Field of Classification Search .......... 540/575; 544/129, 278, 279, 298, 320, 323, 364, 409; 546/118, 187, 188; 514/218, 237.2, 253.01, 514/253.13, 255.05, 260.1, 264.11, 269, 514/273, 275, 303, 316
See application file for complete search history.

(56) References Cited

U.S. PATENT DOCUMENTS

| | | | |
|---|---|---|---|
| 6,221,660 B1 | 4/2001 | Bonini et al. |
| 6,468,756 B1 | 10/2002 | Bonini et al. |
| 7,083,933 B1 | 8/2006 | Griffin |
| 7,108,991 B2 | 9/2006 | Chen et al. |
| 7,135,471 B2 | 11/2006 | Eggenweiler et al. |
| 2007/0078150 A1 | 4/2007 | Jones et al. |
| 2009/0258816 A1 | 10/2009 | Fyee et al. |
| 2009/0286812 A1 | 11/2009 | Erickson et al. |
| 2010/0113479 A1 | 5/2010 | Choudhury et al. |
| 2010/0113480 A1 | 5/2010 | Reuman |
| 2010/0113773 A1 | 5/2010 | Kimura et al. |
| 2010/0292259 A1 | 11/2010 | Kaneko et al. |
| 2011/0021491 A1 | 1/2011 | Tran et al. |
| 2011/0166116 A1 | 7/2011 | Dyck et al. |

FOREIGN PATENT DOCUMENTS

| | | |
|---|---|---|
| CA | 2710182 A1 | 4/2009 |
| CA | 2720049 A1 | 10/2009 |
| EP | 1997484 A2 | 12/2008 |
| WO | 9952868 A1 | 10/1999 |
| WO | 02102783 A1 | 12/2002 |
| WO | 03104205 A1 | 12/2003 |
| WO | 2004043925 A2 | 5/2004 |
| WO | 2005007647 A1 | 1/2005 |
| WO | 2005061489 A1 | 7/2005 |
| WO | 2005121121 A2 | 12/2005 |
| WO | 2006067531 A1 | 6/2006 |
| WO | 2006067532 A1 | 6/2006 |
| WO | 2006070208 A1 | 7/2006 |
| WO | 2006076231 A2 | 7/2006 |
| WO | 2006077364 A1 | 7/2006 |
| WO | 2006077365 A1 | 7/2006 |
| WO | 2006077367 A1 | 7/2006 |
| WO | 2006083491 A2 | 8/2006 |
| WO | 2007003960 A1 | 1/2007 |
| WO | 2007003961 A2 | 1/2007 |
| WO | 2007003962 A2 | 1/2007 |

(Continued)

OTHER PUBLICATIONS

Jones et al., GPR119 agonists for the treatment of type 2 diabetes, Expert Opin. Ther. Patents, 19(10), pp. 1339-1359 (2009).*
Abstract in English for WO2010013849 publication date Feb. 4, 2010.
Abstract in English for WO2010074271 publication date Jul. 1, 2010.
Abstract in English for WO2010084944 publication date Jul. 29, 2010.
Abstract in English for WO2010095663 publication date Aug. 26, 2010.

(Continued)

Primary Examiner — Deepak Rao
(74) Attorney, Agent, or Firm — Michael P. Morris; David L. Kershner

(57) ABSTRACT

New compounds are disclosed which have utility in the treatment of a variety of metabolic related conditions in a patient. The compounds of this invention have the structure (I):

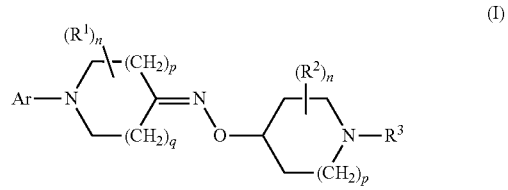

wherein $R^1$, $R^2$, $R^3$, n, p, q, and Ar are as defined herein, including stereoisomers, and pharmaceutically acceptable salts thereof. Also disclosed are pharmaceutical compositions comprising a compound of this invention, as well as methods relating to the use thereof in a patient in need thereof.

20 Claims, No Drawings

FOREIGN PATENT DOCUMENTS

| | | |
|---|---|---|
| WO | 2007003964 A1 | 1/2007 |
| WO | 2007035355 A2 | 3/2007 |
| WO | 2007109045 A1 | 9/2007 |
| WO | 2007116229 A1 | 10/2007 |
| WO | 2007116230 A1 | 10/2007 |
| WO | 2007120689 A2 | 10/2007 |
| WO | 2007120702 A2 | 10/2007 |
| WO | 2007138362 A1 | 12/2007 |
| WO | 2008005569 A2 | 1/2008 |
| WO | 2008005576 A1 | 1/2008 |
| WO | 2008008887 A2 | 1/2008 |
| WO | 2008008895 A1 | 1/2008 |
| WO | 2008009924 A2 | 1/2008 |
| WO | 2008025798 A1 | 3/2008 |
| WO | 2008025799 A1 | 3/2008 |
| WO | 2008025800 A1 | 3/2008 |
| WO | 2008070692 A2 | 6/2008 |
| WO | 2008081204 A1 | 7/2008 |
| WO | 2008081205 A1 | 7/2008 |
| WO | 2008081206 A1 | 7/2008 |
| WO | 2008081207 A1 | 7/2008 |
| WO | 2008081208 A1 | 7/2008 |
| WO | 2008083238 A2 | 7/2008 |
| WO | 2008097428 A2 | 8/2008 |
| WO | 2008109702 A1 | 9/2008 |
| WO | 2008120818 A1 | 10/2008 |
| WO | 2008137435 A1 | 11/2008 |
| WO | 2008137436 A1 | 11/2008 |
| WO | 2009012275 A1 | 1/2009 |
| WO | 2009012277 A1 | 1/2009 |
| WO | 2009014910 A2 | 1/2009 |
| WO | 2009034388 A1 | 3/2009 |
| WO | 2009038974 A1 | 3/2009 |
| WO | 2009050522 A1 | 4/2009 |
| WO | 2009050523 A1 | 4/2009 |
| WO | 2009051119 A1 | 4/2009 |
| WO | 2009055331 A2 | 4/2009 |
| WO | 2009073772 A1 | 6/2009 |
| WO | 2009105715 A1 | 8/2009 |
| WO | 2009105717 A1 | 8/2009 |
| WO | 2009106561 A1 | 9/2009 |
| WO | 2009106565 A1 | 9/2009 |
| WO | 2009123221 A1 | 10/2009 |
| WO | 2009123992 A1 | 10/2009 |
| WO | 2009125434 A2 | 10/2009 |
| WO | 2009126535 A1 | 10/2009 |
| WO | 2009129036 A1 | 10/2009 |
| WO | 2009141238 A1 | 11/2009 |
| WO | 2009150144 A1 | 12/2009 |
| WO | 2010004343 A1 | 1/2010 |
| WO | 2010004344 A1 | 1/2010 |
| WO | 2010004345 A1 | 1/2010 |
| WO | 2010004346 A1 | 1/2010 |
| WO | 2010004347 A1 | 1/2010 |
| WO | 2010004348 A1 | 1/2010 |
| WO | 2010006191 A1 | 1/2010 |
| WO | 2010008739 A2 | 1/2010 |
| WO | 2010009183 A1 | 1/2010 |
| WO | 2010009195 A1 | 1/2010 |
| WO | 2010013849 A1 | 2/2010 |
| WO | 2010014593 A1 | 2/2010 |
| WO | 2010048149 A2 | 4/2010 |
| WO | 2010074271 A1 | 7/2010 |
| WO | 2010075269 A1 | 7/2010 |
| WO | 2010075271 A1 | 7/2010 |
| WO | 2010075273 A1 | 7/2010 |
| WO | 2010084512 A1 | 7/2010 |
| WO | 2010084944 A1 | 7/2010 |
| WO | 2010088518 A2 | 8/2010 |
| WO | 2010095663 A1 | 8/2010 |
| WO | 2010103333 A1 | 9/2010 |
| WO | 2010103334 A1 | 9/2010 |
| WO | 2010103335 A1 | 9/2010 |
| WO | 2010106457 A2 | 9/2010 |
| WO | 2010114957 A1 | 10/2010 |
| WO | 2010114958 A1 | 10/2010 |
| WO | 2010123018 A1 | 10/2010 |
| WO | 2010128414 A1 | 11/2010 |
| WO | 2010128425 A1 | 11/2010 |
| WO | 2010135505 A2 | 11/2010 |
| WO | 2010135506 A1 | 11/2010 |
| WO | 2010140092 A1 | 12/2010 |
| WO | 2010149684 A1 | 12/2010 |
| WO | 2010149685 A1 | 12/2010 |
| WO | 2011138427 A2 | 11/2011 |

OTHER PUBLICATIONS

Abstract in English for WO2010123018 publication date Oct. 28, 2010.

Abstract in English for WO09123221 (2009) is AU2009232721 (2009) cited in NPL.

Chu, Z-L, et al., "A Role for Intestinal Endocrine Cell-Expressed GPR119 in Glycemic Control by Enhancing GLP-1 and GIP Release". The Endocrine Socieity, Endocrinology, first published ahead of print Jan. 17, 2008.

Endocrinology. "G Protein-Coupled Receptors and Isuli Secretion: 119 and Counting". Endocrinology, 2007, 148, 6, p. 2598-2600.

International Search Report for PCT/EP2010/058873 mailed Sep. 2, 2010.

Overton, H.A. et al., "GPR119, a novel G protein-coupled receptor target for the treatment of type 2 diabetes and obesity". Life Sciences 2007, British Journal of Pharmacology, 2007, p. 1-6.

Sakamoto, Y. et al., Expression and distribution of Gpr119 in the pancreatic islets of mice and rats; predominant localization in pancreatic polypeptide-secreting PP-cells. Science Direct, Biochemical and Biophysical Research Communications, 351, 2006, p. 474-480.

Soga, T. et al., "Lysophosphatidylcholine enhances glucose-dependent insulin secretion via an orphan G-protein coupled receptor". Science Direct, Biochemical and Biophysical Research Communications, 326, 2005, p. 744-751.

Winzell, M.S., et al. "G-protein-coupled receptors and islet function—Implications for treatment of type 2 diabetes". Science Direct, Pharmacology and Therapeutics, 116, 2007, p. 437-448.

WO200800839 (Part 1of2), International Publication Date: Jan. 17, 2008. Patentee: Shionogi & Co. Ltd. Inventor: A, Matsumura, Title: Oxime Compounds and their use thereof. Total pp. 599. Part 1 of 2. This foreign patent is too large for EFS submission via the Foreign patent section. Therefore filing in two parts in the NPL section. pp. 1-319.

WO200800839 (Part 2of2), International Publication Date: Jan. 17, 2008. Patentee: Shionogi & Co. Ltd. Inventor: A, Matsumura, Title: Oxime Compounds and their use thereof. Total pp. 599. Part 2 of 2. This foreign patent is too large for EFS submission via the Foreign patent section. Therefore filing in two parts in the NPL section. pp. 319-599.

* cited by examiner

SEQUENCE LISTING

<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Lys Thr Ile Ile Ala Leu Ser Tyr Ile Phe Cys Leu Val Phe Ala
1               5                   10                  15

Asp Tyr Lys Asp Asp Asp Asp Ala
            20

COMPOUNDS, PHARMACEUTICAL COMPOSITION AND METHODS RELATING THERETO

FIELD OF THE INVENTION

This invention relates generally to new compounds of the formula (I), to pharmaceutical compositions and to methods of treating diseases and conditions by administration of such compounds to a patient in need thereof.

BACKGROUND OF THE INVENTION

Diabetes is an increasingly prevalent chronic disease whose impact as a public health concern is felt throughout the world. The American Diabetes Association estimates approximately 7% of the United States population suffers from this disease and that 1 out of every 10 dollars spent on healthcare in the U.S. is spent on diabetes and its complications. Type 1 diabetes generally results from the body's failure to produce insulin. Type 2 diabetes is the more prevalent type of diabetes and generally results from insulin resistance combined with a relative insulin deficiency. Additionally, there are millions of Americans who can be said to have prediabetes, that is, higher than normal blood glucose levels but not yet high enough to be diagnosed with Type 2 diabetes.

Type 2 diabetes is characterized by fasting and postprandial hyperglycemia and by relative insulin insufficiency. Hyperglycemia may cause long-term microvascular and macrovascular complications, such as nephropathy, neuropathy, retinopathy, and peripheral vascular disease. In addition, Type 2 diabetes is a comorbid disease that frequently compounds hyperlipidemia, atherosclerosis and hypertension. Hyperlipidemia is a primary risk factor for cardiovascular disease due to atherosclerosis. Obesity is a well known common risk factor for the development of atherosclerosis, stroke, hypertension and Type 2 diabetes. Type 2 diabetes causes significant morbidity and mortality at considerable expense to patients, their families and society. Furthermore, the incidence of Type 2 diabetes worldwide is increasing such that Type 2 diabetes is now considered to be a worldwide epidemic.

A number of therapies for the treatment of Type II diabetes are in use. A change in diet along with an increase in exercise and weight loss is considered a first line of treatment. However, this may not result in sufficient control of blood glucose levels resulting in the use of medications to help control glucose levels. These medications include insulin, sulfonylureas, meglitinides, biguanides, thiazolidinediones, DPP-4 inhibitors, alpha-glucosidase inhibitors, amylin analogs and incretin mimetics. These medications may be used singly or in combination and may result in reduced glucose levels. However, these medications still may not cause a drop in glucose levels to what would be considered normal or the effect may wear off over time. Some medications may lower glucose levels too much, resulting in a dangerous hypoglycemic episode. Insulin, amylin and incretin mimetics need to be injected, often numerous times a day. Other side effects include weight gain, nausea, and diarrhea.

GPR119 is a class 1 G-protein-coupled receptor which has received attention due to evidence that modulation of the GRP119 receptor may produce favorable effects on glucose homeostasis, food intake, body weight gain and β-cell preservation, any or all of which effects may be useful in the treatment of both diabetes and obesity (*Br. J. Pharm.* 2007 1-6).

The GPR119 receptor and isoforms have been identified in mammalian species including human, rat, mouse, hamster, chimpanzee, rhesus monkey, cattle and dog. The pancreas has been identified as the major site of mRNA expression in the human, with some expression also seen in the gastrointestinal tract. The expression of GPR119 in the pancreas and particularly in the pancreatic β-cells led to the hypothesis that the GPR119 receptor could have effects upon insulin secretion.

The discovery of two endogenous ligands, lysophosphatidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm 2005 744-751, Cell Metabolism 2006 167-175, Endocrinolgy 2007, 2601-9, Endocrinology, 2008, Epub ahead of print). GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Taken together, GPR119 is a novel mechanism by which glycemic control may be facilitated with the added benefit of weight loss.

BRIEF SUMMARY OF THE INVENTION

In brief, this invention is generally directed to new compounds, as well as to methods for their preparation and use, and to pharmaceutical compositions containing the same. More specifically, the new compounds are useful as GPR119 receptor agonists. In a first aspect the present invention relates to a compound of the following general formula (I):

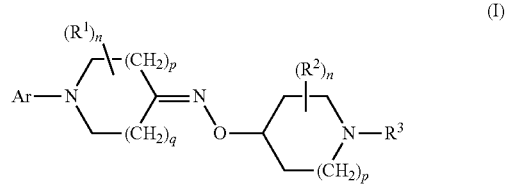

including tautomers and stereoisomers thereof, or a salt thereof, wherein $R^1$, $R^2$, $R^3$, n, p, q, and Ar are as defined below.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

The compounds of this invention may have utility over a wide range of therapeutic applications, and may be used to treat a variety of conditions in both men and women, as well as a mammal in general (also referred to herein as a "patient"). For example, such conditions include diabetes and obesity. The compounds of the present invention may treat these conditions through effects on glucose homeostasis, food intake, body weight gain and β-cell preservation.

Therefore in a further aspect this invention relates to a method for treating diseases or conditions which are mediated by modulating the activity of GPR119 enzyme(s) in a patient in need thereof characterized in that a compound of general formula (I) or a pharmaceutically acceptable salt thereof is administered to a patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided the use of a compound of the general formula (I) or a physiologically acceptable salt thereof for the manufacture of a medicament for a therapeutic method as described hereinbefore and hereinafter.

The methods of this invention include administering an effective amount of a compound of this invention, preferably in the form of a pharmaceutical composition, to a patient in need thereof.

In a further aspect this invention relates to a pharmaceutical composition, comprising one or more compounds of general formula (I) or one or more pharmaceutically acceptable salts thereof according to the invention, optionally together with one or more pharmaceutically acceptable carriers and/or diluents.

Compounds of the present invention may be administered along with additional agents to help lower glucose levels. Additional therapeutic agents which may be used in conjunction with a compound of the current invention include insulin, sulfonylureas, meglitinides, biguanides, thiazolidinediones, DPP-4 inhibitors, alpha-glucosidase inhibitors, amylin analogs and incretin mimetics.

Therefore in a further aspect this invention relates to a method for treating a disease or condition mediated by modulating the activity of GPR119 in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) in combination with one or more additional therapeutic agents for the treatment or prevention of diseases or conditions which are mediated by modulating the activity of GPR119.

In a further aspect this invention relates to a pharmaceutical composition which comprises a compound according to general formula (I) and one or more additional therapeutic agents, optionally together with one or more pharmaceutically acceptable carriers and/or diluents.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as GPR119 receptor agonists. The compounds of this invention have the following structure (I):

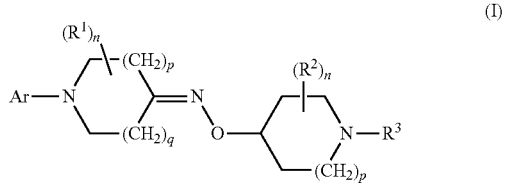

(I)

wherein:
Ar is aryl or heteroaryl, wherein each aryl and heteroaryl are optionally substituted with 1-5 $R^4$;

$R^1$ at each occurrence is independently $C_{1-4}$alkyl, F, hydroxy, $C_{1-4}$alkyl-O—, —$CO_2R^7$, or —C(=O)N($R^6$)$_2$;

$R^2$ at each occurrence is independently $C_{1-4}$alkyl, F, hydroxy, or $C_{1-4}$alkyl-O—;

$R^3$ is $R^{Alk}$, aryl-$C_{1-4}$alkyl, heterocycle-$C_{1-4}$alkyl, —C(=O)$R^6$, —$CO_2R^5$, —$SO_2R^5$, —C(=X)N($R^6$)$_2$, aryl, or heterocycle, wherein each alkyl, $R^{Alk}$, aryl, and heterocycle group is optionally substituted with 1-4 substituents independently of each other selected from $R^8$;

$R^4$ at each occurrence is independently halogen, cyano, hydroxy, $R^{Alk}$, —$NO_2$, —C(=O)H, —C(=O)$R^5$, —$C_{1-3}$-alkyl-C(=O)$R^5$, —$CO_2H$, —$CO_2R^5$, —C(=O)N($R^6$)$_2$, —$C_{1-3}$-alkyl-C(=O)N($R^6$)$_2$, —$SO_2N(R^6)_2$, —S(=O)$R^5$, —S(=O)$_2R^5$, —S(=O)$_2$—O—$R^5$, $R^{Alk}$—O—, $R^{Alk}$—S—, —N($R^6$)$_2$, aryl, aryl-$C_{1-6}$alkyl, heterocycle, heterocycle-$C_{1-6}$alkyl, —$NR^6C$(=O)$R^5$, —$NR^6S$(=O)$_2R^5$, —$NR^6C$(=O)N($R^6$)$_2$, —$NR^6C$(=O)$OR^7$, —$NR^6C$(=$NR^6$)N($R^6$)$_2$, or —$NR^6S$(=O)$_2$N($R^6$)$_2$, wherein each alkyl, $R^{Alk}$, aryl and heterocycle is optionally substituted with 1-5 substituents independently of each other selected from $R^8$;

$R^5$ is $R^{Alk}$, heterocycle, aryl, heterocycle-$C_{1-3}$-alkyl or aryl-$C_{1-3}$-alkyl, wherein each alkyl, $R^{Alk}$, heterocycle and aryl group is optionally substituted with 1-4 independently of each other selected from $R^8$;

$R^6$ at each occurrence is independently H, $R^{Alk}$, heterocycle, heterocycle-$C_{1-6}$-alkyl, aryl or aryl-$C_{1-3}$-alkyl, wherein each $R^{Alk}$, heterocycle, aryl and alkyl are optionally substituted with 1-4 substituents independently of each other selected from halogen, hydroxy, —N($R^7$)$_2$, $C_{1-4}$alkyl-O—, and —$CO_2R^7$;

$R^7$ at each occurrence is independently H or $C_{1-4}$alkyl;

$R^8$ at each occurrence is independently cyano, hydroxy, $R^{Alk}$, aryl, aryl-$C_{1-6}$alkyl, heterocycle, heterocycle-$C_{1-6}$alkyl, halogen, oxo, $C_{1-4}$haloalkyl, —$NO_2$, —C(=O)H, —$CO_2R^7$, —OC(=O)$R^{Alk}$, —C(=O)N($R^6$)$_2$, —$SO_2N(R^6)_2$, —S(=O)$R^{Alk}$, —S(=O)$_2R^{Alk}$, $C_{1-6}$alkyl-O—, halo$C_{1-4}$alkyl-O—, —N($R^6$)$_2$, —$SR^6$, —$NR^6C$(=O)$R^{Alk}$, —$NR^6S$(=O)$_2R^{Alk}$, —$NR^6C$(=O)$OR^{Alk}$, —$NR^6C$(=O)N($R^6$)$_2$ or —$NR^6S$(=O)$_2$N($R^6$)$_2$, wherein each $R^{Alk}$, alkyl, aryl and heterocycle are optionally substituted with 1-4 substituents independently of each other selected from halogen, hydroxy, —N($R^7$)$_2$, $C_{1-4}$alkyl-O—, —$NR^6CO_2R^6$, —$NR^6SO_2R^6$, and —$CO_2R^7$;

$R^{Alk}$ at each occurrence is independently $C_{1-6}$-alkyl, $C_{2-6}$-alkenyl, $C_{2-6}$-alkynyl, $C_{3-8}$-cycloalkyl, $C_{3-8}$-cycloalkyl-$C_{1-3}$-alkyl, $C_{4-8}$-cycloalkenyl or $C_{4-8}$-cycloalkenyl-$C_{1-3}$-alkyl;

X denotes O or S;
n at each occurrence is 0, 1, or 2;
p at each occurrence is 0 or 1; and
q is 0, 1, or 2,
including any tautomers and stereoisomers thereof,
or a salt thereof.

Unless otherwise stated, the groups, residues, and substituents, particularly Ar, X, $R^{Alk}$, $R^N$, $R^1$, $R^2$, $R^3$, $R^4$, $R^5$, $R^6$, $R^7$, $R^8$, are defined as above and hereinafter. If residues, substituents, or groups occur several times in a compound, as for example $R^{Alk}$, $R^N$, $R^4$, $R^5$, $R^6$, $R^7$, $R^8$, they may have the same or different meanings. Some preferred meanings of individual groups and substituents of the compounds according to the invention will be given hereinafter. Any and each of these definitions may be combined with each other.

Ar:

According to an embodiment Ar-E1 the group Ar denotes aryl or heteroaryl, wherein aryl denotes phenyl or naphthyl, and heteroaryl denotes a 5- or 6-membered aromatic monocyclic ring, which comprises 1 to 4 heteroatoms selected from N, O and S, or a 8-, 9- or 10-membered aromatic bicyclic ring, which comprises 1 to 4 heteroatoms selected from N, O and S, wherein in each monocyclic aryl or heteroaryl group two adjacent C and/or N atoms may be linked via a $C_{3-5}$-alkylene or $C_{3-5}$-alkenylene bridging group in which one or two $CH_2$- groups may be replaced by a group selected from O, S, NH, $N(C_{1-3}$-alkyl), —C(=O)—, —S(=O)— and —S(=O)$_2$—, and wherein one or two CH-groups may be replaced by N, wherein said aryl or heteroaryl group is optionally substituted with 1-5 substituents independently of each other selected from $R^4$.

According to another embodiment Ar-E2 the group Ar denotes phenyl, pyridyl, pyrazinyl, pyrimidinyl, pyridazinyl, indazolyl, benzooxazolyl, benzoisoxazolyl, quinazolinyl or tetrahydropyridopyrimidinyl, all of which are optionally substituted with 1-5 substituents independently of each other selected from $R^4$.

According to another embodiment Ar-E3 the group Ar is selected from the group consisting of phenyl, pyridyl, pyrazinyl, pyrimidinyl, pyridazinyl,

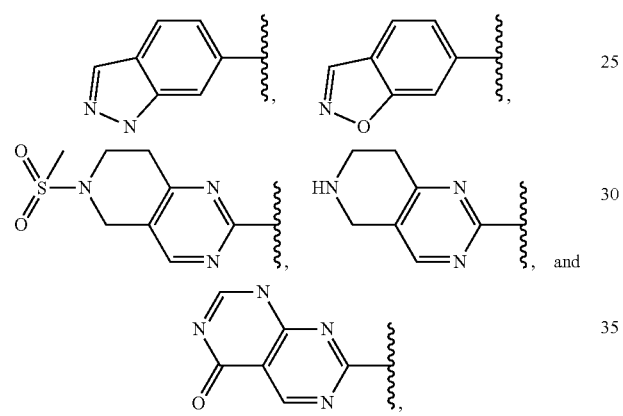

all of which are optionally substituted with 1-5 $R^4$.

According to another embodiment Ar-E4 the group Ar denotes phenyl, pyridyl, pyrazinyl, pyrimidinyl or pyridazinyl, all of which are optionally substituted with 1-5 substituents independently of each other selected from $R^4$.

The group Ar is preferably substituted with 1 to 5 substituents independently of each other selected from $R^4$, even more preferably with 1 to 4 substituents independently of each other selected from $R^4$.

According to another embodiment Ar-E5 the group Ar is selected from the group consisting of

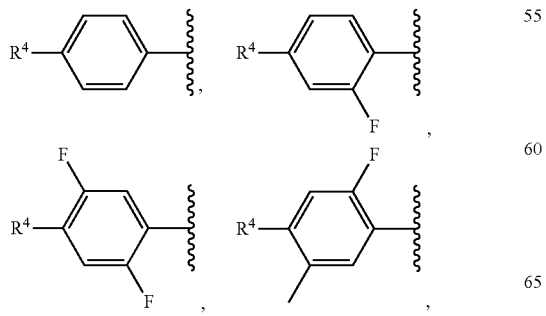

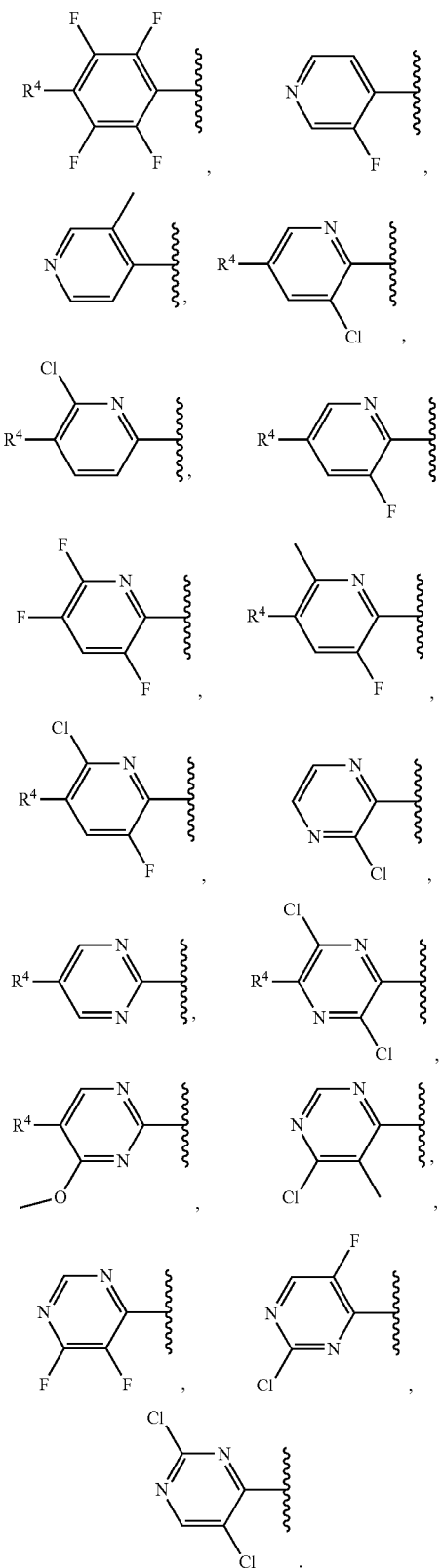

wherein $R^4$ is defined as hereinbefore and hereinafter.

According to another embodiment Ar-E6 the group Ar is selected from the group consisting of

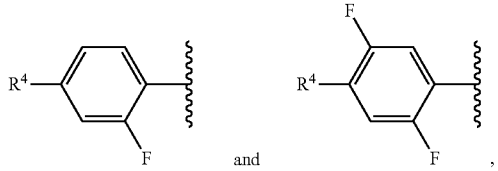

and wherein $R^4$ is defined as hereinbefore and hereinafter.

$R^4$:

According to an embodiment $R^4$-E1 the group $R^4$ at each occurrence denotes independently F, Cl, CN, —NO$_2$, $R^{Alk}$, $R^{Alk}$—O—, HCO, $R^{Alk}$—C(=O)—, HO—C(=O)—, $R^{Alk}$—O—C(=O)—, $R^{Alk}$—S(=O)—, $R^{Alk}$—S(=O)$_2$—, $R^{Alk}$—O—S(=O)$_2$—, $(R^6)_2$N—C(=O)—, $(R^6)_2$N—C(=O)—C$_{1-3}$-alkyl, heterocycle, heterocycle-C$_{1-3}$-alkyl, heterocycle-C(=O)—, heterocycle-C(=O)—C$_{1-3}$-alkyl, heterocycle-N($R^6$)—C(=O)—, heterocycle-N($R^6$)—C(=O)—C$_{1-3}$-alkyl, heterocycle-C$_{1-3}$alkyl-N($R^6$)—C(=O)—, heterocycle-C$_{1-3}$alkyl-N($R^6$)—C(=O)—C$_{1-3}$-alkyl, $(R^6)_2$N—S(=O)$_2$—, $R^{Alk}$—C(=O)—O—C$_{1-3}$-alkyl, $R^{Alk}$—O—C(=O)—N($R^6$)—C$_{1-3}$-alkyl-C(=O)—O—C$_{1-3}$-alkyl, $R^{Alk}$—S(=O)$_2$—C$_{1-3}$-alkyl, $(R^6)_2$N—C$_{1-3}$-alkyl, heterocycle-C$_{1-3}$-alkyl-N($R^6$)—C$_{1-3}$-alkyl, $R^{Alk}$—C(=O)—N($R^6$)—, $R^{Alk}$—C(=O)—N($R^6$)—C$_{1-3}$-alkyl, $R^{Alk}$—O—C(=O)—N($R^6$)—, $R^{Alk}$—O—C(=O)—N($R^6$)—C$_{1-3}$-alkyl, $R^{Alk}$-alkyl-S(=O)$_2$—N($R^6$)—, $R^{Alk}$—S(=O)$_2$—N($R^6$)—C$_{1-3}$-alkyl, $(R^6)_2$N—C(=O)—N($R^6$)—, $(R^6)_2$N—C(=O)—N($R^6$)—C$_{1-3}$-alkyl, $(R^6)_2$N—S(=O)$_2$—N($R^6$)—, $(R^6)_2$N—S(=O)$_2$—N($R^6$)—C$_{1-3}$-alkyl, wherein each $R^{Alk}$, alkyl and heterocycle group is optionally substituted with 1-3 substituents independently of each other selected from $R^8$;

wherein $R^{Alk}$ is defined as hereinbefore and hereinafter or preferably means C$_{1-6}$alkyl, C$_{2-6}$-alkenyl, C$_{2-6}$-alkynyl, C$_{3-8}$-cycloalkyl or C$_{3-8}$-cycloalkyl-C$_{1-3}$-alkyl or even more preferably means C$_{1-6}$alkyl, C$_{3-7}$-cycloalkyl or C$_{3-7}$-cycloalkyl-C$_{1-3}$-alkyl; and wherein heterocycle is defined as hereinbefore and hereinafter or preferably means a 4-, 5- or 6-membered monocyclic or a 8-, 9- or 10-membered bi- or tri-cyclic heterocycle ring which is either saturated, unsaturated or aromatic, and which contains from 1 to 4 heteroatoms independently selected from N, O and S, and wherein the N and S heteroatoms may be optionally oxidized, and the N heteroatom may be optionally quaternized, including bicyclic rings in which any of the above heterocycles are fused to a benzene ring, and wherein the above mentioned rings may comprise a group selected from —C(=O)—, —S(=O)— or —S(=O)$_2$—;

even more preferably the term heterocycle denotes azetidinyl, pyrrolidinyl, piperidinyl, morpholinyl, piperazinyl, azepanyl, diazepanyl, aza-bicyclo[2.2.2]octyl, hexahydro-pyrrolo[3,4-c]pyrrolyl, pyrrolidinonyl, piperidinonyl, oxazolidinonyl, imidazolidinonyl, piperazinonyl, pyrrolyl, pyrrazolyl, imidazolyl, dihydroimidazolyl, triazolyl, oxazolyl, isoxazolyl, thiazolyl, furanyl, thiophenyl, pyridyl, pyridazinyl, pyrimidinyl, pyrazinyl, tetrazolyl and dithianyl-5-oxide, wherein said pyrrolyl, pyrrazolyl, imidazolyl, oxazolyl, isoxazolyl, thiazolyl, furanyl, thiophenyl, pyridyl, pyridazinyl, pyrimidinyl and pyrazinyl may be condensed with a phenyl, pyridyl, pyrrolyl, pyrrazolyl or imidazolyl ring; and wherein $R^6$ is defined as hereinbefore and hereinafter or preferably denotes H, C$_{1-6}$-alkyl, C$_{3-8}$-cycloalkyl, C$_{3-7}$-cycloalkyl-C$_{1-3}$-alkyl, wherein each alkyl group is optionally substituted with 1-4 substituents independently of each other selected from HO—, C$_{1-4}$-alkyl-O—, H$_2$N—, C$_{1-3}$-alkyl-NH—, (C$_{1-3}$-alkyl)$_2$N—, HOOC—, C$_{1-4}$-alkyl-O—C(=O)—, even more preferably $R^6$ denotes H or C$_{1-4}$-alkyl, wherein each alkyl group is optionally substituted as defined hereinbefore; and wherein $R^8$ is defined as hereinbefore and hereinafter or preferably denotes F, Cl, CN, —OH, oxo, C$_{1-4}$-alkyl-, C$_{1-4}$-alkyl-O—, HOOC—, C$_{1-4}$-alkyl-O—(O=)C—, H$_2$N—, C$_{1-3}$-alkyl-NH—, (C$_{1-3}$-alkyl)$_2$N—, H$_2$N—C$_{1-3}$-alkyl-, C$_{1-3}$-alkyl-NH—C$_{1-3}$-alkyl-, (C$_{1-3}$-alkyl)$_2$N—C$_{1-3}$-alkyl-, heterocycle-C$_{1-3}$-alkyl, wherein each alkyl group is optionally substituted with 1-3 F atoms, and wherein heterocycle is defined as hereinbefore and hereinafter or preferably denotes azetidinyl, pyrrolidinyl, piperidinyl, azepanyl, piperazinyl or morpholinyl, wherein each heterocycle group is optionally substituted with 1 or 2 C$_{1-3}$-alkyl groups.

According to an embodiment $R^4$-E2 the group $R^4$ at each occurrence denotes independently F, Cl, CN, —NO$_2$, C$_{1-4}$alkyl, C$_{2-4}$-alkenyl, C$_{1-4}$-alkyl-O—, HCO, C$_{1-4}$-alkyl-C(=O)—, HO—C(=O)—, C$_{1-4}$-alkyl-O—C(=O)—, C$_{1-4}$-alkyl-S(=O)—, C$_{1-4}$-alkyl-S(=O)$_2$—, C$_{3-7}$-cycloalkyl-S(=O)$_2$—, C$_{1-4}$-alkyl-O—S(=O)$_2$—, $(R^6)_2$N—C(=O)—, $(R^6)_2$N—C(=O)—C$_{1-3}$-alkyl, heterocycle, heterocycle-C$_{1-3}$-alkyl, heterocycle-C(=O)—, heterocycle-C(=O)—C$_{1-3}$-alkyl, heterocycle-N($R^6$)—C(=O)—, heterocycle-N($R^6$)—C(=O)—C$_{1-3}$-alkyl, heterocycle-C$_{1-3}$alkyl-N($R^6$)—C(=O)—, heterocycle-C$_{1-3}$alkyl-N($R^6$)—C(=O)—C$_{1-3}$-alkyl, $(R^6)_2$N—S(=O)$_2$—, C$_{1-4}$-alkyl-C(=O)—O—C$_{1-3}$-alkyl, C$_{1-4}$-alkyl-O—C(=O)—N($R^6$)—C$_{1-3}$-alkyl-C(=O)—O—C$_{1-3}$-alkyl, C$_{1-4}$-alkyl-S(=O)$_2$—C$_{1-3}$-alkyl, $(R^6)_2$N—C$_{1-3}$-alkyl, heterocycle-C$_{1-3}$-alkyl-N($R^6$)—C$_{1-3}$-alkyl, C$_{1-4}$-alkyl-C(=O)—N($R^6$)—, C$_{1-4}$-alkyl-C(=O)—N($R^6$)—C$_{1-3}$-alkyl, C$_{1-4}$-alkyl-O—C(=O)—N($R^6$)—, C$_{1-4}$-alkyl-O—C(=O)—N($R^6$)—C$_{1-3}$-alkyl, C$_{1-4}$-alkyl-S(=O)$_2$—N($R^6$)—, C$_{1-4}$-alkyl-S(=O)$_2$—N($R^6$)—C$_{1-3}$-alkyl, $(R^6)_2$N—C(=O)—N($R^6$)—, $(R^6)_2$N—C(=O)—N($R^6$)—C$_{1-3}$-alkyl, $(R^6)_2$N—S(=O)$_2$—N($R^6$)—, $(R^6)_2$N—S(=O)$_2$—N($R^6$)—C$_{1-3}$-alkyl, wherein each alkyl, cycloalkyl, alkenyl, heterocycle group is optionally substituted with 1-3 substituents independently of each other selected from $R^8$;

wherein heterocycle is defined as hereinbefore and hereinafter or preferably means a 4-, 5- or 6-membered monocyclic or a 8-, 9- or 10-membered bi- or tricyclic heterocycle ring which is either saturated, unsaturated or aromatic, and which contains from 1 to 4 heteroatoms independently selected from N, O and S, and wherein the N and S heteroatoms are optionally oxidized, and the N heteroatom is optionally quaternized, including bicyclic rings in which any of the above heterocycles are fused to a benzene ring, and wherein the above mentioned rings may comprise a group selected from —C(=O)—, —S(=O)— or —S(=O)$_2$—;

even more preferably the term heterocycle denotes azetidinyl, pyrrolidinyl, piperidinyl, morpholinyl, piperazinyl, azepanyl, diazepanyl, aza-bicyclo[2.2.2]octyl, hexahydro-pyrrolo[3,4-c]pyrrolyl, pyrrolidinonyl, piperidinonyl, oxazolidinonyl, imidazolidinonyl, piperazinonyl, pyrrolyl, pyrrazolyl, imidazolyl, dihydroimidazolyl, triazolyl, oxazolyl, isoxazolyl, thiazolyl, furanyl, thiophenyl, pyridyl, pyridazinyl, pyrimidinyl, pyrazinyl, tetrazolyl and dithianyl-S-oxide, wherein said pyrrolyl, pyrrazolyl, imidazolyl, oxazolyl, isoxazolyl, thiazolyl, furanyl, thiophenyl, pyridyl, pyridazinyl, pyrimidinyl and pyrazinyl may be condensed with a phenyl, pyridyl, pyrrolyl, pyrrazolyl or imidazolyl ring; and wherein $R^6$ is defined as hereinbefore and hereinafter or preferably denotes H, $C_{1-6}$-alkyl, $C_{3-8}$-cycloalkyl, $C_{3-7}$-cycloalkyl-$C_{1-3}$-alkyl, wherein each alkyl group is optionally substituted with HO—, $C_{1-4}$-alkyl-O—, $H_2N$—, $C_{1-3}$-alkyl-NH—, $(C_{1-3}$-alkyl$)_2N$—, HOOC—, $C_{1-4}$-alkyl-O—C(=O)—, even more preferably $R^6$ denotes H or $C_{1-4}$-alkyl, wherein each alkyl group is optionally substituted as defined hereinbefore; and wherein $R^8$ is defined as hereinbefore and hereinafter or preferably denotes F, Cl, CN, —OH, oxo, $C_{1-4}$-alkyl-, $C_{1-4}$-alkyl-O—, HOOC—, $C_{1-4}$-alkyl-O—(O=)C—, $H_2N$—, $C_{1-3}$-alkyl-NH—, $(C_{1-3}$-alkyl$)_2N$—, $H_2N$—$C_{1-3}$-alkyl-, $C_{1-3}$-alkyl-NH—$C_{1-3}$-alkyl-, $(C_{1-3}$-alkyl$)_2N$—$C_{1-3}$-alkyl-, heterocycle-$C_{1-3}$-alkyl, wherein each alkyl group may be substituted with 1-3 F atoms, and wherein heterocycle is defined as hereinbefore and hereinafter or preferably denotes azetidinyl, pyrrolidinyl, piperidinyl, piperazinyl or morpholinyl, wherein each heterocycle group is optionally substituted with 1 or 2 $C_{1-3}$-alkyl groups.

According to an embodiment $R^4$-E2a the group $R^4$ at each occurrence denotes independently HC(=O)—, HO—$C_{1-4}$-alkyl-, $C_{1-4}$-alkyl-S(=O)$_2$-L-, $C_{1-4}$-alkyl-S(=O)-L-, $C_{3-6}$-cycloalkyl-S(=O)$_2$-L-, $C_{3-6}$-cycloalkyl-$C_{1-3}$-alkyl-S(=O)$_2$-L-, $(R^6)_2N$—C(=O)-L-, heterocycle-C(=O)-L-, heterocycle-N($R^6$)—C(=O)-L-, heterocycle-$C_{1-3}$alkyl-N($R^6$)—C(=O)-L-, $C_{1-4}$-alkyl-O—C(=O)—N($R^6$)-L-, wherein L is a single bond or $C_{1-3}$-alkyl, in particular L is a single bond or —$CH_2$—; and wherein $R^6$ is defined as hereinbefore and hereinafter or preferably denotes H, $C_{1-6}$-alkyl, $C_{3-8}$-cycloalkyl, $C_{3-7}$-cycloalkyl-$C_{1-3}$-alkyl, wherein each alkyl and cycloalkyl group is optionally substituted with HO—, $C_{1-4}$-alkyl-O—, $H_2N$—, $C_{1-3}$-alkyl-NH—, $(C_{1-3}$-alkyl$)_2N$—, HOOC—, $C_{1-4}$-alkyl-O—C(=O)—; and preferably the term heterocycle denotes azetidinyl, pyrrolidinyl, piperidinyl, azepanyl, morpholinyl, piperazinyl, diazepanyl, aza-bicyclo[2.2.2]octyl, hexahydro-pyrrolo[3,4-c]pyrrolyl, wherein the heterocycle group is optionally substituted with halogen, HO—, $C_{1-4}$-alkyl-, $C_{1-4}$-alkyl-O—, $H_2N$—, $C_{1-3}$-alkyl-NH—, $(C_{1-3}$-alkyl$)_2N$—, $C_{1-4}$-alkyl-O—$C_{1-3}$-alkyl-, $H_2N$—$C_{1-3}$-alkyl-, $C_{1-3}$-alkyl-NH—$C_{1-3}$-alkyl- or $(C_{1-3}$-alkyl$)_2N$—$C_{1-3}$-alkyl-; wherein each alkyl group is optionally substituted with 1-3 F-atoms and wherein each alkyl group is optionally substituted with —OH or $C_{1-3}$-alkyl-O—.

According to an embodiment $R^4$-E2b the group $R^4$ at each occurrence denotes independently heterocycle or heterocycle-$C_{1-3}$-alkyl; wherein each heterocycle group is optionally substituted with 1-3 substituents independently of each other selected from $R^8$;

wherein heterocycle is defined as hereinbefore and hereinafter or preferably means a 4-, 5- or 6-membered monocyclic or a 8-, 9- or 10-membered bi- or tricyclic heterocycle ring which is either saturated, unsaturated or aromatic, and which contains from 1 to 4 heteroatoms independently selected from N, O and S, and wherein the N and S heteroatoms are optionally oxidized, and the N heteroatom is optionally quaternized, including bicyclic rings in which any of the above heterocycles are fused to a benzene ring, and wherein the above mentioned rings may comprise a group selected from —C(=O)—, —S(=O)— or —S(=O)$_2$—;

wherein $R^8$ is defined as hereinbefore and hereinafter or preferably denotes F, Cl, CN, $NO_2$, —OH, $C_{1-4}$-alkyl-, $C_{1-4}$-alkyl-O—, HOOC—, $C_{1-4}$-alkyl-O—(O=)C—, $H_2N$—, $C_{1-3}$-alkyl-NH—, $(C_{1-3}$-alkyl$)_2N$—, $H_2N$—$C_{1-3}$-alkyl-, $C_{1-3}$-alkyl-NH—$C_{1-3}$-alkyl-, $(C_{1-3}$-alkyl$)_2N$—$C_{1-3}$-alkyl-, wherein each alkyl group may be substituted with 1-3 F atoms.

According to another aspect of the embodiment $R^4$-E2b the term heterocycle denotes pyrrolidinonyl, piperidinonyl, oxazolidinonyl, imidazolidinonyl, piperazinonyl, pyrrolyl, pyrrazolyl, imidazolyl, dihydroimidazolyl, triazolyl, oxazolyl, isoxazolyl, thiazolyl, furanyl, thiophenyl, pyridyl, pyridazinyl, pyrimidinyl, pyrazinyl, tetrazolyl and dithianyl-S-oxide; wherein each heterocycle group is optionally substituted with 1-3 substituents independently of each other selected from $R^8$ as defined.

According to yet another aspect of the embodiment $R^4$-E2b the term heterocycle denotes imidazolidinonyl, imidazolyl, dihydroimidazolyl, triazolyl, tetrazolyl; wherein each heterocycle group is optionally substituted with 1-3 substituents independently of each other selected from $R^8$ as defined.

According to an embodiment $R^4$-E3 the group $R^4$ at each occurrence denotes independently $(R^6)_2N$—C(=O)—$C_{1-3}$-alkyl, heterocycle-C(=O)—$C_{1-3}$-alkyl, heterocycle-N($R^6$)—C(=O)—$C_{1-3}$-alkyl or heterocycle-$C_{1-3}$alkyl-N($R^6$)—C(=O)—$C_{1-3}$-alkyl, wherein each alkyl, heterocycle group is optionally substituted with 1-3 substituents independently of each other selected from $R^8$;

wherein heterocycle is defined as hereinbefore and hereinafter or preferably means a 4-, 5- or 6-membered monocyclic or a 8-, 9- or 10-membered bi- or tricyclic heterocycle ring which is either saturated, unsaturated or aromatic, and which contains from 1 to 4 heteroatoms independently selected from N, O and S, and wherein the N and S heteroatoms may be optionally oxidized, and the N heteroatom may be optionally quaternized, including bicyclic rings in which any of the above heterocycles are fused to a benzene ring, and wherein the above mentioned rings may comprise a group selected from —C(=O)—, —S(=O)— or —S(=O)$_2$—;

even more preferably the term heterocycle denotes azetidinyl, pyrrolidinyl, piperidinyl, azepanyl, morpholinyl, piperazinyl, diazepanyl, aza-bicyclo[2.2.2]octyl, hexahydro-pyrrolo[3,4-c]pyrrolyl, pyrrolidinonyl, piperidinonyl; and wherein $R^6$ is defined as hereinbefore and hereinafter or preferably denotes H, $C_{1-6}$-alkyl, $C_{3-8}$-cycloalkyl, $C_{3-7}$-cycloalkyl-$C_{1-3}$-alkyl, wherein each alkyl group is optionally substituted with HO—, $C_{1-4}$-alkyl-O—, $H_2N$—, $C_{1-3}$-alkyl-NH—, $(C_{1-3}$-alkyl$)_2N$—, HOOC—, $C_{1-4}$-alkyl-O—C(=O)—, even more preferably $R^6$ denotes H or $C_{1-4}$-alkyl, wherein each alkyl group is optionally substituted as defined hereinbefore; and wherein $R^8$ is defined as hereinbefore and hereinafter or preferably denotes F, Cl, CN, —OH, oxo, $C_{1-4}$-alkyl-, $C_{1-4}$-alkyl-O—, HOOC—, $C_{1-4}$-alkyl-O—(O=)C—, $H_2N$—, $C_{1-3}$-alkyl-NH—, $(C_{1-3}$-alkyl$)_2N$—, $H_2N$—$C_{1-3}$-alkyl-, $C_{1-3}$-alkyl-NH—$C_{1-3}$-alkyl-, $(C_{1-3}$-alkyl$)_2N$—$C_{1-3}$-alkyl-, heterocycle-$C_{1-3}$-alkyl, wherein each alkyl group is optionally substituted with 1-3 F atoms, and wherein heterocycle is defined as hereinbefore and hereinafter or preferably denotes azetidinyl, pyrrolidinyl, piperidinyl, piperazinyl or morpholinyl, wherein each heterocycle group is optionally substituted with 1 or 2 $C_{1-3}$-alkyl groups.

According to an embodiment $R^4$-E4 the group $R^4$ at each occurrence denotes independently HO—$C_{1-3}$-alkyl-, $C_{1-4}$- alkyl-S(=O)$_2$—, C$_{3-6}$-cycloalkyl-S(=O)$_2$— or C$_{3-6}$-cycloalkyl-C$_{1-3}$-alkyl-S(=O)$_2$—.

According to an embodiment R$^4$-E4a the group R$^4$ at each occurrence denotes independently HO—CH$_2$— or CH$_3$—S(=O)$_2$—.

According to another embodiment R$^4$-E5 the group R$_4$ at each occurrence denotes independently F, Cl, CN, —NO$_2$, H$_3$C—, HO—CH$_2$—, HO—CD$_2$-, CH$_3$—CH(OH)—, CH$_3$—O—CH$_2$—,

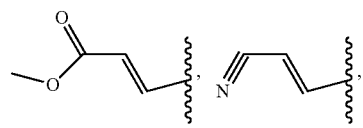

H$_3$C—O—, HC(=O)—, H$_3$C—CO—, H$_5$C$_2$—O—CO—CH$_2$—CO—, HO—C(=O)—, H$_3$C—SO—, H$_3$C—SO$_2$—, H$_3$C—O—SO$_2$—,

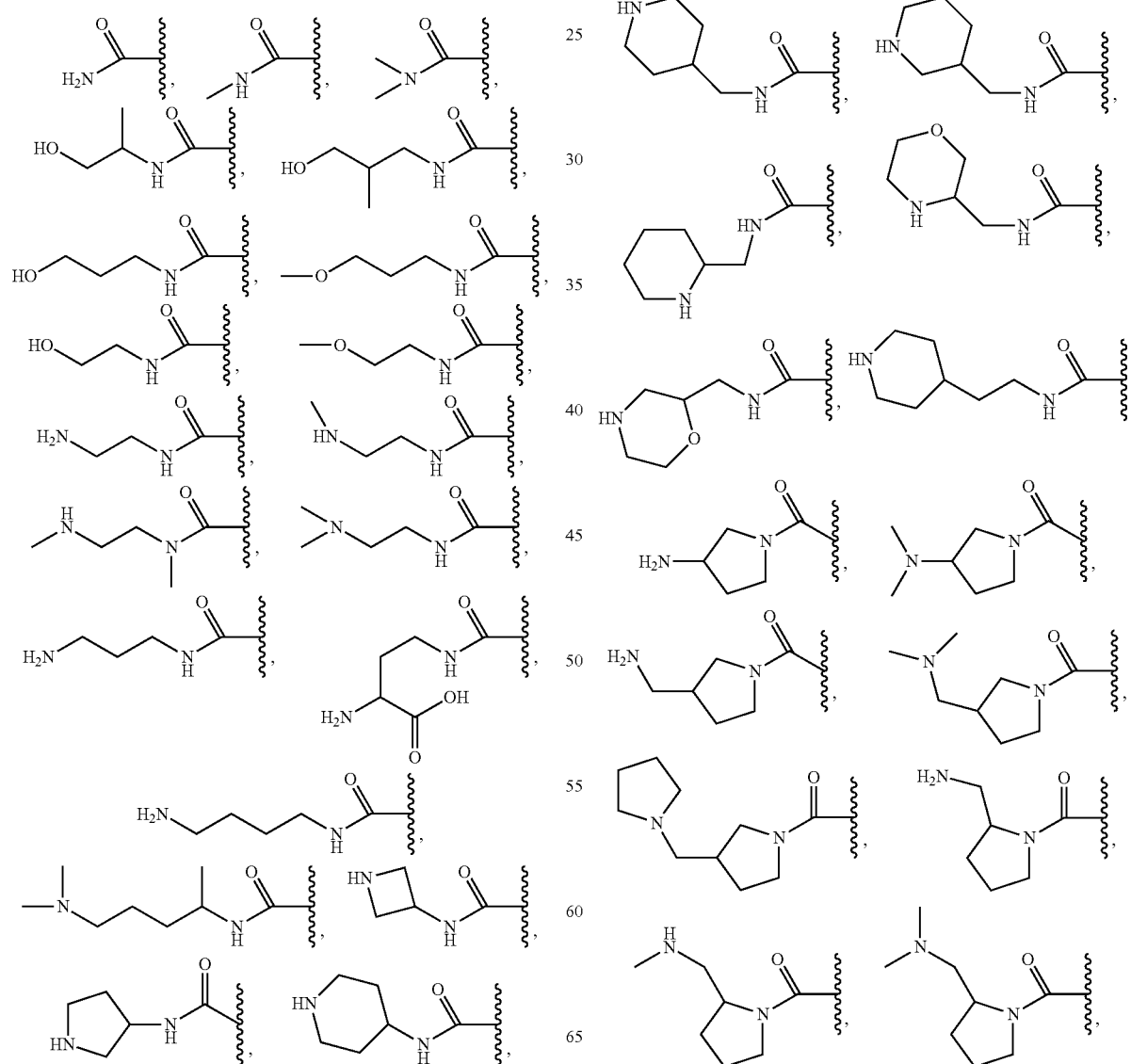

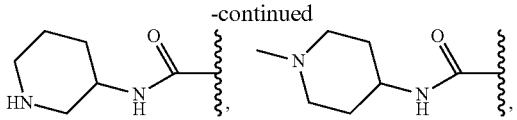
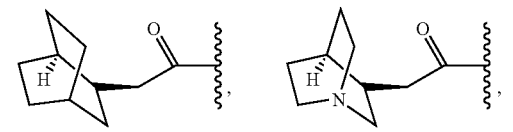
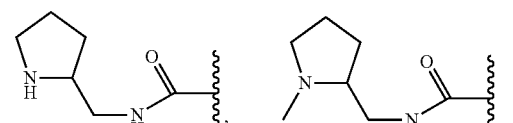
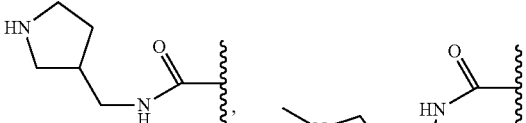
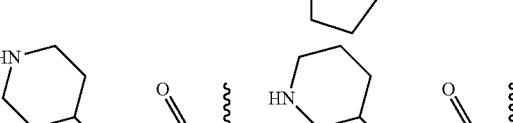
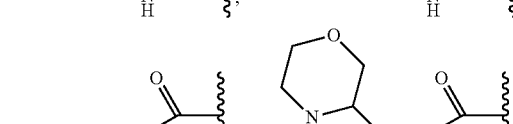
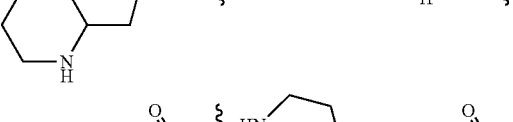
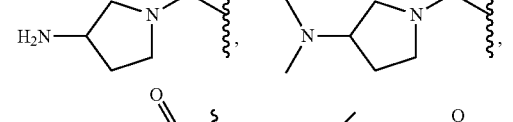
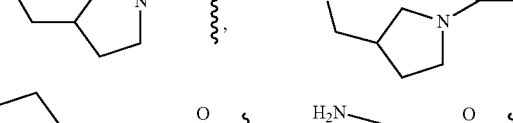
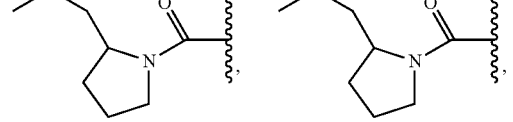

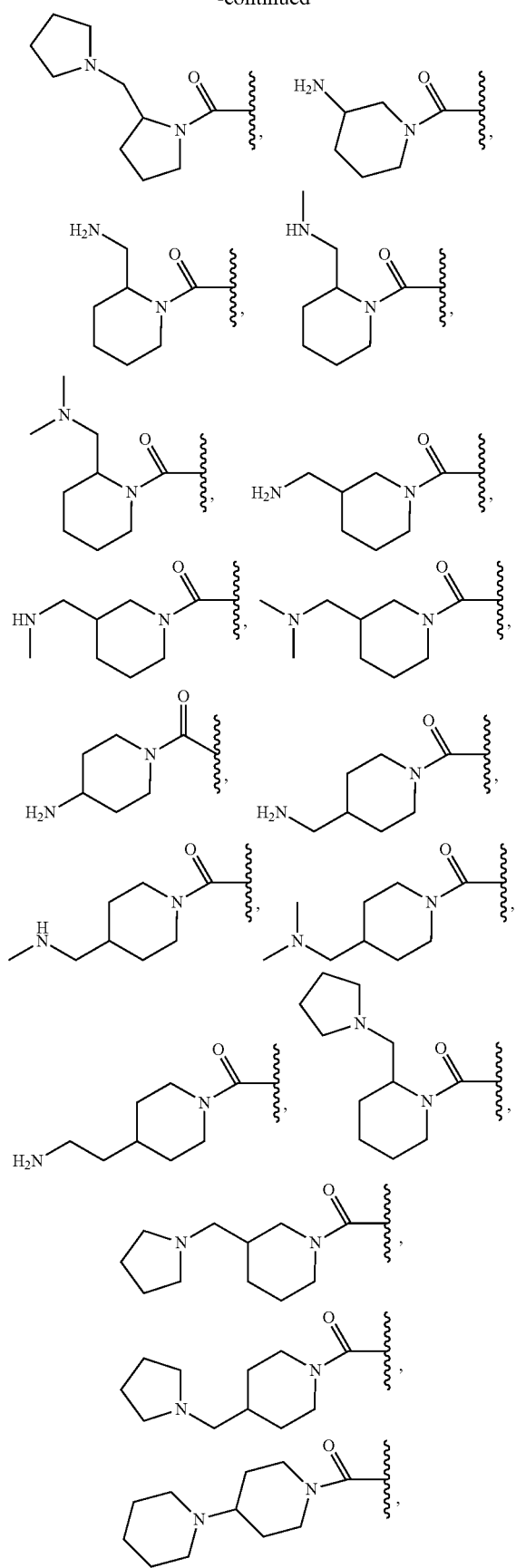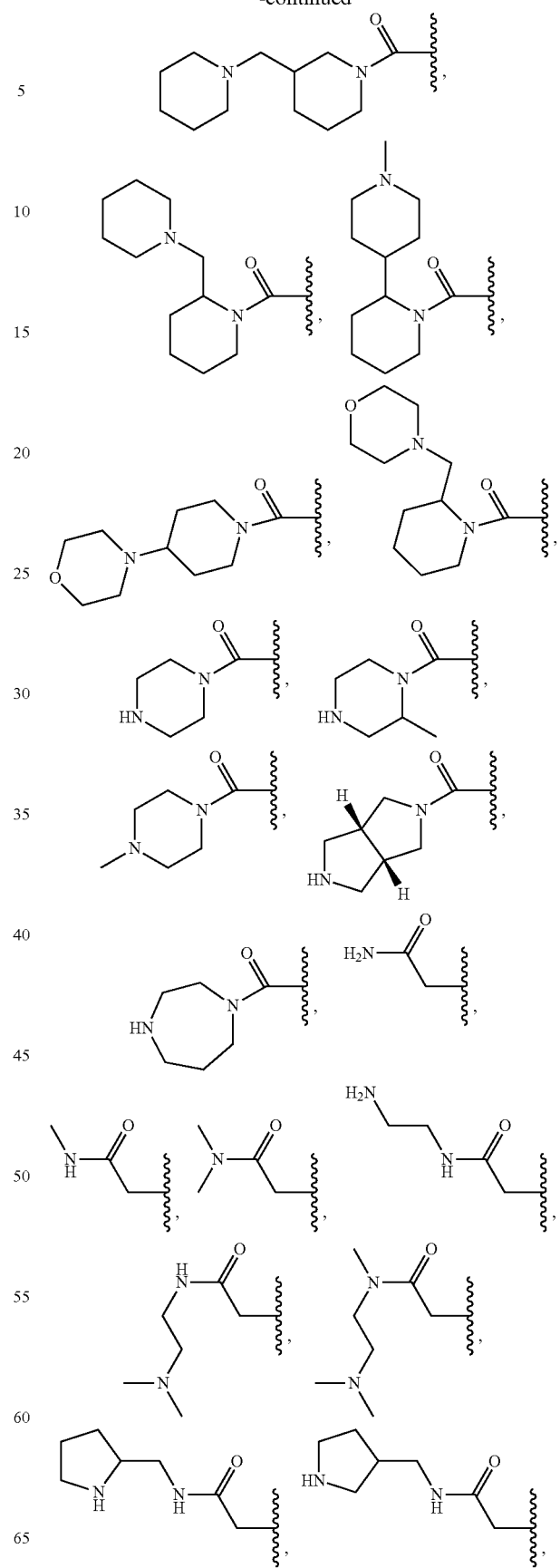

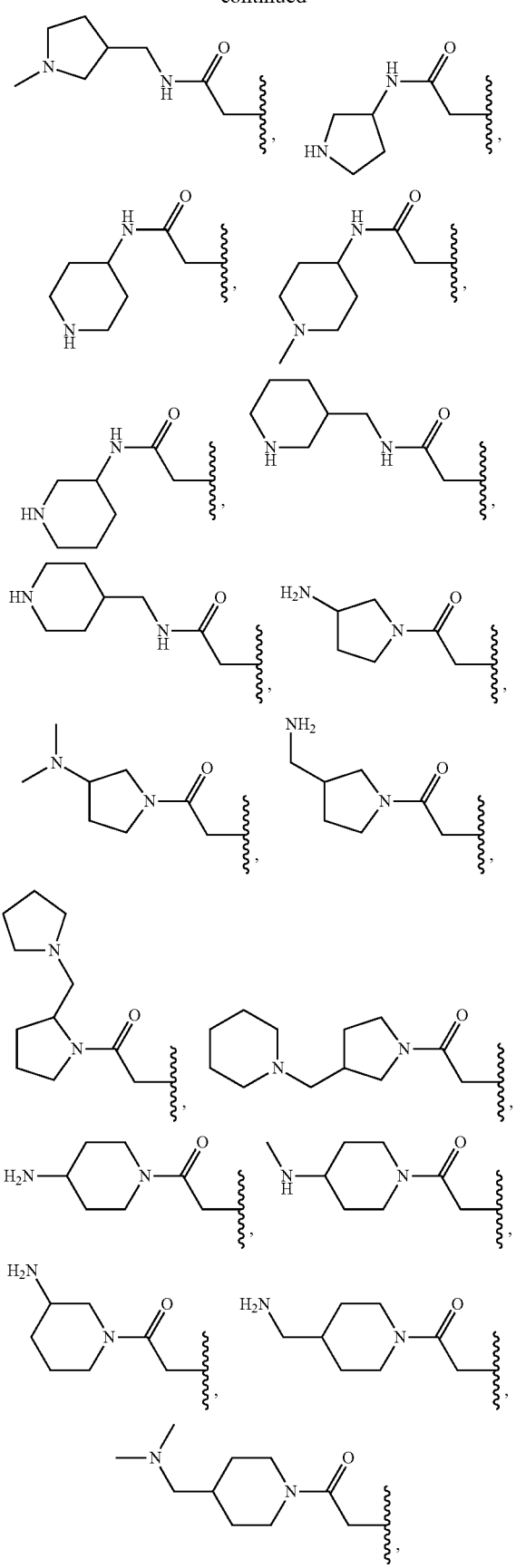
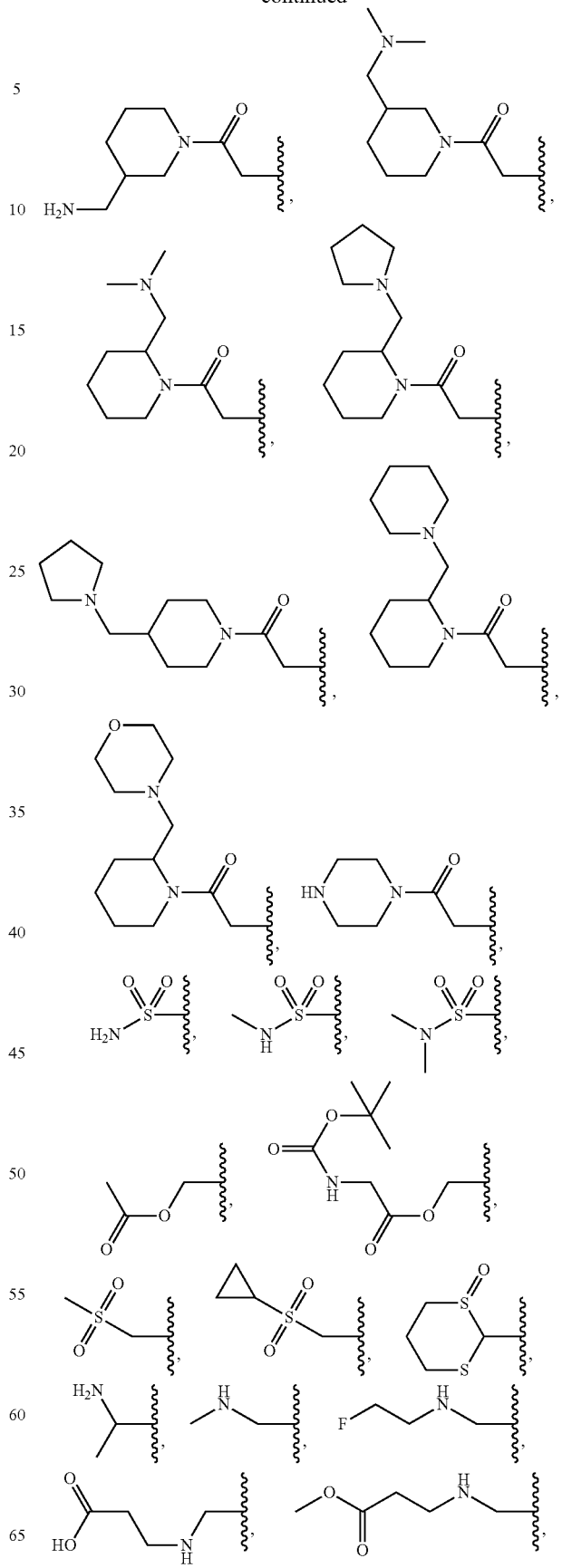

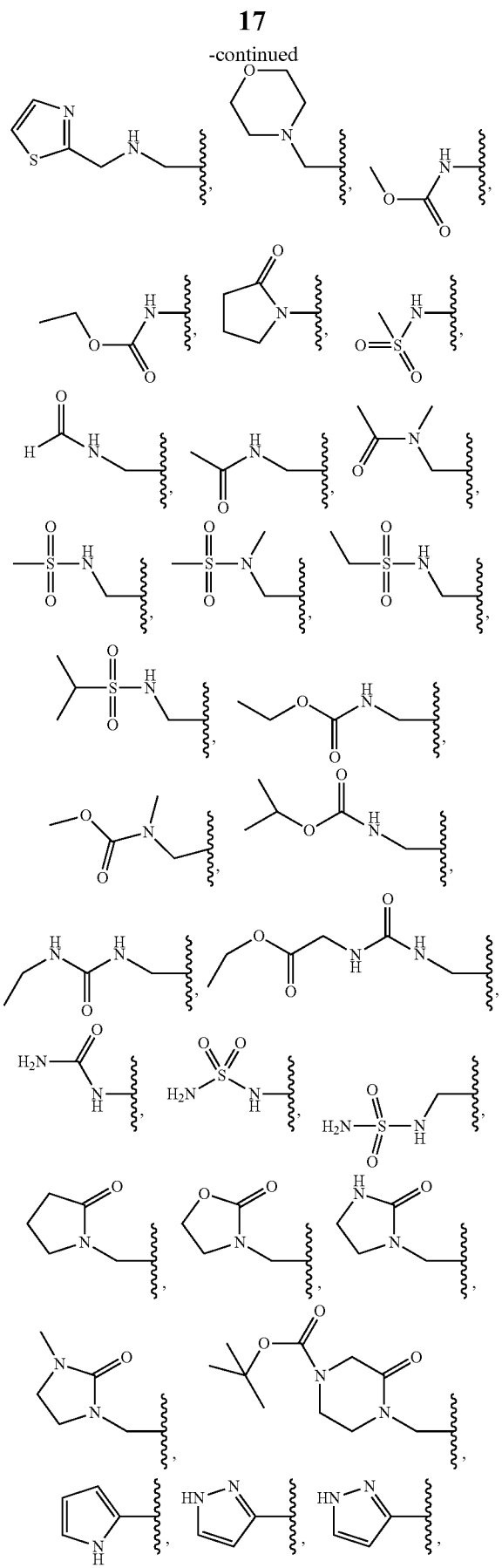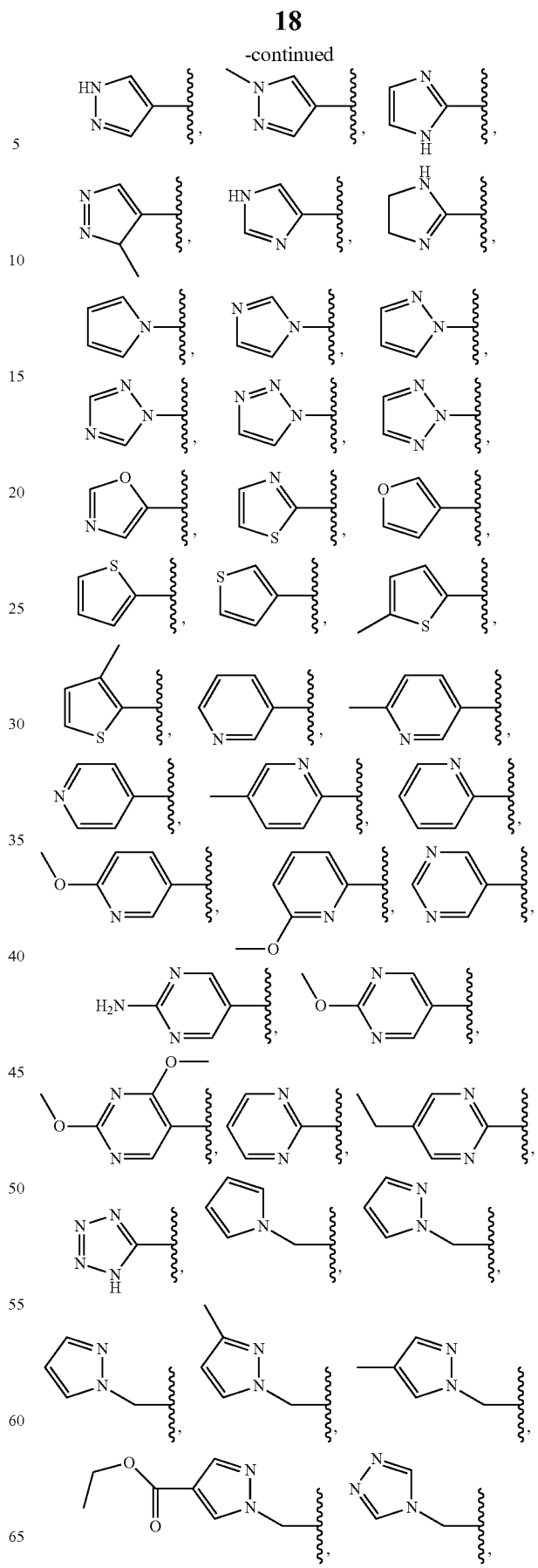

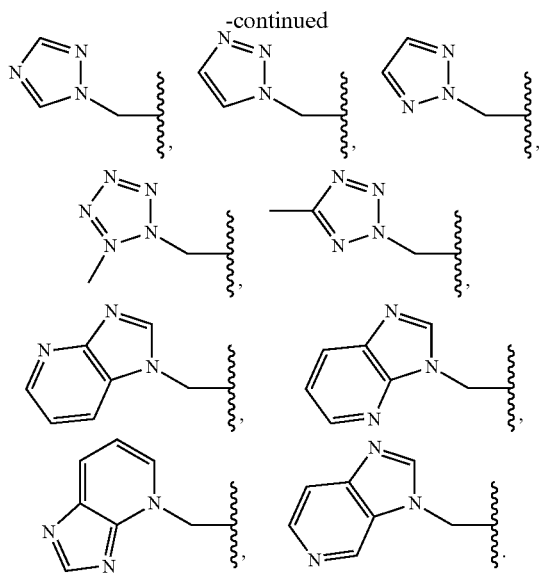

R³:

According to an embodiment R³-E1 the group R³ is selected from the group consisting of $R^{Alk}$, $R^{Alk}$—C(=O)—, aryl-C(=O)—, aryl-$C_{1-3}$-alkyl-C(=O)—, heterocycle-C(=O)—, heterocycle-$C_{1-3}$-alkyl-C(=O)—, $R^{Alk}$—O—C(=O)-L-, aryl-O—C(=O)-L-, aryl-$C_{1-3}$-alkyl-O—C(=O)-L-, heterocycle-O—C(=O)-L-, heterocycle-$C_{1-3}$-alkyl-O—C(=O)-L-, $R^{Alk}$—$NR^N$—C(=X)-L-, heterocycle-$NR^N$—C(=X)-L-, heterocycle-$C_{1-3}$-alkyl-$NR^N$—C(=X)-L-, aryl-$NR^N$—C(=X)-L-, aryl-$C_{1-3}$-alkyl-$NR^N$—C(=X)-L-, $R^{Alk}$—S(=O)$_2$-L-, aryl-S(=O)$_2$-L-, aryl-$C_{1-3}$-alkyl-S(=O)$_2$-L-, heterocycle-S(=O)$_2$—, heterocycle-$C_{1-3}$-alkyl-S(=O)$_2$-L-, aryl-L- and heteroaryl-L-, wherein L is a single bond or $C_{1-3}$-alkyl, preferably a single bond or —CH$_2$—; and wherein each $R^{Alk}$, aryl, heteroaryl and heterocycle group is optionally substituted with 1-5 substituents independently of each other selected from R⁸, preferably 1-3 substituents independently of each other selected from R⁸, wherein $R^{Alk}$ is defined as hereinbefore and hereinafter or preferably means $C_{1-6}$alkyl, $C_{2-6}$-alkenyl, $C_{2-6}$-alkynyl, $C_{3-8}$-cycloalkyl or $C_{3-8}$-cycloalkyl-$C_{1-3}$-alkyl or even more preferably means $C_{1-6}$alkyl, $C_{3-7}$-cycloalkyl or $C_{3-7}$-cycloalkyl-$C_{1-3}$-alkyl; and wherein X denotes O or S, preferably O; and wherein $R^N$ denotes H or $C_{1-4}$-alkyl, preferably H or methyl; and wherein R⁸ is defined as hereinbefore and hereinafter or preferably denotes F, Cl, Br, $C_{1-4}$-alkyl, CF$_3$—, $C_{2-4}$-alkenyl, $C_{1-4}$-alkyl-O—, $C_{1-4}$-alkyl-O—C(=O)—, H$_2$N—, $C_{1-3}$-alkyl-NH—, $(C_{1-3}$-alkyl)$_2$N—, $C_{1-3}$-alkyl-S(=O)$_2$—, phenyl, wherein each alkyl group is optionally substituted with 1-3 F atoms; and wherein phenyl is optionally substituted with one or more substituents selected from the group consisting of halogen, CN, —OH, $C_{1-4}$-alkyl-, $C_{1-4}$-alkyl-O—, H$_2$N—, $C_{1-3}$-alkyl-NH—, $(C_{1-3}$-alkyl)$_2$N—; and heterocycle is defined as hereinbefore and hereinafter or preferably denotes azetidinyl, pyrrolidinyl, piperidinyl, piperazinyl, N—$C_{1-3}$-alkyl-piperazinyl, morpholinyl, pyrrolyl, pyridyl, pyrazinyl, pyrimidinyl, pyridazinyl, thiazolyl; and wherein aryl is defined as hereinbefore and hereinafter or preferably denotes phenyl; and wherein heteroaryl is defined as hereinbefore and hereinafter or preferably denotes pyridyl, pyrazinyl, pyrimidinyl, pyridazinyl, thiazolyl or furanyl; and wherein in each aryl or heteroaryl group two adjacent C and/or N atoms may be linked via a $C_{3-5}$-alkylene or $C_{3-5}$-alkenylene bridging group in which one or two CH$_2$-groups may be replaced by a group selected from O, S, NH, N($C_{1-3}$-alkyl), —C(=O)—, —S(=O)— and —S(=O)$_2$—, and wherein one or two CH-groups may be replaced by N.

According to another embodiment R³-E2 the group R³ is selected from the group consisting of $C_{1-6}$-alkyl-, $C_{3-7}$-cycloalkyl, $C_{3-7}$-cycloalkyl-$C_{1-3}$-alkyl, $C_{1-6}$-alkyl—C(=O)—, $C_{3-6}$-cycloalkyl-C(=O)—, $C_{3-6}$-cycloalkyl-$C_{1-3}$-alkyl-C(=O)—, aryl-C(=O)—, aryl-$C_{1-3}$-alkyl-C(=O)—, heterocycle-C(=O)—, heterocycle-$C_{1-3}$-alkyl-C(=O)—, $C_{1-6}$-alkyl-O—C(=O)—, $C_{3-6}$-cycloalkyl-O—C(=O)—, $C_{3-6}$-cycloalkyl-$C_{1-3}$-alkyl-O—C(=O)—, $C_{2-6}$-alkenyl-O—C(=O)—, $C_{2-6}$-alkynyl-O—C(=O)—, aryl-O—C(=O)—, aryl-$C_{1-3}$-alkyl-O—C(=O)—, heterocycle-O—C(=O)—, heterocycle-$C_{1-3}$-alkyl-O—C(=O)—, $C_{1-6}$-alkyl-$NR^N$—C(=X)—, $C_{3-6}$-cycloalkyl-$NR^N$—C(=X)—, $C_{3-6}$-cycloalkyl-$C_{1-3}$-alkyl-$NR^N$—C(=X)—, heterocycle-$NR^N$—C(=X)—, heterocycle-$C_{1-3}$-alkyl-$NR^N$—C(=X)—, $C_{1-6}$-alkyl-O—C(=O)—$C_{1-3}$-alkyl-, $C_{3-6}$-cycloalkyl-O—C(=O)—$C_{1-3}$-alkyl-, $C_{3-6}$-cycloalkyl-$C_{1-3}$-alkyl-O—C(=O)—$C_{1-3}$-alkyl-, $C_{2-6}$-alkenyl-O—C(=O)—$C_{1-3}$-alkyl-, $C_{2-6}$-alkynyl-O—C(=O)—$C_{1-3}$-alkyl-, aryl-O—C(=O)—$C_{1-3}$-alkyl-, aryl-$C_{1-3}$-alkyl-O—C(=O)—$C_{1-3}$-alkyl-, heterocycle-O—C(=O)—$C_{1-3}$-alkyl-, heterocycle-$C_{1-3}$-alkyl-O—C(=O)—$C_{1-3}$-alkyl-, aryl-S(=O)$_2$—, aryl, heteroaryl, aryl-$C_{1-3}$-alkyl and heteroaryl-$C_{1-3}$-alkyl;

wherein each alkyl, cycloalkyl, alkenyl, alkynyl, cycloalkyl, aryl, heteroaryl and heterocycle group is optionally substituted with 1-5 substituents independently of each other selected from R⁸, preferably 1-3 substituents independently of each other selected from R⁸; and wherein X denotes O or S, preferably O; and wherein $R^N$ denotes H or $C_{1-3}$-alkyl, preferably H or methyl; and wherein R⁸ is defined as hereinbefore and hereinafter or preferably denotes F, Cl, Br, $C_{1-4}$-alkyl, CF$_3$—, $C_{2-4}$-alkenyl, $C_{1-4}$-alkyl-O—, $C_{1-4}$-alkyl-O—C(=O)—, H$_2$N—, $C_{1-3}$-alkyl-NH—, $(C_{1-3}$-alkyl)$_2$N—, $C_{1-3}$-alkyl-S(=O)$_2$—, phenyl, wherein each alkyl group is optionally substituted with 1-3 F atoms; and wherein phenyl is optionally substituted with one or more substituents selected from the group consisting of halogen, CN, —OH, $C_{1-4}$-alkyl-, $C_{1-4}$-alkyl-O—, H$_2$N—, $C_{1-3}$-alkyl-NH— and $(C_{1-3}$-alkyl)$_2$N—; and wherein heterocycle is defined as hereinbefore and hereinafter, preferably heterocycle denotes azetidinyl, pyrrolidinyl, piperidinyl, piperazinyl, N—$C_{1-3}$-alkyl-piperazinyl, morpholinyl, pyrrolyl, pyridyl, pyrazinyl, pyrimidinyl, pyridazinyl or thiazolyl; and wherein aryl is defined as hereinbefore and hereinafter, preferably aryl denotes phenyl; and wherein heteroaryl is defined as hereinbefore and hereinafter, preferably heteroaryl denotes pyridyl, pyrazinyl, pyrimidinyl, pyridazinyl, thiazolyl or furanyl; and wherein in each aryl or heteroaryl group two adjacent C and/or N atoms may be linked via a $C_{3-5}$-alkylene or $C_{3-5}$-alkenylene bridging group in which one or two CH$_2$-groups may be replaced by a group selected from O, S, NH, N($C_{1-3}$-alkyl), —C(=O)—, —S(=O)— and —S(=O)$_2$—, and wherein one or two CH-groups may be replaced by N.

According to an embodiment R³-E3 the group R³ is selected from the group consisting of C₃₋₆-alkyl-, C₁₋₆-alkyl-C(=O)—, C₃₋₆-cycloalkyl-C(=O)—, C₃₋₆-cycloalkyl-CH₂—C(=O)—, phenyl-C(=O)—, phenyl-CH₂—C(=O)—, heterocycle-C(=O)—, heterocycle-CH₂-alkyl-C(=O)—, C₁₋₆-alkyl-O—C(=O)—, C₃₋₆-cycloalkyl-O—C(=O)—, C₃₋₆-cycloalkyl-C₁₋₃-alkyl-O—C(=O)—, C₁₋₄-alkyl-O—C₂₋₄-alkyl-O—C(=O)—, C₁₋₄-alkyl-O—C(=O)—C₂₋₄-alkyl-O—C(=O)—, H₂N—C₂₋₄-alkyl-O—C(=O)—, C₁₋₆-alkyl-NR$^N$—C(=O)—, C₃₋₆-cycloalkyl-NR$^N$—C(=O)—, C₃₋₆-cycloalkyl-C₁₋₃-alkyl-NR$^N$—C(=O)—, C₁₋₃-alkyl-HN—C₂₋₄-alkyl-O—C(=O)—, (C₁₋₃-alkyl)₂N—C₂₋₄-alkyl-O—C(=O)—, C₂₋₆-alkenyl-O—C(=O)—, C₂₋₆-alkynyl-O—C(=O)—, phenyl-O—C(=O)—, phenyl-CH₂—O—C(=O)—, phenyl, pyridyl, pyrimidinyl, thiazolyl, phenyl-CH₂—, pyridyl-CH₂—, pyrimidinyl-CH₂—, pyridylphenyl-CH₂—, pyrimidinylphenyl-CH₂— and furanyl-CH₂—;

wherein in a phenyl ring two adjacent CH groups may be linked via a —O—CH₂—O— or a —O—CH₂—CH₂—O— bridging group, wherein heterocyle is defined as hereinbefore and hereinafter, preferably heterocycle denotes azetidinyl, pyrrolidinyl, piperidinyl, piperazinyl, N—C₁₋₃-alkyl-piperazinyl, morpholinyl, wherein the heterocycle group may be substituted with phenyl; and wherein each heterocycle, phenyl, pyridyl, pyrimidinyl and thiazolyl is optionally substituted with 1 to 4 substituents selected from the group consisting of F, Cl, Br, CN, C₁₋₄-alkyl, C₂₋₄-alkenyl, C₁₋₄-alkyl-O—, CF₃, CF₃—O—, C₁₋₃—O—C(=O)—, H₂N—, C₁₋₃-alkyl-NH—, (C₁₋₃-alkyl)₂N—, wherein alkyl may be substituted with 1 to 3 F atoms, wherein cycloalkyl may be substituted with C₁₋₃-alkyl, wherein R$^N$ denotes H or C₁₋₃-alkyl, preferably H or methyl.

According to an embodiment R³-E4 the group R³ is selected from the group consisting of C₁₋₆-alkyl-O—C(=O)—, C₃₋₆-cycloalkyl-O—C(=O)—, C₃₋₆-cyclo alkyl-C₁₋₃-alkyl-O—C(=O)—, C₁₋₄-alkyl-O—C₂₋₄-alkyl-O—C(=O)—, H₂N—C₂₋₄-alkyl-O—C(=O)—, C₁₋₃-alkyl-HN—C₂₋₄-alkyl-O—C(=O)—, (C₁₋₃-alkyl)₂N—C₂₋₄-alkyl-O—C(=O)— and pyrimidinyl;

wherein each pyrimidinyl may be substituted with 1 to 4 substituents independently of each other selected from the group consisting of F, Cl, Br, CN, C₁₋₄-alkyl, C₂₋₄-alkenyl, C₁₋₄-alkyl-O—, CF₃, CF₃—O—, C₁₋₃—O—C(=O)—, H₂N—, C₁₋₃-alkyl-NH—, (C₁₋₃-alkyl)₂N—, wherein alkyl may be substituted with 1 to 3 F atoms, wherein cycloalkyl may be substituted with C₁₋₃-alkyl.

According to an embodiment R³-E4a the group R³ is selected from the group consisting of i-propyl-O—C(=O)—, and ethyl-pyrimidinyl.

According to another embodiment R³-E5 the group R³ is selected from the group consisting of

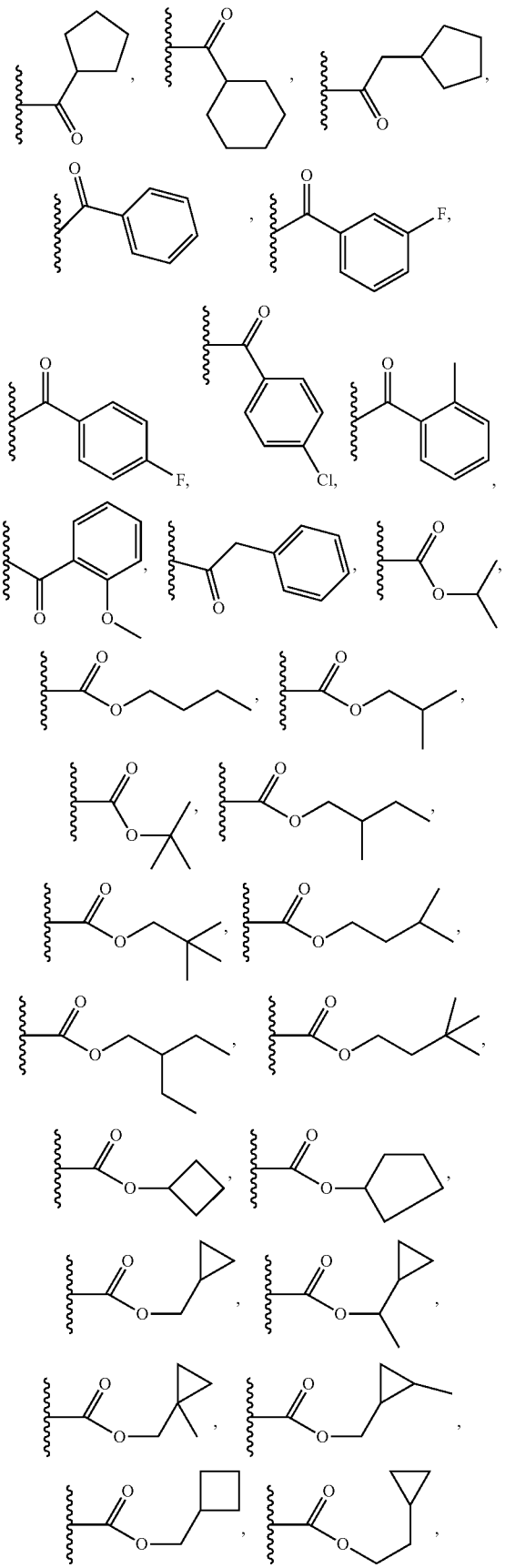

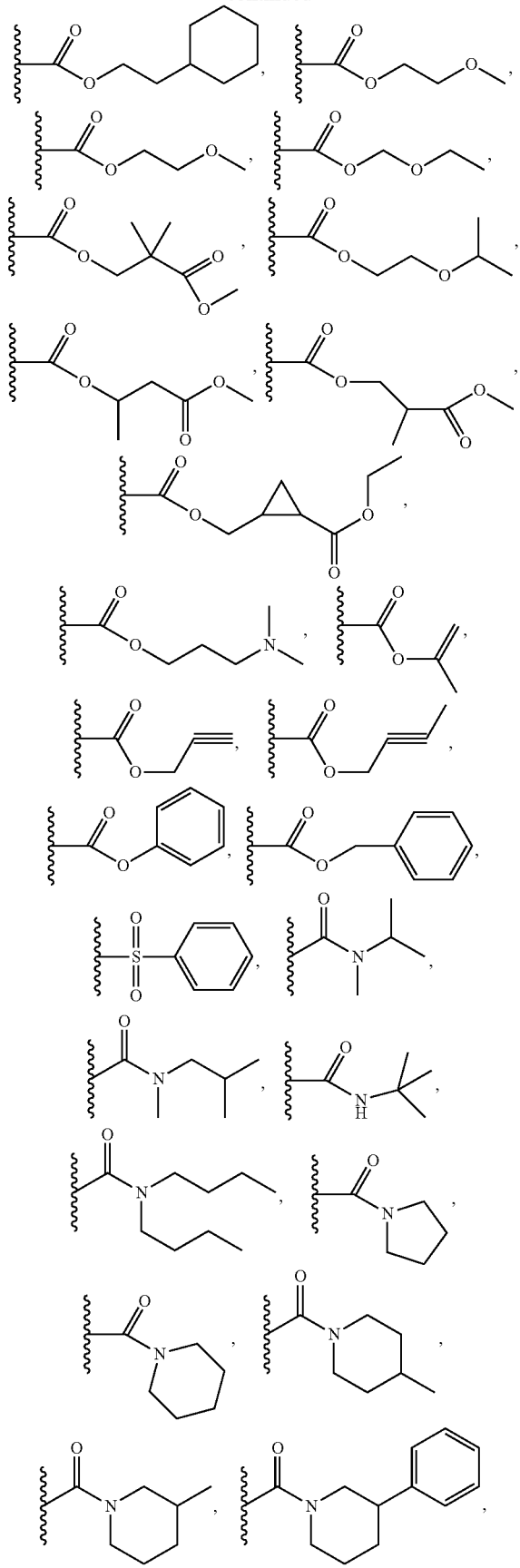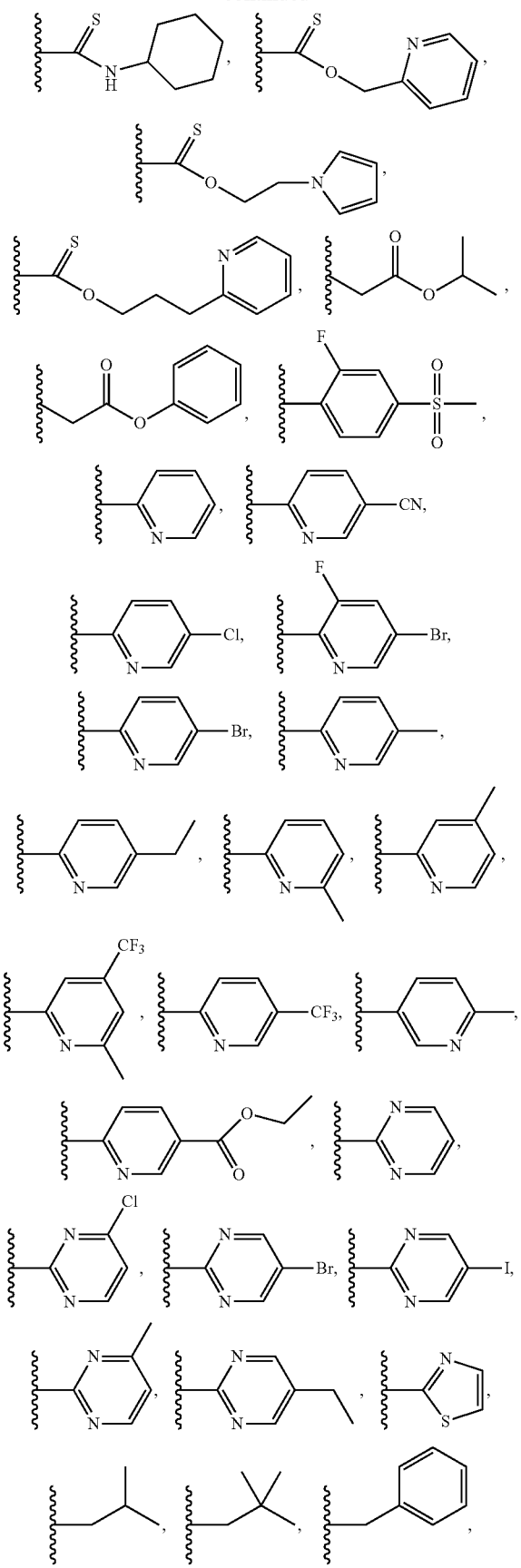

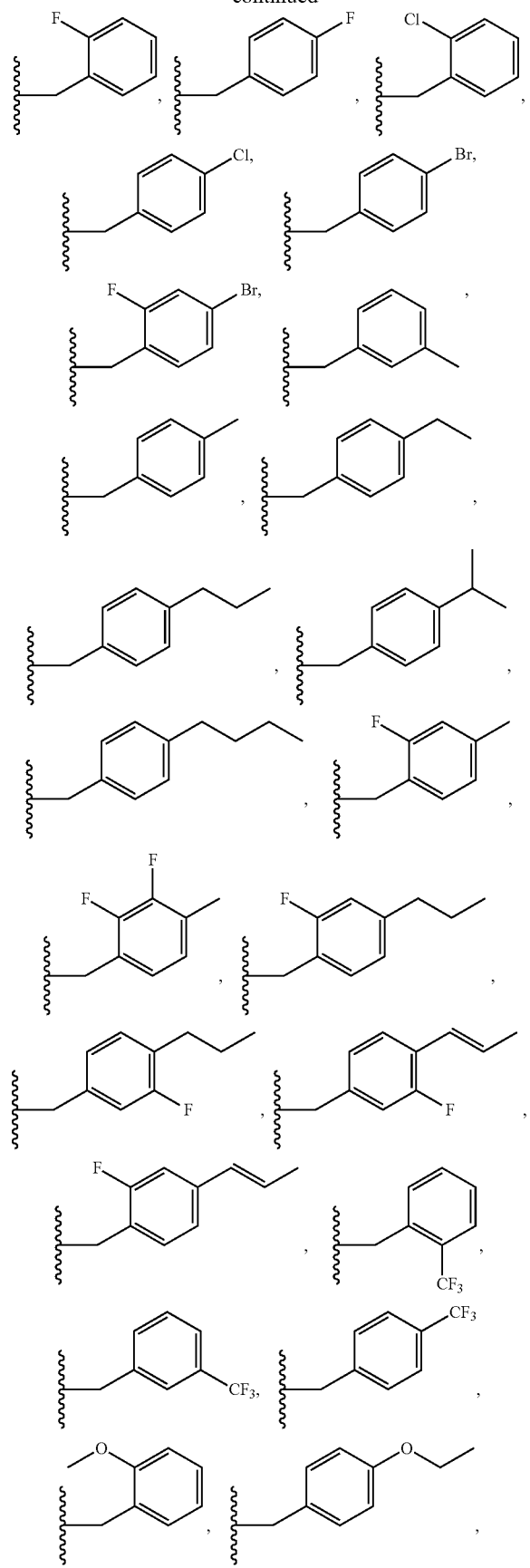
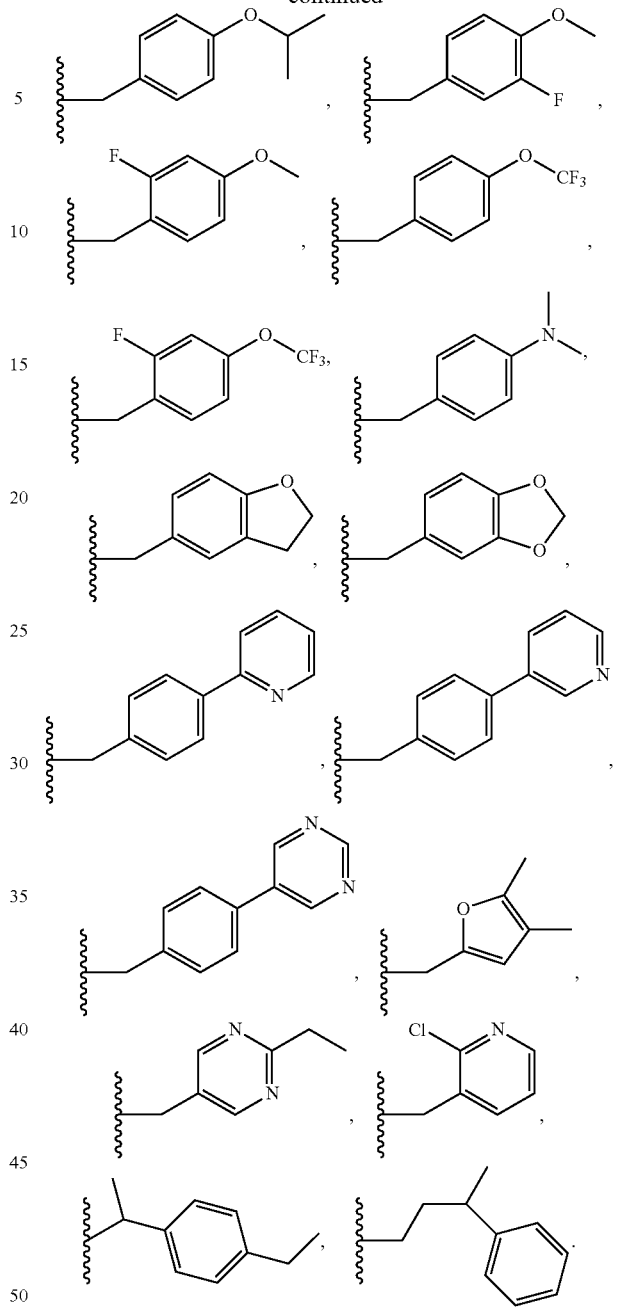

$R^{Alk}$:

According to an embodiment $R^{Alk}$-E1 the group $R^{Alk}$ is selected from the group consisting of $C_{1-6}$-alkyl, $C_{2-6}$-alkenyl, $C_{2-6}$-alkynyl, $C_{3-8}$-cycloalkyl, $C_{3-8}$-cycloalkyl-$C_{1-3}$-alkyl, $C_{4-8}$-cycloalkenyl or $C_{4-8}$-cycloalkenyl-$C_{1-3}$-alkyl.

According to an embodiment $R^{Alk}$-E2 the group $R^{Alk}$ is selected from the group consisting of $C_{1-6}$-alkyl, $C_{3-7}$-cycloalkyl or $C_{3-7}$-cycloalkyl-$C_{1-3}$-alkyl.

According to an embodiment $R^{Alk}$-E3 the group $R^{Alk}$ is selected from the group consisting of $C_{1-4}$-alkyl, $C_{3-6}$-cycloalkyl or $C_{3-6}$-cycloalkyl-$CH_2$—.

$R^1$:

According to an embodiment $R^1$-E1 the group $R^1$ is selected from the group consisting of $C_{1-4}$-alkyl, F, hydroxy, $C_{1-4}$alkyl-O—, —$CO_2R^7$, or —$C(=O)N(R^6)_2$.

According to an embodiment $R^1$-E2 the group $R^1$ is selected from the group consisting of $C_{1-3}$-alkyl, F, hydroxy or $C_{1-3}$alkyl-O—.

$R^2$:

According to an embodiment $R^2$-E1 the group $R^2$ is selected from the group consisting of $C_{1-4}$alkyl, F, hydroxy, or $C_{1-4}$alkyl-O—.

According to an embodiment $R^2$-E2 the group $R^2$ is selected from the group consisting of $C_{1-3}$-alkyl, F, hydroxy or $C_{1-3}$alkyl-O—.

$R^5$:

According to an embodiment $R^5$-E1 the group $R^5$ is selected from the group consisting of $R^{Alk}$, heterocycle, aryl, heterocycle-$C_{1-3}$-alkyl or aryl-$C_{1-3}$-alkyl, wherein each alkyl, $R^{Alk}$, heterocycle and aryl group is optionally substituted with 1-4 substituents independently of each other selected from $R^8$.

According to an embodiment $R^5$-E2 the group $R^5$ is selected from the group consisting of $C_{1-6}$-alkyl optionally substituted with 1-3 substituents independently of each other selected from $R^8$.

According to an embodiment $R^5$-E3 the group $R^5$ is selected from the group consisting of $C_{1-4}$-alkyl optionally substituted with 1-2 substituents independently of each other selected from $R^8$.

According to an embodiment $R^5$-E4 the group $R^5$ is selected from the group consisting of isopropyl and isobutyl.

According to an embodiment $R^5$-E5 the group $R^5$ is selected from the group consisting of heterocycle optionally substituted with 1-3 substituents independently of each other selected from $R^8$.

According to an embodiment $R^5$-E6 the group $R^5$ is selected from the group of heterocycles consisting of azetidinyl, pyrrolidinyl, piperidinyl, morpholinyl, piperazinyl, diazepanyl, aza-bicyclo[2.2.2]octyl and hexahydro-pyrrolo[3,4-c]pyrrolyl, wherein each of the beforementioned groups are optionally substituted with 1-3 substituents independently of each other selected from $R^8$. According to another aspect of this embodiment the heterocycle groups are linked via a N-atom.

$R^6$:

According to an embodiment $R^6$-E1 the group $R^6$ is selected from the group consisting of H, $R^{Alk}$, heterocycle, heterocycle-$C_{1-6}$-alkyl, aryl or aryl-$C_{1-3}$-alkyl, wherein each $R^{Alk}$, heterocycle, aryl and alkyl are optionally substituted with 1-4 substituents independently of each other selected from halogen, hydroxy, —N($R^7$)$_2$, $C_{1-4}$alkyl-O—, and —CO$_2R^7$.

According to an embodiment $R^6$-E2 the group $R^6$ is selected from the group consisting of H, $C_{1-6}$-alkyl, $C_{3-8}$-cycloalkyl, $C_{3-7}$-cycloalkyl-$C_{1-3}$-alkyl, wherein each alkyl group is optionally substituted with 1-3 substituents independently of each other selected from HO—, $C_{1-4}$-alkyl-O—, H$_2$N—, $C_{1-3}$-alkyl-NH—, ($C_{1-3}$-alkyl)$_2$N—, HOOC—, $C_{1-4}$-alkyl-O—C(=O)—.

According to an embodiment $R^6$-E3 the group $R^6$ is selected from the group consisting of H or $C_{1-4}$-alkyl, wherein each alkyl group is optionally substituted with 1 or 2 substituents independently of each other selected from HO—, $C_{1-4}$-alkyl-O—, H$_2$N—, $C_{1-3}$-alkyl-NH—, ($C_{1-3}$-alkyl)$_2$N—, HOOC—, $C_{1-4}$-alkyl-O—C(=O)—.

$R^7$:

According to an embodiment $R^7$-E1 the group $R^7$ is selected from the group consisting of H or $C_{1-4}$alkyl.

$R^8$:

According to an embodiment $R^8$-E1 the group $R^8$ is selected from the group consisting of cyano, hydroxy, $R^{Alk}$, aryl, aryl-$C_{1-6}$alkyl, heterocycle, heterocycle-$C_{1-6}$-alkyl, halogen, oxo, $C_{1-4}$-haloalkyl, NO$_2$, H—C(=O)—, $R^7$O—C(=O)—, $R^{Alk}$—C(=O)—O—, ($R^6$)$_2$N—C(=O)—, ($R^6$)$_2$N—S(=O)$_2$—, $R^{Alk}$—S(=O)—, $R^{Alk}$—S(=O)$_2$—, $C_{1-6}$alkyl-O—, halo$C_{1-4}$alkyl-O—, ($R^6$)$_2$N—, $R^6$S—, $R^{Alk}$C(=O)—$R^6$N—, $R^{Alk}$—S(=O)$_2$—$R^6$N—, $R^{Alk}$O—C(=O)—$R^6$N—, ($R^6$)$_2$N—C(=O)—$R^6$N— or ($R^6$)$_2$N—S(=O)$_2$—$R^6$N—, wherein each $R^{Alk}$, alkyl, aryl and heterocycle are optionally substituted with 1-4 substituents independently of each other selected from halogen, hydroxy, ($R^7$)$_2$N—, $C_{1-4}$alkyl-O—, $R^6$O—C(=O)—$R^6$N—, $R^6$—S(=O)$_2$—$R^6$N— and $R^7$—O—C(=O)—.

According to an embodiment $R^8$-E2 the group $R^8$ is selected from the group consisting of cyano, hydroxy, $C_{1-6}$-alkyl, phenyl, phenyl-$C_{1-3}$alkyl, heterocycle, heterocycle-$C_{1-3}$-alkyl, halogen, oxo, NO$_2$, H—C(=O)—, $R^7$O—C(=O)—, $R^7$—C(=O)—O—, ($R^6$)$_2$N—C(=O)—, ($R^6$)$_2$N—S(=O)$_2$—, $R^7$—S(=O)—, $R^7$—S(=O)$_2$—, $C_{1-6}$alkyl-O—, ($R^6$)$_2$N—, $R^6$S—, $R^7$—C(=O)—$R^6$N—, $R^7$O—C(=O)—$R^6$N— or ($R^6$)$_2$N—C(=O)—$R^6$N—, wherein each alkyl, aryl and heterocycle are optionally substituted with 1-4 substituents independently of each other selected from halogen, hydroxy, ($R^7$)$_2$N—, $C_{1-4}$alkyl-O—, $R^6$O—C(=O)—$R^6$N—, $R^6$—S(=O)$_2$—$R^6$N— and $R^7$—O—C(=O)—.

According to an embodiment $R^8$-E3 the group $R^8$ is selected from the group consisting of F, Cl, CN, —OH, oxo, $C_{1-4}$-alkyl-, $C_{1-4}$-alkyl-O—, HOOC—, $C_{1-4}$-alkyl-O—(O=)C—, H$_2$N—, $C_{1-3}$-alkyl-NH—, ($C_{1-3}$-alkyl)$_2$N—, H$_2$N—$C_{1-3}$-alkyl-, $C_{1-3}$-alkyl-NH—$C_{1-3}$-alkyl-, ($C_{1-3}$-alkyl)$_2$N—$C_{1-3}$-alkyl-, heterocycle-$C_{1-3}$-alkyl, wherein each alkyl group is optionally substituted with 1-3 F atoms, and wherein heterocycle is defined as hereinbefore and hereinafter or wherein heterocycle denotes azetidinyl, pyrrolidinyl, piperidinyl, piperazinyl or morpholinyl, wherein each heterocycle group is optionally substituted with 1 or 2 $C_{1-3}$-alkyl groups.

X:

According to an embodiment X-E1 the group X denotes O or S.

According to an embodiment X-E2 the group X denotes O.

n:

According to an embodiment n-E1 the index n is 0, 1 or 2.

According to an embodiment n-E2 the index n is 0.

p:

According to an embodiment p-E1 the index p is 0 or 1.

According to an embodiment p-E2 the index p is 1.

q:

According to an embodiment q-E1 the index q is 0, 1 or 2.

According to an embodiment q-E2 the index q is 1.

The following preferred embodiments of compounds of the formula (I) are described using generic formulas (I), (I.1) to (I.27), (II), (III), (IV), (V), (VI), (VII), (VIII), (IX), (X), (XI), (XII), (XIII), (XIV) and (XV), wherein any tautomers and stereoisomers, esters, and salts thereof, in particular the pharmaceutically acceptable salts, are encompassed.

In embodiments of the present invention, Ar of structure (I) may be phenyl substituted with 2 $R^4$ as shown in structure (II) and 3-pyridyl substituted in the 4 and 6 positions with $R^4$ as shown in structure (III).

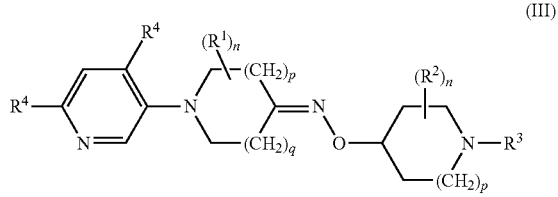
(III)

In an embodiment of structure (I), n at each occurrence is 0, and p and q are all 1 as shown in structure (IV). In an embodiment of structure (IV), Ar is phenyl substituted with 3 $R^4$ functionalities as shown in structure (V).

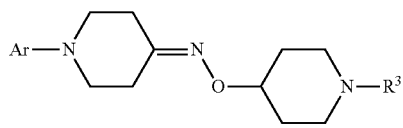
(IV)

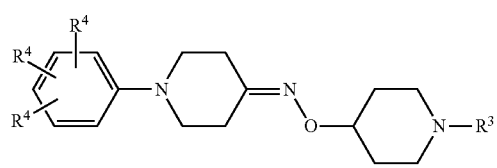
(V)

In an embodiment of structure (V), $R^4$ is F at both the 2- and 5-positions of the phenyl and $C_{1-6}$alkyl substituted with $R^8$ is at the 4-position as shown in structure (VI). In another embodiment of structure (V), $R^3$ is 5-ethyl-pyrimidin-2-yl. In a further embodiment of structure (VI), $R^3$ is —$CO_2R^5$ as shown in structure (VII).

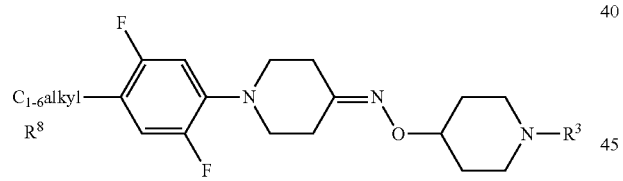
(VI)

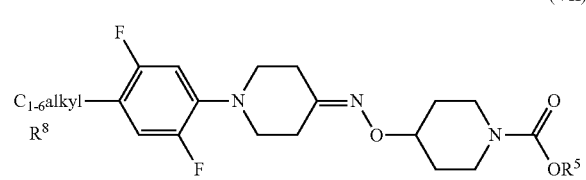
(VII)

In an embodiment of structure (VII), $R^5$ is $C_{1-6}$alkyl.
In an embodiment of structure (VII), $R^5$ is $C_{1-4}$alkyl.
In an embodiment of structure (VII), $R^5$ is isopropyl or isobutyl.
In another embodiment of structure (VII), $R^5$ is $C_{1-6}$alkyl substituted with $R^8$.
In another embodiment of structure (VII), $R^5$ is $C_{1-6}$alkyl and $R_8$ is $N(R^7)_2$.
In two embodiments of structure (IV), $R^3$ is C(=O)$R^6$ as shown in structure (VIII) and $CO_2R^5$ as shown in structure (IX). In another embodiment of structure (IV), $R^3$ is 5-ethyl-pyrimidin-2-yl.

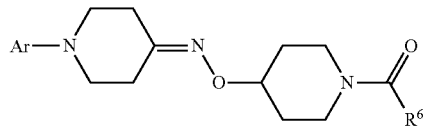
(VIII)

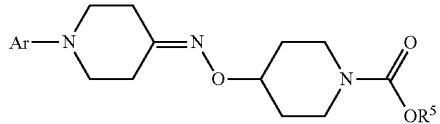
(IX)

In two embodiments of structure (IX), Ar is 2,5-difluoro-4-$R^4$-phenyl as shown in structure (X) and Ar is 2,5-difluoro-4-$R^4$-phenyl where $R^5$ is $C_{1-6}$alkyl as shown in structure (XI).

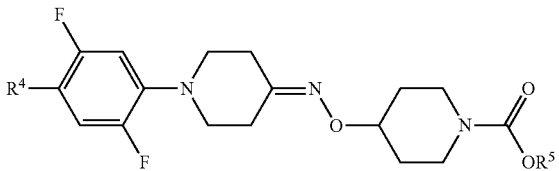
(X)

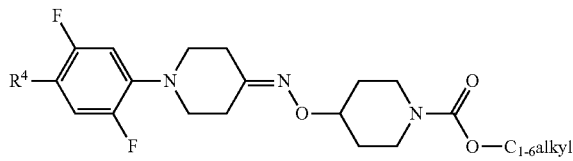
(XI)

In two embodiments of structure (IX), $R^4$ is —$SO_2R^5$ as shown in structure (XII) and $R^4$ is —C(=O)$R^5$ as shown in structure (XIII).

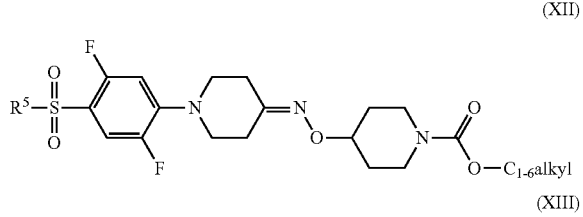
(XII)

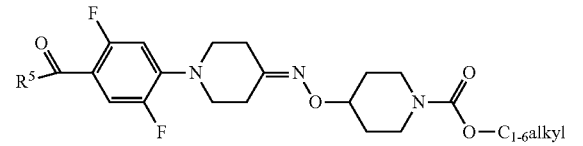
(XIII)

In two embodiments of structure (XIII), $R^5$ is heterocycle substituted with $R^8$ as shown in structure (XIV) and $R^5$ is heterocycle bonded at a nitrogen substituted with $R^8$ as shown in structure (XV).

In an embodiment of structure (XII), $R^8$ is methyl.
In an embodiment of structure (XIII), $C_{1-6}$alkyl is isopropyl.

(XIV)
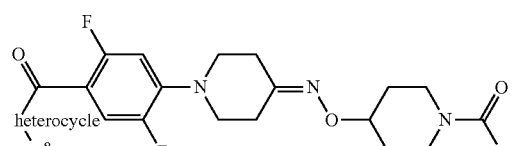
(XV)
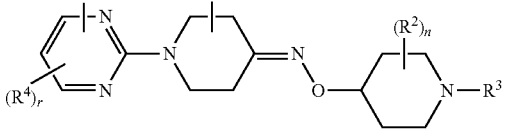
In an embodiment of structures (XIV) and (XV), $R^8$ is heterocycle-$C_{1-6}$alkyl.
In an embodiment of structures (XIV) and (XV), $R^8$ is —$N(R^6)_2$.
In an embodiment of structures (XIV) and (XV), $R^8$ is $C_{1-6}$alkyl substituted with —$N(R^7)_2$.
Further embodiments of compounds of the present invention are depicted by the following structural formulas
(I.1) 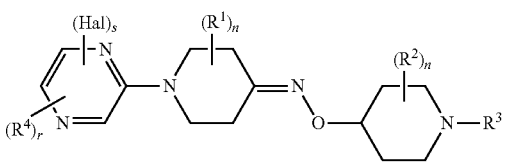
(I.2) 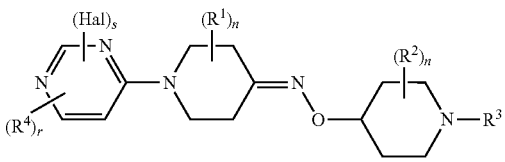
(I.3) 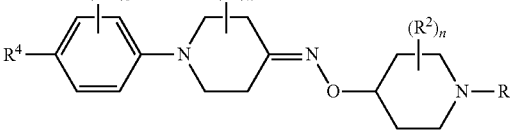
(I.4) 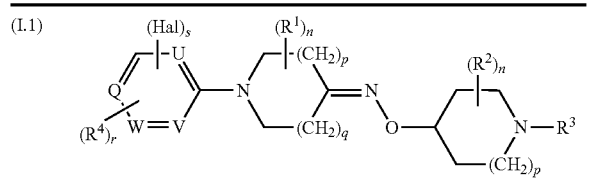
(I.5) 
(I.6) 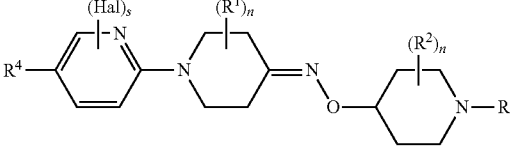
(I.7) 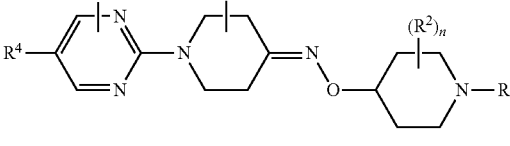
(I.8) 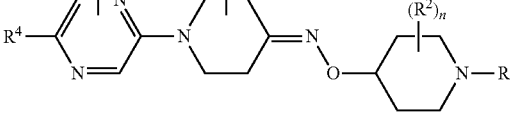
(I.9) 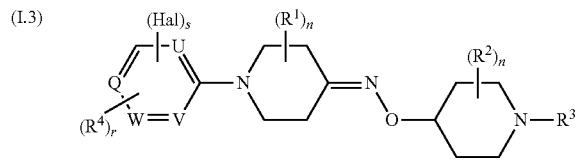
(I.10) 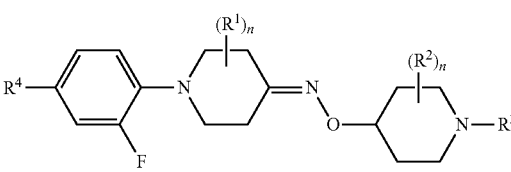
(I.11) 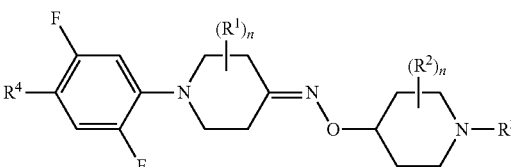
(I.12)
(I.13)
(I.14)

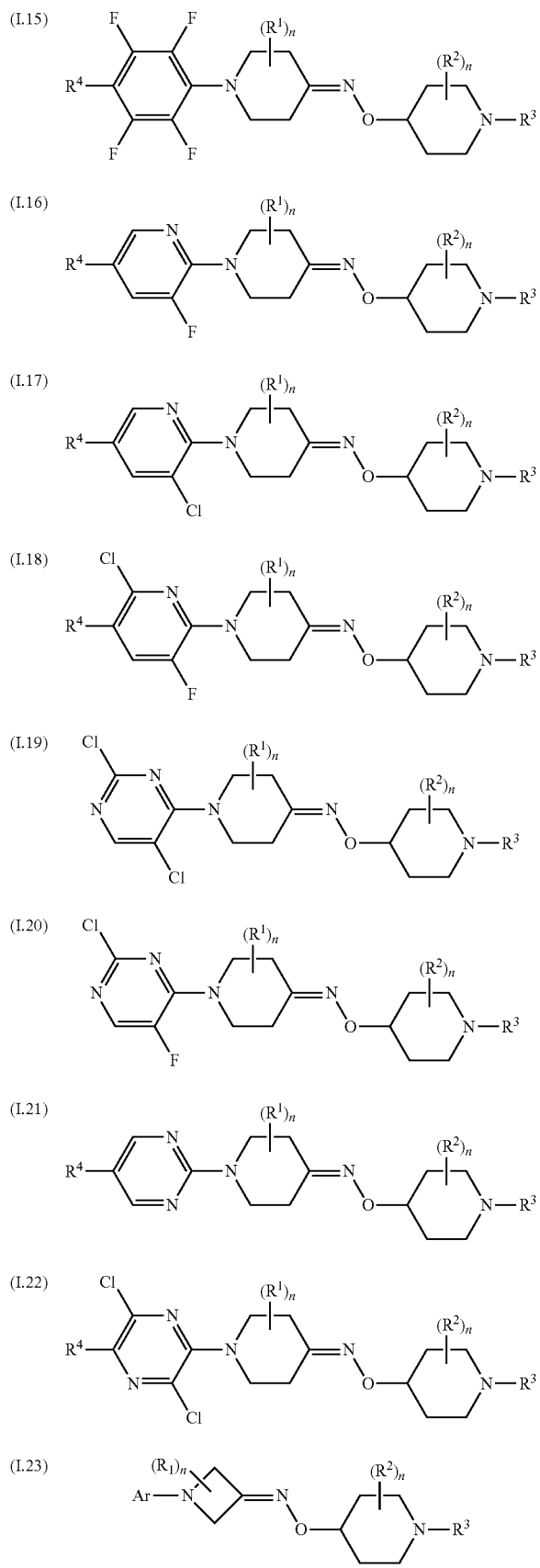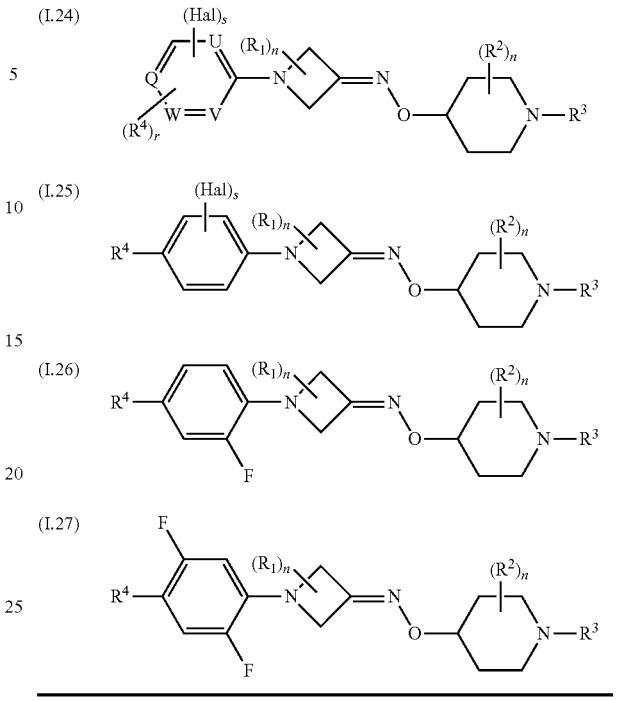

including tautomers, stereoisomers and esters thereof, and salts, particularly pharmaceutically acceptable salts, thereof, wherein in each of the formulas (I), (I.1) to (I.27), (II), (III), (IV), (V), (VI), (VII), (VIII), (IX), (X), (XI), (XII), (XIII), (XIV) and (XV) the groups Ar, $R^1$, $R^2$, $R^3$, $R^4$, $R^5$, $R^6$, $R^7$, $R^8$ and the indexes n, p, q are defined as hereinbefore and hereinafter; and Q, U, V, W denote CH which may be substituted by Hal and/or $R^4$ as defined, wherein one or two of the groups Q, U, V and W may denote N;

n independently is 0, 1 or 2; preferably 0;

p independently is 0 or 1; preferably 1;

q is 0 or 1, preferably 1;

r is 0, 1 or 2, preferably 1;

s is 0, 1, 2, 3 or 4, preferably 1, 2, 3 or 4, even more preferably 1; wherein r+s≦5:

Hal is F or Cl, preferably F;

Ar is selected from an embodiment Ar-E1, Ar-E2, Ar-E3, Ar-E4, Ar-E5 or Ar-E6;

$R^1$ is selected from an embodiment $R^1$-E1 or $R^1$-E2;

$R^2$ is selected from an embodiment $R^2$-E1 or $R^2$-E2;

$R^3$ is selected from an embodiment $R^3$-E1, $R^3$-E2, $R^3$-E3, $R^3$-E4, $R^3$-E4a or $R^3$-E5;

$R^4$ is selected from an embodiment $R^4$-E1, $R^4$-E2, $R^4$-E2a, $R^4$-E2b, $R^4$-E3, $R^4$-E4, $R^4$-E4a or $R^4$-E5.

Examples of particular subgeneric embodiments according to the present invention are set forth in the following table, wherein each substituent group of each embodiment is defined according to the definitions set forth hereinbefore and wherein all other substituents of the given formula are defined according to the definitions set forth hereinbefore and hereinafter:

| Embodiment | Formula | R⁴ | R³ |
|---|---|---|---|
| E-1 | I.1 | R⁴-E1 | R³-E1 |
| E-2 | I.1 | R⁴-E2a and/or R⁴-E2b | R³-E2 |
| E-3 | I.1 | R⁴-E4 | R³-E4 |
| E-4 | I.3 | R⁴-E1 | R³-E1 |
| E-5 | I.3 | R⁴-E2a and/or R⁴-E2b | R³-E2 |
| E-6 | I.3 | R⁴-E4 | R³-E4 |
| E-7 | I.4 | R⁴-E2a and/or R⁴-E2b | R³-E2 |
| E-8 | I.4 | R⁴-E4 | R³-E4 |
| E-9 | I.5 | R⁴-E2a and/or R⁴-E2b | R³-E2 |
| E-10 | I.5 | R⁴-E4 | R³-E4 |
| E-11 | I.7 | R⁴-E2a and/or R⁴-E2b | R³-E2 |
| E-12 | I.7 | R⁴-E4 | R³-E4 |
| E-13 | I.9 | R⁴-E2a and/or R⁴-E2b | R³-E2 |
| E-14 | I.9 | R⁴-E4 | R³-E4 |
| E-15 | I.13 | R⁴-E2a and/or R⁴-E2b | R³-E2 |
| E-16 | I.13 | R⁴-E4 | R³-E4 |
| E-17 | I.14 | R⁴-E2a and/or R⁴-E2b | R³-E2 |
| E-18 | I.14 | R⁴-E4 | R³-E4 |
| E-19 | I.15 | R⁴-E2a and/or R⁴-E2b | R³-E2 |
| E-20 | I.15 | R⁴-E4 | R³-E4 |
| E-21 | I.24 | R⁴-E1 | R³-E1 |
| E-22 | I.24 | R⁴-E2a and/or R⁴-E2b | R³-E2 |
| E-23 | I.24 | R⁴-E4 | R³-E4 | wherein

Q, U, V, W denote CH which may be substituted by Hal and/or R⁴ as defined, wherein one or two of the groups Q, U, V and W may denote N;

Hal is F or Cl, preferably F;

r is 0, 1 or 2, preferably 1;

s is 0, 1, 2, 3 or 4, preferably 1, 2, 3 or 4, even more preferably 1 or 2; wherein r+s≦5;

R¹ is selected from an embodiment R¹-E1 or R¹-E2;

R² is selected from an embodiment R²-E1 or R²-E2;

n independently is 0, 1 or 2; preferably 0;

p independently is 0 or 1; preferably 1;

q is 0 or 1, preferably 1;

including their tautomers stereoisomers, and the salts thereof.

Particularly preferred compounds, including their tautomers and stereoisomers, the salts thereof, are described in the experimental section hereinafter.

Particularly preferred compounds are described in the experimental section hereinafter.

The compounds of the present invention may be prepared by known organic synthesis techniques, including the methods described in more detail in the Examples. In general, the compounds of structure (I) above may be made by the following reaction schemes, wherein all substituents are as defined above unless indicated otherwise.

SCHEME 1

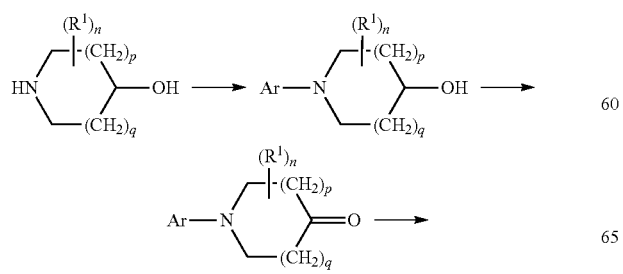

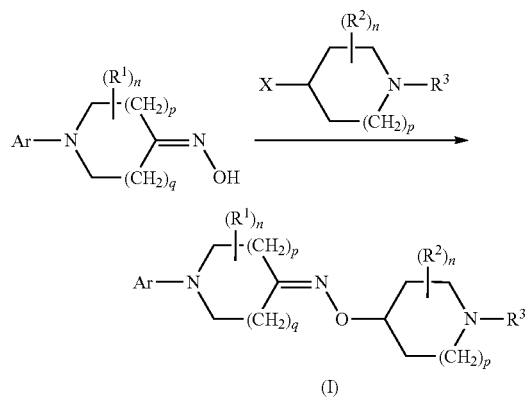

The compounds are prepared by N-arylation of a cyclic amino alcohol (typically by displacement of a haloaromatic by nucleophilic aromatic substitution), followed by oxidation of the alcohol to the ketone with an oxidant such as TPAP and NMO. Reaction with hydroxylamine then leads to the oxime, which can then be reacted with a halo cyclic amine to give the final product.

SCHEME 2

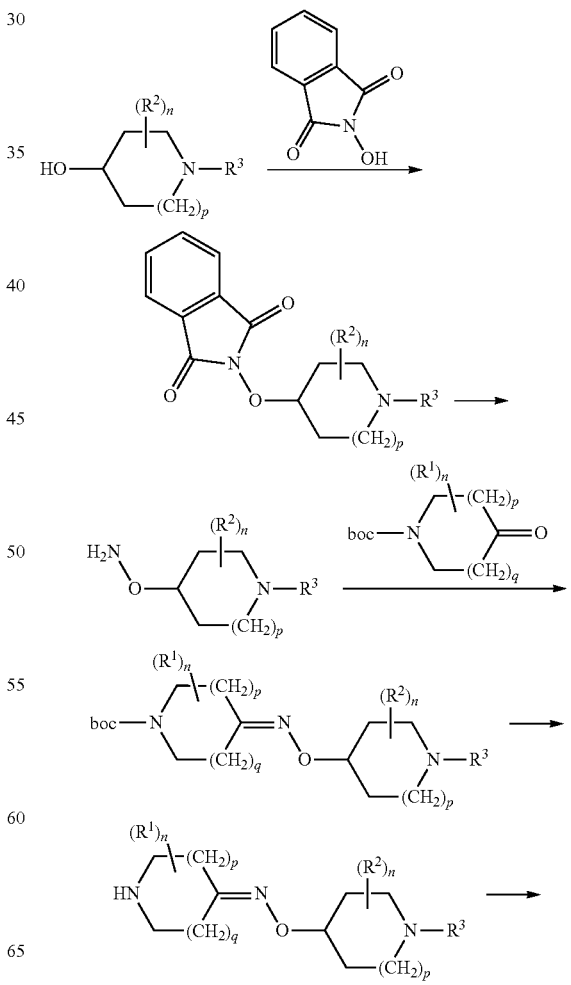

-continued

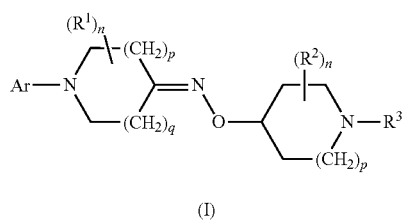

(I)

The compounds can also be prepared by coupling a cyclic amino alcohol with 2-hydroxy-isoindole-1,3-dione under Mitsunobu conditions followed by the deprotection of the phthalimide with hydrazine. The hydroxylamine is then reacted with the Boc-protected cyclic amino ketone and the amine is deprotected in acidic conditions to generate the free secondary amine. Compound (I) may be generated in a number of ways including displacement of a haloaromatic by nucleophilic aromatic substitution, Buckwald coupling with a haloaromatic or by coupling with an aryl boronic acid.

SCHEME 3

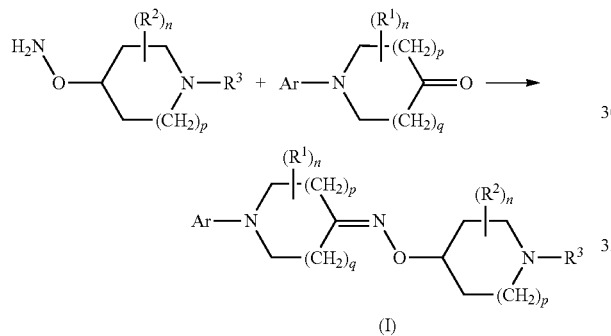

(I)

Alternatively, the hydroxylamine obtained can be reacted with the cyclic amino aryl ketone (prepared as shown previously) in ethanol at reflux.

SCHEME 4

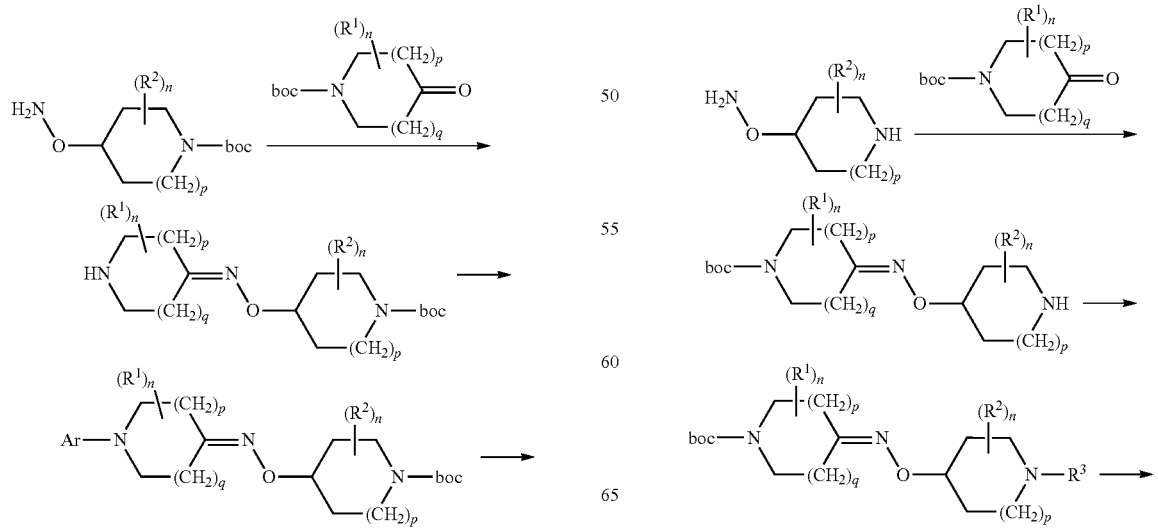

-continued

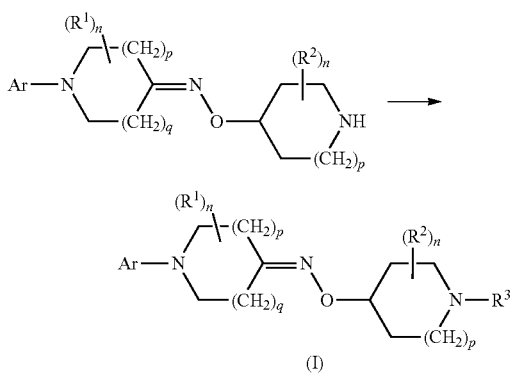

(I)

The hydroxylamine can be reacted with the free amino cyclo ketone to give the oxime. The amine can then be arylated as described previously and the N-Boc can be deprotected to allow derivatization by, for instance, displacement of a haloaromatic by nucleophilic aromatic substitution or, reaction with an electrophilic alkylating agent, reductive amination with an aldehyde or Buckwald coupling with a haloaromatic

SCHEME 5

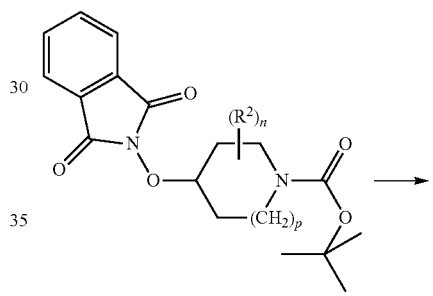

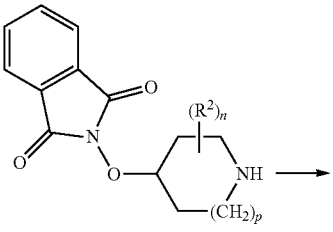

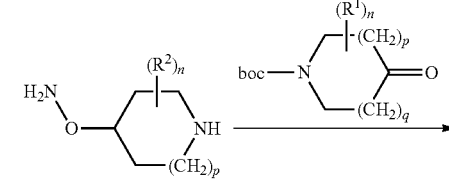

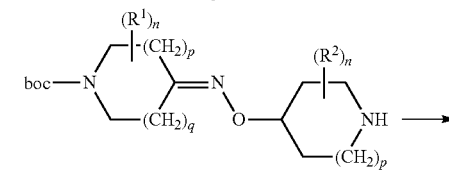

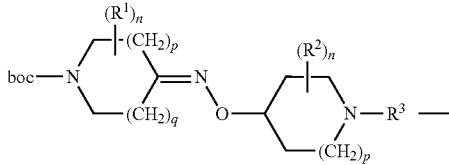

-continued

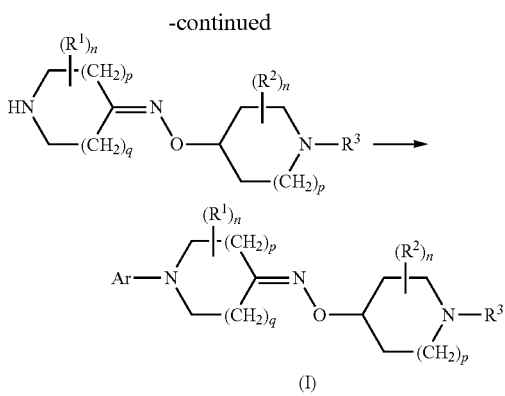

(I)

Alternatively, the phthalimide and boc protected intermediate can be sequentially deprotected, first the N-Boc then the N-phthalimide to give the amino hydroxylamine which can be reacted with the Boc amino cyclic ketone. The free amine can be derivatized as described previously, then the N-boc can be deprotected and the free amine arylated as described previously.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention", "GPR199 receptor agonist(s) according to the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the modulation of the activity of the GPR119 enzyme(s) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk or the sign ┆ is used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

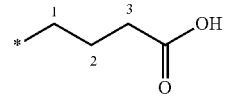

wherein the carboxy group is attached to the third carbon atom of the propyl group. The terms "1-methylpropyl-", "2,2-dimethylpropyl-" or "cyclopropylmethyl-" group represent the following groups:

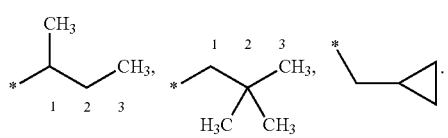

In a definition of a group or substituent the term "oxo" denotes an O-atom which replaces two H-atoms and which is linked to the respective atom via a double bond. A group comprising a —CH$_2$-group may be substituted with an oxo substituent such that the —CH$_2$-group is replaced a —C(=O)— group.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term halogen generally denotes fluorine, chlorine, bromine and iodine.

Alkyl:

The term "C$_{1-n}$-alkyl", wherein n is an integer from 2 to n, either alone or in combination with another radical denotes an acyclic, saturated, branched or linear hydrocarbon radical with 1 to n C atoms. For example the term C$_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Alkylene:

The term "C$_{1-n}$-alkylene" wherein n is an integer 1 to n, either alone or in combination with another radical, denotes an acyclic, straight or branched chain divalent alkyl radical containing from 1 to n carbon atoms. For example the term C$_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

Alkenyl:

The term "C$_{2-n}$-alkenyl", is used for a group as defined in the definition for "C$_{1-n}$-alkyl" with at least two carbon atoms, if at least two of those carbon atoms of said group are bonded to each other by a double bond. For example the term C$_{2-3}$-alkenyl includes —CH=CH$_2$, —CH=CH—CH$_3$, —CH$_2$—CH=CH$_2$.

Alkenylene:

The term "C$_{2-n}$-alkenylene" is used for a group as defined in the definition for "C$_{1-n}$-alkylene" with at least two carbon atoms, if at least two of those carbon atoms of said group are bonded to each other by a double bond. For example the term C$_{2-3}$-alkenylene includes —CH=CH—, —CH=CH—CH$_2$—, —CH$_2$—CH=CH—.

Alkynyl:

The term "C$_{2-n}$-alkynyl", is used for a group as defined in the definition for "C$_{1-n}$-alkyl" with at least two carbon atoms, if at least two of those carbon atoms of said group are bonded to each other by a triple bond. For example the term C$_{2-3}$-alkynyl includes —C≡CH, —C≡C—CH$_3$, —CH$_2$—C≡CH.

Alkynylene:

The term "C$_{2-n}$-alkynylene" is used for a group as defined in the definition for "C$_{1-n}$-alkylene" with at least two carbon atoms, if at least two of those carbon atoms of said group are bonded to each other by a triple bond. For example the term C$_{2-3}$-alkynylene includes —C≡C—, —C≡C—CH$_2$—, —CH$_2$—C≡C—.

Carbocyclyl:

The term "carbocyclyl" as used either alone or in combination with another radical, means a mono- or multi-ring ring structure consisting only of carbon containing between one and four rings wherein such rings may be attached together in a pendent manner or may be fused. The term "carbocycle" refers to fully saturated and aromatic ring systems and partially saturated ring systems. The term "carbocycle" additionally encompasses spiro systems, and bridged systems.

Cycloalkyl:

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Cycloalkenyl:

The term "$C_{3-n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

"Aryl$C_{1-6}$alkyl" means a $C_{1-6}$alkyl having at least one alkyl hydrogen atom replaced with an aryl moiety, such as —$CH_2$-phenyl, —$CH_2$—$CH_2$-phenyl and the like.

Heteroaryl:

"Heteroaryl" means an aromatic heterocycle ring of 5- to 10-members and having at least one heteroatom selected from N, O, S, including —C(═O)—, —S(═O)— and —S(═O)$_2$—, and containing at least 1 carbon atom, including both mono- and bicyclic ring systems, and wherein the N and S heteroatoms may be optionally oxidized, and the N heteroatom may be optionally quaternized. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, oxadiazolyl, thiadiazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

Heterocycle

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from N, O, S, including —C(═O)—, —S(═O)— and —S(═O)$_2$—, and wherein the N and S heteroatoms may be optionally oxidized, and the N heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or acid groups are bonded to any group that, when administered to a patient, cleaves to form the hydroxy, amine or acid groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof.

The compounds of the present invention may exist in a continuum of solid states ranging from fully amorphous to fully crystalline. Furthermore, some of the crystalline forms of the compounds of structure (I) may exist as polymorphs, which are included in the present invention. In addition, some of the compounds of structure (I) may also form solvates with water or organic solvents. The term solvate is used herein to describe a molecular complex comprising a compound of the present invention and one or more pharmaceutically acceptable solvent molecules. Such solvates are similarly included within the scope of this invention.

The present invention also includes all pharmaceutically acceptable isotopically labeled compounds of structure (I) where one or more atoms are replaced by atoms having the same atomic number but a different atomic mass. Examples include $^2H$ and $^3H$ for hydrogen, $^{11}C$, $^{13}C$ and $^{14}C$ for carbon, $^{36}Cl$ for chlorine, $^{18}F$ for fluorine, $^{123}I$ and $^{125}I$ for iodine, $^{13}N$ and $^{15}N$ for nitrogen, and $^{35}S$ for sulfur.

Compounds of the present invention include compounds of structure (I) as defined, including all polymorphs, prodrugs, isomers (including optical, geometric and tautomeric), salts, solvates and isotopes thereof.

In an embodiment, GPR119 agonists of the present invention may be used to treat patients with a variety of diseases and conditions.

In an embodiment, GPR119 agonists of the present invention may be used to treat diseases and conditions which are mediated by the modulating the activity of GPR119.

In an embodiment, GPR119 agonists of the present invention may be used to treat diabetes, in particular type 2 diabetes mellitus or type 1 diabetes mellitus.

In an embodiment, GPR119 agonists of the present invention may be used to treat obesity.

In another embodiment GPR119 agonists of the present invention may be used to treat type 1 diabetes, type 2 diabetes, insufficient glycemic control, insulin resistance, hyperglycemia, hyperlipidemia, hypercholesterinemia, dyslipidemia, syndrome X, metabolic syndrome, obesity, hypertension, chronic systemic inflammation, retinopahtie, neuropathie, nephropathie, atherosclerosis, endothelial dysfunction and bone related conditions such as osteoporosis, rheumatoid arthritis or osteoarthritis.

In another embodiment GPR119 agonists of the present invention may be used to treat, slow, delay or reverse a progression of impaired glucose tolerance, impaired fasting blood, glucose insulin resistance and/or metabolic syndrome to type 2 diabetes.

In another embodiment GPR119 agonists of the present invention may be used to treat or improve the glycemic control and/or to reduce fasting blood glucose, postprandial glucose and/or of glycosylated hemoglobin HbAlc.

In another embodiment GPR119 agonists of the present invention may be used to prevent, slow progression of, delay or treat of a condition or disorder selected from the group consisting of complications of diabetes mellitus, for example cataracts and micro- and macrovascular diseases, such as nephropathy, retinopathy, neuropathy, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis.

In another embodiment GPR119 agonists of the present invention may be used to reduce body weight and/or body fat, or prevent an increase in body weight and/or body fat, or to facilitate a reduction in body weight and/or body fat In another embodiment GPR119 agonists of the present invention may be used to prevent, slow, delay or treat the degeneration of pancreatic beta cells and/or the decline of the functionality of pancreatic beta cells and/or to improve and/or restore the functionality of pancreatic beta cells and/or restore the functionality of pancreatic insulin secretion In another embodiment GPR119 agonists of the present invention may be used to maintain and/or improve the insulin sensitivity and/or to treat or prevent hyperinsulinemia and/or insulin resistance In addition, the compounds of the present invention may be useful in combination with one or more additional therapeutic agents, particularly therapeutic agents suitable for the treatment and/or prevention of the conditions and diseases presented previously. Additional therapeutic agents which may be suitable for combination with one or more compounds of the present invention include insulin and insulin analogs, sulfonylureas (such as glibenclamide, glimepiride, tolbutamide), meglitinides (such as nateglinide, mitiglinide), biguanides (especially metformin), PPAR modulators including the thiazolidinediones (such as pioglitazone, rivoglitazone), DPP-4 inhibitors (such as alogliptin, linagliptin), alpha-glucosidase inhibitors (such as acarbose, miglitol, voglibose), GLP-1 analogs (such as exenitide, liraglutide), SGLT-2 inhibitors (such as dapagliflozin, remogliflozin, sergliflozin), amylin analogs (such as pramlintide) and incretin mimetics.

In another embodiment of the invention, pharmaceutical compositions containing one or more GPR119 receptor agonists are disclosed. For the purposes of administration, the compounds of the present invention may be formulated as pharmaceutical compositions. Pharmaceutical compositions of the present invention comprise a compound of the present invention and a pharmaceutically acceptable carrier and/or diluent. The compound is present in the composition in an amount which is effective to treat a particular disorder, that is, in an amount sufficient to achieve GPR119 receptor agonist activity, and preferably with acceptable toxicity to the patient. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GPR119 receptor agonist, diluents, dispersing and surface active agents, binders, and lubricants. One skilled in this art may further formulate the GPR119 receptor agonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating various diseases and/or conditions as described hereinbefore and hereinafter, in particular obesity and diabetes and related conditions as discussed above. Such methods include administering of a compound of the present invention to a patient in an amount sufficient to treat the condition. In this context, "treat" includes prophylactic administration. Such methods include systemic administration of a GPR119 receptor agonist of this invention, preferably in the form of a pharmaceutical composition as discussed above. As used herein, systemic administration includes oral and parenteral methods of administration.

The dose range of the compounds of general formula (I) applicable per day is usually from 0.001 to 10 mg, preferably from 0.01 to 8 mg per kg body weight of the patient. Each dosage unit may conveniently contain from 0.1 to 1000 mg of a compound according to the invention.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

For oral administration, suitable pharmaceutical compositions of GPR119 receptor agonists include powders, granules, pills, tablets, lozenges, chews, gels, and capsules as well as liquids, syrups, suspensions, elixirs, and emulsions. The compounds of the invention may also be used in fast dissolving, fast disintegrating dosage forms. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the GPR119 receptor agonist, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

The following examples are provided for purposes of illustration, not limitation. In summary, the compounds of this invention may be synthesized and assayed by the general methods disclosed in the following Examples.

EXAMPLES

HPLC Methods for Analyzing the Samples

Retention time, $t_R$, in minutes
Analytical HPLC-MS Method 1
Platform: Agilent 1100 series: equipped with an auto-sampler, an UV detector (220 nM and 254 nM), a MS detector (APCI);
HPLC column: Phenomenex Synergi: MAX-RP, 2.0×50 mm column;
HPLC gradient: 1.0 mL/minute, from 10% acetonitrile in water to 90% acetonitrile in water in 2.5 minutes, maintaining 90% for 1 minute. Both acetonitrile and water have 0.025% TFA.
Analytical HPLC-MS Method 2
Platform: Agilent 1100 series: equipped with an auto-sampler, an UV detector (220 nM and 254 nM), a MS detector (APCI);
HPLC column: Phenomenex Synergi-Max RP, 2.0×50 mm column;
HPLC gradient: 1.0 mL/minute, from 5% acetonitrile in water to 95% acetonitrile in water in 13.5 minutes, maintaining 95% for 2 minute. Both acetonitrile and water have 0.025% TFA.
Analytical HPLC-MS Method 3
Platform: Agilent 1100 series: equipped with an auto-sampler, an UV detector (220 nM and 254 nM), a MS detector (electrospray);
HPLC column: XTerra MS, $C_{18}$, 5µ, 3.0×250 mm column;
HPLC gradient: 1.0 mL/minute, from 10% acetonitrile in water to 90% acetonitrile in water in 46 minutes, jump to 99% acetonitrile and maintain 99% acetonitrile for 8.04 minutes. Both acetonitrile and water have 0.025% TFA.
Analytical HPLC-MS Method 4 Platform: Agilent 1100 series: equipped with an auto-sampler, an UV detector (220 nM and 254 nM), a MS detector (electrospray);
HPLC column: Waters XBridge 5µ C18 110A, 3.0×100 mm
HPLC gradient: 1.5 mL/min, from 5% acetonitrile in water to 90% acetonitrile in water in 9.86 minutes, from 90% acetonitrile in water to 95% acetonitrile in water in 0.1 minutes, hold at 95% for 1.19 minutes. Both acetonitrile and water have 0.04% $NH_4OH$
Analytical HPLC-MS Method 5
Platform: Gilson 215 Auto-sampler, Dionex Thermostatted Column Compartment TCC-100 held at 30° C., Dionex PDA-100 Photodiode Array Detector (220 nm and 254 nm), Dionex P680 HPLC pump, Thermo Finnigan MSQ single quad Mass Spectrometer (APCI)
HPLC column: Phenomenex Gemini 5µ C18 110A, 3.0× 150 mm
HPLC gradient: 1.5 mL/min, from 5% acetonitrile in water to 90% acetonitrile in water in 9.86 minutes, from 90% acetonitrile in water to 95% acetonitrile in water in 0.1 minutes, hold at 95% for 1.19 minutes. Both acetonitrile and water have 0.04% $NH_4OH$
Analytical HPLC-MS Method 6
Platform: Agilent 1100 series: equipped with an auto-sampler, an UV detector (220 nM and 254 nM), a MS detector (APCI);
HPLC column: Phenomenex Synergi-Max RP, 2.0×50 mm column;
HPLC gradient: from 5% B to 95% B in A in 6.43 minutes, 9.17 minutes total run time. A=10 mM $NH_4OH$ in water, B=75% MeOH 25% AcN
Preparative HPLC-MS
Platform: Shimadzu HPLC equipped with a Gilson 215 auto-sampler/fraction collector, UV detector and a PE Sciex API150EX mass detector;
HPLC column: BHK ODS-0/B, 5µ, 30×75 mm
HPLC gradient: 35 mL/minute, 10% acetonitrile in water to 100% acetonitrile in 7 minutes, maintaining 100% acetonitrile for 3 minutes, with 0.025% TFA.
Chiral HPLC
Platform: Dionex P680A and P680P pumps, Dionex PAD 100 photodiode array detector, Jasco CD 2095 plus chiral detector, Gilson 215 liquid handler. Analytical Columns are 0.46×25 cm, 5 µm; preparative columns are 2×25 cm, 5 µm.

Example 1

4-[1-(2-FLUORO-4-METHANESULFONYL-PHENYL)-PIPERIDIN-4-YLIDENEAMINOOXY]-PIPERIDINE-1-CARBOXYLIC ACID TERT-BUTYL ESTER

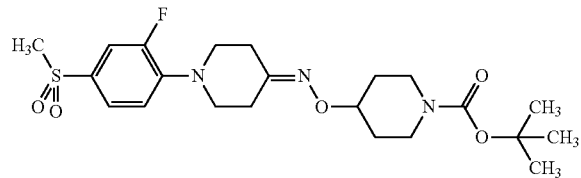

1-1

Step 1A: 1-(2-Fluoro-4-methanesulfonyl-phenyl)-piperidin-4-ol (1a)

4-Hydroxypiperidine (658 mg, 6 5 mmol) and 1,2-difluoro-4-(methanesufonyl)benzene (1.98 g, 5.1 mmol) were combined in DMF (5 mL). Sodium carbonate (705 mg, 6.7 mmol) was added and the mixture was heated at 60 ° C. for 18 h. The mixture was cooled to room temperature and then poured into a mixture of water (10 mL) and a saturated sodium chloride solution (10 mL). The mixture was extracted three times with ethyl acetate (15 mL) and the extracts were combined, washed with brine, dried ($MgSO_4$), and concentrated under vacuum to afford 1.46 g of crude 1a, which was used in the subsequent step without purification: LC-MS 274.1 ($MH^+$).

Step 1B: 1-(2-Fluoro-4-methanesulfonyl-phenyl)-piperidin-4-one (1b)

Compound 1a and NMO (780 mg, 6.66 mmol) were dissolved in DCM (30 mL). Molecular sieves (4 Å, 1.5 g) were added and stiffing was continued for 1 h. TPAP (100 mg, 0.28 mmol) was added and the mixture was stirred for 18 h. The mixture was filtered
(Celite), concentrated, and the residue was purified by flash LC(elution with 10-50% ethyl acetate and 0.1% TEA in hexanes) to afford 1.12 g (81% yield from 1,2-difluoro-4-(methanesulfonyl)benzene) of 1b as a white solid: $^1H$ NMR (300

MHz, CDCl₃) δ 7.67-7.59 (m, 2 H), 7.06 (t, J=8.3 Hz, 1 H), 3.58 (t, J=6.2 Hz, 4 H), 3.04 (s, 3 H), 2.64 (t, J=6.2 Hz, 4 H); LC-MS 272.1 (MFE).

Step 1C: 1-(2-Fluoro-4-methanesulfonyl-phenyl)-piperidin-4-one oxime (1c)

Compound 1b (341 mg, 1.3 mmol) and sodium acetate trihydrate (513 mg, 3.8 mmol) were combined in ethanol (5 mL) and heated to reflux for 15 minutes. Hydroxylamine hydrochloride (131 mg, 1.9 mmol) was added and heating was continued for 3 h. The mixture was cooled to room temperature and diluted with water (30 mL). The mixture was chilled in an ice-bath and the resulting white precipitate was isolated by filtration, washed with water, and dried under vacuum to afford 266 mg (74%) of 1c: $^1$H NMR (300 MHz, CDCl₃) δ 7.98 (br s, 1 H), 7.65-7.56 (m, 2 H), 7.02 (t, J=8.4 Hz, 1 H), 3.42-3.33 (m, 4 H), 3.04 (s, 3 H), 2.82 (t, J=5.9 Hz, 2 H), 2.54 (t, J=5.7 Hz, 2 H); LC-MS 287.1 (MH⁺).

Step 1D: tert-Butyl 4-[1-(2-Fluoro-4-methanesulfonylphenyl)piperidin-4-ylideneaminooxy]piperidine-1-carboxylate (1-1)

Compound 1c (31 mg, 0.11 mmol), 4-iodo-piperidine-1-carboxylic acid tert-butyl ester (38 mg, 0.11 mmol), cesium carbonate (102 mg, 0.31 mmol), and DMSO (0.3 mL) were combined and stirred at room temperature for 6 h and at 60° C. for 18 h. A second quantity of 4-iodo-piperidine-1-carboxylic acid tert-butyl ester (72 mg, 0.23 mmol) and cesium carbonate (102 mg, 0.31 mmol) was added and heating was continued for 4 h. Some starting material persisted so more 4-iodo-piperidine-1-carboxylic acid tert-butyl ester (75 mg, 0.24 mmol) was added and the mixture was heated for a further 2 h. The mixture was then poured into ethyl acetate (5 mL), washed twice with aqueous sodium chloride (5 mL), dried (MgSO₄) and concentrated. The residue was taken up in methanol (1 mL) and purified by preparative HPLC to afford 8 mg (12%) of the TFA salt of 1-1 as an brown oil: $^1$H NMR (300 MHz, CDCl₃) δ 7.64-7.56 (m, 2 H), 7.00 (t, J=8.3 Hz, 1 H), 4.22 (quintet, J=3.9 Hz, 1 H), 3.70-3.66 (m, 2 H), 3.40 (t, J=5.7 Hz, 2 H), 3.33 (t, J=6.2 Hz, 2 H), 3.25-3.17 (m, 2 H), 3.30 (s, 3 H), 2.78 (t, J=5.9 Hz, 2 H), 2.52 (t, J=6.0 Hz, 2 H), 1.94-1.87 (m, 2 H), 1.68-1.57 (m, 2 H), 1.46 (s, 9 H); LC-MS 370.1 (MH⁺-Boc), $t_R$=7.88 (Method 2). EC50: 29 nM.

Example 2

4-[1-(2-FLUORO-4-METHANESULFONYL-PRENYL)-PIPERIDIN-4-YLIDENEAMINOOXY]-PIPERIDINE-1-CARBOXYLIC ACID ISOPROPYL ESTER 2-1

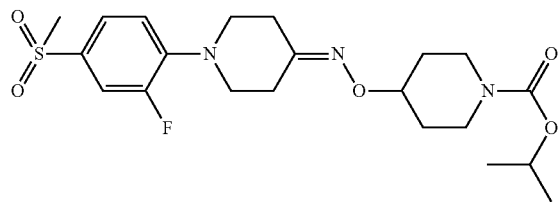

Step 2A: Isopropyl 4-(1,3-Dioxo-1,3-dihydroisoindol-2-yloxy)piperidine-1-carboxylate (2a)

4-Hydroxy-piperidine-1-carboxylic acid isopropyl ester (3.09 g, 17 mmol), N-hydroxyphthalimide (2.69 g, 17 mmol), and triphenylphosphine (4.32 g, 17 mmol) were combined in THF (30 mL). DEAD (2.6 mL, 17 mmol) was added and the mixture was stirred at room temperature for 18 h. The mixture was then concentrated under vacuum and the residue was purified by flash LC(elution with 10-50% ethyl acetate and 0.1% TEA in hexanes) to afford 3.31 g (60%) of 2a as a colorless oil: $^1$H NMR (300 MHz, CDCl₃) δ 7.85-7.81 (m, 2 H), 7.83-7.29 (m, 2 H), 4.91 (quintet, J=6.3 Hz, 1 H), 4.43 (septet, J=3.9 Hz, 1 H), 3.94-3.86 (m, 2 H), 3.32-3.23 (m, 2 H), 1.99-1.78 (m, 4 H), 1.24 (d, J=6.6 Hz, 6 H); LC-MS 333.1 (MH⁺).

Step 2B: Isopropyl 4-Aminooxypiperidine-1-carboxylate (2b)

Compound 2a (3.31 g, 10 mmol) was dissolved in DCM (21 mL) and treated with hydrazine hydrate (1.52 mL, 31 mmol). After stirring for 3 h, the mixture was chilled in an ice-bath and filtered. The precipitate was washed with a minimal volume of DCM and the resulting filtrate was concentrated under vacuum to afford 1.27 g (63%) of 2b as a colorless oil; LC-MS 203.1 (MH⁺).

Step 2C: Isopropyl 4-((1-tert-butyloxycarbonyl)piperidin-4-ylideneaminooxy)-piperidine-1-carboxylate (2c)

4-Oxo-piperidine-1-carboxylic acid tert-butyl ester (1.25 g, 6.3 mmol) and sodium acetate trihydrate (0.52 g, 3.8 mmol) were combined in ethanol (10 mL) and heated to reflux for 15 minutes. Compound 2b (1.27 g, 1.9 mmol) in ethanol (4 mL) was added and heating was continued for 3 h. The mixture was cooled to room temperature and diluted with water (60 mL). The mixture was extracted three times with ethyl acetate (30 mL) and the combined extracts were washed with aqueous sodium chloride (30 mL), dried (MgSO₄) and concentrated under vacuum to afford 2.24 g (93%) of 2c as a colorless oil: $^1$H NMR (300 MHz, CDCl₃) δ 4.91 (quintet, J=6.3 Hz, 1 H), 4.20 (septet, J=3.9 Hz, 1 H), 3.72-3.68 (m, 2 H), 3.56-3.47 (m, 4 H), 3.29-3.20 (m, 2 H), 2.58 (t, J=6.2 Hz, 2 H), 2.33 (t, J=6.2 Hz, 1 H), 1.92-1.86 (m, 2 H), 1.68-1.54 (m, 2 H), 1.47 (s, 9 H), 1.23 (d, J=6.3 Hz, 6 H); LC-MS 384.3 (MFE).

Step 2D: Isopropyl 4-(Piperidin-4-ylideneaminooxy)piperidine-1-carboxylate (2d)

Compound 2c was dissolved in DCM (20 mL) and treated slowly with TFA (20 mL). The mixture was stirred at room temperature for 45 minutes and was then concentrated under vacuum. The residue was dissolved in DCM and PL-HCO₃ MP-Resin (8.9 g, 4.2 mmol) was added. The mixture was gently stirred for 18 h and then filtration and concentration afforded 1.27 g (71%) of 2d as a pale yellow oil: $^1$H NMR (300 MHz, CDCl₃) δ 4.90 (quintet, J=6.3 Hz, 1 H), 4.19 (septet, J=3.9 Hz, 1 H), 3.72-3.65 (m, 2 H), 3.29-3.21 (m, 2 H), 2.97 (t, J=5.7 Hz, 2 H), 2.90 (t, J=5.9 Hz, 2 H), 2.55 (t, J=6.2 Hz, 2 H), 2.27 (t, J=5.7 Hz, 2 H), 1.93-1.84 (m, 2 H), 1.68-1.56 (m, 2 H), 1.28 (d, J=6.0 Hz, 6 H); LC-MS 284.2 (MH⁺).

Step 2E: 4-[1-(2-Fluoro-4-methanesulfonyl-phenyl)-piperidin-4-ylideneaminooxy]-piperidine-1-carboxylic acid isopropyl ester (2-1)

Compound 2d (24 mg, 0.085 mmol), 1,2-difluoro-4-methanesulfonyl-benzene (0.13 mmol), DIEA (0.075 mL, 0.45 mmol), and DMSO (0.3 mL) were combined and heated at 130° C. for 20 h. The mixture was cooled to room temperature, methanol (0.75 mL) was added, and the mixture was purified by preparative HPLC to afford the trifluoroacetic acid salt of 2-1.

The following compounds were made according to this procedure by displacement of the aryl halide (fluoro, chloro or bromo).

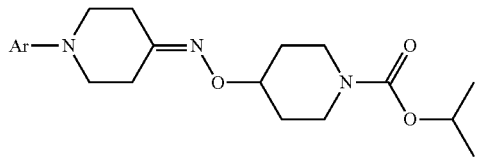
| No. | Ar | MH+ | MW | $t_R$ (Min) | HPLC Gradient | EC50 (nM) |
|---|---|---|---|---|---|---|
| 2-1 | 3-F, 4-(methylsulfonyl)phenyl | 456.4 | 455.5 | 7.46 | Method 6 | 47 |
| 2-2 | 2,5-difluoro-4-cyanophenyl | 421.0 | 420.4 | 8.77 | Method 6 | 397 |
| 2-3 | 2,5-difluoro-4-formylphenyl | 424.1 | 423.4 | 10.67 | Method 5 | 14 |
| 2-4 | 2-hydroxypyridin-4-yl | 377.1 | 376.4 | 5.21 | Method 4 | >10000 |
| 2-5 | pyridine-4-yl N-oxide | 361.4 | 376.4 | 6.39 | Method 4 | >10000 |
| 2-6 | 2-methylpyridin-4-yl | 375.4 | 374.5 | 7.12 | Method 4 | 1485 |
| 2-7 | 3-methylpyridin-2-yl | 375.4 | 374.5 | 8.09 | Method 4 | 55% |
| 2-8 | 6-methylpyridin-2-yl | 375.2 | 374.5 | 10.14 | Method 5 | >10000 |
| 2-9 | pyridin-4-yl | 361.4 | 360.4 | 6.44 | Method 4 | >10000 |

-continued
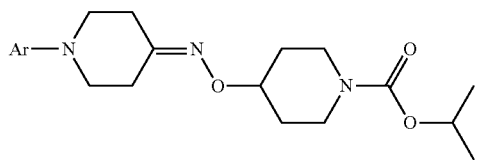
| No. | Ar | MH+ | MW | $t_R$ (Min) | HPLC Gradient | EC50 (nM) |
|---|---|---|---|---|---|---|
| 2-10 | pyrazine-Cl | 396.5 | 395.9 | 8.07 | Method 4 | 363 |
| 2-11 | pyrazine | 362.4 | 361.4 | 6.50 | Method 4 | >10000 |
| 2-12 | 5-iodo-pyridine | 487.0 | 486.3 | 10.72 | Method 5 | 2359 |
| 2-13 | 5-nitro-thiazole | 412.0 | 411.5 | 9.01 | Method 5 | 5112 |
| 2-14 | thiadiazole | 368.4 | 367.5 | 5.88 | Method 4 | >10000 |
| 2-15 | thieno[3,2-d]pyrimidine | 418.4 | 417.5 | 6.95 | Method 4 | 4785 |
| 2-16 | 4-methylsulfonyl-phenyl | 438.1 | 437.6 | 8.37 | Method 5 | 328 |
| 2-17 | 5-bromo-pyrimidine | 440.1 | 440.3 | 10.44 | Method 5 | 1176 |
| 2-18 | 4-amino-5-cyano-pyrimidine | 402.3 | 401.5 | 8.08 | Method 5 | >10000 |
| 2-19 | 4-fluoro-2-formyl-phenyl | 406.1 | 405.4 | 8.27 | Method 2 | 345 |

-continued
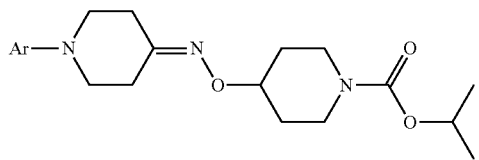
| No. | Ar | MH+ | MW | $t_R$ (Min) | HPLC Gradient | EC50 (nM) |
|---|---|---|---|---|---|---|
| 2-20 | 2-fluoro-4-formylphenyl | 406.1 | 405.4 | 7.60 | Method 6 | 703 |
| 2-21 | 4-chloro-2-fluoro-5-carboxyphenyl | 456.4 | 455.9 | 3.35 | Method 4 | >10000 |
| 2-22 | 4-formyl-2-fluorophenyl | 406.1 | 405.5 | 7.39 | Method 2 | 318 |
| 2-23 | 4-acetyl-2,5-difluorophenyl | 438.5 | 437.5 | 6.41 | Method 5 | 375 |
| 2-24 | 6-chloro-5-cyano-3-fluoropyridin-2-yl | 438.3 | 437.9 | 6.50 | Method 4 | 600 |
| 2-24 | 5-(hydroxymethyl)-3-chloropyridin-2-yl | 425.1 | 424.9 | 5.18 | Method 5 | 182 |
| 2-25 | 5-chloro-4-formylthiazol-2-yl | 428.7 | 428.9 | 5.63 | Method 5 | >10000 |
| 2-26 | 2-chloro-3-(hydroxymethyl)pyridin-6-yl | 424.6 | 424.9 | 5.25 | Method 4 | 758 |

-continued
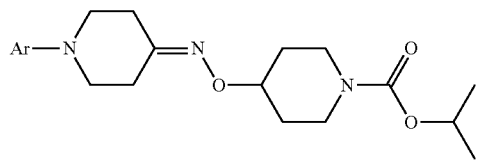
| No. | Ar | MH+ | MW | $t_R$ (Min) | HPLC Gradient | EC50 (nM) |
|---|---|---|---|---|---|---|
| 2-27 | 6-chloro-3-(hydroxymethyl)pyridin-2-yl | 425.3 | 424.9 | 5.54 | Method 4 | >10000 |
| 2-28 | 4-formylphenyl | 388.3 | 387.5 | 5.43 | Method 5 | >10000 |
| 2-29 | 4-formyl-2-methylphenyl | 402.4 | 401.5 | 6.79 | Method 4 | 3168 |
| 2-30 | 4-formyl-3-hydroxyphenyl | 404.2 | 403.5 | 5.14 | Method 5 | >10000 |
| 2-31 | 4-formyl-2-chlorophenyl | 422.2 | 421.9 | 6.79 | Method 4 | 1248 |
| 2-32 | 4-carbamoyl-2,6-difluorophenyl | 439.5 | 438.5 | 5.08 | Method 5 | 25 |
| 2-33 | 6-chloro-3-fluoro-5-(hydroxymethyl)pyridin-2-yl | 425.1 | 442.9 | 7.67 | Method 2 | 27 |
| 2-34 | 3-amino-6-chloro-5-(methoxycarbonyl)pyrazin-2-yl | 468.9 | 468.9 | 5.60 | Method 5 | >10000 |

-continued
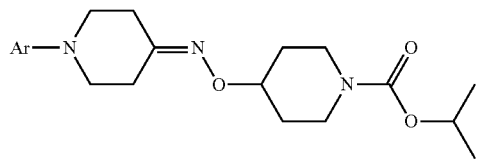
| No. | Ar | MH+ | MW | t_R (Min) | HPLC Gradient | EC50 (nM) |
|---|---|---|---|---|---|---|
| 2-35 | | 453.5 | 452.5 | 5.24 | Method 5 | 34 |
| 2-36 | | 456.8 | 456.5 | 4.93 | Method 5 | 130 |
| 2-37 | | 379.1 | 378.4 | 5.03 | Method 5 | 630 |
| 2-38 | | 414.2 | 413.5 | 5.25 | Method 5 | >10000 |
| 2-39 | | 429.2 | 429.2 | 6.43 | Method 5 | 1685 |
| 2-40 | | 474.4 | 474.4 | 3.28 | Method 1 | 2000 |
| 2-41 | | 458.3 | 457.5 | 38.15 | Method 3 | 58 |
| 2-42 | | 470.1 | 469.6 | 6.67 | Method 2 | 296 |

-continued
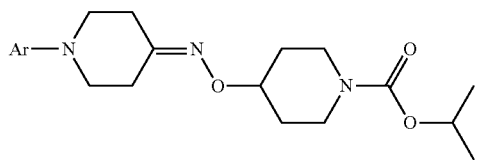
| No. | Ar | MH+ | MW | $t_R$ (Min) | HPLC Gradient | EC50 (nM) |
|---|---|---|---|---|---|---|
| 2-43 | (methylsulfonyl-dimethylamino-pyrimidinyl) | 483.2 | 482.6 | 5.94 | Method 2 | 799 |
| 2-44 | (dimethylamino-pyrimidinyl) | 405.2 | 404.5 | 4.76 | Method 2 | >10000 |
| 2-45 | (methylsulfinyl-dimethylamino-pyrimidinyl) | 467.1 | 466.6 | 4.32 | Method 2 | >10000 |
| 2-46 | (2-chloropyrimidin-4-yl) | 396.1 | 395.9 | 5.20 | Method 5 | 1876 |
| 2-47 | (4-chloropyrimidin-2-yl) | 396.3 | 395.9 | 6.24 | Method 4 | 2010 |
| 2-48 | (ethyl chloro-fluoro-pyridinyl ketoester) | 527.1 | 527.0 | 6.22 | Method 5 | 146 |
| 2-49 | (2,5-dichloropyrimidin-4-yl) | 430.0 | 430.3 | 6.11 | Method 5 | 170 |
| 2-50 | (4,5-dichloropyrimidin-2-yl) | 430.3 | 430.3 | 6.96 | Method 4 | >10000 |

-continued
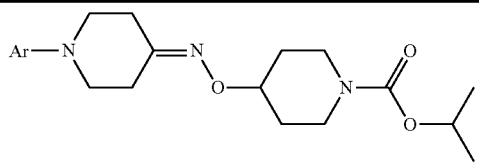
| No. | Ar | MH+ | MW | $t_R$ (Min) | HPLC Gradient | EC50 (nM) |
|---|---|---|---|---|---|---|
| 2-51 | 3-methyl-pyridin-4-yl | 374.9 | 374.5 | 5.10 | Method 5 | 951 |
| 2-52 | 6-chloro-5-methyl-pyrimidin-4-yl | 410.0 | 409.9 | 5.75 | Method 5 | 653 |
| 2-53 | 4-(hydroxymethyl)phenyl | 390.2 | 389.5 | 5.39 | Method 5 | >10000 |
| 2-54 | 5-bromo-4-dimethylamino-pyrimidin-2-yl | 482.9 | 483.4 | 7.04 | Method 5 | >10000 |
| 2-55 | 5-bromo-4-methylthio-pyrimidin-2-yl | 486.0 | 486.4 | 7.39 | Method 5 | >10000 |
| 2-56 | 5-bromo-4-methoxy-pyrimidin-2-yl | 470.0 | 470.4 | 6.70 | Method 5 | >10000 |
| 2-57 | 4-carbamoyl-2,3,5,6-tetrafluorophenyl | 475.1 | 474.4 | 5.22 | Method 5 | 56 |
| 2-58 | 5,6-difluoro-pyrimidin-4-yl | 398.1 | 397.4 | 5.89 | Method 5 | 603 |
| 2-59 | 2-chloro-5-carboxy-pyridin-3-yl | 439.1 | 438.9 | 2.86 | Method 5 | >10000 |

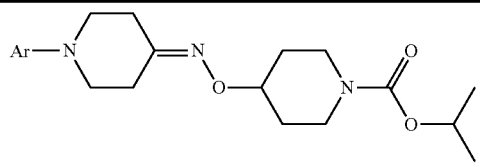
| No. | Ar | MH+ | MW | $t_R$ (Min) | HPLC Gradient | EC50 (nM) |
|---|---|---|---|---|---|---|
| 2-60 | | 474.2 | 473.5 | 5.76 | Method 5 | 28 |
| 2-61 | | 446.1 | 445.5 | 4.03 | Method 5 | >10000 |
| 2-62 | | 441.1 | 440.4 | 6.42 | Method 5 | 304 |
| 2-63 | | 567.1 | 566.6 | 6.01 | Method 5 | >10000 |
| 2-64 | | 409.4 | 408.5 | 4.83 | Method 4 | 79% |
| 2-65 | | 420.1 | 419.5 | 3.46 | Method 5 | >10000 |
| 2-66 | | 430.1 | 429.4 | 6.92 | Method 5 | >10000 |
| 2-67 | | 439.1 | 439.3 | 4.54 | Method 6 | 54% |

-continued
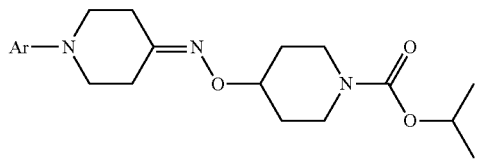
| No. | Ar | MH+ | MW | $t_R$ (Min) | HPLC Gradient | EC50 (nM) |
|---|---|---|---|---|---|---|
| 2-68 | 5-Cl, 3-F pyridin-2-yl | 413.1 | 412.9 | 9.27 | Method 2 | 63% |
| 2-69 | 3,5-diF pyridin-2-yl | 397.4 | 396.4 | 6.40 | Method 5 | 1021 |
| 2-70 | 3,6-diF pyridin-2-yl | 397.2 | 396.4 | 5.91 | Method 5 | 3257 |
| 2-71 | 5,6-diF pyridin-2-yl | 397.1 | 396.4 | 6.32 | Method 5 | 2588 |
| 2-72 | 3-F pyridin-4-yl | 378.9 | 378.4 | 5.08 | Method 5 | 750 |
| 2-73 | 2-Cl, 5-F pyrimidin-4-yl | 414.0 | 413.9 | 5.72 | Method 5 | 110 |
| 2-74 | 2-OH, 5-F pyridin-4-yl | 395.4 | 394.4 | 4.20 | Method 5 | >10000 |
| 2-75 | 3,5,6-triF pyridin-2-yl | 415.3 | 414.4 | 6.53 | Method 4 | 453 |

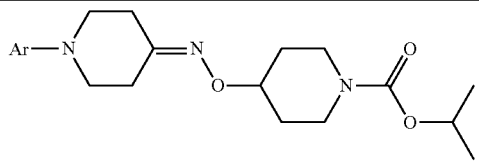

| No. | Ar | MH+ | MW | $t_R$ (Min) | HPLC Gradient | EC50 (nM) |
|---|---|---|---|---|---|---|
| 2-76 | 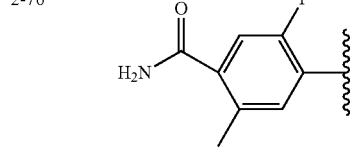 | 435.1 | 434.5 | 4.21 | Method 2 | 534 |
| 2-77 | 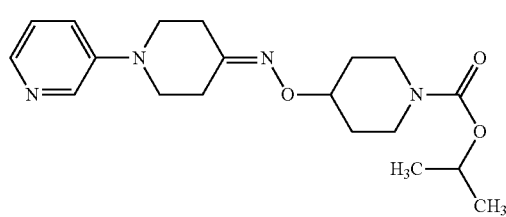 | 511.2 | 510.6 | 5.60 | Method 2 | 47 |

Example 3

4-(2,3,5,6-TETRAHYDRO-[1,3']BIPYRIDINYL-4-YLIDENEAMINOOXY)-PIPERIDINE-1-CARBOXYLIC ACID ISOPROPYL ESTER

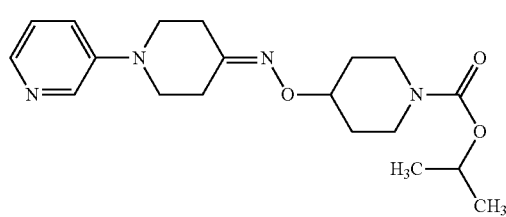

3-1

Step 3A: 4-(2,3,5,6-tetrahydro-[1,3']bipyridinyl-4-ylideneaminooxy)-piperidine-1-carboxylic acid isopropyl ester (3-1)

Compound 2d (44 mg, 0.16 mmol), 3-bromo-pyridine (0.18 mmol), potassium t-butoxide (26 mg, 0.23 mmol), and tri-t-butylphosphonium tetrafluoroborate (9 mg, 0.03 mmol) were combined in THF (0.3 mL) and nitrogen was bubbled through the mixture for 10 minutes. Tris(benzylideneacetone) dipalladium (7 mg, 0.008 mmol) was added and the mixture was heated at 50° C. for 3 days. The mixture was concentrated under a stream of nitrogen and the residue was taken up in methanol (1 mL) and purified by preparative HPLC to afford the trifluoroacetic acid salt of 3-1 as an oil: LC-MS 361.4 (MFE), $t_R$=4.75 (Method 5).

Example 4

ISOPROPYL 4-(2'-METHYL-2,3,5,6-TETRAHYDRO-[1,3]BIPYRIDINYL-4-YLIDENEAMINOOXY)PIPERIDINE-1-CARBOXYLATE

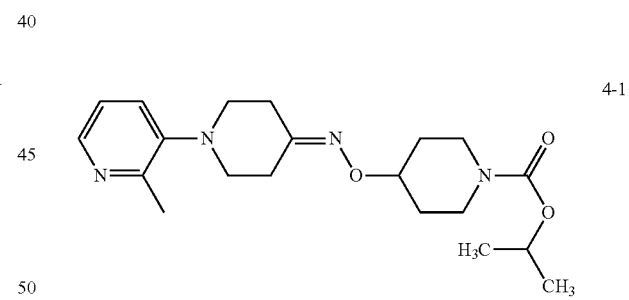

4-1

Step 4A: Isopropyl 4-(2'-Methyl-2,3,5,6-tetrahydro-[1,3']bipyridinyl-4-ylideneaminooxy)piperidine-1-carboxylate (4-1)

Compound 2d (30 mg, 0.11 mmol), 3-bromo-2-methyl-pyridine (0.16 mmol), cesium carbonate (72 mg, 0.22 mmol), PddppfCl$_2$ (10 mg), and triisobutylphosphatrane (15 µL) were combined in toluene (0.5 mL). The mixture was heated at 80° C. for 20 h. The mixture was concentrated under a stream of nitrogen and the residue was partitioned between DCM and water. The DCM layer was concentrated and taken up in methanol and purified by preparative HPLC to afford 4-1: LC-MS 375.4 (MH$^+$), $t_R$=7.88 (Method 6). EC50: 4804 nM.

Example 5

4-[1-(2,5-DIFLUORO-4-PYRROLIDIN-1-YLMETHYL-PHENYL)-PIPERIDIN-4-YLIDENE AMINOOXY]-PIPERIDINE-1-CARBOXYLIC ACID ISOPROPYL ESTER 5-1

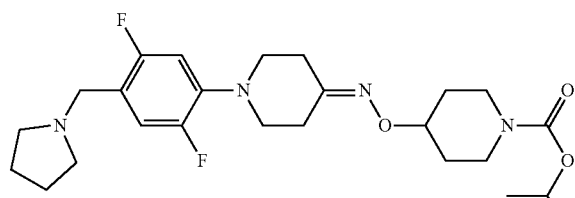

Step 5A: 4-[1-(2,5-Difluoro-4-pyrrolidin-1-ylmethyl-phenyl)-piperidin-4-ylidene aminooxy]-piperidine-1-carboxylic acid isopropyl ester (5-1)

Compound 2-3 (50 mg, 0.12 mmol), pyrrolidine (0.17 mmol), DCM (0.5 mL) and NaBH(OAc)$_3$ (30 mg, 0.14 mmol) were combined and stirred at room temperature for 20 h. The mixture was diluted with 2 mL of DCM, washed with aqueous NaHCO$_3$ (1 mL) and concentrated under a stream of nitrogen. The residue was taken up with methanol and purified by preparative HPLC to afford 5-1.

The following compounds were made according to this procedure using the corresponding amine and using either DCM or DCE as a solvent:

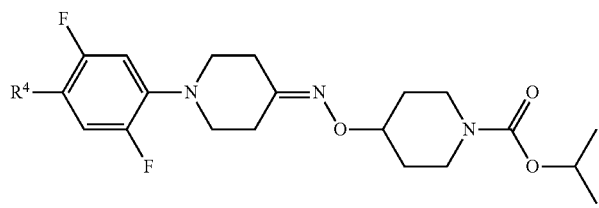

| No. | R$_4$ | MH+ | MW | t$_R$ (Min) | HPLC Gradient | EC50 (nM) |
|---|---|---|---|---|---|---|
| 5-1 | | 479.5 | 478.6 | 11.22 | Method 5 | 7833 |
| 5-2 | | 553.2 | 552.6 | 5.06 | Method 5 | 5885 |
| 5-3 | | 483.2 | 482.6 | 9.01 | Method 5 | >10000 |
| 5-4 | | 495.3 | 494.6 | 6.21 | Method 5 | 69% |
| 5-5 | | 497.4 | 496.6 | 6.49 | Method 5 | >10000 |

-continued

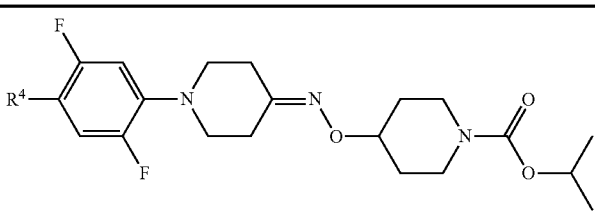

| No. | R₄ | MH+ | MW | $t_R$ (Min) | HPLC Gradient | EC50 (nM) |
|---|---|---|---|---|---|---|
| 5-6 | (methylaminomethyl) | 439.4 | 438.5 | 5.44 | Method 4 | 78% |
| 5-7 | (methyl 3-aminopropanoate-methyl) | 511.5 | 510.6 | 5.66 | Method 4 | 1146 |
| 5-8 | (dimethylaminomethyl) | 453.2 | 452.5 | 6.35 | Method 5 | >10000 |
| 5-9 | (2-fluoroethylaminomethyl) | 471.1 | 470.5 | 5.97 | Method 5 | 703 |
| 5-10 | (4-(N-methyl-N-carboxypropyl)aminomethyl) | 525.5 | 524.6 | 3.59 | Method 4 | >10000 |
| 5-11 | (thiazol-2-ylmethylaminomethyl) | 522.4 | 521.6 | 5.89 | Method 4 | 332 |

Example 6

4-{1-[2,5-DIFLUORO-4-(2-OXO-PYRROLIDIN-1-YLMETHYL)-PHENYL]-PIPERIDIN-4-YLIDE-NEAMINOOXY}-PIPERIDINE-1-CARBOXYLIC ACID ISOPROPYL ESTER 6-1

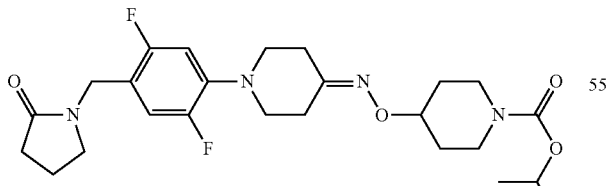

Step 6A: 4-{1-[2,5-Difluoro-4-(2-oxo-pyrrolidin-1-ylmethyl)-phenyl]-piperidin-4-ylideneaminooxy}-piperidine-1-carboxylic acid isopropyl ester (6-1)

Compound 2-3 (30 mg), 4-amino-butyric acid methyl ester (11 mg), DCE (2 mL) and NaBH(OAc)₃ (22 mg) were combined and stirred at room temperature for 48 h. The mixture was diluted with 2 mL of DCM, washed with aqueous NaHCO₃ (1 mL) and concentrated under a stream of nitrogen. The residue was taken up with methanol and purified by preparative HPLC to afford 6-1: LC-MS 493.5 (MH⁺), $t_R$=5.54 (Method 4). EC50: 40 nM.

Example 7

4-(1-{4-[(2-CARBOXY-ETHYLAMINO)-METHYL]-2,5-DIFLUORO-PHENYL}-PIPERIDIN-4-YLIDENEAMINOOXY)-PIPERIDINE-1-CARBOXYLIC ACID ISOPROPYL ESTER 7-1

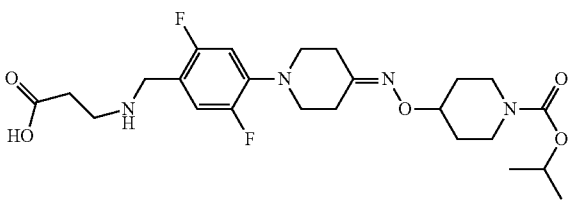

Step 7A: 4-(1-{4-[(2-Carboxy-ethylamino)-methyl]-2,5-difluoro-phenyl}-piperidin-4-ylideneaminooxy)-piperidine-1-carboxylic acid isopropyl ester (7-1)

Compound 5-7 (15 mg) was stirred in a mixture of 1 mL of MeOH and 1 mL of NaOH 1N for 1.5 h. 2 mL of NaOH 1N was added and the mixture was stirred at room temperature for 2 h. The mixture was evaporated; HCl 1N was added until PH 1 and the product was extracted with DCM. Purification on preparative HPLC afforded 7-1: LC-MS 497.5 (MH$^+$), t$_R$=5.32 (Method 2). EC50: 1153 nM.

Example 8-1

4-{1-[4-((R)-1-AMINO-ETHYL)-2,5-DIFLUORO-PHENYL]-PIPERIDIN-4-YLIDENEAMINOOXY}-PIPERIDINE-1-CARBOXYLIC ACID ISOPROPYL ESTER

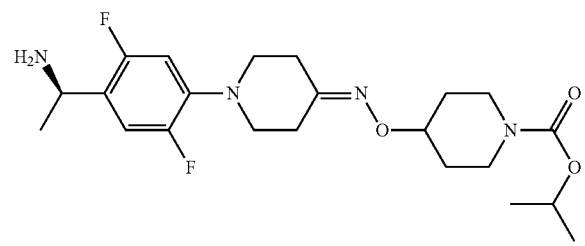

8-1

Step 8A: 4-(1-{2,5-Difluoro-4-[(R)-1-(2-methyl-propane-2-sulfinylamino)-ethyl]-phenyl}-piperidin-4-ylideneaminooxy)-piperidine-1-carboxylic acid isopropyl ester (8a)

Compound 2-3 (500 mg, 1.18 mmol) and (R)-(+) tert-butane sulfonamide (150 mg, 1.24 mmol) were dissolved in 8 mL THF. Ti(OEt)$_4$ (1.04 mL, 1.6 mmol) was added and the mixture stirred at room temperature for 8 hours. The mixture was diluted with DCM (10 mL), quenched with water (5 mL) and filtered through a pad of celite. The organic layer was collected, dried over MgSO$_4$, filtered, concentrated and purified by flash LC (elution with 35% EtOAc in hexanes) to afford 500 mg (81%) of the imine which was dissolved in anhydrous THF (2.7 mL). Me$_3$Al (0.95 mL, 1.9 mmol) was added and the mixture was cooled to −60° C. MeLi (1.49 mL, 2.38 mmol) was added dropwise maintaining the temperature at −60° C. for 30 minutes after completion of addition, then warming the mixture to 0° C. and quenching the reaction with saturated Rochelle salt solution (2.5 mL). The mixture was filtered through a pad of celite and diluted with ether (10 mL). The organic layer was collected, dried over Na$_2$SO$_4$, filtered, and concentrated. Purification by flash LC (elution with 50% EtOAc in hexanes) afforded 135 mg (24%) of 8a: LC-MS 453.2 (MH$^+$).

Step 8B: 4-{1-[4-((R)-1-Amino-ethyl)-2,5-difluoro-phenyl]-piperidin-4-ylideneaminooxy}-piperidine-1-carboxylic acid isopropyl ester (8-1)

The R,R-sulfonylamide (1.78 g, 3.28 mmol) was dissolved in MeOH (14.6 mL) and 4N HCl (0.94 mL, 3.8 mmol) was added dropwise and stirred at room temperature for 1 hour. The reaction was then quenched with 2N NaOH till basic then concentrated and extracted with ether (3×20 mL). The organic layer was dried over Na$_2$SO$_4$, filtered, concentrated and purified by flash LC (elution with 0% to 20% MeOH in DCM) to afford 1.31 g (91%) of 4-{1-[4-((R)-1-amino-ethyl)-2,5-difluoro-phenyl]-piperidin-4-ylideneaminooxy}-piperidine-1-carboxylic acid isopropyl ester 8-1: LC-MS 439.2 (MH$^+$), t$_R$=4.39 (Method 2). EC50: 538 nM.

Example 9

4-[1-(4-CARBOXY-2,5-DIFLUORO-PHENYL)-PIPERIDIN-4-YLIDENEAMINOOXY]-PIPERIDINE-1-CARBOXYLIC ACID ISOPROPYL ESTER 9-1

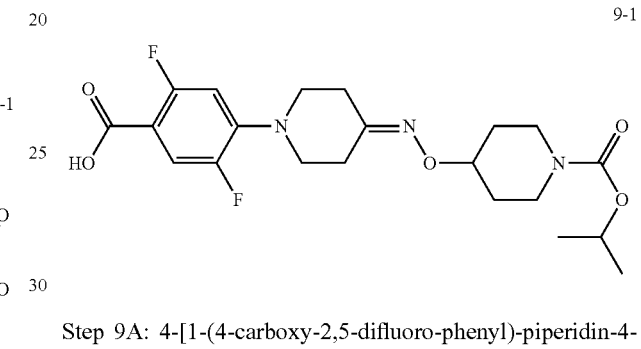

Step 9A: 4-[1-(4-carboxy-2,5-difluoro-phenyl)-piperidin-4-ylideneaminooxy]-piperidine-1-carboxylic acid isopropyl ester (9-1)

To a mixture of 2-3 (0.35 g, 0.83 mmol), NaH$_2$PO$_4$ (26 mg, 0.17 mmol), and 35% H$_2$O$_2$ (0.1 mL, 1.2 mmol) in 4 mL of acetonitrile, was added NaOCl (131 mg, 1.2 mmol) in 2 mL of acetonitrile. The mixture was stirred at room temperature for 20 h, acidified with HCl 1N (15 mL) and extracted with ethyl acetate (3×10 mL). The combined extracts were washed with brine (20 mL), dried over magnesium sulfate and concentrated under vacuum to afford 9-1 as a brown oil: LC-MS 440.0 (MH$^+$), t$_R$=3.01 (Method 5).

Example 10

4-[1-(2,5-DIFLUORO-4-HYDROXYMETHYL-PHENYL)-PIPERIDIN-4-YLIDENEAMINOOXY]-PIPERIDINE-1-CARBOXYLIC ACID ISOPROPYL ESTER 10-1

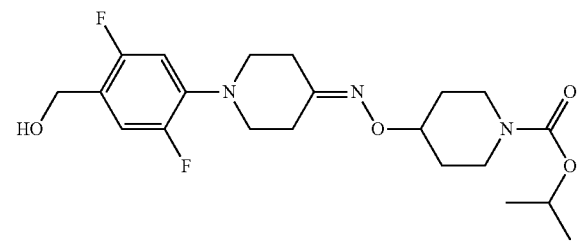

Step 10A: 4-[1-(2,5-Difluoro-4-hydroxymethyl-phenyl)-piperidin-4-ylideneaminooxy]-piperidine-1-carboxylic acid isopropyl ester (10-1)

Sodium borohydride (0.57 g, 15 mmol) was added to compound 2-3 (3.2 g, 7.56 mmol) in 35 mL of methanol at 0° C. and stirring was continued for 2 h. The mixture was quenched with aqueous NaHCO$_3$ (50 mL) and extracted with DCM (3×50 mL). The combined extracts were dried over magnesium sulfate and concentrated. The residue was purified by flash LC(30% EtOAc/hexane) to afford 10-1: LC-MS 408.2 (MH$^+$-18), $t_R$=5.71 (Method 2). EC50: 9 nM.

Example 11

4-[1-(4-acetoxymethyl-2,5-difluoro-phenyl)-piperidin-4-ylideneaminooxy]-piperidine-1-carboxylic acid isopropyl ester 11-1

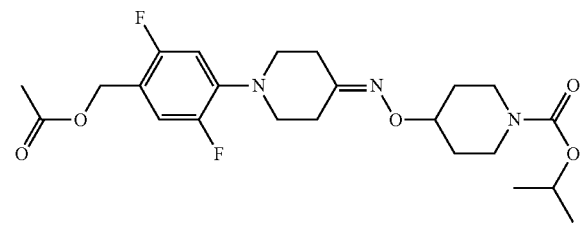

Step 11A: 4-[1-(4-Acetoxymethyl-2,5-difluoro-phenyl)-piperidin-4-ylideneaminooxy]-piperidine-1-carboxylic acid isopropyl (11-1)

Compound 10-1 (37 mg, 0.097 mmol), acetic anhydride (25 μL), triethylamine (24 μL, 0.17 mmol) and DCM (0.5 mL) were combined and stirred at room temperature for 20 h. The mixture was concentrated under a stream of nitrogen, taken up with methanol and purified on preparative HPLC to give 11-1: LC-MS 408.1 (MH$^+$-OAc), $t_R$=6.72 (Method 4). EC50: 67 nM.

Example 12

4-{1-[4-(2-tert-butoxycarbonylamino-acetoxymethyl)-2,5-difluoro-phenyl]-piperidin-4-ylideneaminooxy}-piperidine-1-carboxylic acid isopropyl ester 12-1

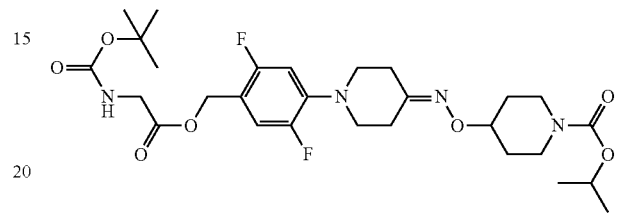

Step 12A: 4-{1-[4-(2-tert-Butoxycarbonylamino-acetoxymethyl)-2,5-difluoro-phenyl]-piperidin-4-ylideneaminooxy}-piperidine-1-carboxylic acid isopropyl ester (12-1)

Compound 10-1 (40 mg, 0.094 mmol), tert-butoxycarbonylamino-acetic acid (17 mg, 0.097 mmol), DMAP (3 mg, 0.024 mmol), EDC(22 mg, 0.11 mmol) and DCM (1 mL) were combined in that order and the reaction mixture was stirred for 20 h. The mixture was then washed with aqueous NaHCO$_3$ (1 mL), concentrated under a stream of nitrogen and purified by Jones flash LC(eluent: 10-40% ethyl acetate+ 0.1% triethylamine in hexanes) to afford 12-1: LC-MS 408.2 (benzylium fragment).

The following compounds were made according to this procedure using the corresponding carboxylic acid:

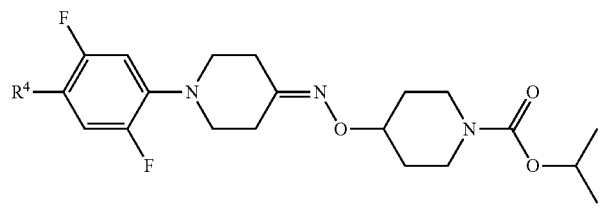

| No. | R$^4$ | M (benzylium fragment) | MW | $t_R$ (Min) | HPLC Gradient |
|---|---|---|---|---|---|
| 12-1 | | 408.2 | 582.6 | 3.07 | Method 1 |

Example 13

4-[1-(2,5-difluoro-4-Methanesulfonylmethyl-phenyl)-piperidin-4-ylidene aminooxy]-piperidine-1-carboxylic acid isopropyl ester

Example 14

4-{1-[2,5-Difluoro-4-(PYRAZOL-1-YLmethyl)-phenyl]-piperidin-4-ylidene aminooxy}-piperidine-1-carboxylic acid isopropyl ester

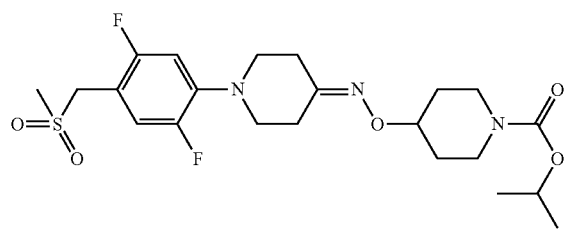

13-1

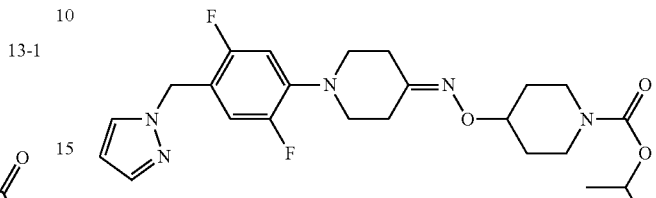

14-1

Step 13A: 4-[1-(2,5-Difluoro-4-methanesulfonylmethyl-phenyl)-piperidin-4-ylidene aminooxy]-piperidine-1-carboxylic acid isopropyl ester (13-1)

Methanesulfonyl anhydride (0.14 mL) was added to compound 10-1 (334 mg, 0.78 mmol) and triethylamine (0.22 mL, 1.6 mmol) in 9.5 mL of DCM at 0° C. The mixture was stirred at room temperature for 2 h and divided into 9 equal portions. One portion was treated with NaSO$_2$Me (2 mmol) and stirred at room temperature for 20 h. 0.5 mL of THF was added and the mixture was heated to 50° C. with the lid off to evaporate the DCM, the vial was then sealed and heated to 50° C. for 18 h. The mixture was concentrated, taken up with methanol and purified on preparative HPLC to give 13-1: LC-MS 488.4 (MH$^+$).

The following compounds were made according to this procedure using the corresponding nucleophile:

Step 14A: 4-{1[2,5-Difluoro-4-(pyrazol-1-ylmethyl)-phenyl]-piperidin-4-ylidene aminooxy}-piperidine-1-carboxylic acid isopropyl ester (14-1)

Methane sulfonyl chloride (30 µL) was added to a mixture of 0.11 g of compound 10-1 and 0.1 mL of triethylamine in 2 mL of DCM. The mixture was stirred at room temperature for 3 h then quenched with water and extracted with DCM twice. The combined DCM fractions were dried over magnesium sulfate and evaporated. The residue was divided in two equal portions and one portion was combined with pyrazole (18 mg), triethylamine (0.1 mL) and 1 mL of DMF in a sealed vial. The vial was heated to 120° C. for 20 minutes in a microwave then water was added and the residue was extracted with ethyl acetate. The solvent was evaporated and the residue was taken up with methanol and purified on preparative HPLC to give 14-1: LC-MS 476.2 (MH$^+$).

The following compounds were made according to this procedure using the corresponding nucleophile:

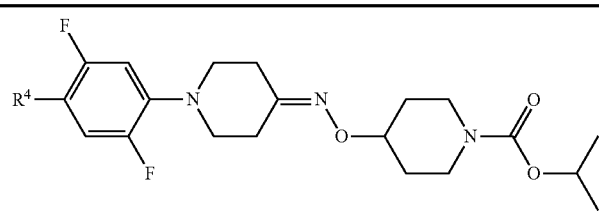

| No. | R$^4$ | MH+ | MW | t$_R$ (Min) | HPLC Gradient | EC50 (nM) |
|---|---|---|---|---|---|---|
| 13-1 | (methanesulfonylmethyl) | 488.4 | 487.6 | 5.52 | Method 4 | 30 |
| 13-2 | (HOOC-CH$_2$-S-CH$_2$-) | 500.4 | 499.6 | 3.53 | Method 4 | 2415 |

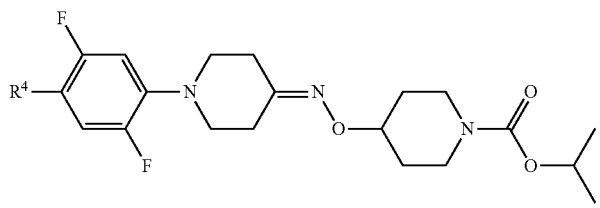
| No. | R⁴ | MH+ | MW | t_R (Min) | HPLC Gradient | EC50 (nM) |
|---|---|---|---|---|---|---|
| 14-1 | pyrazol-1-ylmethyl | 476.2 | 475.5 | 6.01 | Method 5 | 38 |
| 14-2 | methylsulfonylmethyl | 488.1 | 487.5 | 7.35 | Method 2 | 30 |
| 14-3 | cyclopropylsulfonylmethyl | 514.4 | 513.6 | 5.77 | Method 4 | 19 |
| 14-4 | imidazol-1-ylmethyl | 476.4 | 475.5 | 5.43 | Method 4 | 268 |
| 14-5 | imidazo[4,5-b]pyridin-1-ylmethyl | 527.1 | 526.6 | 4.85 | Method 5 | 374 |
| 14-6 | imidazo[4,5-b]pyridin-3-ylmethyl | 527.2 | 526.6 | 5.20 | Method 5 | 647 |
| 14-7 | imidazo[4,5-b]pyridin-7-ylmethyl | 527.2 | 526.6 | 5.66 | Method 5 | 713 |
| 14-8 | imidazo[4,5-c]pyridin-1-ylmethyl | 527.4 | 526.6 | 5.13 | Method 4 | 763 |

-continued
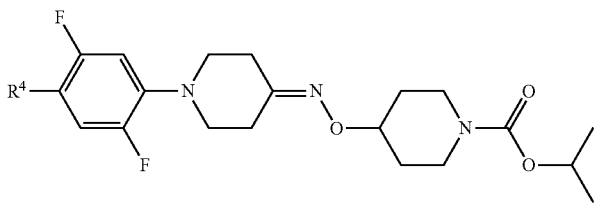
| No. | R⁴ | MH+ | MW | t_R (Min) | HPLC Gradient | EC50 (nM) |
|---|---|---|---|---|---|---|
| 14-9 | 3-methylpyrazol-1-ylmethyl | 490.2 | 489.6 | 6.19 | Method 5 | 257 |
| 14-10 | 4-methylpyrazol-1-ylmethyl | 490.2 | 489.6 | 6.25 | Method 5 | 8 |
| 14-11 | 4-ethoxycarbonylpyrazol-1-ylmethyl | 548.2 | 547.6 | 6.37 | Method 5 | 190 |
| 14-12 | 1,2,3-triazol-1-ylmethyl | 477.2 | 476.5 | 5.41 | Method 5 | 32 |
| 14-13 | 1,2,3-triazol-2-ylmethyl | 477.2 | 476.5 | 6.08 | Method 5 | 16 |
| 14-14 | pyrrol-1-ylmethyl | 475.3 | 474.5 | 6.66 | Method 5 | 467 |
| 14-15 | 5-methyltetrazol-1-ylmethyl | 492.4 | 491.5 | 6.02 | Method 4 | 39 |
| 14-16 | 5-methyltetrazol-2-ylmethyl | 492.4 | 491.5 | 5.48 | Method 4 | 256 |
| 14-17 | 1,2,4-triazol-1-ylmethyl | 477.4 | 476.5 | 5.26 | Method 4 | 28 |

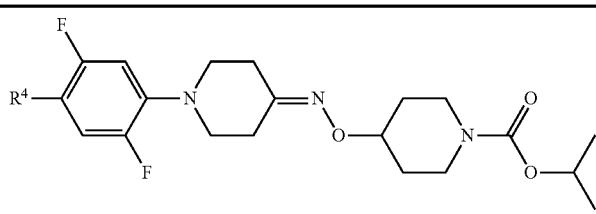

| No. | R⁴ | MH+ | MW | $t_R$ (Min) | HPLC Gradient | EC50 (nM) |
|---|---|---|---|---|---|---|
| 14-18 | (triazolylmethyl) | 477.4 | 476.5 | 4.85 | Method 4 | 1349 |

Example 15
4-{1-[2,5-DIFLUORO-4-(2-OXO-OXAZOLIDIN-3-YLMETHYL)-PHENYL]-PIPERIDIN-4-YLIDE-NEAMINOOXY}-PIPERIDINE-1-CARBOXYLIC ACID ISOPROPYL ESTER 15-1

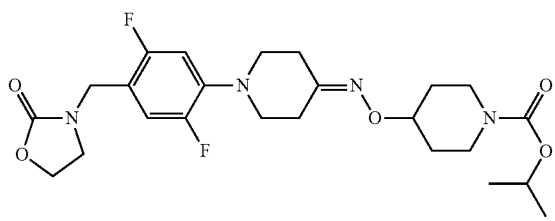

Step 15A: 4-{1-[2,5-Difluoro-4-(2-oxo-oxazolidin-3-ylmethyl)-phenyl]-piperidin-4-ylideneaminooxy}-piperidine-1-carboxylic acid isopropyl (15-1)

Methane sulfonyl chloride (30 µL) was added to a mixture of 0.11 g of compound 10-1 and 0.1 mL of triethylamine in 2 mL of DCM. The mixture was stirred at room temperature for 3 h then quenched with water and extracted with DCM twice. The combined DCM fractions were dried over magnesium sulfate and evaporated. The residue was divided in two equal portions.

In parallel, a solution of oxazolidone (10 mg) in 0.5 mL of DMF was added to a suspension of sodium hydride (20 mg) in 1 mL of DMF at room temperature. The mixture was stirred at room temperature for 3 h. The portion of mesylate made in parallel was added in 1 mL of DMF and the mixture was stirred at room temperature for 1 h. Water was added and the product was extracted with ethyl acetate. The solvent was evaporated and the residue was taken up with methanol and purified on preparative HPLC to give 15-1: LC-MS 495.5 (MH⁺).

The following compounds were made according to this procedure using the corresponding nucleophile in excess (2, 5 or 20 equivalents):

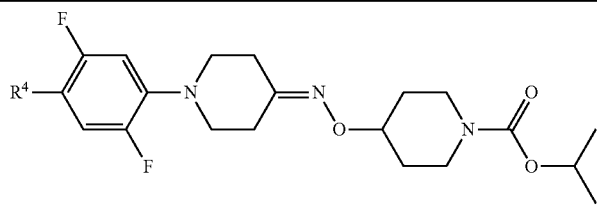

| No. | R⁴ | MH+ | MW | $t_R$ (Min) | HPLC Gradient | EC50 (nM) |
|---|---|---|---|---|---|---|
| 15-1 | 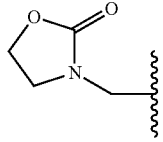 | 495.5 | 494.5 | 5.54 | Method 4 | 140 |
| 15-2 | 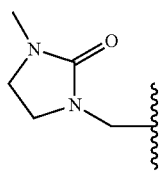 | 508.2 | 507.6 | 5.58 | Method 5 | 282 |

-continued

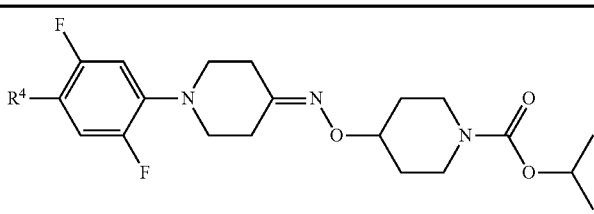

| No. | R⁴ | MH+ | MW | $t_R$ (Min) | HPLC Gradient | EC50 (nM) |
|---|---|---|---|---|---|---|
| 15-3 | *tert*-butyl 3-oxopiperazine-1-carboxylate-N-CH₂- | 608.3 | 607.7 | 6.25 | Method 5 | 408 |
| 15-4 | 2-oxopyrrolidin-1-yl-CH₂- | 493.4 | 492.6 | 5.54 | Method 4 | 40 |
| 15-5 | 2-oxoimidazolidin-1-yl-CH₂- | 494.4 | 493.5 | 5.22 | Method 4 | — |

Example 16

4-(1-{4-[(3-ETHYL-UREIDO)-METHYL]-2,5-DIFLUORO-PHENYL}-PIPERIDIN-4-YLIDENEAMINOOXY)-PIPERIDINE-1-CARBOXYLIC ACID ISOPROPYL ESTER 16-1

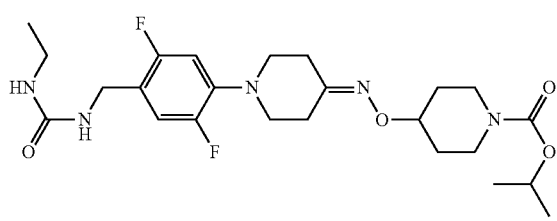

Step 16A: 4-[1-(4-Aminomethyl-2,5-difluoro-phenyl)-piperidin-4-ylideneaminooxy]-piperidine-1-carboxylic acid isopropyl ester (16a)

A mixture of 10-1 (30 mg, 0.07 mmol), triphenylphosphine (19 mg), phthalimide (11 mg) and DEAD (12 µL) in THF (1 mL) was stirred at room temperature for 3 days. The mixture was concentrated under a stream of nitrogen and combined with DCM (0.2 mL), ethanol (0.5 mL) and hydrazine (50 µL). The mixture was stirred at room temperature for 20 h, filtered and concentrated under a stream of nitrogen. The crude mixture was taken up with methanol and purified by preparative HPLC to afford 16a as a brown oil: LC-MS 408.2 (MH⁺-17).

Alternative Synthesis:

To a mixture of 2-2 (0.92 g) and nickel chloride (0.28 g, 1 eq) in 30 mL of ethanol, at 0° C., was added sodium borohydride (0.25 g, 3 eq) in portions. The mixture was stirred at room temperature for 30 minutes, then filtered on celite with ethyl acetate and ethanol and the organic layer was evaporated. Ethyl acetate was added and the product was extracted in HCl 0.1N twice. The combined aqueous layers were washed with ethyl acetate then neutralized with ammonium hydroxide until basic pH and the product was extracted with ethyl acetate to give 0.56 g of 16a.

Step 16B: 4-(1-{4-[(3-Ethyl-ureido)-methyl]-2,5-difluoro-phenyl}-piperidin-4-ylideneaminooxy)-piperidine-1-carboxylic acid isopropyl ester (16-1)

To a solution of 16a (23 mg) and triethylamine (0.1 mL) in 1 mL of DCM was added a drop of ethyl isocyanate (excess) and the reaction mixture was stirred for 30 minutes at room temperature. The mixture was then quenched with water and extracted with DCM to give 33 mg of crude product which was purified on preparative HPLC to give 16-1: LC-MS 496.2 (MH⁺).

The following compounds were made according to this procedure using the corresponding electrophile:

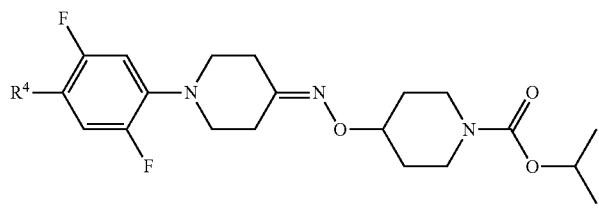
| No. | R⁴ | MH+ | MW | t_R (Min) | HPLC Gradient | EC50 (nM) |
|---|---|---|---|---|---|---|
| 16-1 | | 496.2 | 495.6 | 5.25 | Method 5 | 168 |
| 16-2 | | 467.5 | 466.5 | 5.03 | Method 4 | 141 |
| 16-3 | | 503.4 | 502.6 | 5.38 | Method 4 | 51 |
| 16-4 | | 497.4 | 496.5 | 5.91 | Method 4 | 70 |
| 16-5 | | 531.0 | 530.6 | 5.87 | Method 5 | 142 |
| 16-6 | | 517.1 | 516.6 | 5.63 | Method 5 | 113 |
| 16-7 | | 511.2 | 510.6 | 6.32 | Method 5 | 134 |
| 16-8 | | 453.3 | 452.5 | 5.13 | Method 4 | 120 |
| 16-9 | | 554.4 | 553.6 | 5.44 | Method 2 | 401 |

Example 17

4-[1-(2,5-DIFLUORO-4-SULFONYLUREIDOM-ETHYL-PHENYL)-PIPERIDIN-4-YLIDENEAMI-NOOXY]-PIPERIDINE-1-CARBOXYLIC ACID ISOPROPYL ESTER 17-1

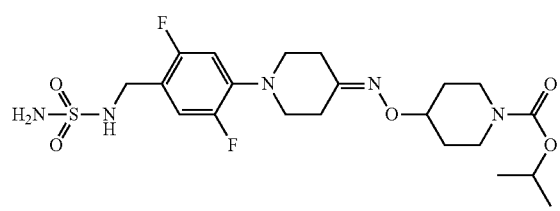

Step 17A: 4-[1-(2,5-Difluoro-4-sulfonylureidomethyl-phenyl)-piperidin-4-ylideneaminooxy]-piperidine-1-carboxylic acid isopropyl ester (17-1)

25 mg of 16a and sulfamide (7 mg, 1.2 eq) were combined in 0.5 mL of water and 0.5 mL of methanol in a sealed vial. The mixture was stirred at 100° C. overnight then the mixture was evaporated, extracted with ethyl acetate and purified on preparative HPLC to give 17-1: LC-MS 504.2 (MH$^+$-17), $t_R$=5.06 (Method 5). EC50: 312 nM.

Example 18

4-(1-{4-[(ACETYL-METHYL-AMINO)-ME-THYL]-2,5-DIFLUORO-PHENYL}-PIPERIDIN-4-YLIDENEAMINOOXY)-PIPERIDINE-1-CAR-BOXYLIC ACID ISOPROPYL ESTER 18-1

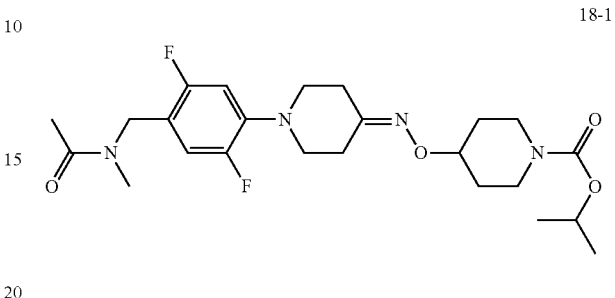

Step 18A: 4-(1-{4-[(Acetyl-methyl-amino)-methyl]-2,5-difluoro-phenyl}-piperidin-4-ylidene aminooxy)-piperidine-1-carboxylic acid isopropyl ester (18-1)

To a suspension of 60% NaH (20 mg) in 0.3 mL of DMF, was added 16-2 (20 mg) in 0.3 mL of DMF. The mixture was stirred at room temperature for 10 minutes then Me$_2$SO$_4$ (30 µL) was added and the mix was stirred at room temperature for 1 h. A saturated solution of NaHCO$_3$ was added and the product was extracted with ethyl acetate. The crude material was purified on preparative HPLC to give 18-1: LC-MS 481.4 (MH$^+$).

The following compounds were made according to this procedure.

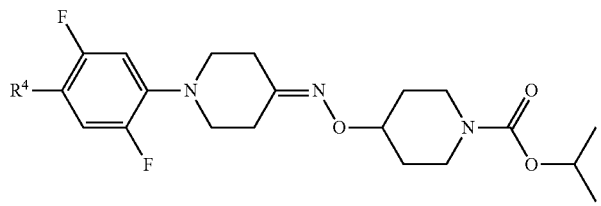

| No. | R$^4$ | MH+ | MW | $t_R$ (Min) | HPLC Gradient | EC50 (nM) |
|---|---|---|---|---|---|---|
| 18-1 | | 481.4 | 480.55 | 5.51 | Method 4 | 127 |
| 18-2 | | 517.2 | 516.6 | 5.82 | Method 5 | 150 |
| 18-3 | | 511.2 | 510.68 | 6.58 | Method 5 | 304 |

Example 19

4-{1-[4-(4,5-DIHYDRO-1H-IMIDAZOL-2-yl)-2,5-DIFLUORO-PHENYL]-PIPERIDIN-4-YLIDENE-AMINOOXY}-PIPERIDINE-1-CARBOXYLIC ACID ISOPROPYL ESTER

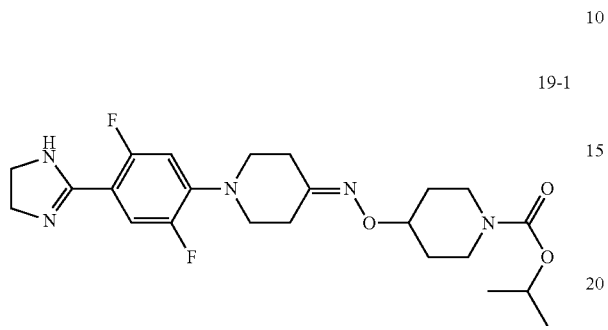

19-1

Step 19A: 4-{1-[4-(4,5-Dihydro-1H-imidazol-2-yl)-2,5-difluoro-phenyl]-piperidin-4-ylideneaminooxy}-piperidine-1-carboxylic acid isopropyl ester (19-1)

20 mg of 2-3 and ethane-1,2-diamine (3 μL, 1 eq) were combined in 1 mL of DCM. At 0° C., NBS(9 mg, 1 eq) was added and the mixture was stirred at room temperature overnight. Aqueous $Na_2S_2O_3$ was added followed by aqueous $NaHCO_3$ and the product was extracted with DCM. The crude material was then purified on preparative HPLC to afford 19-1: LC-MS 464.2 (MH), $t_R$=5.53 (Method 5). 53% stimulation at 10 μM.

Example 20

4-[1-(2,5-DIFLUORO-4-OXAZOL-5-yl-PHENYL)-PIPERIDIN-4-YLIDENEAMINOOXY]-PIPERIDINE-1-CARBOXYLIC ACID ISOPROPYL ESTER

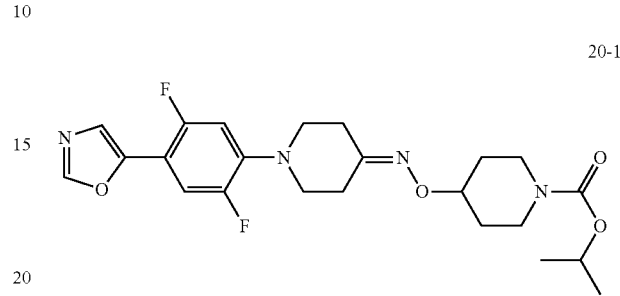

20-1

Step 20A: 4-[1-(2,5-Difluoro-4-oxazol-5-yl-phenyl)-piperidin-4-ylideneaminooxy]-piperidine-1-carboxylic acid isopropyl ester (20-1)

To a mixture of TosMIC(8 mg, 0.9 eq) and $K_2CO_3$ (20 mg, 3 eq) in 1 mL of methanol, at room temperature, was slowly added 2-3 (20 mg, 1 eq) in 1 mL of THF. The reaction mixture was heated at 60° C. for 3 hours then it was cooled to room temperature and water was added. The product was extracted with ethyl acetate and purified on preparative HPLC to give 20-1: LC-MS 463.4 (MH).

The following compounds were made according to this procedure using the corresponding starting material aldehyde:

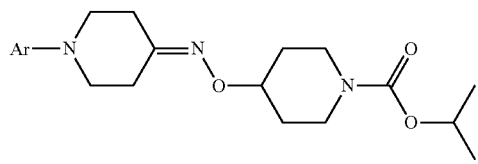

| No. | Ar | MH+ | MW | $t_R$ (Min) | HPLC Gradient | EC50 (nM) |
|---|---|---|---|---|---|---|
| 20-1 | 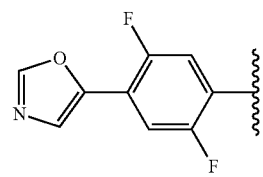 | 463.4 | 462.5 | 6.22 | Method 4 | 100 |
| 20-2 | 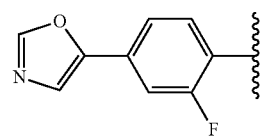 | 445.2 | 444.5 | 5.99 | Method 5 | 498 |

Example 21

4-{1-[2,5-DIFLUORO-4-(1-OXO-1LAMBDA*4*-[1,3]DITHIAN-2-yl)-PHENYL]-PIPERIDIN-4-YLIDENEAMINOOXY}-PIPERIDINE-1-CARBOXYLIC ACID ISOPROPYL ESTER

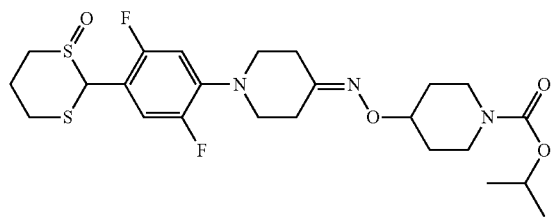

21-1

Step 21A: 4-[1-(4-[1,3]-Dithian-2-yl-2,5-difluoro-phenyl)-piperidin-4-ylideneaminooxy]-piperidine-1-carboxylic acid isopropyl ester (21a)

2-3 (20 mg) and propane-1,3-dithiol (5 μL, 1 eq) were combined in 1 mL of DCM. 1 mg of iodine was added and the reaction mixture was stirred at room temperature overnight. Aqueous $Na_2S_2O_3$ was added and the product was extracted with DCM. Concentration and purification on preparative HPLC gave 21a: LC-MS 514.4 (MH).

**Step 21B: 4-{1-[2,5-Difluoro-4-(1-oxo-1 lambda*4*-[1,3]dithian-2-yl)-phenyl]-piperidin-4-ylideneaminooxy}-piperidine-1-carboxylic acid isopropyl ester (21-1)**

21a (55 mg) was dissolved in 0.5 mL of DCM and cooled to −78° C. mCPBA (24 mg, 1 eq) in 1 mL of DCM was added and the mixture was stirred at room temperature for 2 days. The solution was washed with aqueous $Na_2CO_3$ twice then with water and the crude material obtained was purified on preparative HPLC to give 21-1 as a 15:85 mixture of diastereoisomers: LC-MS 530.2 (MH), $t_R$=5.58 (Method 5). EC50: 143 nM.

Example 22

4-[1-(2,5-DIFLUORO-4-IMIDAZOL-1-yl-PHENYL-PIPERIDIN-4-YLIDENEAMINOOXY]-PIPERIDINE-1-CARBOXYLIC ACID ISOPROPYL ESTER

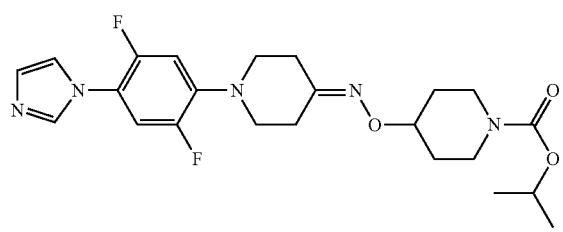

22-1

Step 22A: 4-[1-(2,5-Difluoro-4-imidazol-1-yl-phenyl)-piperidin-4-ylideneaminooxy]-piperidine-1-carboxylic acid isopropyl ester (22-1)

50 mg of 2-40, imidazole (16 mg, 2 eq), CuBr (2 mg, 0.1 eq), 2-oxo-cyclohexanecarboxylic acid ethyl ester (4 mg, 0.2 eq), cesium carbonate (72 mg, 2.1 eq) and DMSO (0.4 mL) were combined in a sealed vial and heated at 120° C. overnight. Water was added and the product was extracted with ethyl acetate. The crude residue was purified on preparative HPLC to give 22-1: LC-MS 462.1 (MH).

The following compounds were made according to this procedure using the corresponding nucleophile:

| No. | R4 | MH+ | MW | $t_R$ (Min) | HPLC Gradient | EC50 (nM) |
|---|---|---|---|---|---|---|
| 22-1 | imidazol-1-yl | 462.1 | 461.5 | 5.51 | Method 5 | 435 |
| 22-2 | pyrrol-1-yl | 461.3 | 460.5 | 7.08 | Method 5 | 767 |
| 22-3 | pyrazol-1-yl | 462.2 | 461.5 | 6.46 | Method 5 | 62 |
| 22-4 | 1,2,4-triazol-1-yl | 463.3 | 462.5 | 5.64 | Method 4 | 33 |
| 22-5 | 1,2,3-triazol-1-yl | 463.3 | 462.5 | 5.70 | Method 4 | — |
| 22-6 | 1,2,3-triazol-2-yl | 463.3 | 462.5 | 5.30 | Method 4 | — |
| 22-7 | 2-oxopyrrolidin-1-yl | 479.2 | 478.5 | 5.51 | Method 5 | 157 |

Example 23

4-[1-(4-CARBAMIMIDOYL-2,5-DIFLUORO-PHENYL)-PIPERIDIN-4-YLIDENEAMINOOXY]-PIPERIDINE-1-CARBOXYLIC ACID ISOPROPYL ESTER

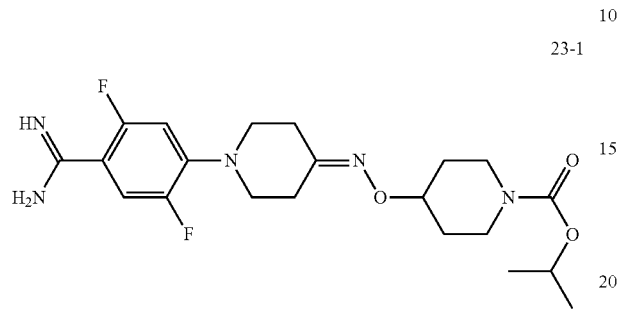

23-1

Step 23A: 4-[1-(4-Carbamimidoyl-2,5-difluoro-phenyl)-piperidin-4-ylideneaminooxy]-piperidine-1-carboxylic acid isopropyl ester (23-1)

To a solution of 2-2 (80 mg) in 2 mL of THF, was added LiHMDS(0.76 mL of a 1M solution, 4 eq). The mix was stirred at room temperature for 1 hour then evaporated and purified on preparative HPLC to afford 23-1: LC-MS 438.3 (MH), $t_R$=5.38 (Method 5). 3% stimulation at 10 μM.

Example 24

4-[1-(3-AMINO-4,7-DIFLUORO-1H—INDAZOL-6-yl)-PIPERIDIN-4-YLIDENEAMINOOXY]-PIPERIDINE-1-CARBOXYLIC ACID ISOPROPYL ESTER

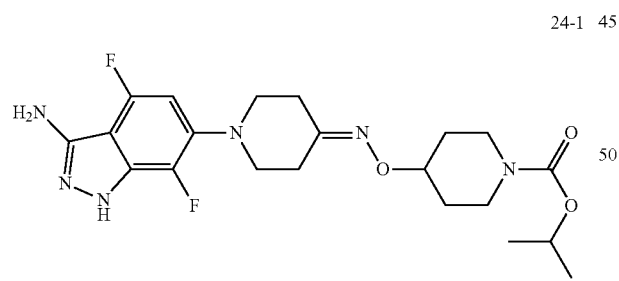

24-1

Step 24A: 4-[1-(3-Amino-4,7-difluoro-1H-indazol-6-yl)-piperidin-4-ylideneaminooxy]-piperidine-1-carboxylic acid isopropyl ester (24-1)

A mixture of 2-2 (50 mg) and hydrazine hydrate (60 μL, 10 eq) in 1 mL of nBuOH was heated at 110° C. in a sealed vial for 2 days. The solvent was evaporated, water was added and the product was extracted with ethyl acetate. The crude material was then purified on preparative HPLC to afford 24-1: LC-MS 433.4 (MH), $t_R$=5.58 (Method 5).

Example 25

4-[1-(3-AMINO-4,7-DIFLUORO-1-METHYL-1H-INDAZOL-6-YL)-PIPERIDIN-4-YLIDENEAMINOOXY]-PIPERIDINE-1-CARBOXYLIC ACID ISOPROPYL ESTER

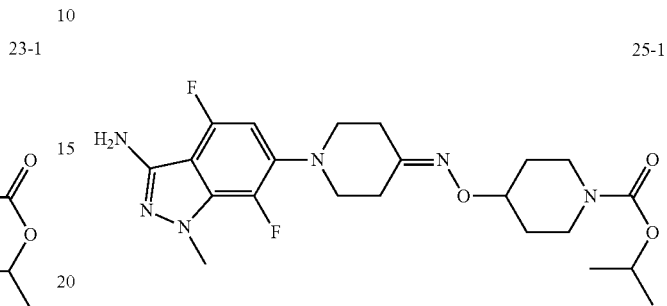

25-1

Step 25A: 4-[1-(3-Amino-4,7-difluoro-1-methyl-1H-indazol-6-yl)-piperidin-4-ylidene aminooxy]-piperidine-1-carboxylic acid isopropyl ester (25-1)

A mixture of 2-2 (50 mg) and methylhydrazine (60 μL, 10 eq) in 1 mL of nBuOH was heated at 110° C. in a sealed vial overnight. The solvent was evaporated, and the crude material was purified on preparative HPLC to afford 25-1: LC-MS 447.1 (MH), $t_R$=5.58 (Method 5).

Example 26

4-[1-(3-AMINO-4,7-DIFLUORO-BENZO[D]ISOXAZOL-6-YL)-PIPERIDIN-4-YLIDENEAMINOOXY]-PIPERIDINE-1-CARBOXYLIC ACID ISOPROPYL ESTER

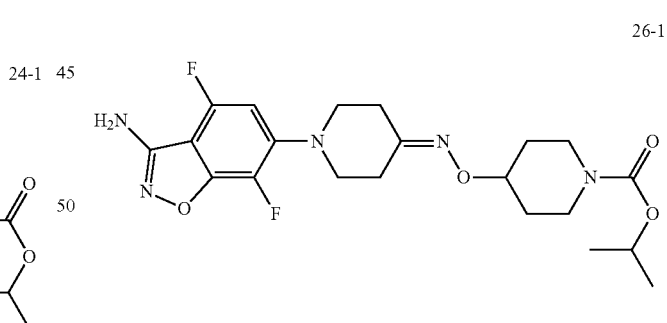

26-1

Step 26A: 4-[1-(3-Amino-4,7-difluoro-benzo[d]isoxazol-6-yl)-piperidin-4-ylideneaminooxy]-piperidine-1-carboxylic acid isopropyl ester (26-1)

To a solution of N-hydroxy-acetamide (27 mg, 3 eq) in 2 mL of DMF was added potassium tert-butoxide (40 mg, 3 eq) and the mixture was stirred at room temperature for 20 minutes. 2-2 (50 mg) was added and the mixture was stirred at room temperature overnight. Water was added and the product was extracted with ethyl acetate. The crude material was purified on preparative HPLC to give 26-1: LC-MS 434.3 (MH), $t_R$=5.58 (Method 5).

Example 27

4-[1-(2,5-DIFLUORO-4-THIOPHEN-2-YL-PHENYL)-PIPERIDIN-4-YLIDENEAMINOOXY]-PIPERIDINE-1-CARBOXYLIC ACID ISOPROPYL ESTER

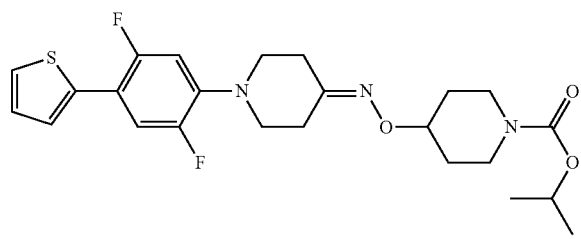

27-1

Step 27A: 4-[1-(2,5-Difluoro-4-thiophen-2-yl-phenyl)-piperidin-4-ylideneaminooxy]-piperidine-1-carboxylic acid isopropyl ester (27-1)

30 mg of 2-40, 41 mg of cesium carbonate (2 eq), 2-thiophene boronic acid (20 mg, 2 eq), a catalytic amount of (PPh$_3$)$_4$ (5% mol) in 1 mL of DMF and 0.2 mL of water were combined in a sealed vial and heated up to 110° C. for 2 h. After cooling down to room temperature, the product was extracted with ethyl acetate and the crude residue was purified on preparative HPLC to give 27-1: LC-MS 478.4 (MH).

The following compounds were made according to this procedure using the corresponding aryl boronic acid:

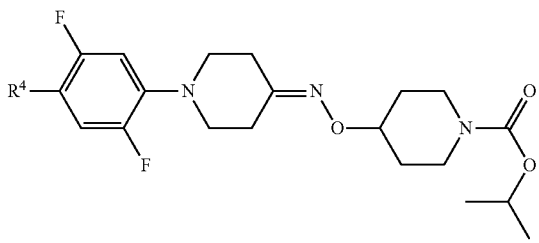

| No. | R$^4$ | MH+ | MW | t$_R$ (Min) | HPLC Gradient | EC50 (nM) |
|-----|-------|-----|-----|-------------|---------------|-----------|
| 27-1 | thiophen-2-yl | 478.4 | 477.6 | 7.47 | Method 4 | 201 |
| 27-2 | 3,5-dimethylisoxazol-4-yl | 491.3 | 490.5 | 6.65 | Method 5 | <10000 |
| 27-3 | furan-3-yl | 462.4 | 461.5 | 7.04 | Method 4 | 591 |
| 27-4 | pyridin-3-yl | 473.2 | 472.5 | 6.18 | Method 5 | 182 |
| 27-5 | pyridin-4-yl | 473.5 | 472.5 | 6.23 | Method 5 | 378 |
| 27-6 | pyrimidin-5-yl | 474.4 | 473.5 | 5.85 | Method 4 | 243 |
| 27-7 | 1H-pyrrol-2-yl | 461.3 | 460.5 | 6.65 | Method 5 | 436 |

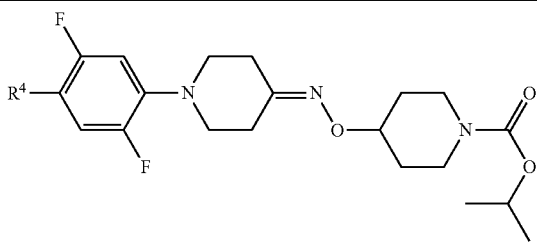
| No. | R⁴ | MH+ | MW | $t_R$ (Min) | HPLC Gradient | EC50 (nM) |
|---|---|---|---|---|---|---|
| 27-8 | N-Boc-pyrrole | 561.2 | 560.6 | 7.72 | Method 5 | nd |
| 27-9 | 1H-pyrazol-3-yl | 462.2 | 461.5 | 5.70 | Method 5 | 232 |
| 27-10 | 1H-pyrazol-4-yl | 462.1 | 461.5 | 5.51 | Method 5 | 177 |
| 27-11 | 6-methoxypyridin-2-yl | 503.4 | 502.5 | 7.73 | Method 5 | 80%* |
| 27-12 | thiophen-3-yl | 478.1 | 477.6 | 7.45 | Method 5 | 245 |
| 27-13 | 1-methylimidazol-5-yl | 476.4 | 475.5 | 4.08 | Method 5 | 68%* |
| 27-14 | 1H-imidazol-4-yl | 462.7 | 461.5 | 3.89 | Method 5 | 152 |
| 27-15 | 2-aminopyrimidin-5-yl | 489.5 | 488.5 | 5.61 | Method 4 | 516 |
| 27-16 | 1-methylimidazol-2-yl | 476.5 | 475.5 | 5.56 | Method 4 | 5554 |
| 27-17 | 1,4-dimethylimidazol-2-yl | 490.5 | 489.5 | 5.78 | Method 4 | +2210000 |

-continued
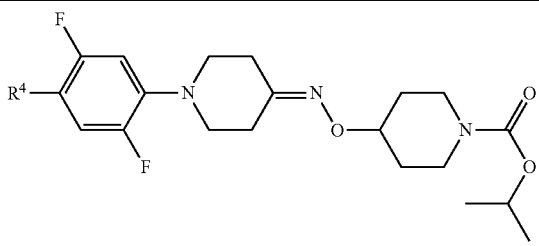
| No. | R⁴ | MH+ | MW | t_R (Min) | HPLC Gradient | EC50 (nM) |
|---|---|---|---|---|---|---|
| 27-18 | thiazol-2-yl | 479.4 | 478.5 | 5.16 | Method 5 | 137 |
| 27-19 | thiazol-4-yl | 479.4 | 478.5 | 6.89 | Method 4 | 3076 |
| 27-20 | pyrimidin-2-yl | 474.1 | 473.5 | 8.07 | Method 2 | 272 |
| 27-21 | 5-ethylpyrimidin-2-yl | 502.4 | 501.5 | 6.74 | Method 4 | 509 |
| 27-22 | 1H-imidazol-2-yl | 462.6 | 461.5 | 3.92 | Method 5 | 54 |
| 27-23 | 5-methylthiophen-2-yl | 492.3 | 491.6 | 5.78 | Method 5 | 274 |
| 27-24 | 3-methylthiophen-2-yl | 492.3 | 491.6 | 5.62 | Method 5 | 329 |
| 27-25 | 2,4-dimethylthiazol-5-yl | 507.5 | 506.6 | 6.83 | Method 4 | <10000 |
| 27-26 | 5-methylpyridin-2-yl | 487.5 | 486.5 | 7.12 | Method 4 | 861 |
| 27-27 | pyridin-2-yl | 473.4 | 472.5 | 6.79 | Method 4 | 159 |
| 27-28 | 1H-tetrazol-5-yl | 464.3 | 463.4 | 2.24 | Method 5 | 86%* |

-continued

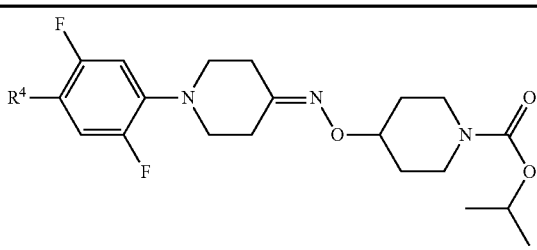

| No. | R⁴ | MH+ | MW | $t_R$ (Min) | HPLC Gradient | EC50 (nM) |
|---|---|---|---|---|---|---|
| 27-29 | 2-methoxypyrimidin-5-yl | 505.1 | 503.5 | 4.71 | Method 5 | 736 |
| 27-30 | 6-methylpyridin-3-yl | 487.5 | 486.5 | 6.51 | Method 4 | 435 |
| 27-31 | 2-methoxy-4-methoxypyrimidin-5-yl | 534.4 | 533.5 | 6.71 | Method 4 | 70%* |
| 27-32 | 1H-indol-5-yl | 511.4 | 510.5 | 6.89 | Method 4 | 1385 |
| 27-33 | 6-methoxypyridin-3-yl | 503.4 | 502.5 | 7.12 | Method 4 | 891 |
| 27-34 | 1-methyl-1H-pyrazol-4-yl | 476.4 | 475.5 | 6.01 | Method 4 | 126 |

*% values mean stimulation in % at 10 μM.

Example 28

4-{1-[2,5-DIFLUORO-4-(4-METHYL-PIPER-AZIN-1-YL)-PHENYL]-PIPERIDIN-4-YLIDENE-AMINOOXY}-PIPERIDINE-1-CARBOXYLIC ACID ISOPROPYL ESTER 28-1

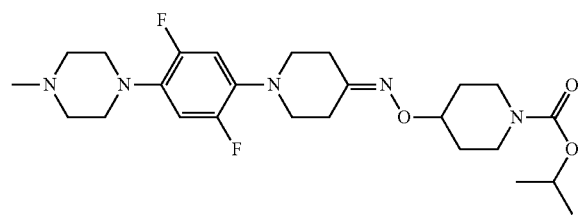

Step 28A: 4-{1-[2,5-Difluoro-4-(4-methyl-piperazin-1-yl)-phenyl]-piperidin-4-ylideneaminooxy}-piperidine-1-carboxylic acid isopropyl ester (28-1)

2-40 (50 mg), Pd₂ dba₃ (10 mg, 10% mol), BINAP (7 mg, 10% mol), N-methyl piperazine (42 mg, 4 eq) and potassium tert-butanol (18 mg, 1.5 eq) were combined in a sealed vial with 0.4 mL of degassed toluene and heated up to 110° C. for 1 h. At room temperature, water was added and the mixture was extracted with ethyl acetate. The crude residue was purified on preparative HPLC to give 28-1: LC-MS 494.1 (MH).

The following compounds were made according to this procedure using the corresponding piperazine:

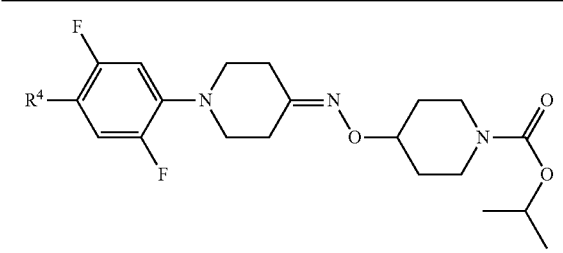

| No. | R⁴ | MH+ | MW | t_R (Min) | HPLC Gradient |
|---|---|---|---|---|---|
| 28-1 | 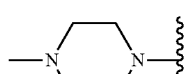 | 494.1 | 493.6 | 5.97 | Method 5 |
| 28-2 | 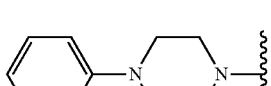 | 557.3 | 556.6 | 7.01 | Method 5 |
| 28-3 | 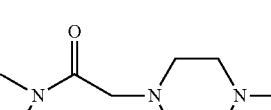 | 579.4 | 578.6 | 6.03 | Method 5 |

Example 29

4-[1-(4-DIMETHYLCARBAMYL-2,5-DIFLUORO-PHENYL)-PIPERIDIN-4-YLIDENEAMINOOXY]-PIPERIDINE-1-CARBOXYLIC ACID ISOPROPYL ESTER 29-1

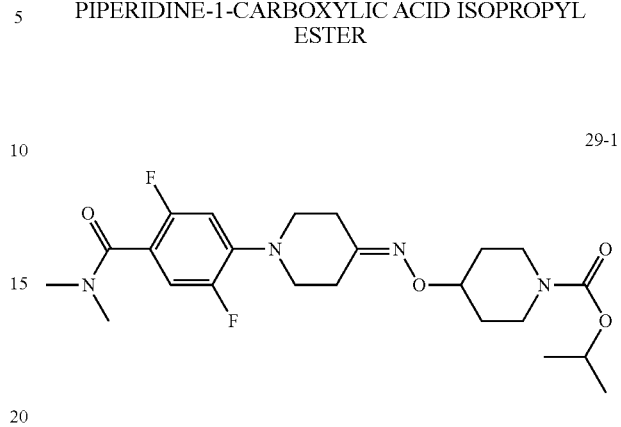

Step 29A: 4-[1-(4-Dimethylcarbamoyl-2,5-difluoro-phenyl)-piperidin-4-ylideneaminooxy]-piperidine-1-carboxylic acid isopropyl ester (29-1)

9-1 (30 mg, 0.071 mmol), dimethylamine (0.1 mmol) and HOBT (0.2 mmol) were combined in DCM (1 mL) and stirred at room temperature for 10 minutes. EDC(0.2 mmol) was added and the mixture was stirred for 18 h. The solution was washed with 2 mL of aqueous NaHCO₃, concentrated, taken up with 1 mL of methanol and purified on preparative HPLC to give 29-1: LC-MS 467.4 (MH).

The following compounds are made according to this procedure using the corresponding amine. An additional step of removing a BOC protecting group from primary and secondary amines with trifluoroacetic acid/dichloromethane is performed when appropriate.

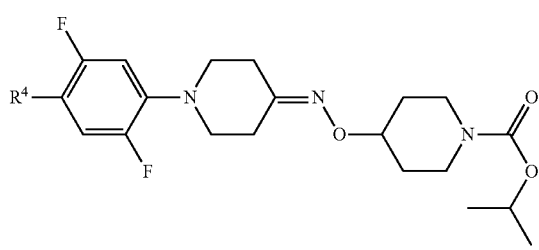

| No. | R⁴ | MH+ | MW | t_R (Min) | HPLC Gradient | EC50 (nM) |
|---|---|---|---|---|---|---|
| 29-1 | 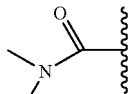 | 467.4 | 466.5 | 5.39 | Method 4 | 129 |
| 29-2 | 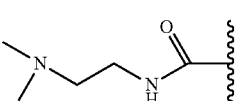 | 510.5 | 509.6 | 5.33 | Method 4 | 450 |
| 29-3 | 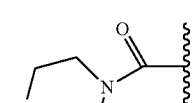 | 508.2 | 507.6 | 5.00 | Method 5 | 512 |

-continued
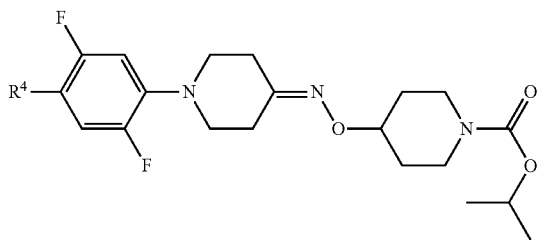
| No. | R⁴ | MH+ | MW | t_R (Min) | HPLC Gradient | EC50 (nM) |
|---|---|---|---|---|---|---|
| 29-4 | | 522.2 | 521.6 | 5.15 | Method 5 | 80 |
| 29-5 | | 510.1 | 509.6 | 5.21 | Method 5 | 215 |
| 29-6 | | 481.8 | 481.5 | 4.72 | Method 5 | 381 |
| 29-7 | | 496.3 | 495.6 | 5.35 | Method 5 | 42 |
| 29-8 | | 497.5 | 496.5 | 4.98 | Method 4 | 81 |
| 29-9 | | 497.5 | 496.5 | 4.87 | Method 4 | 94 |
| 29-10 | | 511.5 | 510.6 | 5.79 | Method 4 | 28 |
| 29-11 | | 483.4 | 482.5 | 4.78 | Method 4 | 84 |
| 29-12 | | 497.5 | 496.5 | 5.43 | Method 4 | 12 |
| 29-13 | | 592.0 | 589.7 | 4.87 | Method 5 | 631 |

-continued
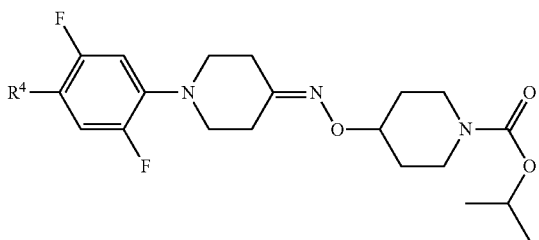
| No. | R⁴ | MH+ | MW | t_R (Min) | HPLC Gradient | EC50 (nM) |
|---|---|---|---|---|---|---|
| 29-14 | morpholine-piperidine-C(O)- | 593.8 | 591.7 | 3.89 | Method 5 | 215 |
| 29-15 | 4-aminopiperidine-NHC(O)- | 523.8 | 521.6 | 4.27 | Method 5 | 27 |
| 29-16 | 1-methylpiperidin-4-yl-NHC(O)- | 538.1 | 535.6 | 4.25 | Method 5 | 319 |
| 29-17 | 4-(aminomethyl)piperidine-C(O)- | 537.5 | 535.6 | 4.13 | Method 5 | 52 |
| 29-18 | 2-(pyrrolidinylmethyl)piperidine-C(O)- | 592.0 | 589.7 | 5.27 | Method 5 | 226 |
| 29-19 | 2-(morpholinylmethyl)piperidine-C(O)- | 607.7 | 605.7 | 4.65 | Method 5 | 269 |
| 29-20 | piperidin-3-yl-NHC(O)- | 523.8 | 521.6 | 4.05 | Method 5 | 129 |
| 29-21 | 3-aminopiperidine-C(O)- | 523.5 | 521.6 | 3.86 | Method 5 | 74 |

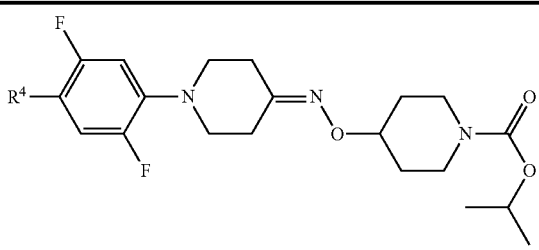
| No. | R⁴ | MH+ | MW | t$_R$ (Min) | HPLC Gradient | EC50 (nM) |
|---|---|---|---|---|---|---|
| 29-22 | | 523.5 | 521.6 | 3.72 | Method 5 | 241 |
| 29-23 | | 509.4 | 507.6 | 3.50 | Method 5 | 595 |
| 29-24 | | 422.8 | 507.6 | 3.62 | Method 5 | 131 |
| 29-25 | | 537.7 | 535.6 | 4.08 | Method 5 | 270 |
| 29-26 | | 537.5 | 535.6 | 3.91 | Method 5 | 247 |
| 29-27 | | 523.3 | 521.6 | 3.65 | Method 5 | 67 |
| 29-28 | | 523.5 | 521.6 | 4.55 | Method 5 | 28 |
| 29-29 | | 523.9 | 521.6 | 4.36 | Method 5 | 34 |
| 29-30 | | 537.6 | 535.6 | 3.86 | Method 5 | 131 |

-continued
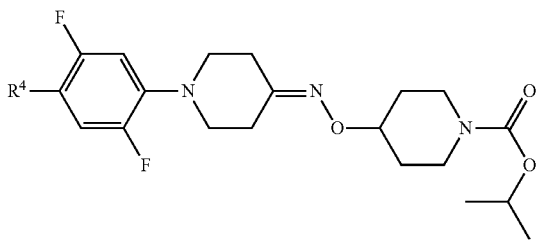
| No. | R⁴ | MH+ | MW | t_R (Min) | HPLC Gradient | EC50 (nM) |
|---|---|---|---|---|---|---|
| 29-31 | 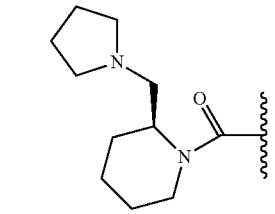 | 589.9 | 589.7 | 4.72 | Method 2 | 225 |
| 29-32 | 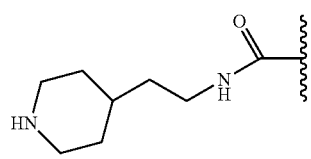 | 550.2 | 549.7 | 5.15 | Method 2 | 73 |
| 29-33 | 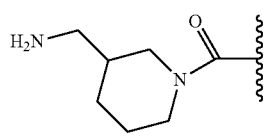 | 537.3 | 535.6 | 3.91 | Method 5 | 41 |
| 29-34 | 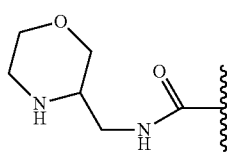 | 539.8 | 537.6 | 3.58 | Method 5 | 200 |
| 29-35 | 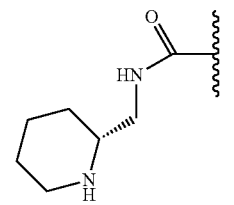 | 537.6 | 535.6 | 4.48 | Method 5 | 78 |
| 29-36 | 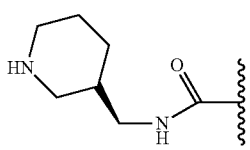 | 537.5 | 535.6 | 4.86 | Method 5 | 114 |
| 29-37 | 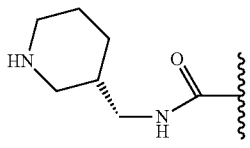 | 537.5 | 535.6 | 4.99 | Method 5 | 8 |

-continued
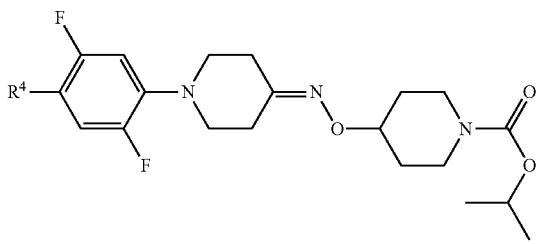
| No. | R⁴ | MH+ | MW | t_R (Min) | HPLC Gradient | EC50 (nM) |
|---|---|---|---|---|---|---|
| 29-38 | | 619.9 | 617.8 | 5.27 | Method 5 | 84 |
| 29-39 | | 606.4 | 603.8 | 4.87 | Method 5 | 131 |
| 29-40 | | 539.5 | 537.6 | 3.57 | Method 5 | 105 |
| 29-41 | | 537.5 | 535.6 | 4.43 | Method 5 | 117 |
| 29-42 | | 537.8 | 535.6 | 4.62 | Method 5 | 71 |
| 29-43 | | 582.0 | 579.7 | 5.32 | Method 5 | 77 |
| 29-44 | | 511.5 | 509.6 | 4.82 | Method 5 | 42 |
| 29-45 | | 523.5 | 521.6 | 5.46 | Method 5 | 189 |

-continued
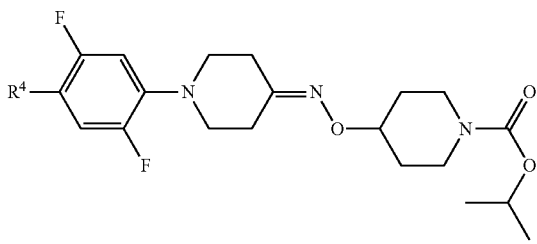
| No. | R⁴ | MH+ | MW | t_R (Min) | HPLC Gradient | EC50 (nM) |
|---|---|---|---|---|---|---|
| 29-46 | | 551.5 | 549.7 | 4.46 | Method 5 | 114 |
| 29-47 | | 564.2 | 563.7 | 4.19 | Method 5 | 264 |
| 29-48 | | 590.2 | 589.7 | 4.86 | Method 5 | 69 |
| 29-49 | | 537.6 | 535.6 | 4.53 | Method 5 | 105 |
| 29-50 | | 522.1 | 521.6 | 3.87 | Method 5 | 133 |
| 29-51 | | 551.5 | 549.7 | 4.22 | Method 5 | 223 |
| 29-52 | | 565.6 | 563.7 | 4.63 | Method 5 | 185 |
| 29-53 | | 551.8 | 549.7 | 4.46 | Method 5 | 43 |

-continued
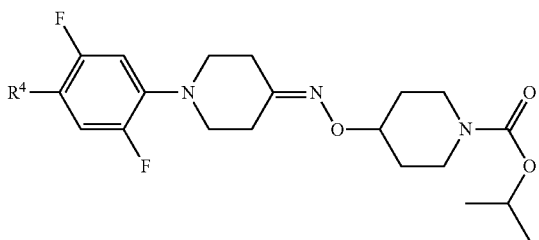
| No. | R⁴ | MH+ | MW | t_R (Min) | HPLC Gradient | EC50 (nM) |
|---|---|---|---|---|---|---|
| 29-54 | | 565.6 | 563.7 | 4.56 | Method 5 | 106 |
| 29-55 | | 591.3 | 589.7 | 5.03 | Method 5 | 90 |
| 29-56 | | 604.3 | 603.8 | 5.13 | Method 5 | 133 |
| 29-57 | | 536.2 | 535.6 | 3.68 | Method 5 | 185 |
| 29-58 | | 522.1 | 521.6 | 3.92 | Method 5 | 189 |
| 29-59 | | 523.4 | 521.6 | 5.12 | Method 5 | 201 |
| 29-60 | | 537.3 | 535.6 | 4.25 | Method 5 | 260 |
| 29-61 | | 537.7 | 535.6 | 4.46 | Method 5 | 173 |

-continued
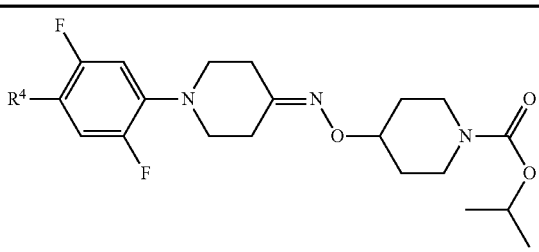
| No. | R⁴ | MH+ | MW | t_R (Min) | HPLC Gradient | EC50 (nM) |
|---|---|---|---|---|---|---|
| 29-62 | ![piperidinylmethyl amide] | 538.7 | 535.6 | 5.18 | Method 5 | 79 |
The following compounds are made according to procedures as described hereinbefore:
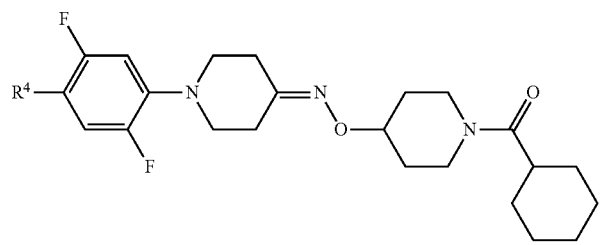
| No. | R⁴ | MH+ | MW | t_R (Min) | HPLC Gradient | EC50 |
|---|---|---|---|---|---|---|
| 29-63 | ![morpholinylmethyl amide] | 563.6 | 561.7 | 3.53 | 5 | — |
| 29-64 | ![piperidinylmethyl piperidine] | 629.8 | 627.8 | 5.63 | 5 | 650 |
| 29-65 | ![methylpiperidinyl piperidine] | 629.8 | 627.8 | 4.86 | 5 | |

-continued
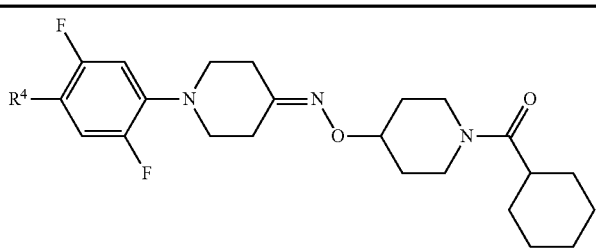
| No. | R⁴ | MH+ | MW | t_R (Min) | HPLC Gradient | EC50 |
|---|---|---|---|---|---|---|
| 29-66 | H₂N~~~N(H)C(O)- | 535.4 | 533.7 | 4.67 | 5 | — |
| 29-67 | piperidin-4-yl-NHC(O)- | 548.0 | 545.7 | 4.27 | 5 | — |
| 29-68 | 4-aminocyclohexyl-NHC(O)- | 561.5 | 559.7 | 4.43 | 5 | — |
| 29-69 | (3-aminopiperidin-1-yl)C(O)- | 547.4 | 545.7 | 3.63 | 5 | — |
| 29-70 | (3-aminopiperidin-1-yl)C(O)- | 547.7 | 545.7 | 3.65 | 5 | — |
The following compounds are made according to procedures as described hereinbefore:
| No. | R⁴ | MH+ | MW | t_R (Min) | HPLC Gradient | EC50 |
|---|---|---|---|---|---|---|
| 29-71 | (morpholin-3-yl)methyl-NHC(O)- | 571.2 | 569.7 | 4.22 | 5 | 624 |
| 29-72 | (piperidin-1-yl-methyl)piperidin-1-yl-C(O)- | 638.8 | 635.8 | 6.34 | 5 | 406 |

-continued
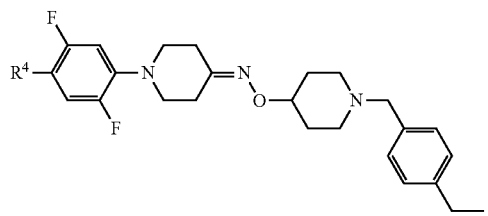
| No. | R⁴ | MH+ | MW | t_R (Min) | HPLC Gradient | EC50 |
|---|---|---|---|---|---|---|
| 29-73 |  | 555.8 | 553.7 | 4.44 | 5 | 1102 |
-continued
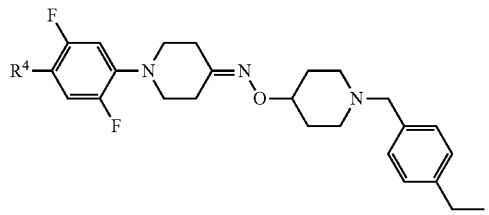
| No. | R⁴ | MH+ | MW | t_R (Min) | HPLC Gradient | EC50 |
|---|---|---|---|---|---|---|
| 29-74 |  | 555.7 | 553.7 | 4.37 | 5 | 723 |
The following compounds are made according to procedures as described hereinbefore:
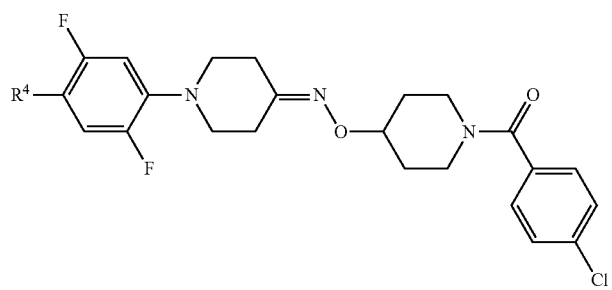
| No. | R⁴ | MH+ | MW | t_R (Min) | HPLC Gradient | EC50 |
|---|---|---|---|---|---|---|
| 29-75 | 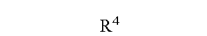 | — | 590.1 | 3.58 | 5 | — |
| 29-76 |  | 591.7 | 588.1 | 4.44 | 5 | — |
| 29-77 | 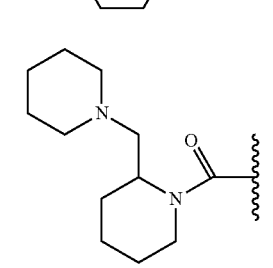 | 658.2 | 656.2 | 5.53 | 5 | 1121 |
| 29-78 | 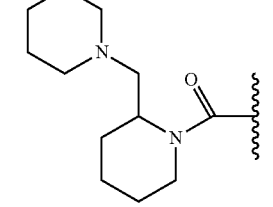 | 575.5 | 574.1 | 3.63 | 5 | — |

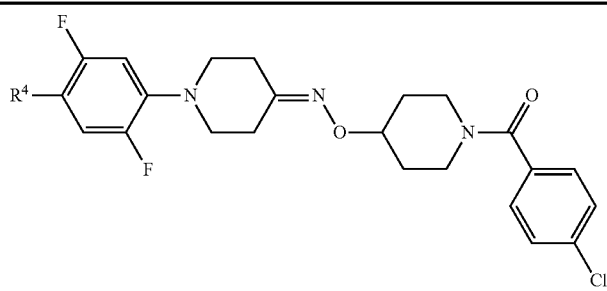
| No. | R⁴ | MH+ | MW | t_R (Min) | HPLC Gradient | EC50 |
|---|---|---|---|---|---|---|
| 29-79 | | 601.6 | 600.1 | 4.29 | 5 | — |
| 29-80 | | 633.7 | 632.2 | 5.17 | 5 | 39 |
| 29-81 | | 563.7 | 562.1 | 4.65 | 5 | — |
| 29-82 | | 575.5 | 574.1 | 3.65 | 5 | — |
The following compounds are made according to procedures as described hereinbefore:
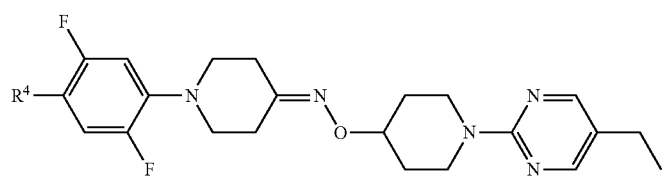
| No. | R⁴ | MH+ | MW | t_R (Mm) | HPLC Gradient | EC 50 |
|---|---|---|---|---|---|---|
| 29-83 | | 625.8 | 623.8 | 5.99 | 5 | 1148 |
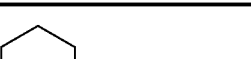

-continued
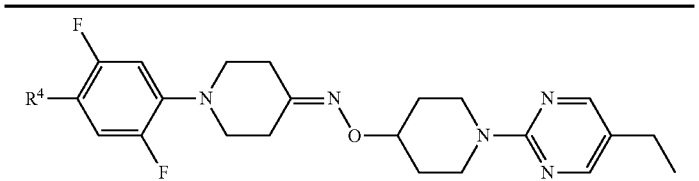
| No. | R⁴ | MH+ | MW | t_R (Mm) | HPLC Gradient | EC 50 |
|---|---|---|---|---|---|---|
| 29-84 | 1-methylpiperidin-4-yl-piperidine-carbonyl | 625.8 | 623.8 | 5.55 | 5 | 85 |
| 29-85 | (dimethylamino)ethyl-NH-C(O)- | 643.0 | 640.8 | 3.91 | 5 | 330 |
| 29-86 | 4-aminocyclohexyl-NH-C(O)- | 557.8 | 555.7 | 4.93 | 5 | 106 |
| 29-87 | morpholin-3-ylmethyl-NH-C(O)- | 558.2 | 557.6 | 3.56 | 5 | 128 |
| 29-88 | (3-aminopiperidin-1-yl)-C(O)- | 542.2 | 541.6 | 3.73 | 5 | 221 |
| 29-89 | (3-aminopiperidin-1-yl)-C(O)- | 542.2 | 541.6 | 3.73 | 5 | 74 |
| 29-90 | pyrrolidin-3-ylmethyl-NH-C(O)- | 542.2 | 541.6 | 4.34 | 5 | 67 |
| 29-91 | piperidin-2-ylmethyl-NH-C(O)- | 557.5 | 555.7 | 4.96 | 5 | 162 |
| 29-92 | piperidin-2-ylmethyl-NH-C(O)- | 557.6 | 555.7 | 4.99 | 5 | 120 |
| 29-93 | piperidin-3-ylmethyl-NH-C(O)- | 556.6 | 555.7 | 5.91 | 5 | 56 |

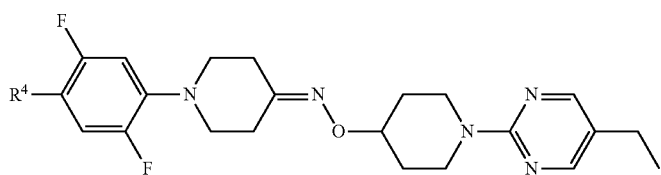
| No. | R⁴ | MH+ | MW | t_R (Mm) | HPLC Gradient | EC 50 |
|---|---|---|---|---|---|---|
| 29-94 | piperidine-CH2-NHC(O)- | 557.6 | 555.7 | 5.91 | 5 | 35 |
| 29-95 | pyrrolidine-CH2-pyrrolidine-C(O)- | 597.7 | 597.7 | 5.27 | 5 | 240 |
| 29-96 | pyrrolidine-CH2-pyrrolidine-C(O)- | 597.7 | 595.7 | 5.24 | 5 | 709 |
| 29-97 | (Me)2N-pyrrolidine-C(O)- | 557.4 | 555.7 | 4.19 | 5 | 181 |
| 29-98 | (Me)2N-pyrrolidine-C(O)- | 557.3 | 555.7 | 4.2 | 5 | 212 |
| 29-99 | pyrrolidine-CH2-piperidine-C(O)- | 611.7 | 609.8 | 5.51 | 5 | 255 |
| 29-100 | morpholine-CH2-piperidine-C(O)- | 627.7 | 625.8 | 5.05 | 5 | 185 |

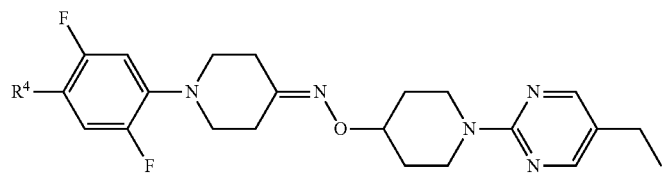
| No. | R⁴ | MH+ | MW | t_R (Mm) | HPLC Gradient | EC 50 |
|---|---|---|---|---|---|---|
| 29-101 | | 614.8 | 611.7 | 4.15 | 5 | 112 |
| 29-102 | | 557.7 | 555.7 | 4.41 | 5 | 108 |
| 29-103 | | 625.9 | 623.8 | 5.80 | 5 | 154 |
| 29-104 | | 557.4 | 555.7 | 4.77 | 5 | 164 |
| 29-105 | | 611.9 | 609.8 | 5.49 | 5 | 71 |
| 29-106 | | 612.5 | 609.8 | 5.46 | 5 | 170 |
| 29-107 | | 585.9 | 583.7 | 4.86 | 5 | 143 |
| 29-108 | | 586.1 | 583.7 | 5.06 | 5 | 141 |

-continued
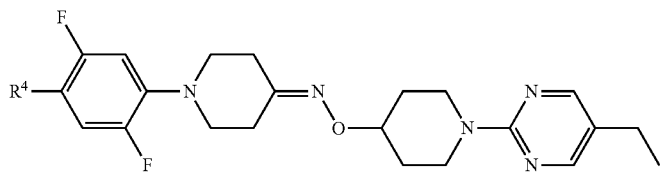
| No. | R⁴ | MH+ | MW | t_R (Mm) | HPLC Gradient | EC 50 |
|---|---|---|---|---|---|---|
| 29-109 | | 585.5 | 583.7 | 4.99 | 5 | 84 |
| 29-110 | | 542.2 | 541.6 | 3.70 | 5 | 256 |
| 29-111 | | 554.2 | 553.7 | 4.15 | 5 | 295 |
| 29-112 | | 570.1 | 569.7 | 4.61 | 2 | 38 |
| 29-113 | | 558.2 | 557.6 | 3.59 | 5 | 26 |
| 29-114 | | 542.2 | 541.6 | 3.80 | 5 | 392 |
| 29-115 | | | 539.6 | 3.46 | 5 | 2011 |
| 29-116 | | 514.1 | 513.6 | 4.68 | 5 | 322 |
| 29-117 | | 560.1 | 559.6 | 2.42 | 5 | 745 |

-continued
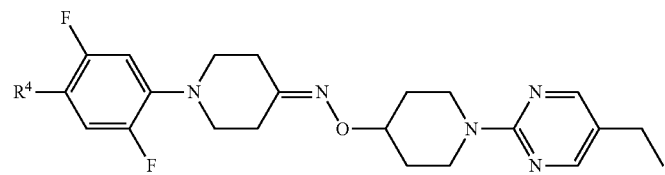
| No. | R⁴ | MH+ | MW | t_R (Mm) | HPLC Gradient | EC 50 |
|---|---|---|---|---|---|---|
| 29-118 | H₂N-(3-aminopyrrolidin-1-yl)carbonyl | 528.1 | 527.6 | 3.45 | 4 | 201 |
| 29-119 | H₂N-(3-aminopyrrolidin-1-yl)carbonyl (enantiomer) | 528.1 | 527.6 | 3.44 | 5 | 75 |
| 29-120 | H₂N-CH₂-(3-pyrrolidinyl)carbonyl | 542.2 | 541.6 | 3.99 | 5 | 202 |
| 29-121 | (pyrrolidin-2-yl)methylaminocarbonyl | 542.1 | 541.6 | 4.45 | 2 | 139 |
| 29-122 | (pyrrolidin-2-yl)methylaminocarbonyl | 542.2 | 541.6 | 4.49 | 2 | 176 |
| 29-123 | (pyrrolidin-3-yl)aminocarbonyl | 528.1 | 527.6 | 4.54 | 5 | 407 |
| 29-124 | H₂N-CH₂-(3-piperidinyl)carbonyl | 556.2 | 555.7 | 4.47 | 5 | 55 |
| 29-125 | H₂N-CH₂-(4-piperidinyl)carbonyl | 556.2 | 555.7 | 4.87 | 5 | 168 |
| 29-126 | (4-aminopiperidin-1-yl)carbonyl | 542.2 | 541.6 | 3.83 | 5 | 469 |

-continued
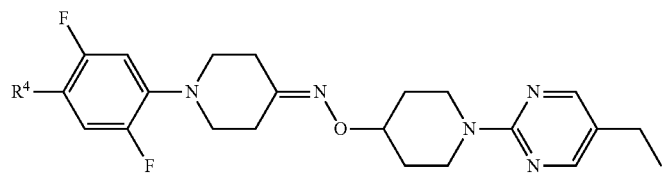
| No. | R⁴ | MH+ | MW | t_R (Mm) | HPLC Gradient | EC 50 |
|---|---|---|---|---|---|---|
| 29-127 | piperidin-3-yl-NHC(O)- | 542.2 | 541.6 | 4.44 | 5 | 322 |
| 29-128 | (piperidin-4-yl)CH₂NHC(O)- | 556.2 | 555.7 | 4.63 | 5 | 70 |
| 29-129 | 3-(methylaminomethyl)piperidin-1-yl-C(O)- | 570.6 | 539.7 | 5.41 | 5 | 50 |
| 29-130 | 4-(methylaminomethyl)piperidin-1-yl-C(O)- | 570.3 | 569.7 | 5.50 | 5 | 206 |
| 29-131 | 2-(aminomethyl)piperidin-1-yl-C(O)- | 556.2 | 555.7 | 4.11 | 5 | 64 |
| 29-132 | (S)-2-(aminomethyl)pyrrolidin-1-yl-C(O)- | 542.2 | 541.6 | 4.28 | 5 | 114 |
| 29-133 | 2-(aminomethyl)pyrrolidin-1-yl-C(O)- | 542.2 | 541.6 | 4.53 | 2 | 164 |
| 29-134 | 2-(methylaminomethyl)pyrrolidin-1-yl-C(O)- | 556.2 | 555.7 | 5.22 | 5 | 437 |

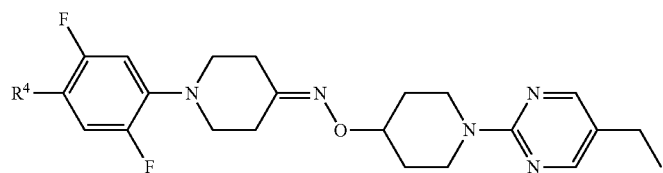
| No. | R⁴ | MH+ | MW | t_R (Mm) | HPLC Gradient | EC 50 |
|---|---|---|---|---|---|---|
| 29-135 | | 556.3 | 555.7 | 4.63 | 2 | 297 |
| 29-136 | | 570.2 | 569.7 | 4.80 | 5 | 120 |
| 29-137 | | 556.2 | 555.7 | 4.80 | 5 | 212 |
| 29-138 | | 556.2 | 555.7 | 4.72 | 5 | 185 |
| 29-139 | | 542.2 | 541.6 | 4.34 | 5 | 92 |

Example 30

4-{1-[4-(CARBOXYMETHYL-CARBAMOYL)-2,5-DIFLUORO-PHENYL]-PIPERIDIN-4-YLIDENEAMINOOXY}-PIPERIDINE-1-CARBOXYLIC ACID ISOPROPYL ESTER

Example 31

4-{1-[2,5-DIFLUORO-4-(2-METHYLAMINO-ETHYLCARBAMOYL)-PHENYL]-PIPERIDIN-4-YLIDENEAMINOOXY}-PIPERIDINE-1-CARBOXYLIC ACID ISOPROPYL ESTER

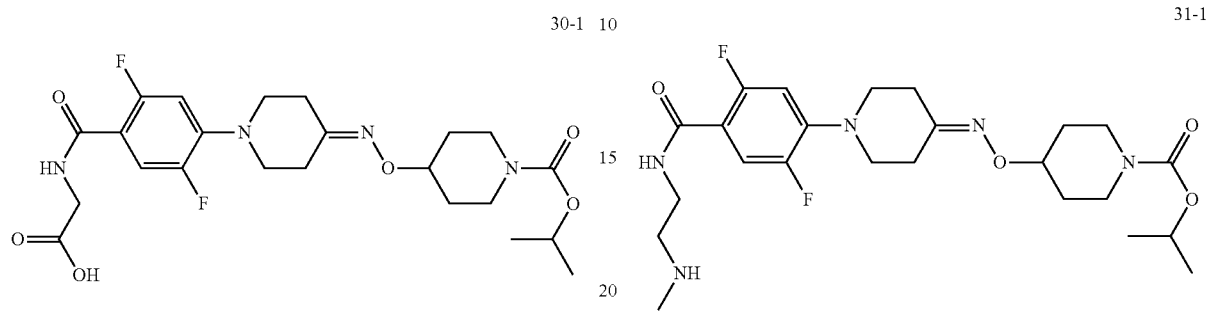

Step 30A: 4-{1-[4-(Carboxymethyl-carbamoyl)-2,5-difluoro-phenyl]-piperidin-4-ylideneaminooxy}-piperidine-1-carboxylic acid isopropyl ester (30-1)

9-1 (32 mg, 0.073 mmol), amino-acetic acid methyl ester (0.11 mmol) and HOBT (15 mg, 0.11 mmol) were combined in DCM (1 mL) and stirred at room temperature for 10 minutes. EDC(19 mg, 0.1 mmol) was added and the mixture was stirred for 18 h. The solution was washed with 2 mL of aqueous NaHCO$_3$, concentrated and taken up with 0.5 mL of dioxane. 0.5 mL of 1N NaOH was added and the mixture was stirred at 60° C. for 1 h. It was then cooled to room temperature, acidified with 0.5 mL of 2N HCl and extracted with ethyl acetate (1.5 mL). The organic layer was concentrated under a stream of nitrogen and purified on preparative HPLC to give 30-1: LC-MS 497.4 (MH).

The following compounds were made according to this procedure using the corresponding amine:

Step 31A: 4-{1-[2,5-Difluoro-4-(2-methylamino-ethylcarbamoyl)-phenyl]-piperidin-4-ylideneaminooxy}-piperidine-1-carboxylic acid isopropyl ester (31-1)

9-1 (32 mg, 0.073 mmol), amino-acetic acid methyl ester (0.11 mmol) and HOBT (15 mg, 0.11 mmol) were combined in DCM (1 mL) and stirred at room temperature for 10 minutes. EDC(19 mg, 0.1 mmol) was added and the mixture was stirred for 18 h. The solution was washed with 2 mL of aqueous NaHCO$_3$, concentrated and taken up with 1 mL of DCM. 1 mL of TFA was added and the mixture was stirred at room temperature for 1 h. It was then concentrated under a stream of nitrogen and purified on preparative HPLC to give 31-1: LC-MS 496.5 (MH).

The following compounds were made according to this procedure:

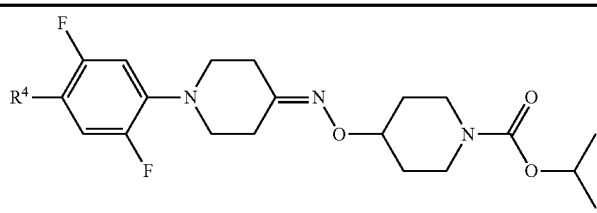

| No. | R$^4$ | MH+ | MW | $t_R$ (Min) | HPLC Gradient | EC50 (nM) |
|---|---|---|---|---|---|---|
| 30-1 | 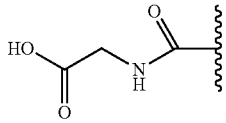 | 497.4 | 496.5 | 3.56 | Method 4 | 1132 |
| 30-2 |  | 511.4 | 510.5 | 3.2 | Method 4 | 1153 |

| No. | R⁴ | MH+ | MW | $t_R$ (Min) | HPLC Gradient | EC50 (nM) |
|---|---|---|---|---|---|---|
| 31-1 | HN(CH₃)-CH₂CH₂-NH-C(O)- | 496.5 | 495.6 | 4.87 | Method 4 | 424 |
| 31-2 | H₂N-CH₂CH₂-NH-C(O)- | 481.8 | 481.5 | 4.72 | Method 5 | 348 |
| 31-3 | H₂N-CH₂CH₂CH₂-NH-C(O)- | 496.3 | 495.6 | 5.35 | Method 5 | 542 |

Example 32

4-(1-PHENYL-PIPERIDIN-4-YLIDENEAMINOOXY)-PIPERIDINE-1-CARBOXYLIC ACID ISOPROPYL ESTER

Step 32A: 4-(1-Phenyl-piperidin-4-ylideneaminooxy)-piperidine-1-carboxylic acid isopropyl ester (32-1)

2d (50 mg, 0.18 mmol), $Pd_2dba_3$ (3 mg), xantphos (5 mg), NaOtBu (23 mg) and phenyl bromide (75 μL) were combined with 0.5 mL of toluene and heated at 100° C. for 20 h. The mixture was concentrated and taken up with methanol and purified on preparative HPLC to give 32-1: LC-MS 360.4 (MH).

The following compounds were made according to this procedure using the corresponding aryl bromide:

| No. | Ar | MH+ | MW | $t_R$ (Min) | HPLC Gradient | EC50 (nM) |
|---|---|---|---|---|---|---|
| 32-1 | phenyl | 360.4 | 359.5 | 6.14 | Method 4 | >10000 |
| 32-2 | 2,5-difluorophenyl | 396.4 | 395.4 | 6.41 | Method 4 | 2855 |
| 32-3 | 3-methylsulfonylphenyl | 438.2 | 437.5 | 5.39 | Method 5 | >10000 |

Example 33

4-(3'-CHLORO-2,3,5,6-TETRAHYDRO-[1,4']BIPY-RIDINYL-4-YLIDENEAMINOOXY)-PIPERI-DINE-1-CARBOXYLIC ACID ISOPROPYL ESTER

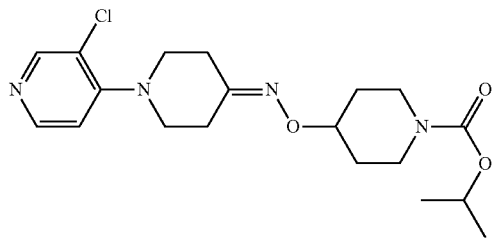

33-1

Step 33A: 4-(3'-Chloro-2,3,5,6-tetrahydro-[1,4]bipyridinyl-4-ylideneaminooxy)-piperidine-1-carboxylic acid isopropyl ester (33-1)

2d (50 mg, 0.18 mmol) was added to a mixture of the boronic acid (0.35 mmol), 4 angstrom molecular sieves (150 mg) and Cu(OAc)$_2$ (5 mg, 0.025 mmol) in 1 mL of DCM. The mixture was stirred at room temperature for 3 days then filtered, concentrated, taken up with methanol and purified on preparative HPLC to give 33-1: LC-MS 395.1 (MH).

The following compounds were made according to this procedure using the corresponding boronic acid:

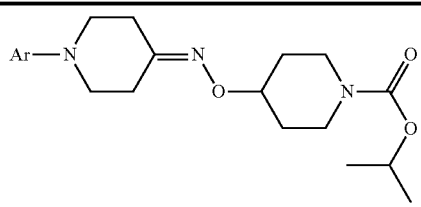

| No. | Ar | MH+ | MW | t$_R$ (Min) | HPLC Gradient |
|---|---|---|---|---|---|
| 33-1 | 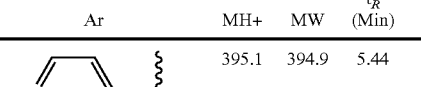 | 395.1 | 394.9 | 5.44 | Method 5 |
| 33-2 | 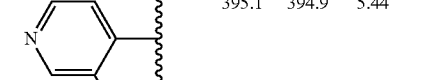 | 361.5 | 360.4 | 4.75 | Method 5 |
| 33-3 | 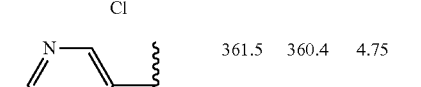 | 426.2 | 425.5 | 6.39 | Method 5 |
| 33-4 | 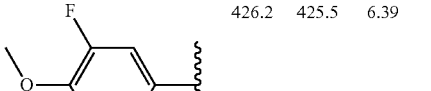 | 420.3 | 419.5 | 5.56 | Method 5 |

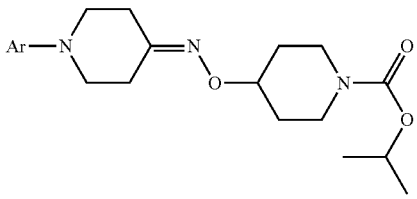

| No. | Ar | MH+ | MW | t$_R$ (Min) | HPLC Gradient |
|---|---|---|---|---|---|
| 33-5 | 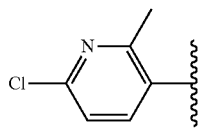 | 409.2 | 408.9 | 6.15 | Method 5 |
| 33-6 | 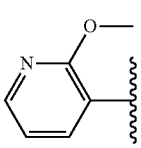 | 391.3 | 390.5 | 5.55 | Method 5 |
| 33-7 | 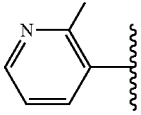 | 379.1 | 378.4 | 5.47 | Method 5 |

Example 34

4-[1-(4-AMINO-2,5-DIFLUORO-PHENYL)-PIPERIDIN-4-YLIDENEAMINOOXY]-PIPERIDINE-1-CARBOXYLIC ACID ISOPROPYL ESTER

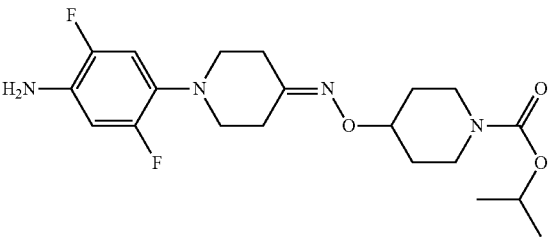

34-1

Step 34A: 4-[1-(4-Amino-2,5-difluoro-phenyl)-piperidin-4-ylideneaminooxy]-piperidine-1-carboxylic acid isopropyl ester (34-1)

To a solution of 2-62 (1.54 g, 3.49 mmol) in 16 mL of acetonitrile, was added sodium hydrosulfite (85% pure, 3.82 g, 18.7 mmol) in 2N NaOH (1.3 g of NaOH in 1 mL of water). The mixture was stirred at room temperature for 18 h. The acetonitrile was removed under vacuum, the residue was diluted with water (200 mL) and ethyl acetate (150 mL) and the layers were separated. The aqueous layer was extracted

Example 35

4-[1-(4-ACETYLAMINO-2,5-DIFLUORO-PHENYL-PIPERIDIN-4-YLIDENEAMINOOXY]-PIPERIDINE-1-CARBOXYLIC ACID ISOPROPYL ESTER

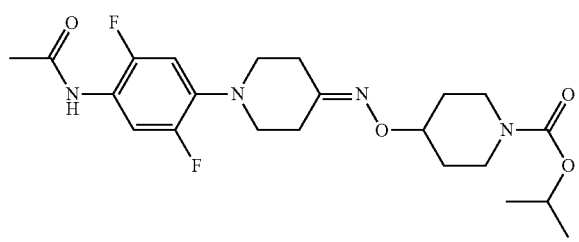

35-1

Step 35A: 4-[1-(4-Acetylamino-2,5-difluoro-phenyl)-piperidin-4-ylideneaminooxy]-piperidine-1-carboxylic acid isopropyl ester (35-1)

To a solution of 34-1 (72.5 mg, 0.18 mmol) and triethylamine (0.15 mL, 1.07 mmol) in 1 mL of DCM, was added acetic anhydride (0.02 mL, 0.21 mmol) and the mixture was stirred at room temperature for 16 h. The solvent was removed under a stream of nitrogen, redissolved in DCM and purified on preparative HPLC to give 35-1: LC-MS 453.1 (MH).

The following compounds were made according to this procedure using the corresponding electrophile (anhydride or chloroformate):

Example 36

4-[1-(2,5-DIFLUORO-4-GUANIDINO-PHENYL)-PIPERIDIN-4-YLIDENEAMINOOXY]-PIPERIDINE-1-CARBOXYLIC ACID ISOPROPYL ESTER

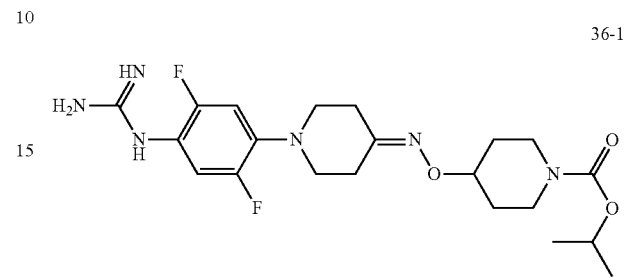

36-1

Step 36A: 4-[1-(2,5-Difluoro-4-guanidino-phenyl)-piperidin-4-ylideneaminooxy]-piperidine-1-carboxylic acid isopropyl ester (36-1)

To a solution of 34-1 (72.5 mg, 0.18 mmol) and triethylamine (0.15 mL, 1.07 mmol) in 1 mL of DCM, was added mercury chloride (60 mg, 0.22 mmol) and di-Boc-thiourea (60 mg, 0.22 mmol). The mixture was stirred at room temperature for 4 h. It was then diluted with DCM (40 mL), filtered through a pad of celite, water (40 mL) was added to the filtrate and the layers were separated. The aqueous layer was extracted with DCM (2×40 mL), the combined extracts were dried over magnesium sulfate, filtered and the solvent was removed under vacuum to give a yellow oil. The oil was dissolved in DCM (5 mL) and TFA (2 mL, 25.96 mmol) was added. The mixture was stirred at room temperature for 1 h and then concentrated and dissolved in DCM for purification on preparative HPLC to give 36-1: LC-MS 453.1 (MH), $t_R$=5.05 (Method 2). EC50: 1320 nM.

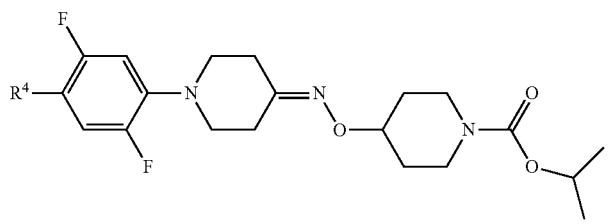

| No. | R⁴ | MH+ | MW | $t_R$ (Min) | HPLC Gradient | EC50 (nM) |
|---|---|---|---|---|---|---|
| 35-1 | 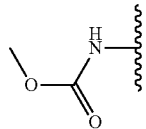 | 453.1 | 452.5 | 7.05 | Method 2 | 17 |
| 35-2 | 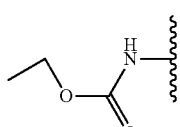 | 483.2 | 482.5 | 8.48 | Method 2 | 18 |

Example 37

4-[1-(2,5-DIFLUORO-4-UREIDO-PHENYL)-PIPERIDIN-4-YLIDENEAMINOOXY]-PIPERIDINE-1-CARBOXYLIC ACID ISOPROPYL ESTER

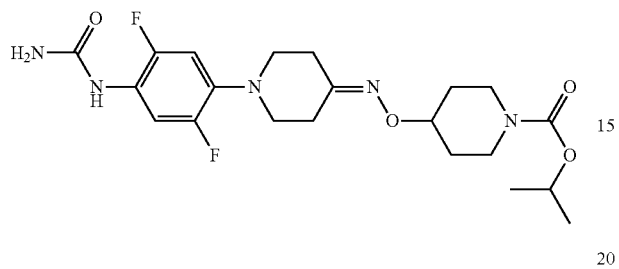

37-1

Step 37A: 4-[1-(2,5-Difluoro-4-ureido-phenyl)-piperidin-4-ylideneaminooxy]-piperidine-1-carboxylic acid isopropyl ester (37-1)

To a solution of 34-1 (72.5 mg, 0.18 mmol) in THF (1 mL) and water (1 mL), was added potassium cyanate (30 mg, 0.37 mmol), acetic acid (0.2 mL) and water (1.8 mL). The biphasic solution was stirred at room temperature for 2 h then concentrated, dissolved in DCM and purified on preparative HPLC to give 37-1: LC-MS 454.1 (MH), $t_R$=6.42 (Method 2). EC50: 71 nM.

Example 38

4-[1-(2,5-DIFLUORO-4-SULFONYLUREIDO-PHENYL)-PIPERIDIN-4-YLIDENEAMINOOXY]-PIPERIDINE-1-CARBOXYLIC ACID ISOPROPYL ESTER

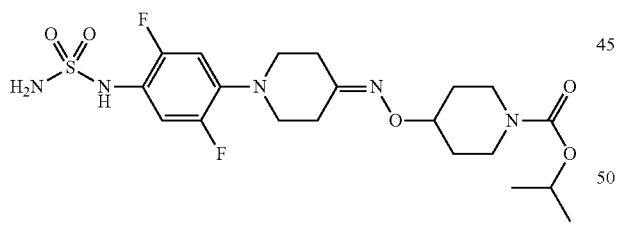

38-1

Step 38A: 4-[1-(2,5-Difluoro-4-sulfonylureido-phenyl)-piperidin-4-ylideneaminooxy]-piperidine-1-carboxylic acid isopropyl ester (38-1)

To a solution of chlorosulfonyl isocyanate (1.51 mL, 17.39 mmol) in benzene (6.5 mL) was slowly added a solution of t-BuOH (1.7 mL, 17.77 mmol) in 1 mL of benzene. The mixture was stirred at room temperature for 1 h. Hexane was added (15 mL) and the solution was stirred for 3 h. The precipitate formed was filtered and washed with hexane to give 3.5 g of a white solid (93% yield).

60 mg of this solid (0.28 mmol) was added to a solution of 34-1 (72.5 mg, 0.18 mmol) and triethylamine (0.15 mL, 1.07 mmol) in 1 mL of DCM. The mixture was stirred at room temperature for 3 days, diluted with DCM (20 mL) and brine (20 mL) and the layers were separated. The aqueous layer was extracted with DCM (2×20 mL) and the combined extracts were dried over magnesium sulfate, filtered and evaporated to give an oil. The oil was taken up with DCM (5 mL) and TFA (2 mL, 26 mmol) was added. The mixture was stirred at room temperature for 2 h, concentrated, dissolved in DCM and purified on preparative HPLC to give 38-1: LC-MS 490.1 (MH), $t_R$=6.74 (Method 2). EC50: 197 nM.

Example 39

4-{1-[2,5-DIFLUORO-4-((E)-2-METHOXYCARBONYL-VINYL)-PHENYL]-PIPERIDIN-4-YLIDENEAMINOOXY}-PIPERIDINE-1-CARBOXYLIC ACID ISOPROPYL ESTER

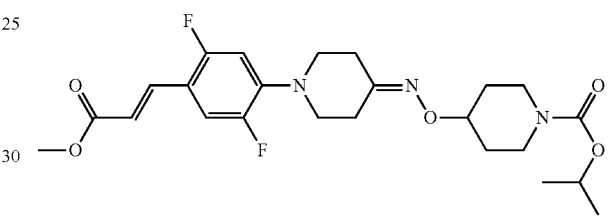

39-1

Step 39A: 4-{1-[2,5-Difluoro-4-((E)-2-methoxycarbonyl-vinyl)-phenyl]-piperidin-4-ylideneaminooxy}-piperidine-1-carboxylic acid isopropyl ester (39-1)

2-3 (50 mg, 0.12 mmol) and methyl(triphenylphosphoranylidene) acetate (50 mg, 0.15 mmol) were combined in 1 mL of DCM and stirred at room temperature for 20 h. The solution was evaporated and purified on preparative HPLC to afford 39-1: LC-MS 480.4 (MH).

The following compounds were made according to this procedure using the corresponding ylide:

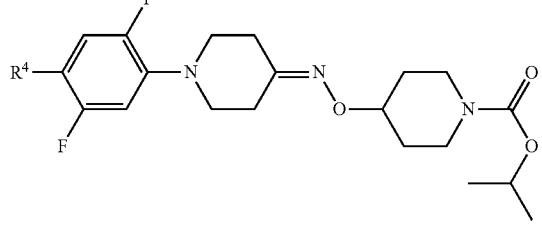

| No. | R⁴ | MH+ | MW | $t_R$ (Min) | HPLC Gradient | EC50 (nM) |
|---|---|---|---|---|---|---|
| 39-1 |  | 480.4 | 479.5 | 10.81 | Method 5 | 46 |

-continued

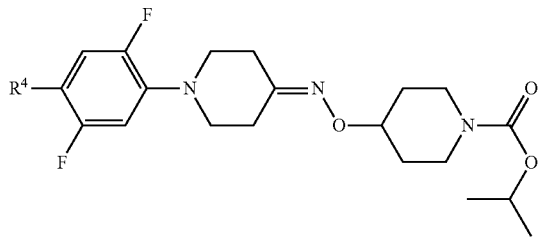

| No. | R⁴ | MH+ | MW | $t_R$ (Min) | HPLC Gradient | EC50 (nM) |
|---|---|---|---|---|---|---|
| 39-2 | (nitrile-vinyl group) | 447.4 | 446.5 | 10.44 | Method 5 | 157 |

Example 40

4-{1-[4-((E)-2-CARBOXY-VINYL)-2,5-DIFLUORO-PHENYL]-PIPERIDIN-4-YLIDENEAMINOOXY}-PIPERIDINE-1-CARBOXYLIC ACID ISOPROPYL ESTER

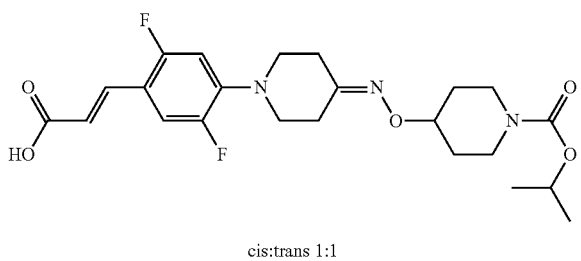

40-1 cis:trans 1:1

Step 40A: 4-{1-[4-((E)-2-Carboxy-vinyl)-2,5-difluoro-phenyl]-piperidin-4-ylideneaminooxy}-piperidine-1-carboxylic acid isopropyl ester (40-1)

2-3 (50 mg, 0.12 mmol) and the ylide (50 mg, 0.15 mmol) were combined in 1 mL of DCM and stirred at room temperature for 18 h. The solution was evaporated and diluted with THF (0.5 mL), 1N NaOH (0.3 mL) was added and the solution was heated to 55° C. for 4 h. The mixture was diluted with HCl 1N (3 mL) and extracted with DCM (2×3 mL). The combined extracts were concentrated and purified on preparative HPLC to afford 40-1: LC-MS 466.3 (MH), $t_R$=3.29 (Method 5). EC50: 2571 nM.

Example 41

4-{1-[2-FLUORO-4-FORMYL-5-(2-HYDROXY-ETHOXY)-PHENYL]-PIPERIDIN-4-YLIDENE-AMINOOXY}-PIPERIDINE-1-CARBOXYLIC ACID ISOPROPYL ESTER

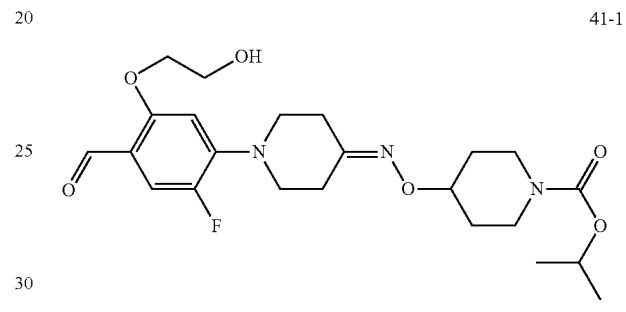

41-1

Step 41A: 4-{1-[2-Fluoro-4-formyl-5-(2-hydroxy-ethoxy)-phenyl]-piperidin-4-ylideneaminooxy}-piperidine-1-carboxylic acid isopropyl ester (41-1)

2-3 (30 mg, 0.007 mmol), cesium carbonate (60 mg, 0.18 mmol) and ethylene glycol (0.2 mL) were combined and heated to 100° C. for 2 h. The mixture was cooled, diluted with methanol and purified on preparative HPLC to afford 41-1: LC-MS 448.4 (MH—OH), $t_R$=5.56 (Method 5).

Example 42

4-{1-[4-((S)-2-TERT-BUTOXYCARBONYLAMINO-3-METHYL-BUTYRYLOXYMETHYL)-2,5-DIFLUORO-PHENYL]-PIPERIDIN-4-YLIDENEAMINOOXY}-PIPERIDINE-1-CARBOXYLIC ACID ISOPROPYL ESTER

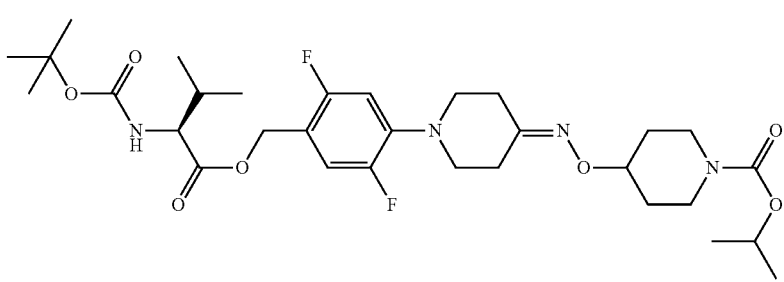

42-1

157

Step 42A: 4-{1-[4-((S)-2-tert-Butoxycarbonylamino-3-methyl-butyryloxymethyl)-2,5-difluoro-phenyl]-piperidin-4-ylideneaminooxy}-piperidine-1-carboxylic acid isopropyl ester (42-1)

10-1 (0.5 g, 1.19 mmol), Boc-L-valine (0.27 g, 1.28 mmol), DMAP (36 mg) and EDC(0.27 g) were combined in 10 mL of DCM and stirred at room temperature for 18 h. The mixture was concentrated and purified by flash LC(eluent: 0 to 40% EtOAc in hexane with 0.1% of triethylamine) to afford 42-1 as a colorless oil: LC-MS 525.2 (MH-Boc), $t_R$=10.38 (Method 2). EC50: 928 nM.

Example 43

4-[1-(2,5-DIFLUORO-4-METHANESULFINYL-PHENYL)-PIPERIDIN-4-YLIDENEAMINOOXY]-PIPERIDINE-1-CARBOXYLIC ACID ISOPROPYL ESTER

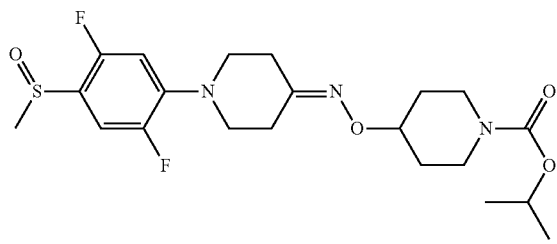

43-1

Step 43A: 1,2,4-Trifluoro-5-methylsulfanyl-benzene (43a)

BuLi (11.5 mL of a 2.5M solution in hexane, 29 mmol) was added to 2,4,5-trifluorobromobenzene (4.69 g, 22 mmol) in ether (55 mL) at −78° C. and the mixture was stirred for 10 minutes. $Me_2S_2$ (4.3 mL, 49 mmol) was added and the mixture was warmed to room temperature over 30 minutes. 5 mL of water was added and the mixture was concentrated, taken up with hexane (75 mL), washed with water (3×40 mL) and brine (40 mL), dried and concentrated to afford crude 1,2,4-trifluoro-5-methylsulfanyl-benzene 43a, which was used without further purification in the next step.

Step 43B: 1,2,4-Trifluoro-5-methanesulfinyl-benzene (43b)

MCPBA (4.93 g, 22 mmol) in DCM (20 mL) was added to an ice cooled solution of 43a (22 mmol) in DCM (40 mL). After 2 h, the mixture was diluted with water (30 mL) and saturated $NaHCO_3$ (30 mL) and stirred for 20 minutes. The organic layer was removed and the aqueous layer was extracted with DCM (2×20 mL). The combined organic extracts were dried and concentrated. The residue was purified by flash LC(10 to 40% EtOAc+0.1% triethylamine in hexane) to afford 1,2,4-trifluoro-5-methanesulfinyl-benzene 43b (0.41 g, 24% yield, HPLC, LC-MS 195.0 (MH)) and 1,2,4-trifluoro-5-methanesulfonyl-benzene 43c (0.63 g, 14%) as white powders.

Step 43C: 4-[1-(2,5-Difluoro-4-methanesulfinyl-phenyl)-piperidin-4-ylideneaminooxy]-piperidine-1-carboxylic acid isopropyl ester (43-1)

2d (0.78 g, 1.76 mmol) and 43b (0.66 g, 3.39 mmol) were combined with diisopropylethylamine (0.91 mL, 5.5 mmol) in DMSO (8 mL) and heated to 120° C. overnight. The mixture was cooled to room temperature and poured into 20 mL of ethyl acetate, washed with water (20 mL) and brine (3×20 mL), dried and concentrated. The residue was purified by flash chromatography (eluent: 50 to 90% of EtOAc+0.1%

158 triethylamine in hexane) to afford 4-[1-(2,5-difluoro-4-methanesulfinyl-phenyl)-piperidin-4-ylideneaminooxy]-piperidine-1-carboxylic acid isopropyl ester 43-1. This material was recrystallized from toluene and hexane to afford 43-1 as a white powder: HPLC, LC-MS 458.1 (MH), $t_R$=6.98 (Method 2). EC50: 58 nM.

Example 44

4-[1-(2,5-DIFLUORO-4-METHANESULFONYLAMINO-PHENYL)-PIPERIDIN-4-YLIDENEAMINOOXY]-PIPERIDINE-1-CARBOXYLIC ACID ISOPROPYL ESTER

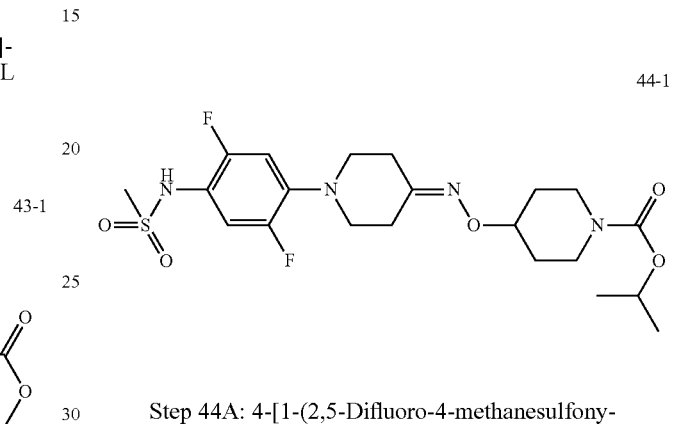

44-1

Step 44A: 4-[1-(2,5-Difluoro-4-methanesulfonylamino-phenyl)-piperidin-4-ylideneaminooxy]-piperidine-1-carboxylic acid isopropyl ester (44-1)

To a solution of 34-1 (49 mg, 0.12 mmol) and triethylamine (17 μL, 0.12 mmol) in 2 mL of DCM, was added mesyl chloride (10 μL, 0.13 mmol). After 2 h, a second equivalent of triethylamine (17 μL, 0.12 mmol) and mesyl chloride (10 μL, 0.13 mmol) was added. After 1 h, the mixture was washed with brine, concentrated and purified on preparative HPLC to give 44-1: LC-MS 489.1 (MH), $t_R$=7.31 (Method 2). EC50: 170 nM.

Example 45

4,5-DIFLUORO-2-METHYL-BENZAMIDE

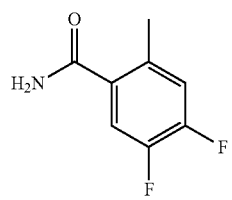

45a

Step 45A: 4,5-Difluoro-2-methyl-benzamide (45a)

To a solution of 4,5-difluoro-3-methylbenzoic acid (0.59 g, 3.4 mmol) in 10 mL of DCM, was added oxalyl chloride (0.5 mL, 5.7 mmol) and DMF (0.01 mL, 0.13 mmol). The mixture was stirred at room temperature for 2 h. It was then concentrated and taken up in THF (7 mL) Ammonium hydroxide (14N, 1 mL, 14 mmol) was added at 0° C. and the mixture was stirred for 30 minutes. The solution was concentrated, dissolved in DCM (2×50 mL) and the combined extracts were washed with brine (75 mL), dried, filtered and evaporated to afford 45a as a white solid (527 mg, 90% yield).

Example 46

4 (5'-METHYLSULFONYL-3'-FLUORO-2,3,5,6-TETRAHYDRO-[1,2']BIPYRIDINYL-4-YLIDENEAMINOOXY)-PIPERIDINE-1-CARBOXYLIC ACID ISOPROPYL ESTER

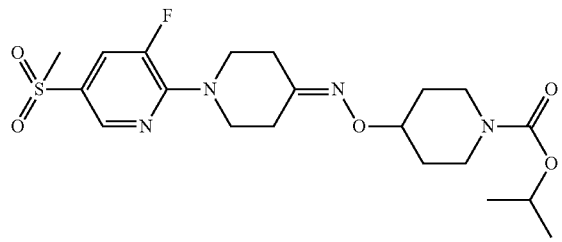

46-1

Step 46A: 4-(5'-Bromo-3'-fluoro-2,3,5,6-tetrahydro-[1,2']bipyridinyl-4-ylideneaminooxy)-piperidine-1-carboxylic acid isopropyl ester (46a)

2d (0.22 g, 0.71 mmol), 3-bromo-6-chloro-5-fluoro-pyridine (0.2 g, 0.95 mmol) and diisopropylethylamine (0.2 mL, 1.2 mmol) in 2 mL of DMSO were heated at 130° C. for 20 h. The mixture was cooled to room temperature and purified by flash LC(0 to 30% EtOAc+0.1% triethylamine in hexane) to afford 46a (92 mg, 28% yield): HPLC, LC-MS 457.1 (MH).

Step 46B: 4,4-(5'-Bromo-3'-fluoro-2,3,5,6-tetrahydro-[1,2]bipyridinyl-4-ylideneaminooxy)-piperidine-1-carboxylic acid isopropyl ester (46-1)

46a (92 mg, 0.2 mmol), sodium methanesulfinate (29 mg, 0.28 mmol), copper iodide (5 mg, 0.03 mmol), L-Proline (6 mg, 0.06 mmol) and sodium hydroxide (3 mg, 0.06 mmol) were combined in 0.6 mL of DMSO and heated at 100° C. for 2 days. The mixture was cooled, poured into water (5 mL) and extracted with EtOAc (5 mL). The EtOAc was evaporated and the residue was purified on preparative TLC(elution with EtOAc) to afford 46-1 as a colorless oil (38 mg, 42% yield): HPLC, LC-MS 457.0 (MH).

The following compounds were made according to this procedure using the corresponding bromo-halo-aryl reagent (the purification was generally done by preparative HPLC instead of preparative TLC):

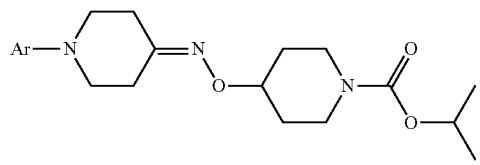

| No. | Ar | MH+ | MW | $t_R$ (Min) | HPLC Gradient | EC50 (nM) |
|---|---|---|---|---|---|---|
| 46-1 | ![5-methylsulfonyl-3-fluoropyridin-2-yl] | 457.1 | 456.5 | 7.10 | Method 2 | 131 |
| 46-2 | ![2-fluoro-5-methylsulfonyl-4-fluorophenyl] | 474.4 | 473.5 | 5.70 | Method 4 | 28 |
| 46-3 | ![5-methylsulfonylpyridin-2-yl] | 439.6 | 438.5 | 7.97 | Method 5 | 614 |
| 46-4 | ![5-methylsulfonylpyrimidin-2-yl] | 440.5 | 439.5 | 8.18 | Method 5 | 157 |

Example 47

4-[1-(4-CYCLOPROPANESULFONYL-2,5-DIFLUORO-PHENYL)-PIPERIDIN-4-YLIDENEAMINOOXY]-PIPERIDINE-1-CARBOXYLIC ACID ISOPROPYL ESTER AND 4-{1-[5-((S)-2-CARBOXY-PYRROLIDIN-1-YL)-4-CYCLOPROPANESULFONYL-2-FLUORO-PHENYL}-PIPERIDIN-4-YLIDENEAMINOOXY]-PIPERIDINE-1-CARBOXYLIC ACID ISOPROPYL ESTER

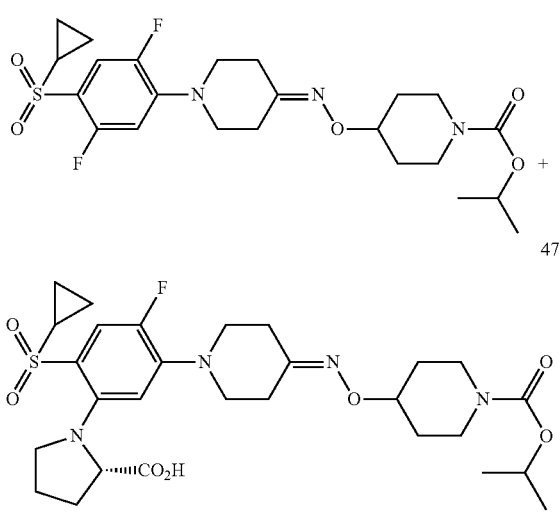

Step 47A: 4-[1-(4-Cyclopropanesulfonyl-2,5-difluoro-phenyl)-piperidin-4-ylideneaminooxy]-piperidine-1-carboxylic acid isopropyl ester (47-1) and 4-{1-[5-((S)-2-carboxy-pyrrolidin-1-yl)-4-cyclopropanesulfonyl-2-fluoro-phenyl]-piperidin-4-ylideneaminooxy}-piperidine-1-carboxylic acid isopropyl ester (47b)

2-40 (25 mg), sodium cyclopropanesulfinate (13 mg, 2 eq), copper iodide (1 mg, 10% mmol), L-Proline (2 mg, 25% mmol) and sodium hydroxide (0.5 mg, 25% mmol) were combined in 0.4 mL of DMSO and heated at 110° C. for 2 days. The mixture was cooled, poured into water and extracted with EtOAc. The EtOAc was evaporated and the residue was purified on preparative HPLC to afford 47-1, LC-MS 500.2 (MH), $t_R$=6.01 (Method 5), EC50: 43 nM and 47b as a side product, LC-MS 595.3 (MH), $t_R$=3.72 (Method 5).

Example 48

4-[1-(2,5-DIFLUORO-4-HYDROXYMETHYL-PHENYL)-PIPERIDIN-4-YLIDENEAMINOOXY]-PIPERIDINE-1-CARBOXYLIC ACID ISOPROPYL ESTER

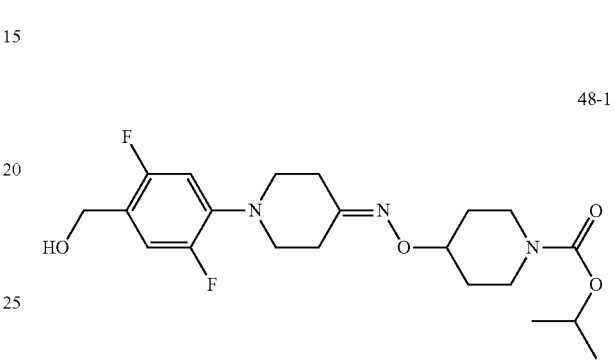

Step 48A: 4-[1-(2,5-Difluoro-4-hydroxymethyl-phenyl)-piperidin-4-ylideneaminooxy]-piperidine-1-carboxylic acid isopropyl ester (48-1)

To a solution of 40 mg of 9-1 (0.09 mmol) and triethylamine (20 µL, 0.13 mmol) in 1 mL of THF at 0° C., was added ethyl chloroformate (12 µL, 0.13 mmol). The mixture was stirred at room temperature for 4 h then added to a stirred suspension of NaBH$_4$ (15 mg, 0.39 mmol) in water (0.5 mL). After 1 h of stirring, the mixture was diluted with aqueous NaHCO$_3$ (4 mL) and extracted with ethyl acetate (2×4 mL). The combined extracts were dried under a stream of nitrogen and the residue was purified by preparative HPLC to afford 48-1: LC-MS 408.1 (MH$^+$-18).

The following compounds were made according to this procedure using the corresponding reducing agent (NaBH$_4$ or NaBD$_4$):

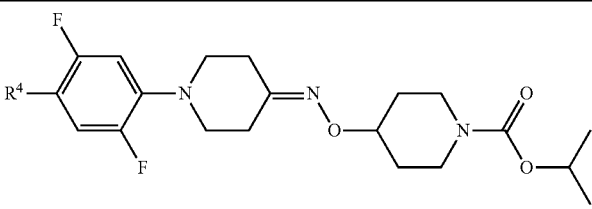

| No. | R⁴ | MH-18 | MW | $t_R$ (Min) | HPLC Gradient | EC50 (nM) |
|---|---|---|---|---|---|---|
| 48-1 | HO–CH₂–⌇ | 408.2 | 425.5 | 7.10 | Method 2 | 9 |
| 48-2 | D,D HO–C–⌇ | 410.1 | 427.5 | 7.11 | Method 2 | 18 |

Example 49

4-[1-(2,5-DIFLUORO-4-METHOXYMETHYL-PHENYL)-PIPERIDIN-4-YLIDENEAMINOOXY]-PIPERIDINE-1-CARBOXYLIC ACID ISOPROPYL ESTER

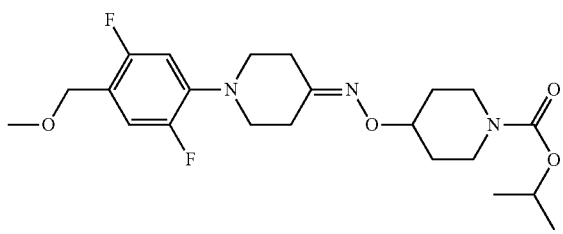

49-1

Step 49A: 4-[1-(2,5-Difluoro-4-methoxymethyl-phenyl)-piperidin-4-ylideneaminooxy]-piperidine-1-carboxylic acid isopropyl ester (49-1)

NaH (60%, 10 mg, 0.25 mmol) was added to a solution of 48-1 (36 mg, 0.085 mmol) in 0.3 mL of DMF at 0° C. After 10 minutes, methyl iodide in MTBE (2M, 0.6 mL, 1.2 mmol) was added and the reaction was stirred at room temperature for 2 h. The mixture was quenched with water (2 mL) and extracted with 1 mL of ethyl acetate. The organic extract was dried under a stream of nitrogen and the residue was purified by preparative TLC(eluent: 30% EtOAc in hexane) to afford 49-1: LC-MS 408.1 (MH$^+$-MeOH), $t_R$=8.77 (Method 2). EC50: 265 nM.

Example 50

4-{1-[2,5-DIFLUORO-4-(1-HYDROXY-ETHYL)-PHENYL]-PIPERIDIN-4-YLIDENEAMINOOXY}-PIPERIDINE-1-CARBOXYLIC ACID ISOPROPYL ESTER

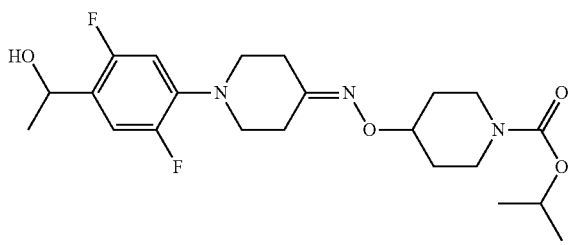

50-1

Step 50A: 4-[1-(4-Acetyl-2,5-difluoro-phenyl)-piperidin-4-ylideneaminooxy]-piperidine-1-carboxylic acid isopropyl ester (50a)

Compound 2d (0.22 g, 0.78 mmol), 1-(2,4,5-trifluoro-phenyl)-ethanone (0.22 mL), DIEA (0.22 mL, 1.33 mmol), and DMSO (2 mL) were combined and heated at 130° C. for 20 h. The mixture was cooled to room temperature and purified by flash chromatography (eluent: 10 to 40% EtOAc+0.1% triethylamine in hexane) to afford 211 mg (62% yield) of 4-[1-(4-acetyl-2,5-difluoro-phenyl)-piperidin-4-ylideneaminooxy]-piperidine-1-carboxylic acid isopropyl ester 50a: LC-MS 438.0 (MH$^+$).

Step 50B: 4-{1-[2,5-Difluoro-4-(1-hydroxy-ethyl)-phenyl]-piperidin-4-ylideneaminooxy}-piperidine-1-carboxylic acid isopropyl ester (50-1)

NaBH$_4$ (0.15 g, 3.9 mmol) was added at 0° C. to a stirred solution of 50a (0.15 g, 0.34 mmol) in 5 mL of methanol. After 1 h, the mixture was diluted with 10 mL of saturated NaHCO$_3$ and stirred for 20 minutes. The mixture was poured into ethyl acetate (25 mL), washed twice with brine (25 mL), dried and concentrated under vacuum. The residue was purified on an AS-H column (elution with 5% EtOH+0.1% triethylamine in hexane) to afford the 2 enantiomers of 4-{1-[2,5-difluoro-4-(1-hydroxy-ethyl)-phenyl]-piperidin-4-ylideneaminooxy}-piperidine-1-carboxylic acid isopropyl ester 50-1, LC-MS 422.2 (MFE-18), $t_R$=6.45 (Method 2). EC50: 48 nM. 78 mg of the first enantiomer and 46 mg of the second enantiomer were obtained.

Example 51

4-(3'-FLUORO-5'-[1,2,4]TRIAZOL-1-Yl-2,3,5,6-TETRAHYDRO-[1,2]BIPYRIDINYL-4-YLIDENE-AMINOOXY)-PIPERIDINE-1-CARBOXYLIC ACID ISOPROPYL ESTER

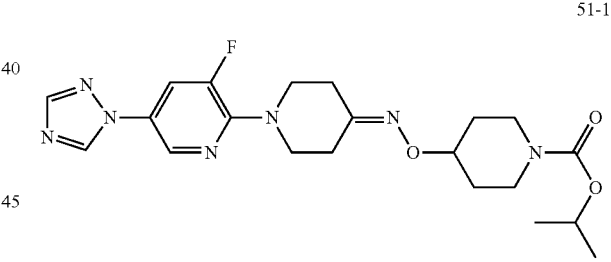

51-1

Step 51A: 4-(3'-Fluoro-5'-[1,2,4]triazol-1-yl-2,3,5,6-tetrahydro-[1,2]bipyridinyl-4-ylideneaminooxy)-piperidine-1-carboxylic acid isopropyl ester (51-1)

46a (30 mg, 0.07 mmol), 1,2,4-triazole (0.1 mmol), copper iodide (12 mg, 0.063 mmol) and trans-1,2-diaminocyclohexane (12 µL, 0.07 mmol) were combined in DMSO (0.5 mL) and heated at 100° C. for 2 days. The mixture was cooled to room temperature, diluted with water (2 mL) and extracted with ethyl acetate (2 mL). The organic layer was concentrated under a stream of nitrogen and the residue was purified on preparative HPLC to afford 51-1: LC-MS 446.2 (MH).

The following compounds were made according to this procedure using the corresponding starting material (46a or 2-17) and the corresponding nucleophile (azole or pyrrolidin-2-one):

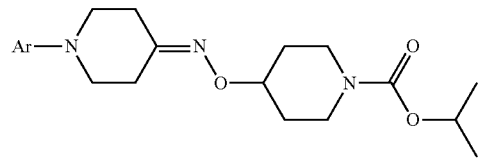
| No. | Ar | MH+ | MW | t_R (Min) | HPLC Gradient | EC50 (nM) |
|---|---|---|---|---|---|---|
| 51-1 | | 446.2 | 445.5 | 5.29 | Method 5 | 327 |
| 51-2 | | 445.2 | 444.5 | 6.10 | Method 5 | 558 |
| 51-3 | | 462.4 | 461.5 | 5.35 | Method 4 | 401 |
| 51-4 | | 429.1 | 428.5 | 4.79 | Method 5 | 735 |
| 51-5 | | 428.3 | 427.5 | 5.53 | Method 4 | 96%* |
| 51-6 | | 445.4 | 444.5 | 4.78 | Method 4 | 98%* |
*% values mean stimulation in % at 10 μM.

Example 52

4-[1-(3-FLUORO-4-HYDROXYMETHYL-PHENYL)-PIPERIDIN-4-YLIDENEAMINOOXY]-PIPERIDINE-1-CARBOXYLIC ACID ISOPROPYL ESTER

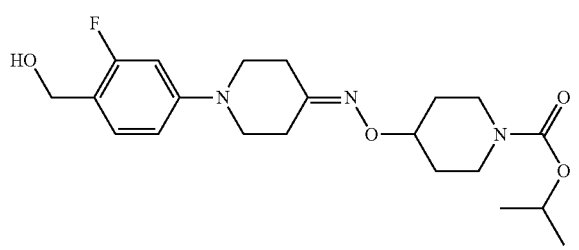

52-1

Step 52A: 4-[1-(3-Fluoro-4-hydroxymethyl-phenyl)-piperidin-4-ylideneaminooxy]-piperidine-1-carboxylic acid isopropyl ester (52-1)

NaBH$_4$ (20 mg, 0.52 mmol) was added to a stirred solution of 2-20 (0.047 mmol) in methanol (0.4 mL). The mixture was stirred for 1 h and quenched with 3 mL of aqueous NaHCO$_3$. It was then extracted with ethyl acetate (2×2 mL) and the combined extracts were concentrated under a stream of nitrogen, taken up with methanol and purified on preparative HPLC to afford 52-1: LC-MS 390.1 (MH-18).

The following compounds were made according to this procedure using the corresponding starting material aldehyde (2-20, 2-22 or 2-23):

Example 53

4-(3'-FLUORO-5'-HYDROXYMETHYL-2,3,5,6-TETRAHYDRO-[1,2]BIPYRIDINYL-4-YLIDENEAMINOOXY)-PIPERIDINE-1-CARBOXYLIC ACID ISOPROPYL ESTER

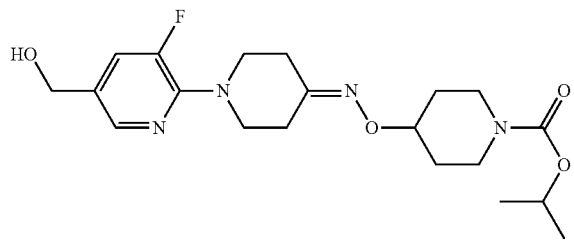

53-1

Step 53A: 6-Chloro-5-fluoro-pyridine-3-carbaldehyde (53a)

Butyl lithium (2.5 M in hexane, 2.5 mL, 6.3 mmol) was added to 5-bromo-2-chloro-3-fluoro-pyridine (1 g, 4.75 mmol) in 10 mL of ether at −78° C. After 10 minutes, DMF (5 mL) was added and the mixture was warmed to room temperature over 1 h. The mixture was poured into 20 mL of EtOAc and the mixture was washed with water (20 mL) and brine (20 mL), dried over magnesium sulfate and concentrated to afford the crude 53a (0.92 g) as a brown oil: LC-MS 160.0 (MH$^+$).

Step 53B: 4-(3'-Fluoro-5'-formyl-2,3,5,6-tetrahydro-[1,2]bipyridinyl-4-ylideneaminooxy)-piperidine-1-carboxylic acid isopropyl ester (53b)

2d (0.45 g, 1.6 mmol), 6-chloro-5-fluoro-pyridine-3-carbaldehyde 53a (0.6 g, 3.76 mmol) and diisopropylethylamine (0.75 mL, 4.5 mmol) were combined in 5 mL of DMSO and

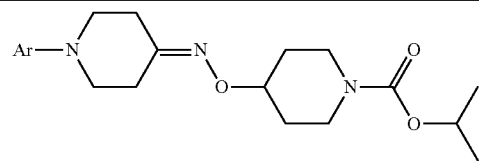

| No. | Ar | MH+ | MW | t$_R$ (Min) | HPLC Gradient | EC50 (nM) |
|---|---|---|---|---|---|---|
| 52-1 | HO—CH$_2$—C$_6$H$_3$(F)— | 390.1 | 407.5 | 4.34 | Method 4 | >10000 |
| 52-2 | (F)(HO-CH(CH$_3$))-C$_6$H$_2$(F)— | 422.2 | 439.5 | 6.45 | Method 2 | 71 |
| 52-3 | HO-CH$_2$-C$_6$H$_3$(F)— | 408.2 | 407.5 | 5.57 | Method 2 | 128 | heated at 60° C. for 18 h. The mixture was poured into ethyl acetate (30 mL), washed with water (2×20 mL) and brine (2×20 mL) and concentrated to give the crude 53b.

Step 53C: 4-(3'-Fluoro-5'-hydroxymethyl-2,3,5,6-tetrahydro-[1,2']bipyridinyl-4-ylideneaminooxy)-piperidine-1-carboxylic acid isopropyl ester (53-1)

The crude 53b was taken up with methanol (10 mL), cooled in an ice bath and treated with NaBH$_4$ (0.52 g, 13.7 mmol). The mixture was stirred for 2 h and treated with aqueous NaHCO$_3$ (10 mL). The mixture was extracted with 40 mL of ethyl acetate, washed with brine (3×30 mL) and concentrated under vacuum. The residue was purified by flash chromatography (eluent: 20 to 70% ethyl acetate+0.1% triethylamine in hexane) to afford 296 mg (44% yield) of 53-1: LC-MS 409.2 (MH$^+$), t$_R$=5.59 (Method 2). EC50: 224 nM.

Example 54

4-[3'-FLUORO-5'-(4-METHYL-PYRAZOL-1-YL-METHYL)-2,3,5,6-TETRAHYDRO-[1,2]BIPYRIDINYL-4-YLIDENEAMINOOXY]-PIPERIDINE-1-CARBOXYLIC ACID ISOPROPYL ESTER 54-1

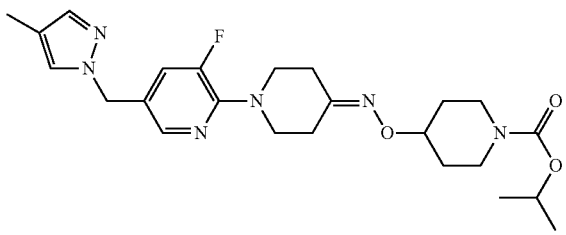

Step 54A: 4-[3'-Fluoro-5'-(4-methyl-pyrazol-1-ylmethyl)-2,3,5,6-tetrahydro-[1,2]bipyridinyl-4-ylideneaminooxy]-piperidine-1-carboxylic acid isopropyl ester (54-1)

Mesyl chloride (96 µL, 1.2 mmol) was added to an ice cooled solution of 53-1 (0.25 g, 0.62 mmol) and triethylamine (0.26 mL, 1.9 mmol) in 5 mL of DCM. After 2 h, the mixture was diluted with DCM (30 mL), washed with brine (15 mL) and water (15 mL), dried and concentrated under vacuum. The residue was taken up in DMF and added to a mixture of 4-methyl-1H-pyrazole (0.8 mmol) and sodium hydride (30 mg, 60%, 0.8 mmol) in DMF which had been pre-stirred for 5 minutes. The mixture was heated to 100° C. for 2 h then allowed to cool down to room temperature, diluted with water (1.5 mL) and extracted with DCM (2 mL). The organic layer was concentrated under a stream of nitrogen, the residue was taken up in methanol and the mixture was purified by HPLC to afford 54-1: LC-MS 473.2 (MH$^+$).

The following compounds were made according to this procedure using the corresponding nucleophile:

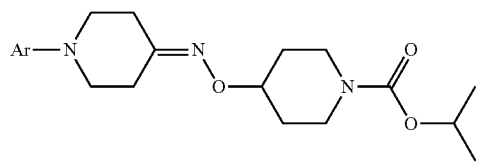

| No. | Ar | MH+ | MW | t$_R$ (Min) | HPLC Gradient | EC50 (nM) |
|---|---|---|---|---|---|---|
| 54-1 | ![pyrazole-methyl-pyridine-F] | 473.2 | 472.5 | 5.82 | Method 5 | 445 |
| 54-2 | ![triazole-methyl-pyridine-F] | 460.2 | 459.5 | 5.00 | Method 5 | 1058 |
| 54-3 | ![pyrazole-methyl-pyridine-F] | 460.2 | 459.5 | 5.73 | Method 5 | 765 |

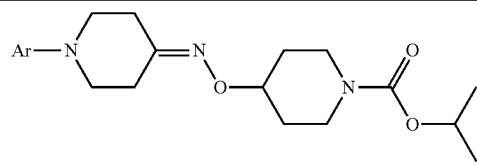

| No. | Ar | MH+ | MW | $t_R$ (Min) | HPLC Gradient | EC50 (nM) |
|---|---|---|---|---|---|---|
| 54-4 | (pyrrolidinone-methyl-fluoropyridinyl) | 476.4 | 475.5 | 6.12 | Method 4 | 93%* |
| 54-5 | (methyl-tetrazol-2-yl-methyl-fluoropyridinyl) | 475.1 | 474.5 | 5.11 | Method 5 | 75%* |
| 54-6 | (methyl-tetrazol-1-yl-methyl-fluoropyridinyl) | 475.3 | 474.5 | 5.63 | Method 5 | 1147 |
| 54-7 | (methylsulfonylmethyl-fluoropyridinyl) | 471.2 | 470.5 | 4.99 | Method 5 | 484 |

*% values mean stimulation in % at 10 μM.

Example 55

4-(3'-FLUORO-5'-HYDROXYMETHYL-6'-METHYL-2,3,5,6-TETRAHYDRO-[1,2]BIPYRIDINYL-4-YLIDENEAMINOOXY)-PIPERIDINE-1-CARBOXYLIC ACID ISOPROPYL ESTER

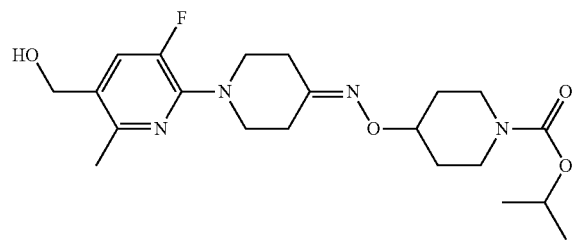

55-1

Step 55A: (2,6-Dichloro-5-fluoro-pyridin-3-yl)-methanol (55a)

To a solution of 2,6-dichloro-5-fluoro-nicotinic acid (1.11 g, 5.29 mmol) in 20 mL of THF at 0° C., was added BH₃.THF (1M, 8 mL, 8 mmol) and the mixture was stirred at room temperature for 5 h. K₂CO₃ (4 g) was added and the mixture was stirred for 2 h, filtered and concentrated. The residue was purified by flash chromatography (eluent: 10 to 50% ethyl acetate+0.1% triethylamine in hexane) to afford 55a as a white solid (0.57 g, 55% yield).

Step 55B: 4-(6'-Chloro-3'-fluoro-5'-hydroxymethyl-2,3,5,6-tetrahydro-[1,2']bipyridinyl-4-ylideneaminooxy)-piperidine-1-carboxylic acid isopropyl ester (55b)

2d (0.48 g, 1.7 mmol), 55a (0.36 g, 1.86 mmol) and diisopropylethylamine (0.31 mL, 1.9 mmol) were combined in 5 mL of DMSO and heated at 130° C. for 2 days. The mixture was cooled, poured into ethyl acetate (15 mL), washed with water (10 mL) and brine (10 mL), dried and concentrated. The residue was purified by flash chromatography (eluent: 10 to 50% ethyl acetate+0.1% triethylamine in hexane) to afford 55b as a yellow oil (0.22 g, 30% yield): LC-MS 425.1 (MH⁺).

Step 55C: 4-(3'-Fluoro-5'-hydroxymethyl-6'-methyl-2,3,5,6-tetrahydro-[1,2']bipyridinyl-4-ylideneaminooxy)-piperidine-1-carboxylic acid isopropyl ester (55-1)

55b (30 mg, 0.068 mmol), trimethylboroxine (25 mg, 0.2 mmol) and potassium carbonate (50 mg, 0.36 mmol) were combined in 0.5 mL of dioxane and heated at 100° C. for 20 h. The mixture was cooled, concentrated under a stream of nitrogen, diluted with water (2 mL) and extracted with ethyl acetate (2×2 mL). The combined extracts were dried under a stream of nitrogen and the residue was purified by preparative HPLC to afford 55-1 as a colorless oil: LC-MS 423.1 (MH⁺), $t_R$=5.95 (Method 2). EC50: 206 nM.

Example 56

4-[1-(3,6-DICHLORO-5-HYDROXYMETHYL-PYRAZIN-2-YL)-PIPERIDIN-4-YLIDENEAMINOOXY]-PIPERIDINE-1-CARBOXYLIC ACID ISOPROPYL ESTER

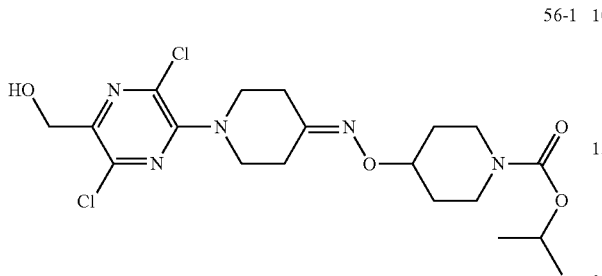

56-1

Step 56A: 3,5,6-Trichloro-pyrazine-2-carboxylic acid methyl ester (56a)

Methyl 3-amino-5,6-dichloro-2-pyrazinecarboxylate (2.6 g, 11.8 mmol), $CuCl_2$ (2.37 g, 17.6 mmol) and iso-amylnitrite (2.07 g, 17.7 mmol) were combined in 100 mL of acetonitrile and heated at 65° C. for 18 h. The solution was cooled, acidified with 2N HCl (50 mL), diluted with water (100 mL), and extracted with DCM (3×30 mL). The combined extracts were dried, concentrated and the residue was purified by flash chromatography (eluent: 10 to 50% EtOAc+0.1% triethylamine in hexane) to afford 56a (1.21 g, 42% yield).

Step 56B: 3,6-Dichloro-5-[4-(1-isopropoxycarbonyl-piperidin-4-yloxyimino)-piperidin-1-yl]-pyrazine-2-carboxylic acid methyl ester (56b)

2d (99 mg, 0.35 mmol), 56a (92 mg, 0.35 mmol) and diisopropylethylamine (0.1 mL, 0.6 mmol) were combined in 0.5 mL of DMSO and stirred at room temperature for 18 h. The mixture was diluted with aqueous $NaHCO_3$ (5 mL) and extracted with EtOAc (5 mL). The organic layer was concentrated under vacuum to afford the crude 56b. 20 mg of this crude material was purified by preparative HPLC to afford 56b: LC-MS 488.3 ($MH^+$).

Step 56C: 3,6-Dichloro-5-[4-(1-isopropoxycarbonyl-piperidin-4-yloxyimino)-piperidin-1-yl]-pyrazine-2-carboxylic acid (56c)

The crude 56b obtained in the previous step was taken up with THF (1 mL) and 1N NaOH (1 mL) and heated to 50° C. for 3 h. The mixture was cooled, diluted with 5 mL of 1N HCl and extracted with EtOAc (3×5 mL). The combined extracts were dried and concentrate to afford 0.13 g of crude 56c. 25 mg of this material was purified by preparative HPLC to afford 56c: LC-MS 474.7 ($MH^+$).

Step 56D: 4-[1-(3,6-Dichloro-5-hydroxymethyl-pyrazin-2-yl)-piperidin-4-ylideneaminooxy]-piperidine-1-carboxylic acid isopropyl ester (56-1)

The crude 56c obtained in the previous step was combined with triethylamine (50 µL, 0.36 mmol) in 2 mL of THF and treated at 0° C. with ethyl chloroformate (30 µL, 0.31 mmol). The mixture was stirred at room temperature for 4 h then it was added to a stirred suspension of sodium borohydride (32 mg, 0.84 mmol) in water and the stirring was continued for 3 h. The mixture was quenched with aqueous $NaHCO_3$ (5 mL) and water (5 mL) and extracted with EtOAc (3×5 mL). The combined extracts were dried and concentrated and the residue was purified by reparative TLC(eluent: EtOAc) to afford 56-1: LC-MS 442.0 ($MH^+$-18), $t_R$=7.43 (Method 2). EC50: 35 nM.

Example 57

4-[1-(5-METHYLCARBAMOYL-4-TRIFLUOROMETHYL-PYRIMIDIN-2-YL)-PIPERIDIN-4-YLIDENEAMINOOXY]-PIPERIDINE-1-CARBOXYLIC ACID ISOPROPYL ESTER

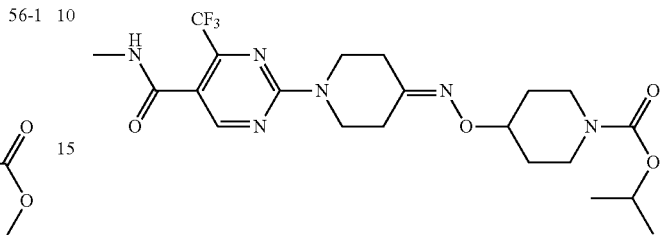

57-1

Step 57A: 2-[4-(1-Isopropoxycarbonyl-piperidin-4-yloxyimino)-piperidin-1-yl]-4-trifluoromethyl-pyrimidine-5-carboxylic acid methyl ester (57a)

2-Chloro-4-trifluoromethyl-pyrimidine-5-carboxylic acid methyl ester (0.2 g, 0.78 mmol), 2d (0.2 g, 0.71 mmol), and diisopropylethylamine (0.2 mL, 1.2 mmol) were combined in 2 mL of DMSO and stirred at 110° C. for 18 h. The mixture was cooled to room temperature, diluted with aqueous $NaHCO_3$ (5 mL) and extracted with EtOAc (5 mL). The organic layer was concentrated under vacuum to afford the crude 57a.

Step 57B: 2-[4-(1-Isopropoxycarbonyl-piperidin-4-yloxyimino)-piperidin-1-yl]-4-trifluoromethyl-pyrimidine-5-carboxylic acid (57b)

The crude 57a obtained in the previous step was taken up with THF (3 mL) and 1N NaOH (0.6 mL) and heated to 50° C. for 2 h. The mixture was cooled, diluted with 10 mL of 1N HCl and extracted with DCM (3×5 mL). The combined extracts were dried and concentrate to afford the crude 57b.

Step 57C: 4-[1-(5-Methylcarbamoyl-4-trifluoromethyl-pyrimidin-2-yl)-piperidin-4-ylideneaminooxy]-piperidine-1-carboxylic acid isopropyl ester (57-1)

Half of the crude 57b was combined with methylamine (0.06 mmol), HOBT (7 mg, 0.06 mmol) and EDC(10 mg, 0.05 mmol) in 1 mL of DCM. The mixture was stirred at room temperature for 18 h, washed with aqueous $NaHCO_3$ and concentrated. The residue was purified by preparative HPLC to afford 57-1: LC-MS 487.3 ($MH^+$), $t_R$=5.20 (Method 5).

Example 58

4-[1-(5-HYDROXYMETHYL-4-TRIFLUROMETHYL-PYRIMIDIN-2-YL)-PIPERIDIN-4-YLIDENEAMINOOXY]-PIPERIDINE-1-CARBOXYLIC ACID ISOPROPYL ESTER

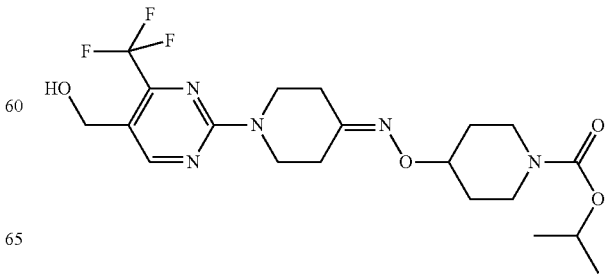

58-1

Step 58A: 4-[1-(5-Hydroxymethyl-4-trifluoromethyl-pyrimidin-2-yl)-piperidin-4-ylideneaminooxy]-piperidine-1-carboxylic acid isopropyl ester (58-1)

Half of the crude 57b was combined with triethylamine (50 μL, 0.36 mmol) in 2 mL of THF and treated at 0° C. with ethyl chloroformate (30 μL, 0.31 mmol). The mix was stirred at room temperature for 4 h then it was added to a stirred suspension of sodium borohydride (32 mg, 0.84 mmol) in water and the stirring was continued for 3 h. The mixture was quenched with aqueous NaHCO$_3$ (5 mL) and water (5 mL) and extracted with EtOAc (3×5 mL). The combined extracts were dried and concentrated and the residue was purified by preparative HPLC to afford 58-1: LC-MS 460.1 (MH$^+$), $t_R$=7.49 (Method 2).

Example 59

4-[1-(6-METHANESULFONYL-5,6,7,8-TETRAHYDRO-PYRIDO[4,3-D]PYRIMIDIN-2-Yl)-PIPERIDIN-4-YLIDENEAMINOOXY]-PIPERIDINE-1-CARBOXYLIC ACID ISOPROPYL ESTER

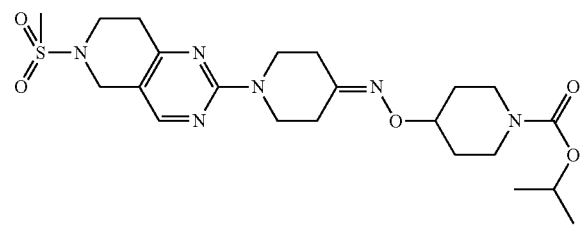

59-1

Step 59A: 2-Bromo-6-methanesulfonyl-5,6,7,8-tetrahydro-pyrido[4,3-d]pyrimidine (59a)

To a mixture of 2-bromo-5,6,7,8-tetrahydro-pyrido[4,3-d]pyrimidine (0.1 g, 0.47 mmol) and triethylamine (0.2 mL) in 2 mL of DCM, at 0° C., was added MsCl (0.1 mL). The mixture was stirred at room temperature for 1 h then diluted with 20 mL of DCM and washed with a mixture of saturated NaHCO$_3$ (15 mL) and water (15 mL). The DCM was evaporated to afford the crude 59a.

Step 59B: 4-[1-(6-Methane sulfonyl-5,6,7,8-tetrahydro-pyrido[4,3-d]pyrimidin-2-yl)-piperidin-4-ylideneaminooxy]-piperidine-1-carboxylic acid isopropyl ester (59b)

Crude 59a, 2d (51 mg) and diisopropylethylamine (0.07 mL) in 0.4 mL of DMSO was heated at 100° C. for 3 h. The mixture was cooled to room temperature, diluted with EtOAc (5 mL) and washed with brine (3×5 mL). The organic layer was dried, concentrated and purified by preparative HPLC to afford 59b: LC-MS 495.4 (MH$^+$), $t_R$=5.11 (Method 4). EC50: 328 nM.

Example 60

4-[1-(6-FLUORO-3H-BENZOIMIDAZOL-5-Yl)-Piperidin-4-YLIDENEAMINOOXY]-PIPERIDINE-1-CARBOXYLIC ACID ISOPROPYL ESTER

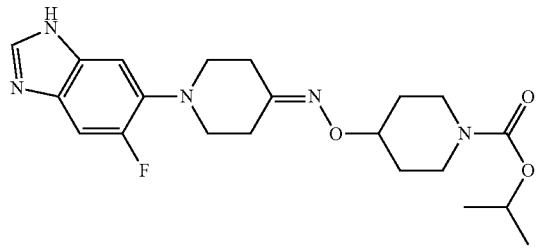

60-1

Step 60A: 4-[1-(5-Amino-2-fluoro-4-nitro-phenyl)-piperidin-4-ylideneaminooxy]-piperidine-1-carboxylic acid isopropyl ester (60a)

2d (0.12 g), 5-chloro-4-fluoro-2-nitro-phenylamine (0.1 g) and diisopropylethylamine (0.1 mL) were combined in 1.2 mL of DMSO and stirred at 110° C. for 3 days. The mixture was cooled to room temperature, diluted with aqueous NaHCO$_3$ (5 mL) and extracted with EtOAc (5 mL). The organic layer was concentrated under vacuum and purified on column chromatography (eluent: 10 to 50% EtOAc in hexane+0.1% triethylamine) to yield 60a.

Step 60B: 4-[1-(4,5-Diamino-2-fluoro-phenyl)-piperidin-4-ylideneaminooxy]-piperidine-1-carboxylic acid isopropyl ester (60b)

60a obtained in the previous step was dissolved in acetonitrile (4 mL) and treated with Na$_2$S$_2$O$_3$ (0.42 g) in 1N NaOH (4 mL). After 20 h, the mixture was poured in water and extracted with EtOAc twice. The combined extracts were dried and concentrated to afford the crude 60b.

Step 60C: 4-[1-(6-Fluoro-3H-benzoimidazol-5-yl)-piperidin-4-ylideneaminooxy]-piperidine-1-carboxylic acid isopropyl ester (60-1)

The crude 60b was combined with TsOH.H$_2$O (50 mg) in 2 mL of DMF and treated with HC(OMe)$_3$ (1 mL). The mixture was stirred for 16 h then concentrated and purified on preparative HPLC to afford 60-1: LC-MS 418.4 (MH$^+$), $t_R$=4.64 (Method 4).

Example 61

4-[1-(2-FLUORO-4-METHANESULFONYL-PHENYL)-PIPERIDIN-(3Z)-YLIDENEAMINOOXY]-PIPERIDINE-1-CARBOXYLIC ACID ISOPROPYL ESTER

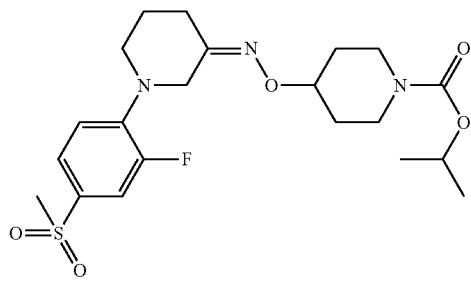

61-1

Step 61A: 4-[Piperidin-(3Z)-ylideneaminooxy]-piperidine-1-carboxylic acid isopropyl ester (61a)

3-Boc-piperidinone (0.83 mmol) and NaOAc.3H$_2$O (30 mg) were combined in 1 mL of ethanol and heated to 65° C. for 15 minutes. 2b (167 mg, 0.83 mmol) was added and the mixture was heated at 65° C. for 18 h. The mixture was concentrated, taken up with DCM (5 mL), washed with aqueous NaHCO$_3$ (5 mL) and the organic layer was separated and treated with TFA (5 mL). The mixture was stirred at room temperature for 45 minutes, concentrated, diluted with NaHCO$_3$ (8 mL) and extracted with EtOAc (2×5 mL). The extracts were dried and concentrated to afford the crude 61a: LC-MS 284.2 (MH$^+$).

Step 61B: 4-[1-(2-Fluoro-4-methanesulfonyl-phenyl)-piperidin-(3Z)-ylideneaminooxy]-piperidine-1-carboxylic acid isopropyl ester (61-1)

61a and 3,4-difluoro methanesulfonylbenzene (30 mg, 0.16 mmol) were combined with diisopropylethylamine (0.07 mL) in 0.3 mL of DMSO and heated to 110° C. for 3 days. The mixture was cooled to room temperature, diluted with aqueous NaHCO$_3$ (5 mL) and extracted with EtOAc (5 mL). The organic layer was concentrated under vacuum and the residue was purified on preparative HPLC to afford 61-1: LC-MS 456.2 (MH$^+$).

The following compounds were made according to this procedure using the corresponding ketone:

Example 62

2-CHLORO-5-ETHYL-PYRIDINE

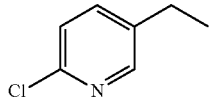

62c

Step 62A: Benzyl-((E)-but-1-enyl)-amine (62a)

To benzylamine (5.46 mL, 50 mmol), at 0° C., was added butyraldehyde (4.51 mL, 50 mmol). The mixture was warmed to room temperature and KOH (1.5 g) was added. The mix was stirred at room temperature for 15 minutes, the water was removed and 0.5 g of KOH was added. The mixture was stirred at room temperature overnight and filtered to remove the KOH to yield 6 g (74%) of 62a.

Step 62B: N-Benzyl-N-((E)-but-1-enyl)-acetamide (62b)

To 62a (3.22 g, 20 mmol) in 10 mL of toluene, was added triethylamine (2.79 mL, 20 mmol). The mixture was cooled to 0° C. and acetic anhydride (1.89 mL, 20 mmol) was added dropwise. The mixture was warmed to room temperature and stirred overnight. It was then concentrated on high vacuum to give crude 62b.

| No. | RR'C=N—O— | MH+ | MW | $t_R$ (Min) | HPLC Gradient | EC50 (nM) |
|---|---|---|---|---|---|---|
| 61-1 | | 456.2 | 455.5 | 5.61 Mixture E/Z | Method 5 | >10000 |
| 61-2 | | 442.3 | 441.5 | 5.34 / 5.45 (E/Z or Z/E) | Method 4 | 1153/542 |
| 61-3 | | 428.3 | 427.5 | 5.37 | Method 4 | 161 |

Step 62C: 2-Chloro-5-ethyl-pyridine (62c)

To DMF (3.8 mL) at 5° C., was added POCl₃ (1.4 mL) dropwise. After 5 minutes, 62b (1 g, 4.9 mmol) was added dropwise in 2 mL of DMF. The mixture was heated to 100° C. overnight. The mixture was allowed to cool to room temperature and was added dropwise to 50 mL of 1N HCl. The solution was extracted 3 times with ethyl acetate. The combined organic layer was dried, evaporated, then purified by column chromatography (eluent: 0 to 30% EtOAc in hexane) to give 0.13 g of 62c (19% yield).

Example 63

1-(2-FLUORO-4-METHANESULFONYL-PHENYL)-PIPERIDIN-4-ONE O-(3,4,5,6-TETRAHYDRO-2H-[1,2]BIPYRIDINYL-4-YL)-OXIME

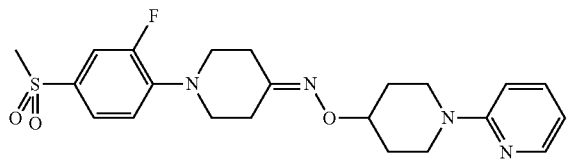

63-1

Step 63A: 1-(2-Fluoro-4-methanesulfonyl-phenyl)-piperidin-4-one O-piperidin-4-yl-oxime (63a).

To a solution of 1-1 (1.88 g, 4 mmol) in 30 mL of DCM, was added TFA (3 mL, 40 mmol) and the reaction mixture was stirred at room temperature for 3 h. It was quenched with saturated NaHCO₃, extracted with DCM 3 times, dried and concentrated to give 1.37 g (3.7 mmol) of 63a.

Step 63B: 1-(2-Fluoro-4-methanesulfonyl-phenyl)-piperidin-4-one O-(3,4,5,6-tetrahydro-2H-[1,2']bipyridinyl-4-yl)-oxime (63-1).

30 mg of 63a (0.08 mmol), diisopropylethylamine (75 µL, 0.43 mmol), DMSO (0.3 mL) and 2-fluoropyridine (11.7 mg, 0.12 mmol) were combined and heated to 120° C. overnight. The mixture was diluted with methanol and purified on preparative HPLC to give 63-1: LC-MS 447.4 (MH⁺).

The following compounds were made according to this procedure by displacement of the corresponding aryl halide (fluoro, chloro, bromo).

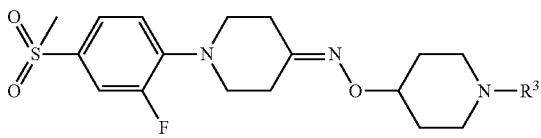

| No. | R³ | MH+ | MW | $t_R$ (Min) | HPLC Gradient | EC50 (nM) |
|---|---|---|---|---|---|---|
| 63-1 | 2-pyridyl | 447.4 | 446.5 | 5.49 | Method 5 | 459 |
| 63-2 | 6-methyl-2-pyridyl | 461.2 | 460.6 | 5.84 | Method 5 | 1253 |
| 63-3 | 3-methyl-2-pyridyl | 460.9 | 460.6 | 6.06 | Method 5 | >10000 |
| 63-4 | 4-pyridyl | 447.3 | 446.5 | 4.82 | Method 2 | >10000 |
| 63-5 | 2-chloropyrimidin-4-yl | 482.1 | 482.0 | 5.20 | Method 5 | >10000 |

-continued
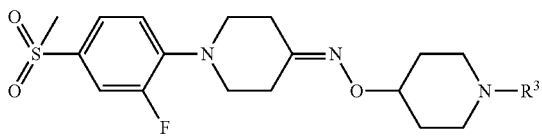
| No. | R³ | MH+ | MW | t_R (Min) | HPLC Gradient | EC50 (nM) |
|---|---|---|---|---|---|---|
| 63-6 | 4-Cl-pyrimidin-2-yl | 482.5 | 482.0 | 6.25 | Method 5 | 1344 |
| 63-7 | thiazol-2-yl | 452.9 | 452.6 | 5.22 | Method 5 | 447 |
| 63-8 | pyrimidin-2-yl | 448.1 | 447.5 | 5.23 | Method 5 | 238 |
| 63-9 | 5-ethyl-pyrimidin-2-yl | 475.6 | 475.6 | 6.13 | Method 5 | 47 |
| 63-10 | 4-CF₃-pyridin-2-yl | 515.1 | 514.5 | 6.65 | Method 5 | >10000 |
| 63-11 | 4-CF₃-pyrimidin-2-yl | 515.7 | 515.5 | 6.51 | Method 5 | >10000 |
| 63-12 | 4-methyl-pyridin-2-yl | 462.0 | 460.6 | 5.69 | Method 5 | 1755 |
| 63-13 | 4-CF₃-6-methyl-pyridin-2-yl | 528.8 | 528.6 | 7.12 | Method 5 | 1493 |
| 63-14 | 5-CF₃-pyridin-2-yl | 515.5 | 514.5 | 6.57 | Method 5 | 495 |
| 63-15 | 6-CF₃-pyridin-2-yl | 514.4 | 514.5 | 6.57 | Method 5 | >10000 |

-continued

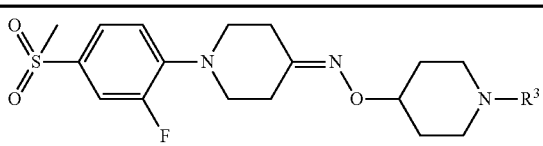

| No. | R³ | MH+ | MW | t_R (Min) | HPLC Gradient | EC50 (nM) |
|---|---|---|---|---|---|---|
| 63-16 | 4-methylpyrimidin-2-yl | 462.0 | 461.6 | 6.04 | Method 5 | 765 |
| 63-17 | 4-methylthiazol-2-yl | 467.3 | 466.6 | 5.77 | Method 5 | >10000 |
| 63-18 | 4,6-dimethylpyrimidin-2-yl | 476.1 | 475.6 | 6.48 | Method 5 | >10000 |
| 63-19 | 5-bromopyrimidin-2-yl | 525.9 | 526.4 | 6.54 | Method 5 | 77 |
| 63-20 | 5-bromopyridin-2-yl | 525.0 | 525.4 | 6.71 | Method 5 | 387 |
| 63-21 | methyl pyrimidine-5-carboxylate-2-yl | 506.1 | 505.6 | 7.63 | Method 2 | 260 |
| 63-22 | 2-fluoro-4-(methylsulfonyl)phenyl | 542.1 | 541.6 | 7.38 | Method 2 | 397 |
| 63-23 | 5-cyanopyridin-2-yl | 472.4 | 471.5 | 5.49 | Method 4 | 1302 |
| 63-24 | 5-chloropyridin-2-yl | 481.1 | 481.0 | 6.32 | Method 4 | 977 |
| 63-25 | 5-bromo-3-fluoropyridin-2-yl | 545.2 | 543.4 | 6.80 | Method 4 | 195 |
| 63-26 | ethyl pyridine-5-carboxylate-2-yl | 519.2 | 518.6 | 5.96 | Method 5 | >10000 |

Example 64

4-[1-(2-FLUORO-4-METHANESULFONYL-PHENYL)-PIPERIDIN-4-YLIDENEAMINOOXY]-PIPERIDINE-1-CARBOXYLIC ACID CYCLOBUTYL ESTER 64-1

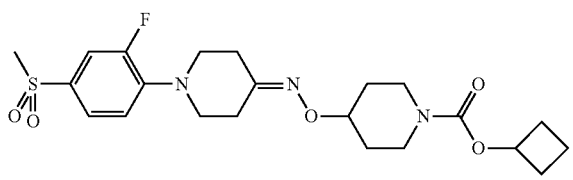

Step 64A: Carbonic acid cyclobutyl ester 4-nitro-phenyl ester (64a)

To 4-nitrophenyl chloroformate (80 mg, 0.4 mmol) in DCM, was added cyclobutanol (31.4 mg, 0.4 mmol). Triethylamine (0.17 mL, 1.2 mmol) was added dropwise and the mixture was stirred at room temperature overnight. The reaction mix containing 64a was used directly in the next step.

Step 64B: 4-[1-(2-Fluoro-4-methanesulfonyl-phenyl)-piperidin-4-ylideneaminooxy]-piperidine-1-carboxylic acid cyclobutyl ester (64-1)

To the reaction mixture of 64a obtained above was added 63a (30 mg, 0.08 mmol) in 0.3 mL of DCM. The mixture was stirred at room temperature for 2 h, concentrated and purified on preparative HPLC to give 64-1: LC-MS 468.4 (MH$^+$).

The following compounds were made according to this procedure using the corresponding alcohol. An additional step of removing a BOC protecting group from primary and secondary amines with trifluoroacetic acid/dichloromethane was performed when appropriate

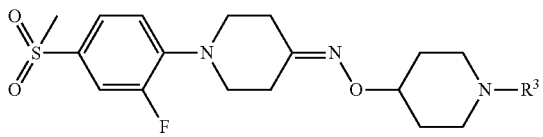

| No. | R³ | MH+ | MW | $t_R$ (Min) | HPLC Gradient | EC50 (nM) |
|---|---|---|---|---|---|---|
| 64-1 | ![cyclobutyl carbonate] | 468.4 | 467.6 | 5.43 | Method 4 | 81 |
| 64-2 | ![cyclopropylmethyl carbonate] | 468.4 | 467.6 | 5.37 | Method 4 | 101 |
| 64-3 | ![propargyl carbonate] | 452.0 | 451.5 | 4.96 | Method 5 | 446 |
| 64-4 | ![2-butynyl carbonate] | 466.3 | 465.5 | 5.34 | Method 5 | 152 |
| 64-5 | ![1-cyclopropylethyl carbonate] | 482.1 | 481.6 | 7.95 | Method 2 | 90 |
| 64-6 | ![cyclobutylmethyl carbonate] | 482.1 | 481.6 | 5.97 | Method 5 | 36 |
| 64-7 | ![cyclopropylmethyl homolog] | 482.0 | 481.6 | 6.03 | Method 5 | 67 |
| 64-8 | ![methylcyclopropylmethyl] | 482.9 | 481.6 | 5.96 | Method 5 | 32 |

-continued

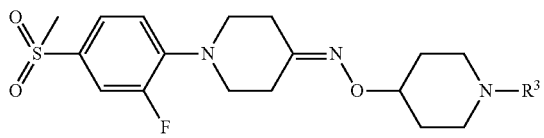

| No. | R³ | MH+ | MW | t_R (Min) | HPLC Gradient | EC50 (nM) |
|---|---|---|---|---|---|---|
| 64-9 | cyclopentyl ester | 481.6 | 481.6 | 5.90 | Method 5 | 41 |
| 64-10 | 2-ethoxyethyl ester | 485.8 | 485.6 | 4.98 | Method 5 | 1276 |
| 64-11 | (R)-5-oxopyrrolidin-3-yl ester | 497.4 | 496.6 | 3.83 | Method 5 | >10000 |
| 64-12 | (S)-5-oxopyrrolidin-3-yl ester | 498.9 | 496.6 | 3.90 | Method 5 | >10000 |
| 64-13 | 1-methylpyrrolidin-3-yl ester | 497.1 | 496.6 | 4.56 | Method 5 | >10000 |
| 64-14 | 1-(dimethylamino)propan-2-yl ester | 498.9 | 498.6 | 5.05 | Method 5 | >10000 |
| 64-15 | 3-(dimethylamino)propyl ester | 499.4 | 498.6 | 4.87 | Method 5 | >10000 |
| 64-16 | 2-isopropoxyethyl ester | 499.5 | 499.6 | 5.24 | Method 5 | 693 |
| 64-17 | pyridin-2-ylmethyl ester | 504.9 | 504.6 | 4.77 | Method 5 | 1067 |
| 64-18 | 2-(1H-pyrrol-1-yl)ethyl ester | 507.3 | 506.6 | 5.41 | Method 5 | 461 |

-continued
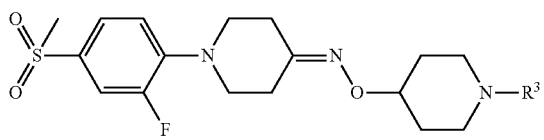
| No. | R³ | MH+ | MW | t_R (Min) | HPLC Gradient | EC50 (nM) |
|---|---|---|---|---|---|---|
| 64-19 | | 511.5 | 510.6 | 5.11 | Method 5 | >10000 |
| 64-20 | | 511.2 | 510.6 | 4.87 | Method 5 | >10000 |
| 64-21 | | 512.8 | 512.6 | 5.00 | Method 5 | >10000 |
| 64-22 | | 513.8 | 513.6 | 5.11 | Method 5 | 193 |
| 64-23 | | 514.5 | 513.6 | 5.10 | Method 5 | 928 |
| 64-24 | | 514.1 | 513.6 | 5.17 | Method 5 | 708 |
| 64-25 | | 518.6 | 518.6 | 4.82 | Method 5 | 1603 |
| 64-26 | | 518.8 | 518.6 | 4.81 | Method 5 | >10000 |
| 64-27 | | 525.0 | 524.6 | 5.05 | Method 5 | >10000 |

-continued
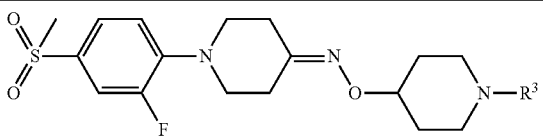
| No. | R³ | MH+ | MW | t_R (Min) | HPLC Gradient | EC50 (nM) |
|---|---|---|---|---|---|---|
| 64-28 | (ethyl piperidinyl ester) | 525.1 | 524.6 | 5.34 | Method 5 | >10000 |
| 64-29 | (propyl diethylamino ester) | 527.1 | 526.7 | 5.45 | Method 5 | >10000 |
| 64-30 | (dimethyl methyl ester) | 528.4 | 527.6 | 5.39 | Method 5 | 277 |
| 64-31 | (cyclopropyl ethyl ester) | 540.4 | 539.6 | 5.32 | Method 5 | 107 |
| 64-32 | (ethyl diisopropylamino ester) | 541.4 | 540.7 | 6.36 | Method 5 | >10000 |
| 64-33 | (azetidinyl ester) | 469.4 | 468.5 | 4.12 | Method 5 | >10000 |
| 64-34 | (amino propyl ester) | 471.4 | 470.6 | 5.22 | Method 5 | >10000 |
| 64-35 | (amino propyl ester) | 471.4 | 470.6 | 4.17 | Method 5 | >10000 |
| 64-36 | (pyrrolidinyl ester) | 483.4 | 482.6 | 4.27 | Method 5 | >10000 |
| 64-37 | (amino isobutyl ester) | 499.5 | 498.6 | 4.56 | Method 5 | >10000 |

-continued
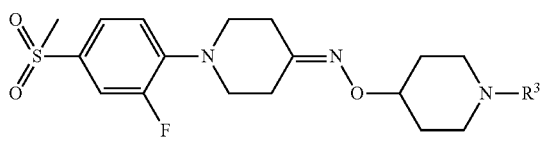
| No. | R³ | MH+ | MW | t_R (Min) | HPLC Gradient | EC50 (nM) |
|---|---|---|---|---|---|---|
| 64-38 | (CH2-O-C(=O)-)-CH2-morpholine (2-yl) | 513.4 | 512.6 | 3.99 | Method 5 | >10000 |
| 64-39 | -C(=O)-O-CH2CH2-cyclopropyl | 482.4 | 481.6 | 5.92 | Method 4 | 127 |
| 64-40 | -C(=O)-O-CH2CH2-CH(CH3)2 | 484.4 | 483.6 | 6.22 | Method 4 | 89 |
| 64-41 | -C(=O)-O-CH2CH2-C(CH3)3 | 498.4 | 497.6 | 6.46 | Method 4 | 202 |
| 64-42 | -C(=O)-O-CH2CH2-cyclohexyl | 524.4 | 523.7 | 6.97 | Method 4 | 350 |
| 64-43 | -C(=O)-O-CH2CH2-N-morpholine | 527.1 | 526.6 | 4.10 | Method 2 | >10000 |
| 64-44 | -C(=O)-O-CH2-CH(NH2)-CH(CH3)2 | 499.2 | 498.6 | 4.68 | Method 5 | >10000 |
| 64-45 | -C(=O)-O-CH2CH2CH2CH3 | 470.4 | 469.6 | 5.85 | Method 4 | 54 |
| 64-46 | -C(=O)-O-CH2CH2-OCH3 | 472.4 | 471.5 | 4.63 | Method 4 | |
| 64-47 | -C(=O)-O-CH2-CH(CH3)-CH2CH3 | 484.3 | 483.6 | 6.24 | Method 5 | 43 |
| 64-48 | -C(=O)-O-CH2-CH(CH3)-CH2CH3 (S) | 484.2 | 483.6 | 6.22 | Method 5 | 54 |

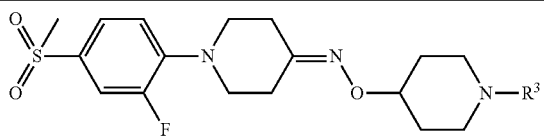

| No. | R³ | MH+ | MW | t_R (Min) | HPLC Gradient | EC50 (nM) |
|---|---|---|---|---|---|---|
| 64-49 | 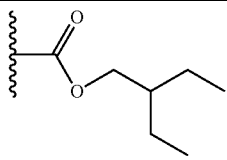 | 498.2 | 497.6 | 6.56 | Method 5 | 54 |

Example 65

N,N-DIETHYL-2-{4-[1-(2-FLUORO-4-METH-ANESULFONYL-PHENYL)-PIPERIDIN-4-YLIDENEAMINOOXY]-PIPERIDIN-1-YL}-ACETAMIDE 65-1

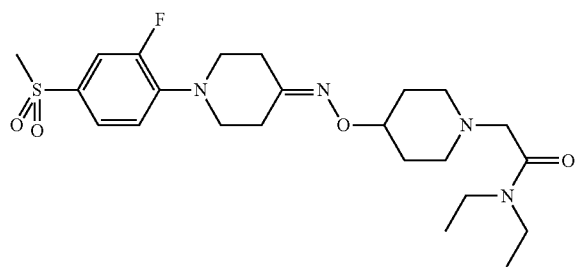

Step 65A: N,N-Diethyl-2-{4-[1-(2-fluoro-4-methanesulfonyl-phenyl)-piperidin-4-ylideneaminooxy]-piperidin-1-yl}-acetamide (65-1)

To a solution of 63a (30 mg, 0.08 mmol) in DCM, was added triethylamine (33.5 µL, 0.24 mmol) and 2-chloro-N,N-diethylacetamide (14.4 µL, 0.096 mmol). The mixture was stirred at room temperature overnight, concentrated and purified on preparative HPLC to give 65-1: LC-MS 482.8 (MH⁺).

The following compounds were made according to this procedure using the corresponding electrophile (alkyl chloro or bromo, acid chloride, chloroformate, isocyanate, isothiocyanate or sulfonyl chloride):

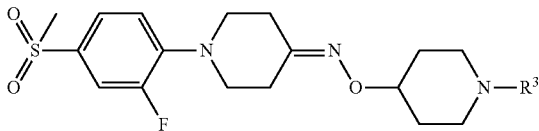

| No. | R³ | MH+ | MW | t_R (Min) | HPLC Gradient | EC50 (nM) |
|---|---|---|---|---|---|---|
| 65-1 | 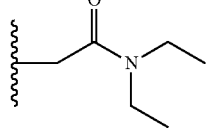 | 482.8 | 482.6 | 4.79 | Method 5 | >10000 |
| 65-2 | 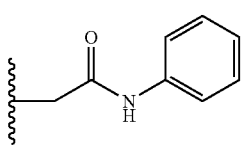 | 503.0 | 502.6 | 5.34 | Method 5 | >10000 |
| 65-3 | 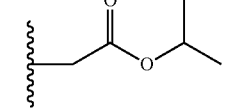 | 470.3 | 469.6 | 5.17 | Method 5 | 64%* |

-continued
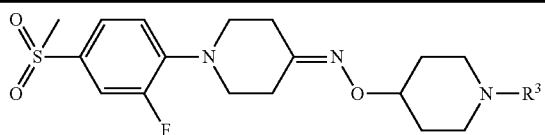
| No. | R³ | MH+ | MW | t_R (Min) | HPLC Gradient | EC50 (nM) |
|---|---|---|---|---|---|---|
| 65-4 | | 469.1 | 468.6 | 4.65 | Method 5 | >10000 |
| 65-5 | | 518.3 | 517.6 | 5.61 | Method 5 | 3382 |
| 65-6 | | 504.0 | 503.6 | 5.46 | Method 5 | 854 |
| 65-7 | | 484.2 | 483.6 | 6.32 | Method 5 | 57 |
| 65-8 | | 455.2 | 454.6 | 4.58 | Method 5 | >10000 |
| 65-9 | | 511.2 | 510.7 | 6.04 | Method 5 | 1797 |
| 65-10 | | 469.1 | 468.6 | 4.92 | Method 5 | >10000 |
| 65-11 | | 469.2 | 468.6 | 5.23 | Method 5 | 1036 |
| 65-12 | | 490.0 | 489.6 | 5.84 | Method 5 | 57 |
| 65-13 | | 470.2 | 469.6 | 6.00 | Method 5 | 82 |
| 65-14 | | 504.1 | 503.6 | 5.95 | Method 5 | 153 |

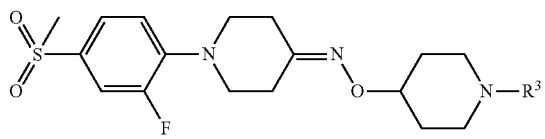
| No. | R³ | MH+ | MW | t_R (Min) | HPLC Gradient | EC50 (nM) |
|---|---|---|---|---|---|---|
| 65-15 | | 454 | 453.5 | 5.51 | Method 5 | 64 |
| 65-16 | | 476.0 | 475.6 | 5.11 | Method 5 | >10000 |
| 65-17 | | 489.0 | 488.6 | 5.06 | Method 5 | 2037 |
| 65-18 | | 510.1 | 509.6 | 5.66 | Method 5 | 1102 |
| 65-19 | | 481.1 | 479.6 | 4.10 | Method 5 | 88 |
| 65-20 | | 467.1 | 465.6 | 3.98 | Method 5 | 39 |
| 65-21 | | 474.2 | 473.6 | 4.91 | Method 5 | 747 |
| 65-22 | | 492.8 | 491.6 | 3.86 | Method 5 | 132 |
| 65-23 | | 509.3 | 508.0 | 4.08 | Method 5 | 55 |

-continued
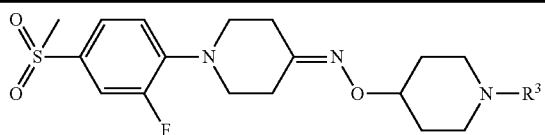
| No. | R³ | MH+ | MW | t_R (Min) | HPLC Gradient | EC50 (nM) |
|---|---|---|---|---|---|---|
| 65-24 | 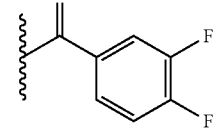 | 511.2 | 509.5 | 4.00 | Method 5 | 640 |
*% values mean stimulation in % at 10 μM.
The following compounds are made according to procedures as described hereinbefore:
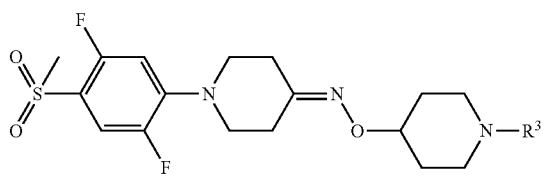
| No. | R³ | MH+ | MW | t_R (Min) | HPLC Gradient | EC50 (nM) |
|---|---|---|---|---|---|---|
| 65-25 | 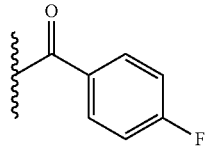 | 511.2 | 509.5 | 3.94 | Method 5 | 73 nM |
| 65-26 | 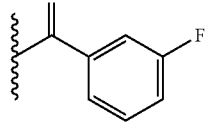 | 511.4 | 509.5 | 4.03 | Method 5 | 74 nM |
| 65-27 | 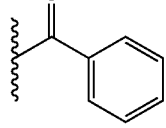 | 493.3 | 491.6 | 3.96 | Method 5 | 175 nM |
| 65-28 | 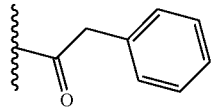 | 505.6 | 507.4 | 3.96 | Method 5 | 240 nM |
| 65-29 | 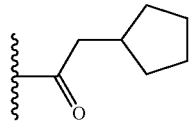 | 499.2 | 497.6 | 4.22 | Method 5 | 72 nM |

-continued
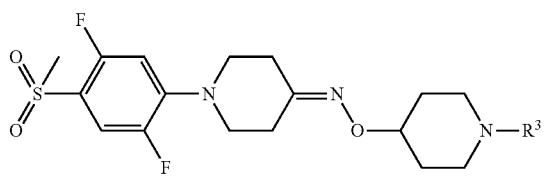
| No. | R³ | MH+ | MW | t_R (Min) | HPLC Gradient | EC50 (nM) |
|---|---|---|---|---|---|---|
| 65-30 | cyclopentyl-C(=O)- | 485.3 | 483.6 | 4.12 | Method 5 | 36 nM |
| 65-31 | 4-chlorobenzoyl | 527.4 | 526.0 | 4.19 | Method 5 | 302 nM |
| 65-32 | 2,4-difluorobenzoyl | 529.5 | 527.5 | 4.06 | Method 5 | 880 nM |
| 65-33 | propyl-C(=O)- | 459.0 | 457.5 | 3.69 | Method 5 | 273 nM |
| 65-34 | 2-methoxybenzoyl | 523.3 | 521.6 | 3.84 | Method 5 | 344 nM |
| 65-35 | 2-methylbenzoyl | 507.3 | 505.6 | 4.03 | Method 5 | 303 nM |
| 65-36 | butyl-C(=O)- | 473.0 | 471.6 | 3.94 | Method 5 | 112 nM |

Example 66

1-(2-FLUORO-4-METHANESULFONYL-PHENYL)-PIPERIDIN-4-ONE O-[1-(1-METHYL-1H-PYRROL-2-YLMETHYL)-PIPERIDIN-4-YL]-OXIME

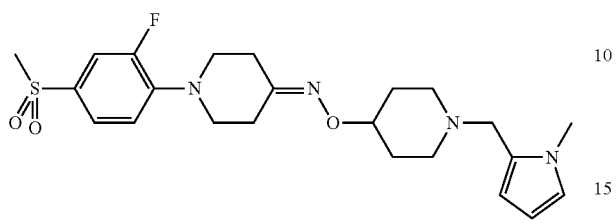

66-1

Step 66A: 1-(2-Fluoro-4-methanesulfonyl-phenyl)-piperidin-4-one O-[1-(1-methyl-1H-Pyrrol-2-ylmethyl)-piperidin-4-yl]-oxime (66-1)

To 63a (24 mg, 0.065 mmol) in 1 mL of DCM, was added 1-methyl-1H-pyrrole-2-carbaldehyde (10.6 g, 0.098 mmol), triethylamine (27 μL, 0.19 mmol) and sodium triacetoxyborohydride (27.6 mg, 0.13 mmol). The mixture was stirred overnight at room temperature, concentrated and purified on preparative HPLC to give 66-1: LC-MS 463.0 (MH$^+$).

The following compounds were made according to this procedure using the corresponding aldehyde:

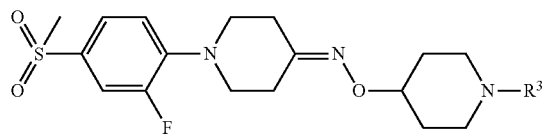

| No. | R³ | MH+ | MW | t$_R$ (Min) | HPLC Gradient | EC50 (nM) |
|---|---|---|---|---|---|---|
| 66-1 | | 463.0 | 462.6 | 5.70 | Method 5 | >10000 |
| 66-2 | | 450.4 | 449.5 | 3.71 | Method 4 | >10000 |
| 66-3 | | 461.4 | 460.6 | 4.42 | Method 4 | >10000 |
| 66-4 | | 461.4 | 460.6 | 4.40 | Method 4 | >10000 |
| 66-5 | | 498.2 | 498.0 | 4.78 | Method 5 | >10000 |
| 66-6 | | 467.2 | 466.6 | 4.77 | Method 5 | 63%* |

-continued
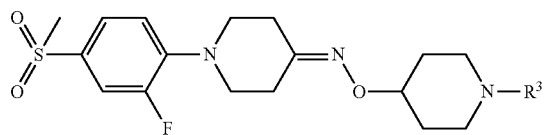
| No. | R³ | MH+ | MW | $t_R$ (Min) | HPLC Gradient | EC50 (nM) |
|---|---|---|---|---|---|---|
| 66-7 | | 478.5 | 477.6 | 4.31 | Method 4 | >10000 |
| 66-8 | | 464.4 | 463.6 | 3.64 | Method 4 | >10000 |
| 66-9 | | 464.4 | 463.6 | 3.91 | Method 4 | >10000 |
| 66-10 | | 464.4 | 463.6 | 4.12 | Method 4 | >10000 |
| 66-11 | | 467.4 | 466.6 | 4.38 | Method 4 | >10000 |
| 66-12 | | 464.2 | 463.6 | 4.17 | Method 5 | >10000 |
| 66-13 | | 478.2 | 477.6 | 4.66 | Method 5 | >10000 |
| 66-14 | | 481.2 | 480.6 | 4.60 | Method 5 | >10000 |
| 66-15 | | 460.1 | 459.6 | 6.15 | Method 5 | 982 |

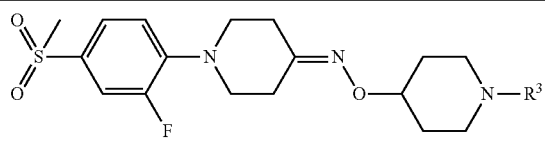
| No. | R³ | MH+ | MW | t_R (Min) | HPLC Gradient | EC50 (nM) |
|---|---|---|---|---|---|---|
| 66-16 | 2-F-benzyl | 478.2 | 477.6 | 5.93 | Method 5 | 560 |
| 66-17 | 2-Cl-benzyl | 494.1 | 494.0 | 6.75 | Method 5 | 661 |
| 66-18 | 2-OMe-benzyl | 490.1 | 489.6 | 6.02 | Method 5 | 66%* |
| 66-19 | 2-CN-benzyl | 485.1 | 484.6 | 6.01 | Method 5 | >10000 |
| 66-20 | oxazolyl | 451.1 | 450.53 | 4.39 | Method 5 | >10000 |
| 66-21 | isobutyl | 426.2 | 425.6 | 6.26 | Method 5 | 64%* |
| 66-22 | neopentyl | 440.0 | 439.6 | 7.49 | Method 5 | 1365 |
| 66-23 | isopentyl | 440.2 | 439.6 | 6.07 | Method 5 | >10000 |
| 66-24 | 1-methyl-3-phenylpropyl | 502.1 | 501.7 | 6.56 | Method 5 | 53%* |
| 66-25 | 3-methylbenzyl | 474.4 | 473.6 | 6.20 | Method 4 | 605 |

-continued
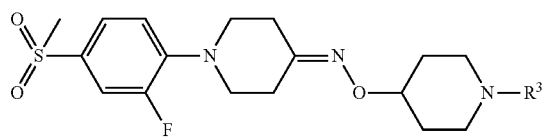
| No. | R³ | MH+ | MW | t_R (Min) | HPLC Gradient | EC50 (nM) |
|---|---|---|---|---|---|---|
| 66-26 | 4-methylbenzyl | 474.4 | 473.6 | 6.19 | Method 4 | 288 |
| 66-27 | 4-ethylbenzyl | 488.3 | 487.6 | 6.50 | Method 5 | 109 |
| 66-28 | 4-chlorobenzyl | 494.0 | 494.0 | 6.37 | Method 5 | 363 |
| 66-29 | 2-CF₃-benzyl | 528.4 | 527.6 | 6.94 | Method 4 | 1216 |
| 66-30 | 3-CF₃-benzyl | 528.3 | 527.6 | 6.47 | Method 4 | 1740 |
| 66-31 | 4-CF₃-benzyl | 528.4 | 527.6 | 6.48 | Method 4 | 354 |
| 66-32 | 4-isopropylbenzyl | 502.2 | 501.7 | 5.60 | Method 2 | 332 |
| 66-33 | 4-fluorobenzyl | 478.3 | 477.6 | 5.91 | Method 5 | 822 |

-continued
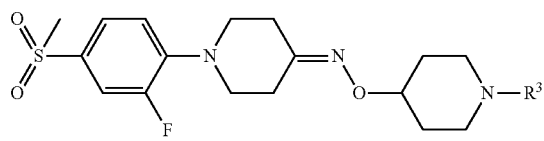
| No. | R³ | MH+ | MW | $t_R$ (Min) | HPLC Gradient | EC50 (nM) |
|---|---|---|---|---|---|---|
| 66-34 | (2,4-dimethylfuran-5-yl)methyl | 478.1 | 477.6 | 5.73 | Method 5 | 75%* |
| 66-35 | (2,3-dihydrobenzofuran-5-yl)methyl | 502.2 | 501.6 | 5.60 | Method 5 | 61%* |
| 66-36 | (4-dimethylaminophenyl)methyl | 503.2 | 502.6 | 5.80 | Method 5 | 83%* |
| 66-37 | (benzo[1,3]dioxol-5-yl)methyl | 504.2 | 503.6 | 5.65 | Method 5 | 87%* |
| 66-38 | (3-fluoro-4-methoxyphenyl)methyl | 508.2 | 507.6 | 5.67 | Method 5 | 435 |
| 66-39 | (4-acetamidophenyl)methyl | 517.2 | 516.6 | 4.44 | Method 5 | >10000 |
| 66-40 | (4-isopropoxyphenyl)methyl | 518.2 | 517.7 | 6.28 | Method 5 | 332 |
| 66-41 | (4-bromophenyl)methyl | 540.1 | 538.5 | 6.49 | Method 5 | 609 |

-continued
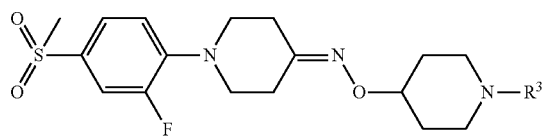
| No. | R³ | MH+ | MW | t_R (Min) | HPLC Gradient | EC50 (nM) |
|---|---|---|---|---|---|---|
| 66-42 | 4-OCF₃-phenyl-CH₂ | 544.3 | 543.6 | 6.59 | Method 5 | 503 |
| 66-43 | 3-F-4-OCF₃-phenyl-CH₂ | 546.3 | 545.6 | 6.60 | Method 5 | 1369 |
| 66-44 | 2-F-4-Br-phenyl-CH₂ | 556.1 | 556.5 | 6.58 | Method 5 | 753 |
| 66-45 | 4-OMe-phenyl-CH₂ | 490.1 | 489.6 | 5.56 | Method 5 | 6000 |
| 66-46 | 4-OEt-phenyl-CH₂ | 504.4 | 503.6 | 6.05 | Method 4 | 418 |
| 66-47 | 2-F-4-Me-phenyl-CH₂ | 492.4 | 491.6 | 6.27 | Method 4 | 909 |
| 66-48 | 2,3-diF-4-Me-phenyl-CH₂ | 510.1 | 509.6 | 6.38 | Method 4 | 99%* |
| 66-49 | 2-Et-pyrimidin-5-yl-CH₂ | 490.2 | 489.6 | 4.52 | Method 4 | 75%* |

-continued
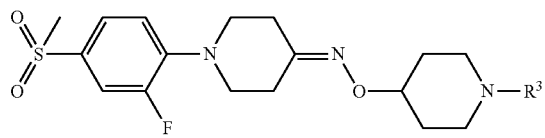
| No. | R³ | MH+ | MW | $t_R$ (Min) | HPLC Gradient | EC50 (nM) |
|---|---|---|---|---|---|---|
| 66-50 | F, OMe-phenyl | 508.2 | 507.6 | 5.72 | Method 5 | 1013 |
| 66-51 | Cl-pyridyl | 495.4 | 495.0 | 5.40 | Method 4 | 66%* |
*% values mean stimulation in % at 10 μM.
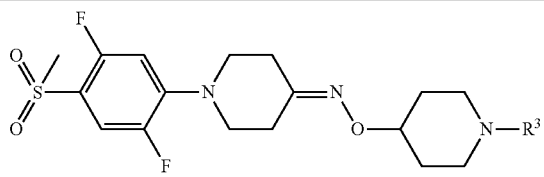
| No. | R³ | MH+ | MW | $t_R$ (Min) | HPLC Gradient | EC50 (nM) |
|---|---|---|---|---|---|---|
| 66-52 | | 555.9 | 554.66 | 4.29 | Method 5 | 926 |
| 66-53 | | 520.6 | 519.65 | 5.18 | Method 2 | 35 |
| 66-54 | | 492.7 | 491.60 | 4.72 | Method 5 | 44 |
| 66-55 | | 506.3 | 505.63 | 4.93 | Method 5 | 37 |

-continued
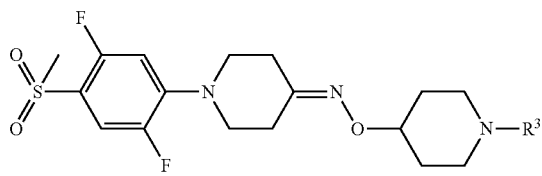
| No. | R³ | MH+ | MW | t_R (Min) | HPLC Gradient | EC50 (nM) |
|---|---|---|---|---|---|---|
| 66-56 | (4-Cl-benzyl) | 511.9 | 512.02 | 4.81 | Method 5 | 50 |
| 66-57 | (4-butyl-benzyl) | 534.2 | 533.68 | 5.47 | Method 5 | 29 |
| 66-58 | (1-(4-ethylphenyl)ethyl) | 519.7 | 519.65 | 5.78 | Method 2 | 72 |
| 66-59 | (3-F-4-propyl-benzyl) | 538.4 | 537.64 | 7.02 | Method 4 | 53 |
| 66-60 | (3-F-4-propyl-benzyl) | 538.4 | 537.64 | 7.17 | Method 4 | 31 |
| 66-61 | (3-F-4-propenyl-benzyl) | 536.3 | 535.63 | 6.99 | Method 4 | 49 |
| 66-62 | (3-F-4-propenyl-benzyl) | 536.3 | 535.63 | 6.77 | Method 4 | 136 |
| 66-63 | (R)-1-(4-ethylphenyl)ethyl | 520.2 | 519.65 | 5.70 | Method 2 | 294 |
| 66-64 | (S)-1-(4-ethylphenyl)ethyl | 520.0 | 519.65 | 5.70 | Method 2 | >10000 |

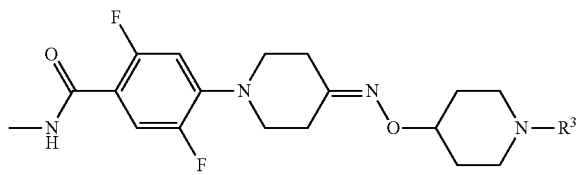
| No. | R³ | MH+ | MW | t_R (Min) | HPLC Gradient | EC50 (nM) |
|---|---|---|---|---|---|---|
| 66-65 | 4-(pyridin-2-yl)benzyl | 534.2 | 533.62 | 4.22 | Method 2 | 792 |
| 66-66 | 4-(pyridin-3-yl)benzyl | 534.3 | 533.62 | 4.08 | Method 2 | 1273 |
| 66-67 | 4-(trifluoromethyl)benzyl | 525.3 | 524.53 | 6.33 | Method 2 | 155 |
| 66-68 | 4-chlorobenzyl | 490.9 | 490.98 | 5.13 | Method 2 | 365 |
| 66-69 | 4-(pyrimidin-5-yl)benzyl | 535.3 | 534.61 | 4.46 | Method 2 | 2262 |
| 66-70 | 4-methylbenzyl | 471.3 | 470.56 | 6.67 | Method 2 | 193 |
| 66-71 | 4-ethylbenzyl | 485.5 | 484.59 | 6.98 | Method 2 | 79 |
| 66-72 | 4-propylbenzyl | 499.2 | 498.61 | 5.05 | Method 2 | 109 |

Example 67

1-(2-FLUORO-4-METHANESULFONYL-PHENYL)-PIPERIDIN-4-ONE O-(5'-METHYL-3,4,5,6-TETRAHYDRO-2H-[1,2']BIPYRIDINYL-4-YL)-OXIME 67-1

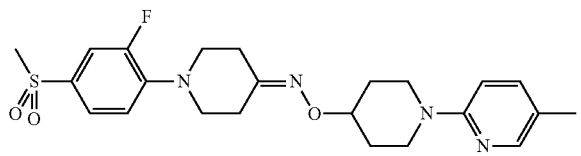

Step 67A: 1-(2-Fluoro-4-methanesulfonyl-phenyl)-piperidin-4-one O-(5'-methyl-3,4,5,6-tetrahydro-2H-[1,2']bipyridinyl-4-yl)-oxime (67-1)

Pd₂dba₃ (1.5 mg, 0.0016 mmol), Xantphos (2.8 mg, 0.0048 mmol), NaOtBu (11.5 mg, 0.12 mmol), 63a (29.5 mg, 0.08 mmol) and 2-bromo-5-methyl-pyridine (27.5 mg, 0.16 mmol) were combined. Toluene (0.3 mL) was added and the mixture was flushed with nitrogen, sealed and heated at 100° C. overnight. The solvent was removed and the crude mixture was purified on preparative HPLC to give 67-1: LC-MS 461.2 (MH⁺).

The following compounds were made according to this procedure by reaction with the corresponding aryl halide (chloro or bromo).

| No. | R³ | MH+ | MW | $t_R$ (Min) | HPLC Gradient | EC50 (nM) |
|---|---|---|---|---|---|---|
| 67-1 | 5-methylpyridin-2-yl | 461.2 | 460.6 | 5.74 | Method 5 | 386 |
| 67-2 | 5-ethylpyridin-2-yl | 475.2 | 474.6 | 6.03 | Method 5 | 558 |
| 67-3 | 6-methylpyridin-3-yl | 461.4 | 460.6 | 4.91 | Method 4 | 745 |

Example 68

1-(2-FLUORO-4-METHANESULFONYL-PHENYL)-PIPERIDIN-4-ONE O-[1-(3-ISOPROPYL-[1,2,4]OXADIAZOL-5-YL)-PIPERIDIN-4-YL]-OXIME 68-1

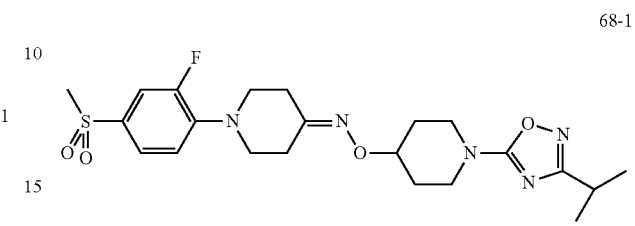

Step 68A: N-Hydroxy-isobutyramidine (68a)

To sodium methoxide (43 mL, 200 mmol) in 100 mL of methanol, was added hydroxylamine hydrochloride (10.5 g, 150 mmol) and isobutyronitrile (9 mL, 100 mmol). The mixture was heated at reflux overnight. The mixture was concentrated, water added, extracted with DCM and the solvent was evaporated to give 1.78 g (17% yield) of 68a as a solid.

Step 68B: 4-[1-(2-Fluoro-4-methanesulfonyl-phenyl)-piperidin-4-ylideneaminooxy]-piperidine-1-carbonitrile (68b)

To sodium bicarbonate (34 mg, 0.4 mmol), was added water (17 µL) and 63a (74 mg, 0.2 mmol) in 1 mL of DCM. The mixture was cooled to 0° C. and cyanogen bromide (25 mg, 0.24 mmol) was added. The mixture was stirred at room temperature overnight. Sodium carbonate was added as well as magnesium sulfate and the solids were filtered and rinsed with DCM. The filtrate was concentrated to give 107 mg of 68b.

Step 68C: 1-(2-Fluoro-4-methanesulfonyl-phenyl)-piperidin-4-one O-[1-(3-isopropyl-[1,2,4]oxadiazol-5-yl)-piperidin-4-yl]-oxime (68-1)

68b (35 mg, 0.066 mmol) and 68a (8 mg, 0.08 mmol) were combined in ethyl acetate (1 mL) and 1N ZnCl₂ (80 µL, 0.08 mmol) was added dropwise. After 1 h, the solvent was evaporated. 1 mL of ethanol and 0.5 mL of concentrated HCl were added and the mixture was heated to reflux. The solvent was removed and the crude mixture was purified on preparative HPLC to give 68-1: LC-MS 480.2 (MH⁺), $t_R$=5.57 (Method 5).

Example 69

4-(PIPERIDIN-4-YLIDENEAMINOOXY)-PIPERIDINE-1-CARBOXYLIC ACID TERT-BUTYL ESTER

69c

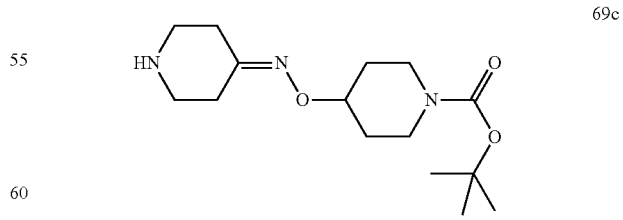

Step 69A: 4-(1,3-Dioxo-1,3-dihydro-isoindol-2-yloxy)-piperidine-1-carboxylic acid tert-butyl ester (69a)

To 4-hydroxypiperidine tert-butyl carboxylate (10 g, 50 mmol), N-hydroxyphthalimide (8.15 g, 50 mmol), triphenylphosphine (13.1 g, 50 mmol) and 80 mL of THF was added DEAD (7.87 mL, 50 mmol) in 20 mL of THF. The mix was stirred at room temperature overnight and the solvent was evaporated. The mixture was azeotroped twice with 50 mL of ether. Ether (40 mL) was added under stirring and the precipitate was filtered and washed with 60 mL of a mixture 1:1 of ether in hexane. The solid was resuspended in 50 mL of a mixture 1:1 of ether in hexane and filtered. The filtrate was evaporated to give 20 g of material which was dissolved in 7 mL of refluxing isopropanol and 3.5 mL of water was added dropwise. The mixture was heated to reflux and cooled to room temperature with vigorous stirring. The solid which crystallized was filtered and washed with 10 mL of a mixture 1:1 of isopropanol and water to give 10 g of material. This solid was dissolved in 15 mL of refluxing isopropanol and 5 mL of water was added slowly. The mixture was cooled to room temperature while stirring. The solid was filtered and washed with cold isopropanol to give 7.84 g (45% yield) of 69a.

Step 69B: 4-Aminooxy-piperidine-1-carboxylic acid tert-butyl ester (69b)

To 69a (6.93 g, 20 mmol) in 40 mL of DCM was added hydrazine hydrate (2.91 mL, 60 mmol). The mixture was stirred at room temperature for 4 h, cooled in an ice bath for 30 minutes, then filtered. The solid was rinsed with 10 mL of DCM and the filtrate was evaporated. After cooling in the fridge, more solid precipitated and the oil was dissolved in 10 mL of DCM and filtered. The filtrate was evaporated to give 4.31 g (99% yield) of 69b.

Step 69C: 4-(Piperidin-4-ylideneaminooxy)-piperidine-1-carboxylic acid tert-butyl ester (69c)

To a solution of 4-piperidinone (2.5 mmol) in 25 mL of DCM, was added 69b (0.43 g, 2 mmol). The mixture was stirred at room temperature for 2 h. NaOAc (0.27 g, 2 mmol) and ethanol (10 mL) were added and the reaction mixture was heated at 70° C. for 2 h. The solution was allowed to cool down to room temperature and the ethanol was evaporated. The residue was extracted with ethyl acetate, washed with water, dried and concentrated to give 0.59 g of 69c.

Example 70

4-(PIPERIDIN-4-YLOXYIMINO)-PIPERIDINE-1-CARBOXYLIC ACID TERT-BUTYL ESTER

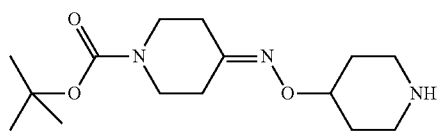

70c

Step 70A: 2-(Piperidin-4-yloxy)-isoindole-1,3-dione (70a)

1.5 g of 69a was taken up with isopropanol (10 mL) and 1 mL of concentrated HCl. The mixture was stirred at room temperature for 3 h, then 1 mL of concentrated HCl was added and the mixture was stirred at 50° C., cooled to room temperature and 10 mL of ether was added. The mixture was cooled to −78° C., filtered; and the solid was washed with ether to yield 0.6 g of solid 70a as an HCl salt.

Step 70B: O-Piperidin-4-yl-hydroxylamine (70b)

To 0.28 g (1 mmol) of 70a in 2 mL of DCM, was added hydrazine hydrate (0.14 mL, 3 mmol). The mixture was stirred at room temperature for 20 minutes. The mixture was concentrated, the solid was filtered and washed with 10 mL of DCM. The filtrate was concentrated to give crude 70b.

Step 70C: 4-(Piperidin-4-yloxyimino)-piperidine-1-carboxylic acid tert-butyl ester (70c)

1.16 g (10 mmol) of crude 70b in 20 mL of ethanol was treated with boc-piperidinone (1.99 g, 10 mmol) and NaOAc.3H$_2$O (2.04 g, 15 mmol). The reaction was heated up to 70° C. overnight. The ethanol was evaporated to 3 mL and the solution was diluted with water and a fine precipitate was filtered. The solid was dissolved in DCM, dried and concentrated to give 0.65 g of solid. The filtrate was extracted with ethyl acetate 3 times, dried and combined with the solid to give 1.1 g of crude 70c.

Example 71

2-CHLORO-5-METHANESULFONYL-PYRIMIDIN-4-OL

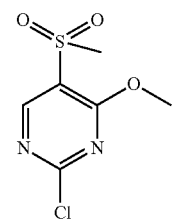

71-1

Step 71A: 2-Chloro-5-methanesulfonyl-pyrimidin-4-ol (71a)

Butyl lithium (0.88 mL, 2.5 M in hexane, 2.2 mmol) was added to a solution of 5-bromo-2-chloro-pyrimidin-4-ol (378 mg, 1.69 mmol) in 5 mL of ether at −78° C. The mixture was stirred for 30 minutes then Me$_2$S$_2$ (0.34 mL) was added. The mixture was allowed to warm up to room temperature over 1 h and quenched with water (2 mL), poured into EtOAc (15 mL) and hexane (15 mL), washed with water (3×20 mL) and brine (20 mL) and concentrated under vacuum. The residue was taken up with 10 mL of DCM and treated with mCPBA (77% pure, 1.14 g, 5.1 mmol) at −78° C. and warmed up to room temperature overnight. Saturated NaHCO$_3$ (15 mL) was added and stiffing was continued for 15 minutes. The organic layer was separated, dried and concentrated under vacuum to afford 71a: LC-MS 223.0 (MH$^+$).

The following compounds were made according to this procedure using the corresponding bromoamyl starting material.

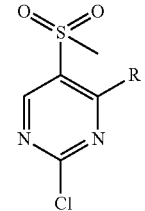

| No. | R | MH+ | MW | Retention Time (Min) | HPLC Gradient |
|---|---|---|---|---|---|
| 71a | methoxy | 223.0 | 222.6 | 2.45 | Method 1 |
| 71b | dimethylamino | 235.0 | 235.1 | 2.44 | Method 1 |

Example 72

(2,6-DICHLORO-PYRIDIN-3-YL)-METHANOL

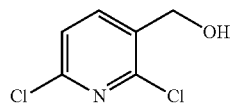

72a

Step 72A: (2,6-Dichloro-pyridin-3-yl)-methanol (72a)

Sodium borohydride (125 mg, 4.49 mmol) was added to 2,6-dichloro-pyridine-3-carbaldehyde (0.62 g, 3.5 mmol) in 20 mL of methanol at 0° C. After 30 minutes, the mixture was quenched with NaHCO$_3$ (20 mL) and water (20 mL) and extracted with EtOAc (2×20 mL). The combined extracts were dried and concentrated under vacuum to afford 72a: LC-MS178.0 (MH$^+$)

(2-Chloro-6-fluoro-pyridin-3-yl)-methanol 72b was also synthesized using this procedure: LC-MS162.0 (MH$^+$)

Example 73

1-(2-FLUORO-4-METHANESULFONYL-PHENYL)-PIPERIDIN-4-ONE O-[1-(PIPERIDINE-1-CARBONYL)-PIPERIDIN-4-YL]-OXIME 73-1

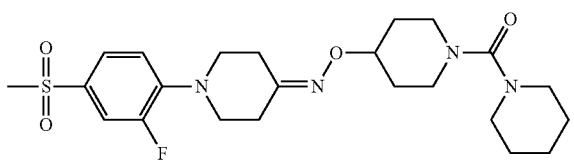

Step 73A

A solution of 63a (135 mg, 0.35 mmol) and pyridine (85 µL, 1.05 mmol) in DCM (5 mL) was added to a solution of triphosgene (37 mg, 0.123 mmol) in DCM (6 mL) and stirred at r.t. for 1 h. 0.5 mL of this solution was transferred to a vial, piperidine (0.01 mL) was added and the mixture stirred at r.t. for 2 h, diluted with methanol and purified by HPLC yielding 73-1. LC-MS 481.4 (MH$^+$).

The following compounds were made according to this procedure using the corresponding amine.

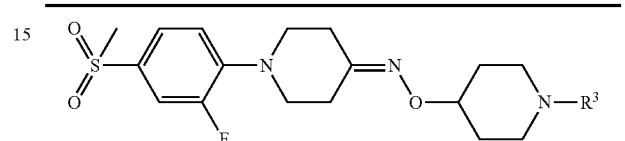

| No. | R$^3$ | MH+ | MW | t$_R$ (Min) | HPLC Gradient | EC50 |
|---|---|---|---|---|---|---|
| 73-1 |  | 481.4 | 480.6 | 5.17 | Method 5 | 425 |
| 73-2 |  | 467.6 | 466.6 | 4.68 | Method 5 | 1508 |

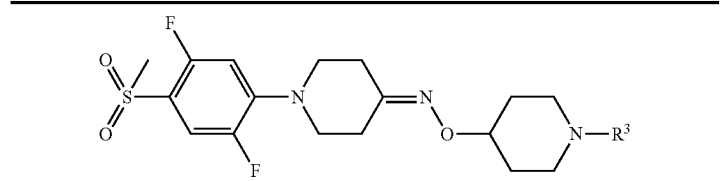

| No. | R$^3$ | MH+ | MW | t$_R$ (Min) | HPLC Gradient | EC50 |
|---|---|---|---|---|---|---|
| 73-3 | 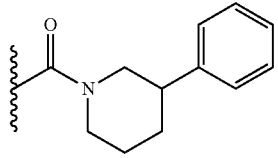 | 576.7 | 574.7 | 4.65 | Method 5 | 332 |
| 73-4 | 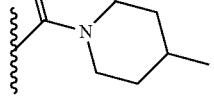 | 514.2 | 512.6 | 4.36 | Method 5 | 189 |
| 73-5 | 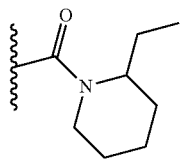 | 528.6 | 526.6 | 4.48 | Method 5 | 1273 |

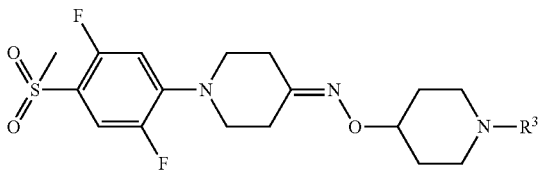

| No. | R³ | MH+ | MW | $t_R$ (Min) | HPLC Gradient | EC50 |
|---|---|---|---|---|---|---|
| 73-6 | | 514.4 | 512.6 | 4.34 | Method 5 | 534 |
| 73-7 | | 502.2 | 500.6 | 4.20 | Method 5 | 405 |
| 73-8 | | 544.5 | 542.7 | 5.01 | Method 5 | 478 |
| 73-9 | | 502.2 | 500.6 | 4.27 | Method 5 | 1115 |
| 73-10 | | 488.3 | 486.6 | 3.94 | Method 5 | 983 |

Example 74

1-(2,5-DIFLUORO-4-METHANESULFONYL-PHENYL)-PIPERIDIN-4-ONE O-[1-(5-IODO-PYRIMIDIN-2-YL)-PIPERIDIN-4-YL]-OXIME

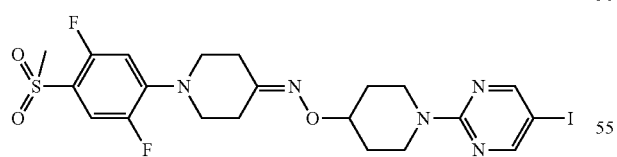

74a

Step 74A: 1-(2,5-Difluoro-4-methanesulfonyl-phenyl)-piperidin-4-one O-[1-(5-iodo-pyrimidin-2-yl)-piperidin-4-yl]-oxime 63-19 (30 mg, 0.055 mmol), CuI (7.6 mg, 0.04 mmol), NaI (33 mg, 0.22 mmol) and N,N'-dimethylethylenediamine (7.3 mg, 0.083 mmol) were added to 1,4-dioxane (0.5 mL) and heated at 120° C. for 16 h. The residue was purified by chromatography on silica gel eluting with EtOAc/Hexane to give 1-(2,5-difluoro-4-methanesulfonyl-phenyl)-piperidin-4-one O-[1-(5-iodo-pyrimidin-2-yl)-piperidin-4-yl]-oxime 74a (17 mg). LC-MS 591.8 (MH⁺), $t_R$=8.30 (Method 2).

Example 75

4-(1-{4-[(2-DIMETHYLAMINO-ETHYLCARBAMOYL)-METHYL]-2,5-DIFLUORO-PHENYL}-PIPERIDIN-4-YLIDENEAMINOOXY)-PIPERIDINE-1-CARBOXYLIC ACID ISOPROPYL ESTER

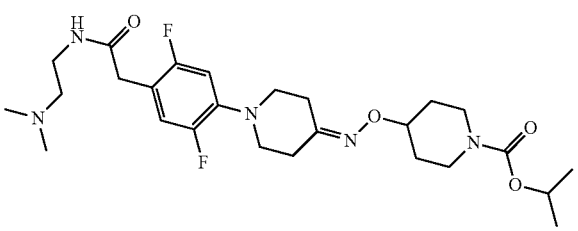

75-1

Step 75A: 4-[1-(4-tert-Butoxycarbonylmethyl-2,5-difluoro-phenyl)-piperidin-4-ylideneaminooxy]-piperidine-1-carboxylic acid isopropyl ester 2-40 (700 mg, 1.47 mmol) was dissolved in 1,4-dioxane (10 mL) and degassed by bubbling N₂ through the solution for 5 mins. Bis(tri-tertbutylphosphine)palladium (112 mg) was added followed by 2-tert-butoxy-2-oxoethylzinc chloride (5.25 mL, 0.5 M in diethylether) and the mixture was stirred at r.t. under N$_2$ for 16 h. Solvent was removed in vacuo and the crude mixture was purified by chromatography on silica gel eluting with EtOAc/Hexane to give 4-[1-(4-tert-butoxycarbonylmethyl-2,5-difluoro-phenyl)-piperidin-4-ylideneaminooxy]-piperidine-1-carboxylic acid isopropyl ester 75a (368 mg).

Step 75B: 4-[1-(4-Carboxymethyl-2,5-difluoro-phenyl)-piperidin-4-ylideneaminooxy]-piperidine-1-carboxylic acid isopropyl ester 4-[1-(4-tert-Butoxycarbonylmethyl-2,5-difluoro-phenyl)-piperidin-4-ylideneaminooxy]-piperidine-1-carboxylic acid isopropyl ester 75a (368 mg) was dissolved in DCM (5 mL) and TFA (3 mL) and stirred at r.t. for 4 h. The solvent was removed in vacuo, DCM and water were added and the organic phase was dried over MgSO$_4$ and concentrated to give 4-[1-(4-carboxymethyl-2,5-difluoro-phenyl)-piperidin-4-ylideneaminooxy]-piperidine-1-carboxylic acid isopropyl ester 75b (300 mg).

Step 75C: 4-(1-{4-[(2-Dimethylamino-ethylcarbamoyl)-methyl]-2,5-difluoro-phenyl}-piperidin-4-ylideneaminooxy)-piperidine-1-carboxylic acid isopropyl ester 4-[1-(4-carboxymethyl-2,5-difluoro-phenyl)-piperidin-4-ylidene aminooxy]-piperidine-1-carboxylic acid isopropyl ester 75b (8 mg, 0.017 mmol) was dissolved in DCE (0.5 mL) and N,N-dimethylethylenediamine (0.01 mL). HOBt (4.5 mg, 0.034 mmol) and EDC(6.5 mg, 0.034 mmol) were added and the mixture was stirred at r.t. for 16 h. MeOH was added and the mixture purified by HPLC to give 4-(1-{4-[(2-dimethylamino-ethylcarbamoyl)-methyl]-2,5-difluoro-phenyl}-piperidin-4-ylideneaminooxy)-piperidine-1-carboxylic acid isopropyl ester 75-1. LC-MS 525.9 (MH$^+$).

The following compounds were made according to this procedure using the corresponding amine. An additional step of removing a BOC protecting group from primary and secondary amines with trifluoroacetic acid/dichloromethane was performed when appropriate.

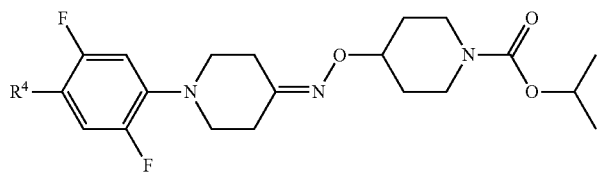

| No. | R$^4$ | MH+ | MW | t$_R$ (Min) | HPLC Gradient | EC50 |
|---|---|---|---|---|---|---|
| 75-1 | | 525.9 | 523.6 | 3.89 | Method 5 | 254 nM |
| 75-2 | | 468.4 | 466.5 | 3.84 | Method 5 | 172 nM |
| 75-3 | | 482.2 | 480.6 | 4.17 | Method 5 | 11 nM |
| 75-4 | | 454.1 | 452.5 | 3.67 | Method 5 | 83 nM |
| 75-5 | | 551.7 | 549.7 | 3.91 | Method 5 | 37 nM |

-continued
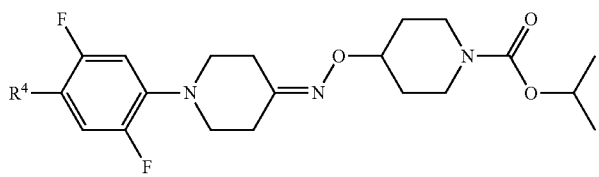
| No. | R⁴ | MH+ | MW | t_R (Min) | HPLC Gradient | EC50 |
|---|---|---|---|---|---|---|
| 75-6 | 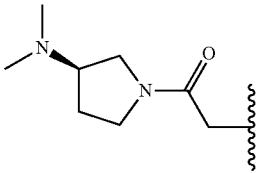 | 551.8 | 549.7 | 3.93 | Method 5 | 58 nM |
| 75-7 | 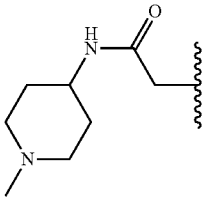 | 551.7 | 549.7 | 3.86 | Method 5 | 79 nM |
| 75-8 | 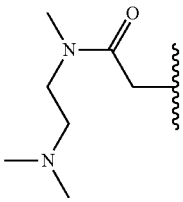 | 539.6 | 537.7 | 4.06 | Method 5 | 136 nM |
| 75-9 | 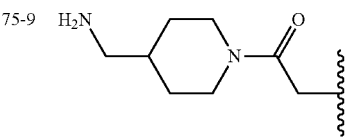 | 550.2 | 549.7 | 4.46 | Method 5 | 144 nM |
| 75-10 | 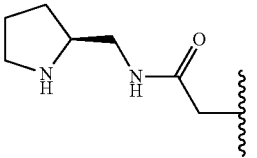 | 536.2 | 535.6 | 5.05 | Method 5 | 203 nM |
| 75-11 | 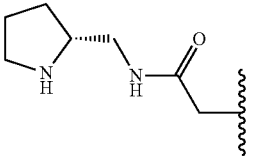 | 536.2 | 535.6 | 5.99 | Method 2 | 161 nM |
| 75-12 | 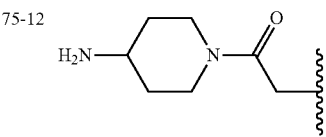 | 536.1 | 535.6 | 3.54 | Method 5 | 92 nM |

-continued
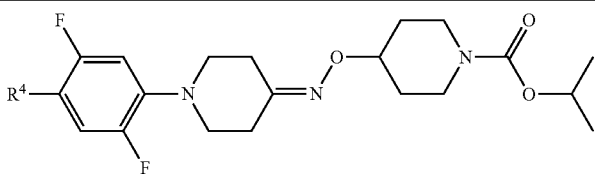
| No. | R⁴ | MH+ | MW | t_R (Min) | HPLC Gradient | EC50 |
|---|---|---|---|---|---|---|
| 75-13 | 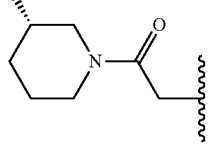 | 536.2 | 535.6 | 3.47 | Method 5 | 116 nM |
| 75-14 | 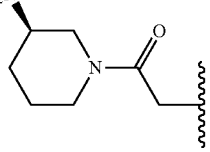 | 536.2 | 535.6 | 3.49 | Method 5 | 51 nM |
| 75-15 | 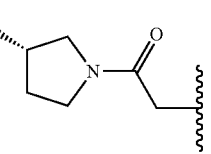 | 536.2 | 535.6 | 3.75 | Method 5 | 29 nM |
| 75-16 | 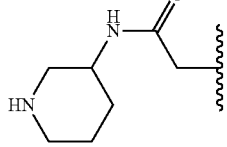 | 536.2 | 535.6 | 3.78 | Method 5 | 122 nM |
| 75-17 | 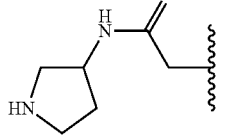 | 522.1 | 521.6 | 3.95 | Method 5 | 152 nM |
| 75-18 | 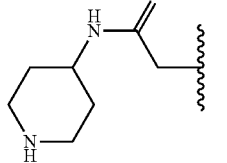 | 536.2 | 535.6 | 4.20 | Method 5 | 98 nM |
| 75-19 | 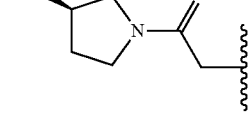 | 522.1 | 521.6 | 3.23 | Method 5 | 78 nM |
| 75-20 | 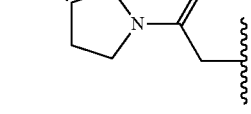 | 522.1 | 521.6 | 3.25 | Method 5 | 45 nM |

-continued
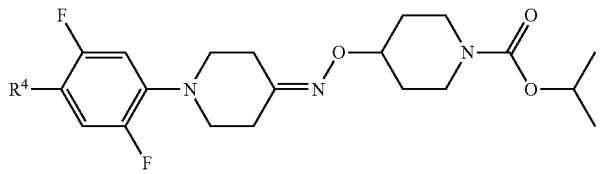
| No. | R⁴ | MH+ | MW | t_R (Min) | HPLC Gradient | EC50 |
|---|---|---|---|---|---|---|
| 75-21 | (4-aminopiperidin-1-yl)carbonyl | 550.1 | 549.7 | 4.04 | Method 5 | 126 nM |
| 75-22 | (3-aminomethylpiperidin-1-yl)carbonyl | 550.2 | 549.7 | 4.09 | Method 5 | 108 nM |
| 75-23 | (piperidin-3-ylmethyl)aminocarbonyl | 550.1 | 549.7 | 4.93 | Method 2 | 380 nM |
| 75-24 | (2-aminoethyl)aminocarbonyl | 496.1 | 495.6 | 3.42 | Method 5 | 410 nM |
| 75-25 | piperazin-1-ylcarbonyl | 522.2 | 521.6 | 3.28 | Method 5 | 92 nM |
| 75-26 | (piperidin-4-ylmethyl)aminocarbonyl | 550.2 | 549.7 | 4.40 | Method 5 | 236 nM |
| 75-27 | (pyrrolidin-3-ylmethyl)aminocarbonyl | 536.1 | 535.6 | 4.84 | Method 2 | 797 nM |

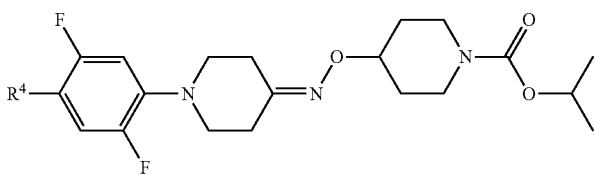
| No. | R⁴ | MH+ | MW | t_R (Min) | HPLC Gradient | EC50 |
|---|---|---|---|---|---|---|
| 75-28 | | 590.1 | 589.7 | 5.64 | Method 2 | 246 nM |
| 75-29 | | 590.1 | 589.7 | 5.64 | Method 2 | 2908 nM |
| 75-30 | | 604.3 | 603.7 | 5.06 | Method 5 | 333 nM |
| 75-31 | | 620.3 | 619.7 | 4.34 | Method 5 | 192 nM |
| 75-32 | | 618.1 | 617.8 | 5.67 | Method 2 | 300 nM |

-continued
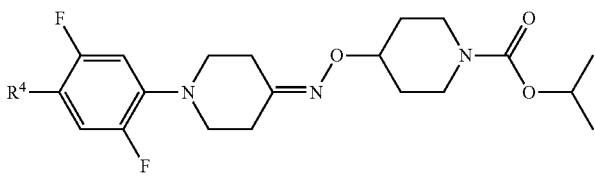
| No. | R⁴ | MH+ | MW | t_R (Min) | HPLC Gradient | EC50 |
|---|---|---|---|---|---|---|
| 75-33 | 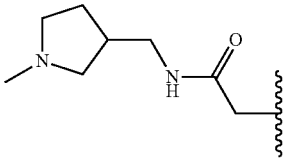 | 550.2 | 549.7 | 4.23 | Method 5 | 128 nM |
| 75-34 | 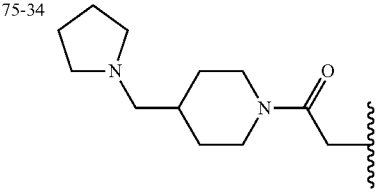 | 604.3 | 603.7 | 5.20 | Method 5 | 146 nM |
| 75-35 | 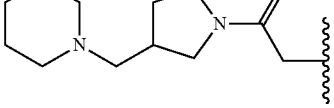 | 604.3 | 603.7 | 5.15 | Method 5 | 171 nM |
| 75-36 | 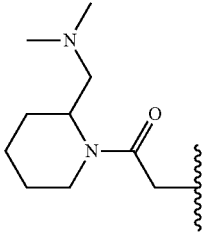 | 578.3 | 577.7 | 5.58 | Method 2 | 322 nM |
| 75-37 | 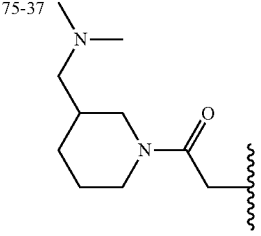 | 578.2 | 577.7 | 4.35 | Method 5 | 155 nM |
| 75-38 | 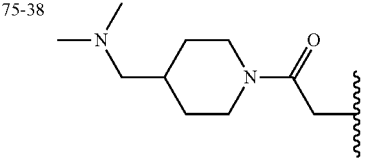 | 578.2 | 577.7 | 4.37 | Method 5 | 92 nM |

Example 76

4-{4-[1-(5-ETHYL-PYRIMIDIN-2-YL)-PIPERIDIN-4-YLOXYIMINO]-PIPERIDIN-1-YL}-2,5-DIFLUORO-BENZOIC ACID

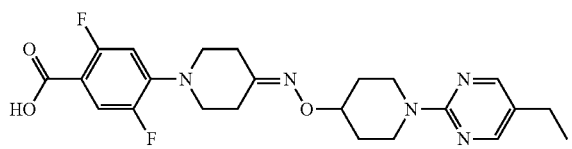

76-1

Step 76A: 2,5-Difluoro-4-(4-oxo-piperidin-1-yl)-benzoic acid methyl ester

Methyl 2,4,5 trifluorobenzoate (5 g, 26.3 mmol), 4-hydroxypiperidine (2.7 g, 26.3 mmol) and DIEA (13 mL, 79 mmol) were dissolved in DMSO (20 mL) in a sealed flask and heated to 120° C. overnight. The reaction mixture was diluted with EtOAc (100 mL) and extracted with sat. $NH_4Cl$ (25 ml) and brine (25 mL), dried over $MgSO_4$ and filtered and concentrated. The crude reaction mixture was purified via chromatography on silica gel eluting with MeOH/DCM to give the alcohol (6 g, 22.3 mmol) in an 85% yield. The alcohol (5.5 g, 20.3 mmol) was dissolved in anhydrous DCM (200 mL) and 4 A° molecular sieves (3 g), NMO (3 g, 25.4 mmol) and TPAP (356 mg, 1 mmol) were added and the reaction mixture was stirred overnight. The crude reaction mixture was filtered over celite, concentrated and purified via chromatography on silica gel eluting with EtOAc/Hexanes to give 2,5-difluoro-4-(4-oxo-piperidin-1-yl)-benzoic acid methyl ester 76a (4.53 g, 16.8 mmol) in 83% yield.

Step 76B: 2,5-Difluoro-4-[4-(piperidin-4-yloxyimino)-piperidin-1-yl]-benzoic acid methyl ester Compound 76a (3.5 g, 13 mmol) and 69b (2.8 g, 13 mmol) were dissolved in EtOH (15 mL) and the mixture was stirred overnight. The solvent was removed in vacuo and the crude reaction mixture was purified via chromatography on silica gel eluting with EtOAc/Hexanes to give the oxime (6 g, 12.8 mmol) in 99% yield. The oxime (3 g, 6.4 mmol) was dissolved in DCM (100 mL) and TFA (20 mL) was added. The reaction stirred at room temperature for 1 hr then the solvents were removed in vacuo. The crude reaction mixture was redissolved in DCM (100 mL) and the organic layer was extracted with sat. $NaHCO_3$ (50 mL). The organic layer was dried over $MgSO_4$, filtered and concentrated to give 2,5-difluoro-4-[4-(piperidin-4-yloxyimino)-piperidin-1-yl]-benzoic acid methyl ester 76b (2.4 g, 6.4 mmol) in quantitative yield.

Step 76C: 4-{4-[1-(5-Ethyl-pyrimidin-2-yl)-piperidin-4-yloxyimino]-piperidin-1-yl}-2,5-difluoro-benzoic acid Compound 76b (1 g, 2.8 mmol) was dissolved in DMSO (5 mL) and 2-chloro-5-ethyl pyrimidine (0.5 mL, 4.1 mmol) and DIEA (1.37 mL, 8.3 mmol) were added. The tube was sealed and heated to 120° C. overnight. The reaction mixture was diluted with EtOAc (100 mL) and extracted with brine (50 mL). The organic layer was dried over $MgSO_4$, filtered and concentrated. The crude reaction mixture was purified via chromatography on silica gel eluting with EtOAc/Hexanes to give the ethyl pyrimidine (1 g, 2.1 mmol) in 75% yield. Next, the ester was saponified with KOH (0.6 g, 10.5 mmol) in MeOH (20 mL) and $H_2O$ (20 mL). The MeOH was removed in vacuo and the reaction mixture was diluted with EtOAc (100 mL) and extracted with 1N HCl (20 mL). The organic layer was dried over $MgSO_4$, filtered and concentrated to give 4-{4-[1-(5-ethyl-pyrimidin-2-yl)-piperidin-4-yloxyimino]-piperidin-1-yl}-2,5-difluoro-benzoic acid 76-1 (0.96 g, 2.1 mmol) in quantitative yield.

Example 77

2-(4-{4-[1-(5-ETHYL-PYRIMIDIN-2-YL)-PIPERIDIN-4-YLOXYIMINO]-PIPERIDIN-1-YL}-2,5-DIFLUORO-PHENYL)-N-(1-METHYL-PIPERIDIN-4-YL)-ACETAMIDE

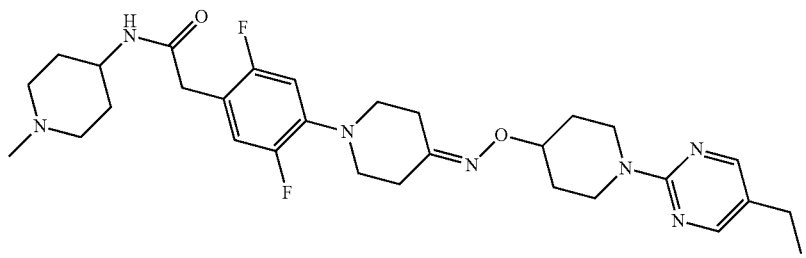

77-1

Step 77A: 4-[1-(4-Bromo-2,5-difluoro-phenyl)-piperidin-4-ylideneaminooxy]-piperidine-1-carboxylic acid tert-butyl ester Compound 69c (1.0 g, 3.4 mmol) and 1-bromo-2,4,5-trifluorobenzene were heated with $iPr_2NEt$ (1.7 mL, 10.2 mmol) in DMSO (5 mL) at 140° C. for 40 min 1M HCl and EtOAc were added and the organic phase dried over $MgSO_4$ and concentrated. The mixture was purified by chromatography on silica gel eluting with EtOAc/Hexane to give 4-[1-(4-Bromo-2,5-difluoro-phenyl)-piperidin-4-ylideneaminooxy]-piperidine-1-carboxylic acid tert-butyl ester 77a (720 mg).

Step 77B: 1-(4-Bromo-2,5-difluoro-phenyl)-piperidin-4-one O-piperidin-4-yl-oxime Compound 77a (300 mg, 0.61 mmol) was dissolved in 20% TFA/DCM (2 mL) and stirred at r.t. for 2 h. The solvents were removed in vacuo and the residue re-dissolved in DCM. This solution was washed with 2M NaOH then water and dried over $MgSO_4$ and concentrated to give 1-(4-bromo-2,5-difluoro-phenyl)-piperidin-4-one O-piperidin-4-yl-oxime 77b.

Step 77C: 1-(4-Bromo-2,5-difluoro-phenyl)-piperidin-4-one O-[1-(5-ethyl-pyrimidin-2-yl)-piperidin-4-yl]-oxime Compound 77b and 2-chloro-5-ethyl-pyrimidine (300 mg) were heated with diisopropylethylamine (300 mg) in DMSO at 130° C. for 0.5 h. Water and EtOAc were added and the organic phase separated, dried over $MgSO_4$ and concentrated.

The mixture was purified by chromatography on silica gel eluting with EtOAc/Hexane to give 1-(4-bromo-2,5-difluoro-phenyl)-piperidin-4-one O-[1-(5-ethyl-pyrimidin-2-yl)-piperidin-4-yl]-oxime 77c (170 mg).

Step 77D: (4-{4-[1-(5-Ethyl-pyrimidin-2-yl)-piperidin-4-yloxyimino]-piperidin-1-yl}-2,5-difluoro-phenyl)-acetic acid tert-butyl ester Compound 77c (170 mg, 0.34 mmol) was dissolved in 1,4-dioxane (4 mL) and degassed by bubbling $N_2$ through the solution for 5 mins Bis(tri-tert-butylphosphine)palladium (32 mg) was added followed by 2-tert-butoxy-2-oxoethylzinc chloride (3 mL, 0.5 M in diethylether) and the mixture was stirred at r.t. under $N_2$ for 16 h. Water and DCM were added and the organic phase was separated, dried over $MgSO_4$ and concentrated. The crude mixture was purified by chromatography on silica gel eluting with EtOAc/Hexane to give (4-{4-[1-(5-ethyl-pyrimidin-2-yl)-piperidin-4-yloxyimino]-piperidin-1-yl}-2,5-difluoro-phenyl)-acetic acid tert-butyl ester 77d (141 mg).

Step 77E: (4-{4-[1-(5-Ethyl-pyrimidin-2-yl)-piperidin-4-yloxyimino]-piperidin-1-yl}-2,5-difluoro-phenyl)-acetic acid Compound 77d (141 mg) was dissolved in DCM (2 mL) and TFA (2 mL) and stirred at r.t. for 1 h. The solvent was removed in vacuo, DCM and 1M HCl were added and the organic phase was separated, dried over $MgSO_4$ and concentrated to give (4-{4-[1-(5-Ethyl-pyrimidin-2-yl)-piperidin-4-yloxyimino]-piperidin-1-yl}-2,5-difluoro-phenyl)-acetic acid 77e (126 mg).

Step 77F: 2-(4-{4-[1-(5-Ethyl-pyrimidin-2-yl)-piperidin-4-yloxyimino]-piperidin-1-yl}-2,5-difluoro-phenyl)-N-(1-methyl-piperidin-4-yl)-acetamide Compound 77e (9 mg, 0.019 mmol) was dissolved in DCE (0.5 mL) and 4-amino-1-methylpiperidine (0.01 mL) was added followed by HOBt (4 mg, 0.03 mmol) and EDC (12 mg, 0.06 mmol) and stirred at r.t. for 16 h. MeOH was added and the mixture purified by HPLC to give 2-(4-{4-[1-(5-ethyl-pyrimidin-2-yl)-piperidin-4-yloxyimino]-piperidin-1-yl}-2,5-difluoro-phenyl)-N-(1-methyl-piperidin-4-yl)-acetamide 77-1. LC-MS 570.2 (MFE).

The following compounds were made according to this procedure using the corresponding amine. An additional step of removing a BOC protecting group from primary and secondary amines with trifluoroacetic acid/dichloromethane was performed when appropriate.

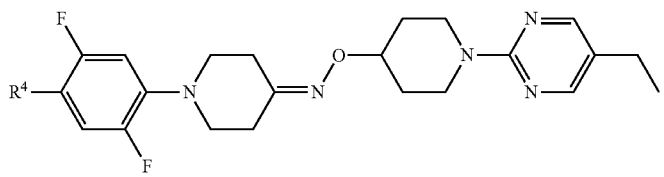

| No. | R4 | MH+ | MW | $t_R$ (Min) | HPLC Gradient | EC50 (nM) |
|---|---|---|---|---|---|---|
| 77-1 | 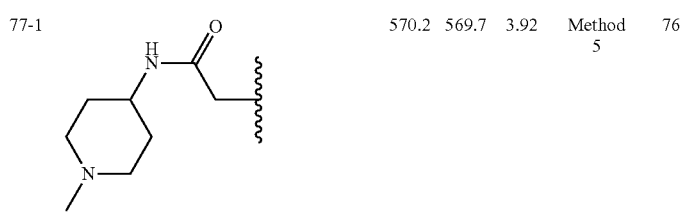 | 570.2 | 569.7 | 3.92 | Method 5 | 76 |
| 77-2 | 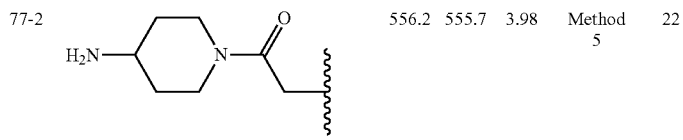 | 556.2 | 555.7 | 3.98 | Method 5 | 22 |
| 77-3 |  | 501.1 | 500.6 | 4.19 | Method 5 | 18 |
| 77-4 | 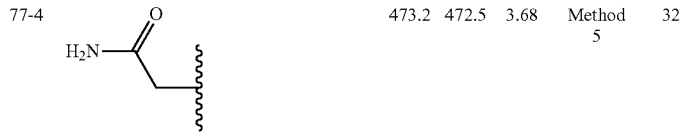 | 473.2 | 472.5 | 3.68 | Method 5 | 32 |

-continued
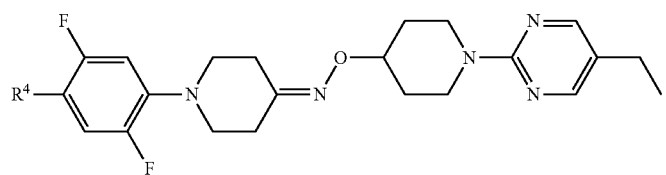
| No. | R4 | MH+ | MW | t_R (Min) | HPLC Gradient | EC50 (nM) |
|---|---|---|---|---|---|---|
| 77-5 | (S)-3-(dimethylamino)pyrrolidine-1-carbonyl | 570.2 | 569.7 | 3.97 | Method 5 | 6 |
| 77-6 | (R)-3-(dimethylamino)pyrrolidine-1-carbonyl | 570.2 | 569.7 | 3.96 | Method 5 | 9 |
| 77-7 | (S)-3-aminopiperidine-1-carbonyl | 556.2 | 555.7 | 3.81 | Method 5 | 45 |
| 77-8 | (R)-3-aminopiperidine-1-carbonyl | 556.2 | 555.7 | 3.83 | Method 5 | 30 |
| 77-9 | (S)-3-(aminomethyl)pyrrolidine-1-carbonyl | 556.2 | 555.7 | 4.04 | Method 5 | 8 |
| 77-10 | piperidin-4-ylamide | 556.2 | 555.7 | 4.70 | Method 5 | 20 |
| 77-11 | (S)-3-aminopyrrolidine-1-carbonyl | 542.2 | 541.6 | 3.57 | Method 5 | 47 |

-continued

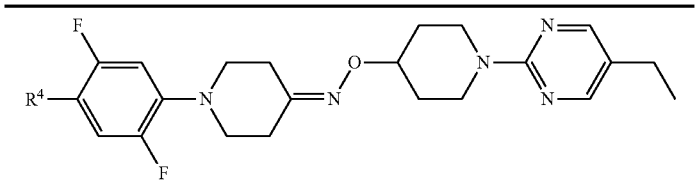

| No. | R₄ | MH+ | MW | $t_R$ (Min) | HPLC Gradient | EC50 (nM) |
|---|---|---|---|---|---|---|
| 77-12 | H₂N-pyrrolidinyl-C(O)- | 542.2 | 541.6 | 3.56 | Method 5 | 19 |
| 77-13 | HN-piperazinyl-C(O)- | 542.2 | 541.6 | 3.63 | Method 5 | 39 |
| 77-14 | MeN(Me)CH₂-piperidinyl-C(O)- | 598.3 | 597.8 | 4.63 | Method 5 | 6 |

Example 78

In Vivo OGTT Methods

Nine to 13 week old Male Sprague Dawley rats weighing 250 g-350 g or 9 week old male Zucker Diabetic Fatty rats weighing 300 g-450 g were fasted overnight for 16 hours. At time zero, blood was collected using the tail-nick method and glucose was measured with a glucometer (Bayer HealthCare) Animals then immediately received either vehicle (80% Labrasol, Gattefossé, France) or 3, 10, or 30 mg/kg GPR119 agonist (p.o., volume 2 mL/kg). Thirty minutes later blood glucose was again measured preceding the administration of a glucose bolus (p.o. 2 g/kg, volume 6 mL/kg). Blood glucose was then determined at 10, 20, 30, 60, 90, 120, and 180 minutes post glucose bolus or 20, 40, 60, 80, 100, and 120 minutes past glucose bolus.

Nine week old male ZDF rats were dosed with either 30 mg/kg of Compound 2-35 or 30 mg/kg of Compound 8-1 30 minutes prior to administration of the glucose bolus. Glucose excursion was greatly reduced by both compounds when compared to vehicle controls. Compound 2-35 resulted in a 75% reduction of glucose excursion compared to vehicle in the 2 hrs post glucose bolus (measuring every 20 minutes and comparing glucose area under the curve) while compound 8-1 resulted in a 70% reduction.

Example 79 cAMP Assay Methods

Quantitative detection of cAMP accumulation from cells expressing human GPR119 receptor was achieved using Perkin Elmer's LANCE cAMP-384 Kit (Cat#AD0264) according to the manufacturer's protocol. Briefly, HEK293 cells stably expressing a mutant form of the human GPR119 receptor (Methionine 1 replaced with the amino acid sequence MKTIIALSYIFCLVFADYKDDDDA (SEQ ID NO: 1), and T327 & S329 changed to alanines) were grown to 50-70% confluency in cell culture media (DMEM, 10% heat inactivated Fetal Bovine Serum, 50 I.U./mL penicillin, 50 µg/mL streptomycin, 10 mM HEPES, 20 µg/mL G418 Sulfate). On the day of the assay, GPR119 stable HEK293 cells were lifted from the tissue culture plate and 1000 cells/well were incubated along with various concentrations of test compounds for 20 min at 37° C. Detection Buffer (50mM HEPES, 10mM calcium chloride, 0.35% Triton X-100, 1 mg/mL BSA) containing cAMP-specific antibody was then added to all wells and allowed to equilibrate in the dark for 10 minutes at room temperature. Upon equilibration, Detection Buffer containing europium-labeled cAMP tracer complex was added to all wells and allowed to react for 1 hour at room temperature. After 1 hour, bound europium-labeled cAMP tracer was measured using a Perkin Elmer ViewLux. The quantity of cAMP generated in each well was derived from a standard curve. EC50 was determined using nonlinear regression analysis of the cAMP values over a range of agonist concentration (12 points spanning the range from 30 µM to 100pM).

For some compounds for which no EC50 value could be determined, the efficacy is provided at a single concentration (10 µM) yielding % stimulation values.

Example 80

Insulin Secretion Assay in Isolated Rat Pancreatic Islets

Rat pancretic islets are isolated and allowed to recover overnight in RPMI cell culture media (10% FBS, 50 I.U./mL penicillin, 50 µg/mL streptomycin, 10 mM HEPES) containing 11 mM Glucose. After incubating overnight at 37° C. and 5% $CO_2$/95% air, the islets were thoroughly washed 5× in 1× Krebes Ringes HEPES buffer (118 mM NaCl, 4.8 mM KCl, 2.5 mM $CaCl_2$, 1.2 mM $MgSO_4$, 20 mM HEPES, 0.1% BSA, adjusted to a pH of 7.4 with NaOH) with 5 mM Glucose. Islets were allowed to preincubate for 30 minutes in 1×KRH with 5 mM Glucose at 37° C. before assay initiation.

Test compounds are diluted in 1×KRH containing an appropriate concentration of glucose so that at the initiation of the islet assay the final glucose concentration was 8.3 mM. At time zero, compound solutions were added to islets in wells to give a final volume of 2.4 mL of 1×KRH with 8.3 mM glucose and allowed to incubate at 37° C. Aliquots of supernatant were removed at various times points and were assayed for insulin using a commercially available insulin RIA kit (Linco Research Labs).

Immediately following the assay, the islets are removed from the 24 well plates into separate 1.5 mL epindorf tubes containing 1 mL of 1×KRH with no glucose and then placed on ice. Islets are allowed to settle for 5 mM before the supernatant is removed and 300 μL of acid/ethanol is added to each tubes. Following brief sonication tubes are stored at −20° C. for at least 24 hours before assayed for total insulin content by radioimmunoassay (Linco Research). For quantification purposes, the amount of stimulated insulin secretion is expressed as a fraction of total insulin in the assay well.

It will be appreciated that, although specific embodiments of the invention have been described herein for purposes of illustration, various modifications may be made without departing from the spirit and scope of the invention. Accordingly, the invention is not limited except as by the appended claims.

$R^1$ at each occurrence is independently $C_{1-4}$alkyl, F, hydroxy, $C_{1-4}$alkyl -O—, —$CO_2R^7$, or —C(=O)N$(R^6)_2$;

$R^2$ at each occurrence is independently $C_{1-4}$alkyl, F, hydroxy, or $C_{1-4}$alkyl-O—;

$R^3$ is $R^{Alk}$, aryl-$C_{1-4}$alkyl, heterocycle-$C_{1-4}$alkyl, —C(=O)$R^6$, —$CO_2R^5$, —$SO_2R^5$, —C(=X)N$(R^6)_2$, aryl, or heterocycle, wherein each alkyl, $R^{Alk}$, aryl, and heterocycle group is optionally substituted with 1-4 substituents independently of each other selected from $R^8$;

$R^4$ at each occurrence is independently halogen, cyano, hydroxy, $R^{Alk}$, —$NO_2$, —C(=O)H, —C(=O)$R^5$, —$C_{1-3}$-alkyl-C(=O)$R^5$, —$CO_2H$, —$CO_2R^5$, —C(=O)N$(R^6)_2$, —$C_{1-3}$-alkyl-C(=O)N$(R^6)_2$, —$SO_2N(R^6)_2$, —S(=O)$R^5$, —S(=O)$_2R^5$, —S(=O)$_2$—O—$R^5$, $R^{Alk}$—O—, $R^{Alk}$—S—, —N$(R^6)_2$, aryl, aryl-$C_{1-6}$alkyl, heterocycle, heterocycle-$C_{1-6}$alkyl, —$NR^6$C(=O)$R^5$, —$NR^6$S(=O)$_2R^5$, —$NR^6$C(=O)N$(R^6)_2$, —$NR^6$C(=O)O$R^7$, —$NR^6$C(=N$R^6$)N$(R^6)_2$, or —$NR^6$S(=O)$_2$N$(R^6)_2$, wherein each alkyl, $R^{Alk}$, aryl and heterocycle is optionally substituted with 1-5 substituents independently of each other selected from $R^8$;

$R^5$ is $R^{Alk}$, heterocycle, aryl, heterocycle-$C_{1-3}$-alkyl or aryl-$C_{1-3}$-alkyl, wherein each alkyl, $R^{Alk}$, heterocycle and aryl group is optionally substituted with 1-4 substituents independently of each other selected from $R^8$;

$R^6$ at each occurrence is independently H, $R^{Alk}$, heterocycle, heterocycle-$C_{1-6}$-alkyl, aryl or aryl-$C_{1-3}$-alkyl, wherein each $R^{Alk}$, heterocycle, aryl and alkyl are optionally substituted with 1-4 halogen, hydroxy, —N$(R^7)_2$, $C_{1-4}$alkyl-O—, and —$CO_2R^7$;

$R^7$ at each occurrence is independently H or $C_{1-4}$alkyl;

What is claimed is:

1. A compound of the formula (I):

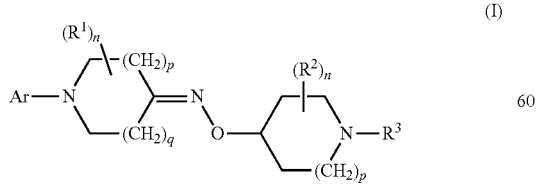

(I)

wherein:

Ar is aryl or heteroaryl, wherein said aryl and heteroaryl are optionally substituted with 1-5 $R^4$;

$R^8$ at each occurrence is independently cyano, hydroxy, $R^{Alk}$, aryl, aryl-$C_{1-6}$alkyl, heterocycle, heterocycle-$C_{1-6}$alkyl, halogen, oxo, $C_{1-4}$haloalkyl, —$NO_2$, —C(=O)H, —$CO_2R^7$, —OC(=O)$R^{Alk}$, —C(=O)N$(R^6)_2$, —$SO_2N(R^6)_2$, —S(=O)$R^{Alk}$, —S(=O)$_2R^{Alk}$, $C_{1-6}$alkyl-O—, halo$C_{1-4}$alkyl-O—, —N$(R^6)_2$, —$SR^6$, —$NR^6$C(=O)$R^{Alk}$, —$NR^6$S(=O)$_2R^{Alk}$, —$NR^6$C(=O)O$R^{Alk}$, —$NR^6$C(=O)N$(R^6)_2$, or —$NR^6$S(=O)$_2$N$(R^6)_2$, wherein each $R^{Alk}$, alkyl, aryl and heterocycle are optionally substituted with 1-4 substituents independently of each other selected from halogen, hydroxy, —N$(R^7)_2$, $C_{1-4}$alkyl-O—, —$NR^6CO_2R^6$, —$NR^6SO_2R^6$, and —$CO_2R^7$;

$R^{Alk}$ at each occurrence is independently $C_{1-6}$-alkyl, $C_{2-6}$-alkenyl, $C_{2-6}$-alkynyl, $C_{3-8}$-cycloalkyl, $C_{3-8}$-cycloalkyl-$C_{1-3}$-alkyl, $C_{4-8}$-cycloalkenyl or $C_{4-8}$-cycloalkenyl-$C_{1-3}$-alkyl;

X denotes O or S;

n at each occurrence is 0, 1, or 2;

p at each occurrence is 0 or 1; and q is 0, 1, or 2, including any tautomers and stereoisomers thereof, or a salt thereof.

2. The compound according to claim 1 having the following structure (I.1):

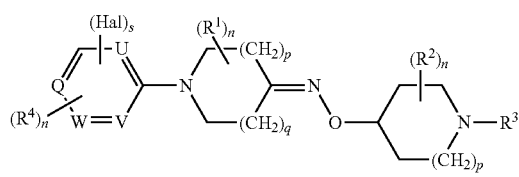

wherein

Q, U, V, W denote CH which may be substituted with Hal and/or $R^4$ as defined in the formula (I.1), wherein one or two of the groups Q, U, V and W may denote N;

r is 0, 1 or 2;

s is 0, 1, 2, 3 or 4, wherein r+s≦5:

Hal is F or Cl;

$R^1$, $R^2$, $R^3$, $R^4$, n, p, q are defined as in claim 1, or a salt thereof.

3. The compound according to claim 1 having the following structure (I.2) or (I.23):

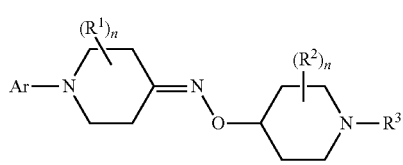

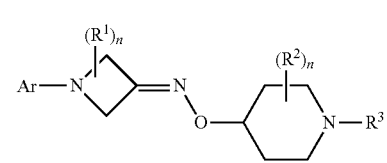

wherein Ar, $R^1$, $R^2$, $R^3$, n are defined as in claim 1, or a salt thereof.

4. The compound according to claim 1 having the following structure (I.3) or (I.24):

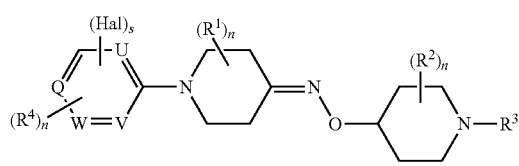

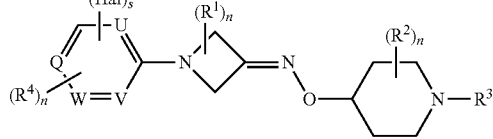

wherein

Q, U, V, W denote CH which may be substituted with Hal and/or $R^4$ as defined in the formula (I.3) and (I.24), wherein one or two of the groups Q, U, V and W may denote N;

r is 0, 1 or 2;

s is 0, 1, 2, 3 or 4, wherein r+s≦5:

Hal is F or Cl;

$R^1$, $R^2$, $R^3$, $R^4$, n are defined as in claim 1, or a salt thereof.

5. The compound according to claim 1 wherein Ar denotes aryl or heteroaryl, wherein aryl denotes phenyl or naphthyl, and heteroaryl denotes a 5- or 6-membered aromatic monocyclic ring, which comprises 1 to 4 heteroatoms selected from N, O and S, or a 8-, 9- or 10-membered aromatic bicyclic ring, which comprises 1 to 4 heteroatoms selected from N, O and S, wherein in each monocyclic aryl or heteroaryl group two adjacent C and/or N atoms may be linked via a $C_{3-5}$-alkylene or $C_{3-5}$-alkenylene bridging group in which one or two $CH_2$-groups may be replaced by a group selected from O, S, NH, $N(C_{1-3}$-alkyl), —C(=O)—, —S(=O)— and —S(=O)$_2$—, and wherein one or two CH-groups may be replaced by N, wherein said aryl or heteroaryl group is optionally substituted with 1-5 substituents independently of each other selected from $R^4$ and wherein $R^4$ is defined as in claim 1, or a salt thereof.

6. The compound according to claim 1 wherein $R^3$ is selected from the group consisting of $R^{Alk}$, $R^{Alk}$—C(=O)—, aryl-C(=O)—, aryl-$C_{1-3}$-alkyl-C(=O)—, heterocycle-C(=O)—, heterocycle-$C_{1-3}$-alkyl-C(=O)—, $R^{Alk}$—O—C(=O)-L-, aryl-O—C(=O)-L-, aryl-$C_{1-3}$-alkyl-O—C(=O)-L-, heterocycle-O—C(=O)-L-, heterocycle-$C_{1-3}$-alkyl-O—C(=O)-L-, $R^{Alk}$—$NR^N$—C(=X)-L-, heterocycle-$NR^N$—C(=X)-L-, heterocycle-$C_{1-3}$-alkyl-$NR^N$—C(=X)-L-, aryl-$NR^N$—C(=X)-L-, aryl-$C_{1-3}$-alkyl-$NR^N$—C(=OX)-L-, $R^{Alk}$—S(=O)$_2$-L-, aryl-S(=O)$_2$-L-, aryl-$C_{1-3}$-alkyl-S(=O)$_2$-L-, heterocycle-S(=O)$_2$-L-, heterocycle-$C_{1-3}$-alkyl-S(=O)$_2$-L-, aryl-L- and heteroaryl-L-, wherein L is a single bond or $C_{1-3}$-alkyl; and wherein each $R^{Alk}$, aryl, heteroaryl and heterocycle group is optionally substituted with 1-5 substituents independently of each other selected from $R^8$; and wherein $R^{Alk}$ denotes $C_{1-6}$-alkyl, $C_{2-6}$-alkenyl, $C_{2-6}$-alkynyl, $C_{3-8}$-cycloalkyl, $C_{3-8}$-cycloalkyl-$C_{1-3}$-alkyl, $C_{4-8}$-cycloalkenyl or $C_{4-8}$-cycloalkenyl-$C_{1-3}$-alkyl and wherein X denotes O or S; and wherein $R^N$ denotes H or $C_{1-4}$-alkyl; and wherein $R^8$ is defined as in claim 1, or a salt thereof.

7. The compound according to claim 1 wherein $R^4$ is selected from F, Cl, CN, —$NO_2$, $R^{Alk}$, $R^{Alk}$—O—, HCO, $R^{Alk}$—C(=O)—, HO—C(=O)—, $R^{Alk}$—O—C(=O)—, $R^{Alk}$—S(=O)—, $R^{Alk}$—S(=O)$_2$—, $R^{Alk}$—O—S(=O)$_2$—, $(R^6)_2$N—C(=O)—, $(R^6)_2$N—C(=O)—$C_{1-3}$-alkyl, heterocycle, heterocycle-$C_{1-3}$-alkyl, heterocycle-C(=O)—, heterocycle-C(=O)—$C_{1-3}$-alkyl, heterocycle -$N(R^6)$—C(=O)—, heterocycle-$N(R^6)$—C(=O)—$C_{1-3}$-alkyl, heterocycle-$C_{1-3}$alkyl-$N(R^6)$—C(=O)—, heterocycle-$C_{1-3}$alkyl-$N(R^6)$—C(=O)—$C_{1-3}$-alkyl, $(R^6)_2$N—S(=O)$_2$—, $R^{Alk}$—C(=O)—O—$C_{1-3}$-alkyl, $R^{Alk}$—O—C(=O)—N($R^6$)—$C_{1-3}$-alkyl-C(=O)—O—$C_{1-3}$-alkyl, $R^{Alk}$—S(=O)$_2$—$C_{1-3}$-alkyl, ($R^6$)$_2$N—$C_{1-3}$-alkyl, heterocycle-$C_{1-3}$-alkyl-N($R^6$)—$C_{1-3}$-alkyl, $R^{Alk}$—C(=O)—N($R^6$)—, $R^{Alk}$—C(=O)—N($R^6$)—$C_{1-3}$-alkyl, $R^{Alk}$—O—C(=O)—N($R^6$)—, $R^{Alk}$—O—C(=O)—N($R^6$)—$C_{1-3}$-alkyl, $R^{Alk}$-alkyl-S(=O)$_2$—N($R^6$)—, $R^{Alk}$—S(=O)$_2$—N($R^6$)—$C_{1-3}$-alkyl, ($R^6$)$_2$N—C(=O)—N($R^6$)—, ($R^6$)$_2$N—C(=O)—N($R^6$)—$C_{1-3}$-alkyl, ($R^6$)$_2$N—S(=O)$_2$—N($R^6$)—, ($R^6$)$_2$N—S(=O)$_2$—N($R^6$)—$C_{1-3}$-alkyl, wherein each $R^{Alk}$, alkyl and heterocycle group is optionally substituted with 1-3 substituents independently of each other selected from $R^8$;

wherein $R^{Alk}$ denotes $C_{1-6}$-alkyl, $C_{2-6}$-alkenyl, $C_{2-6}$-alkynyl, $C_{3-8}$-cycloalkyl, $C_{3-8}$-cycloalkyl-$C_{1-3}$-alkyl, $C_{4-8}$-cycloalkenyl or $C_{4-8}$-cycloalkenyl-$C_{1-3}$-alkyl; and wherein $R^6$ and $R^8$ are defined as in claim 1, or a salt thereof.

8. The compound according to claim 1 wherein $R^6$ is selected from H, $C_{1-6}$-alkyl, $C_{3-8}$-cycloalkyl and $C_{3-7}$-cycloalkyl-$C_{1-3}$-alkyl, wherein each alkyl group is optionally substituted with 1-3 substituents independently of each other selected from HO—, $C_{1-4}$-alkyl-O—, $H_2N$—, $C_{1-3}$-alkyl-NH—, ($C_{1-3}$-alkyl)$_2$N—, HOOC— and $C_{1-4}$-alkyl-O—C(=O)—, or a salt thereof.

9. The compound according to claim 1 wherein $R^8$ is selected from cyano, hydroxy, $C_{1-6}$-alkyl, phenyl, phenyl-$C_{1-3}$alkyl, heterocycle, heterocycle-$C_{1-3}$-alkyl, halogen, oxo, $NO_2$, H—C(=O)—, $R^7$O—C(=O)—, $R^7$—C(=O)—O—, ($R^6$)$_2$N—C(=O)—, ($R^6$)$_2$N—S(=O)$_2$—, $R^7$—S(=O)—, $R^7$—S(=O)$_2$—, $C_{1-6}$alkyl-O—, ($R^6$)$_2$N—, $R^6$S—, $R^7$—C(=O)—$R^6$N—, $R^7$O—C(=O)—$R^6$N— or ($R^6$)$_2$N—C(=O)—$R^6$N—, wherein each alkyl, aryl and heterocycle are optionally substituted with 1-4 substituents independently of each other selected from halogen, hydroxy, ($R^7$)$_2$N—, $C_{1-4}$alkyl-O—, $R^6$O—C(=O)—$R^6$N—, $R^6$—S(=O)$_2$—$R^6$N— and $R^7$—O—C(=O)—, wherein $R^7$ denotes H or $C_{1-4}$alkyl, and wherein $R^6$ is defined as in claim 1, or a salt thereof.

10. The compound according to claim 1 wherein $R^5$ is selected from $C_{1-6}$-alkyl optionally substituted with 1-3 substituents independently of each other selected from $R^8$, wherein $R^8$ is defined as in claim 1, or a salt thereof.

11. The compound of claim 1 wherein each n is 0, p is 1 and q is 1, or a salt thereof.

12. The pharmaceutically acceptable salt of a compound according to claim 1.

13. A pharmaceutical composition comprising a compound according to claim 1, or a pharmaceutically acceptable salt thereof, and one or more pharmaceutically acceptable carriers and/or diluents.

14. A method for treating type I diabetes mellitus, type II diabetes mellitus, or obesity characterized in that a compound according to claim 1, or a pharmaceutically acceptable salt thereof, is administered to a patient in need thereof.

15. A method for treating type I diabetes mellitus, type II diabetes mellitus, or obesity comprising the step of administering to a patient in need thereof a therapeutically effective amount of a compound according to claim 1, or a pharmaceutically acceptable salt thereof, in combination with a therapeutically effective amount of one or more additional therapeutic agents.

16. A pharmaceutical composition comprising a compound according to claim 1, or a pharmaceutically acceptable salt thereof, and one or more additional therapeutic agents, optionally together with one or more pharmaceutically acceptable carriers and/or diluents.

17. The method according to claim 14 for the treatment of type I diabetes mellitus.

18. The method according to claim 14 for the treatment of type II diabetes mellitus.

19. The method according to claim 15 for the treatment of type I diabetes mellitus.

20. The method according to claim 15 for the treatment of type II diabetes mellitus.

* * * * *